(12) United States Patent
Green et al.

(10) Patent No.: US 9,315,498 B2
(45) Date of Patent: *Apr. 19, 2016

(54) ARLETHYNYL DERIVATIVES

(71) Applicant: Hoffmann-La Roche Inc., Nutley, NJ (US)

(72) Inventors: Luke Green, Basel (CH); Wolfgang Guba, Muelheim (DE); Georg Jaeschke, Basel (CH); Synese Jolidon, Blauen (CH); Lothar Lindemann, Basel (CH); Antonio Ricci, Birsfelden (CH); Daniel Rueher, Raedersdorf (FR); Heinz Stadler, Basel (CH); Eric Vieira, Frenkendorf (CH)

(73) Assignee: HOFFMAN-LA ROCHE INC., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/085,064

(22) Filed: Nov. 20, 2013

(65) Prior Publication Data

US 2014/0155602 A1    Jun. 5, 2014

Related U.S. Application Data

(62) Division of application No. 13/914,336, filed on Jun. 10, 2013, now Pat. No. 8,618,296, which is a division of application No. 13/779,782, filed on Feb. 28, 2013, now Pat. No. 8,513,273, which is a division of application No. 13/066,044, filed on Apr. 5, 2011, now Pat. No. 8,420,661.

(30) Foreign Application Priority Data

Apr. 13, 2010 (EP) .................... 10159754

(51) Int. Cl.
| | | |
|---|---|---|
| *A61K 31/50* | (2006.01) | |
| *A61K 31/501* | (2006.01) | |
| *A61K 31/4965* | (2006.01) | |
| *A61K 31/505* | (2006.01) | |
| *A61K 31/44* | (2006.01) | |
| *C07D 401/04* | (2006.01) | |
| *C07D 401/14* | (2006.01) | |
| *C07D 401/00* | (2006.01) | |
| *C07D 403/00* | (2006.01) | |
| *C07D 405/00* | (2006.01) | |
| *C07D 409/00* | (2006.01) | |
| *C07D 239/02* | (2006.01) | |
| *C07D 471/04* | (2006.01) | |
| *C07D 403/04* | (2006.01) | |
| *C07D 413/04* | (2006.01) | |
| *C07D 413/14* | (2006.01) | |
| *C07D 498/04* | (2006.01) | |
| *C07D 491/107* | (2006.01) | |
| *C07D 241/02* | (2006.01) | |
| *C07D 241/00* | (2006.01) | |

(52) U.S. Cl.
CPC ............ *C07D 471/04* (2013.01); *C07D 401/04* (2013.01); *C07D 401/14* (2013.01); *C07D 403/04* (2013.01); *C07D 413/04* (2013.01); *C07D 413/14* (2013.01); *C07D 491/107* (2013.01); *C07D 498/04* (2013.01)

(58) Field of Classification Search
None
See application file for complete search history.

(56) References Cited

U.S. PATENT DOCUMENTS 4,886,817 A * 12/1989 Takeda et al. ............. 514/341
8,420,661 B2 * 4/2013 Green ................. C07D 401/04
                                                      514/278

(Continued)

FOREIGN PATENT DOCUMENTS

| WO | 01/16121 | 3/2001 |
| WO | 2005/094822 | 10/2005 |
| WO | 2007/050050 | 5/2007 |

(Continued)

OTHER PUBLICATIONS

The English translation of the Japanese Office Action, issued on Jan. 28, 2014, in the corresponding Japanese Application No. 2013-504215.

(Continued)

*Primary Examiner* — Rita Desai
*Assistant Examiner* — Ben S Michelson

(57) ABSTRACT

The present invention relates to ethynyl compounds of formula I-C1

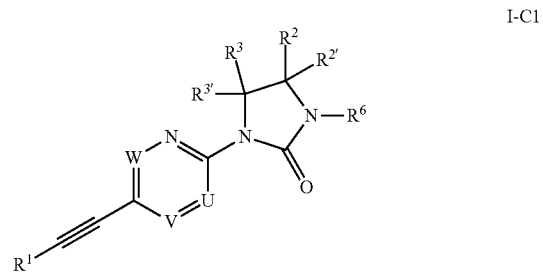

wherein
$R^1$, $R^2$, $R^{2'}$, $R^3$, $R^{3'}$, $R^6$, U, V and W are as defined herein and to a pharmaceutically acceptable acid addition salts, to a racemic mixtures, or to its corresponding enantiomers and/or optical isomers and/or stereoisomers thereof, which are allosteric modulators of the metabotropic glutamate receptor subtype 5 (mGluR5).

8 Claims, No Drawings

(56) References Cited

U.S. PATENT DOCUMENTS

| | | | |
|---|---|---|---|
| 8,716,316 B2* | 5/2014 | Green | A61K 31/44 514/336 |
| 8,969,338 B2* | 3/2015 | Jaeschke | C07D 401/04 514/228.8 |
| 2007/0105899 A1 | 5/2007 | Suzuki et al. | |

FOREIGN PATENT DOCUMENTS

| | | |
|---|---|---|
| WO | 2008/151184 | 12/2008 |
| WO | 2010/063487 | 6/2010 |
| WO | 2011/015343 | 2/2011 |
| WO | 2011/051201 | 5/2011 |

OTHER PUBLICATIONS

Chua et al., "Cyclohexenyl- and dehydropiperidinyl-alkynyl pyridines as potent metabotropic glutamate subtype 5 (mGlu5) receptor antagonists," Bioorganic & Medicinal Chemistry Letters, 2005, vol. 15, pp. 4589-4593.

Bach et al., "Metabotropic glutamate receptor 5 modulators and their potential therapeutic applications," Expert Opin. Ther. Patents (2007) 17(4):371-384.

Rodriguez et al., "Discovery of Novel Allosteric Modulators of Metabotropic Glutamate Receptor Subtype 5 Reveals Chemical and Functional Diversity and In Vivo Activity in Rat Behavioral Models of Anxiolytic and Antipsychotic Activity," Molecular Pharmacology, 2010, vol. 78, No. 6, pp. 1105-1123.

* cited by examiner

ARLETHYNYL DERIVATIVES

CROSS-REFERENCE TO RELATED APPLICATIONS

This application is a Divisional of U.S. patent application Ser. No. 13/914,336, filed Jun. 10, 2013, which is a Divisional of U.S. patent application Ser. No. 13/779,782, filed Feb. 28, 2013, now U.S. Pat. No. 8,513,273, which is a Divisional of U.S. patent application Ser. No. 13/066,044, filed Apr. 5, 2011, now U.S. Pat. No. 8,420,661, which claims the benefit of European Patent Application No. 10159754.0, filed Apr. 13, 2010. Each of these applications is hereby incorporated by reference herein in its entirety.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:
mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

A new avenue for developing selective modulators is to identify compounds which act through allosteric mechanism, modulating the receptor by binding to a site different from the highly conserved orthosteric binding site. Allosteric modulators of mGluR5 have emerged recently as novel pharmaceutical entities offering this attractive alternative. Allosteric modulators have been described, for example in WO2008/151184, WO2006/048771, WO2006/129199 and WO2005/044797 and in *Molecular Pharmacology*, 40, 333-336, 1991; *The Journal of Pharmacology and Experimental Therapeutics*, Vol 313, No. 1, 199-206, 2005;

In recent years there have been significant advantages in understanding the pathophysiology of several disorders of brain development, suggesting that protein synthesis at synapses is triggered by activation of group I metabotropic glutamate receptors. Such disorders include fragile X syndrome, autism, idiopathic autism, tuberous sclerosis complex disorder, neurofibromatosis type 1 or Rett syndrome (*Annu. Rev. Med.*, 2011, 62, 31.1-31.19 and *Neuroscience* 156, 2008, 203-215).

Described in the prior art are positive allosteric modulators. They are compounds that do not directly activate receptors by themselves, but markedly potentiate agonist-stimulated responses, increase potency and maximum of efficacy. The binding of these compounds increases the affinity of a glutamate-site agonist at its extracellular N-terminal binding site. Allosteric modulation is thus an attractive mechanism for enhancing appropriate physiological receptor activation. There is a scarcity of selective allosteric modulators for the mGluR5 receptor. Conventional mGluR5 receptor modulators typically lack satisfactory aqueous solubility and exhibit poor oral bioavailability.

Therefore, there remains a need for compounds that overcome these deficiencies and that effectively provide selective allosteric modulators for the mGluR5 receptor.

SUMMARY OF THE INVENTION

The present invention provides ethynyl compounds of formula I

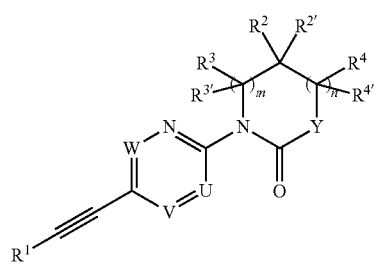

wherein
U is =N— or =C($R^5$)—;
V is —CH= or —N=;
W is =CH— or =N—;
 with the proviso that only one of U, V or W is nitrogen,
$R^5$ is hydrogen, methyl or halogen;
Y is —N($R^6$)—, —O—, —C($R^7$)($R^7$)—, —CH$_2$O— or —CH$_2$S(O)$_2$—;
 wherein $R^6$ is hydrogen or lower alkyl and $R^7$ and $R^{2'}$ are each independently hydrogen, hydroxy, lower alkyl or lower alkoxy;
$R^1$ is phenyl or heteroaryl, each of which is optionally substituted by one or two substituents, selected from halogen, lower alkyl and lower alkoxy;
$R^2$ and $R^{2'}$ are each independently hydrogen, lower alkyl, hydroxy, lower alkoxy, $C_3$-$C_6$-cycloalkyl, or CH$_2$-lower alkoxy, or together with the carbon atom to which they are attached form a $C_3$-$C_6$-cycloalkyl group or a ring containing —$CH_2OCH_2$—;

m is 0, 1 or 2;

when m is 1, $R^3$ and $R^{3'}$ are each independently hydrogen, lower alkyl, or $CH_2$-lower alkoxy or together with the carbon atom to which they are attached form a $C_3$-$C_6$-cycloalkyl group; or $R^3$ and $R^2$ together with the carbon atom to which they are attached form a $C_{3-6}$-cycloalkyl group or a ring containing —$(CH_2)_2OCH_2$—;

n is 0 or 1; and when n is 1, $R^4$ and $R^{4'}$ are each independently hydrogen, lower alkyl, or $CH_2$-lower alkoxy or together with the carbon atom to which they are attached form a $C_3$-$C_6$-cycloalkyl; or $R^4$ and $R^2$ together with the carbon atom to which they are attached form a $C_{3-6}$-cycloalkyl group;

or when n is 0 and Y is —$N(R^6)$—, then $R^6$ and $R^2$ together with the carbon atom and the nitrogen atom to which they are attached form a $C_{3-6}$-cycloalkyl group;

or when n and m are 0, then $R^2$ and $R^7$ together with the carbon atoms to which they are attached form a $C_{3-6}$-cycloalkyl group;

or a pharmaceutically acceptable acid addition salt, a racemic mixture, an enantiomer, an isomer, and/or a stereoisomer thereof.

The present invention provides compounds of formula I per se, their pharmaceutically acceptable salts, and mixtures of enantiomers or diastereomers or their enantiomerically or diastereomerically pure forms. The invention also provides pharmaceutical compositions containing a therapeutically effective amount of such compounds and process for the production of such compounds and compositions.

Compounds of formula I are allosteric modulators of the metabotropic glutamate receptor subtype 5 (mGluR5). They can be used in the treatment or prevention of disorders relating to allosteric modulators for the mGluR5 receptor. For example, the compounds can be used for the treatment or prevention of disorders, relating to allosteric modulators for the mGluR5 receptor, such as schizophrenia, cognition, fragile X syndrome or autism, and to pharmaceutical compositions containing the compounds of formula I. The most preferred indications are schizophrenia and cognition.

DETAILED DESCRIPTION OF THE INVENTION

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-4 carbon atoms. Examples for "alkyl" are methyl, ethyl, n-propyl, and isopropyl.

The term "lower alkoxy" denotes a group —O—R' wherein R' is lower alkyl as defined above.

The term "halogen" denotes the chlorine, fluorine, bromine, or iodine.

The term "ethynyl" denotes the group —C≡C—.

The term "cycloalkyl" denotes a saturated carbon ring, containing from 3 to 6 carbon ring atoms, for example cyclopropyl, cyclobutyl, cyclopentyl or cyclohexyl.

The term "heteroaryl" denotes a 5 or 6-membered aromatic ring, containing at least one N, O or S-heteroatom, for example pyridinyl, pyrimidinyl, pyrazolyl, pyridazinyl, imidazolyl, triazolyl, thienyl or pyrazinyl.

"Pharmaceutically acceptable," such as pharmaceutically acceptable carrier, excipient, etc., denotes pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" denotes an amount that is effective to prevent, alleviate or ameliorate symptoms of disease or prolong the survival of the subject being treated.

One embodiment of the invention provides compounds of formula I-1

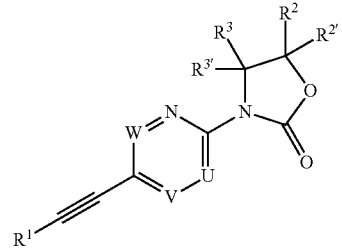

I-A1 wherein

U is =N— or =C($R^5$)—;

V is —CH= or —N=;

W is =CH— or =N—;

with the proviso that only one of U, V or W is nitrogen.

$R^5$ is hydrogen, methyl or halogen;

$R^1$ is phenyl or heteroaryl, each of which is optionally substituted by one or two substituents, selected from halogen, lower alkyl and lower alkoxy;

$R^2$ and $R^{2'}$ are each independently hydrogen, lower alkyl, hydroxy, lower alkoxy, $C_3$-$C_6$-cycloalkyl, or $CH_2$-lower alkoxy, or together with the carbon atom to which they are attached form a $C_3$-$C_6$-cycloalkyl group or a ring containing —$CH_2OCH_2$—; and $R^3$ and $R^{3'}$ are each independently hydrogen, lower alkyl, or $CH_2$-lower alkoxy or together with the carbon atom to which they are attached form a $C_3$-$C_6$-cycloalkyl group; or $R^3$ and $R^2$ together with the carbon atom to which they are attached form a $C_{3-6}$-cycloalkyl group or a ring containing —$(CH_2)_2OCH_2$—;

or a pharmaceutically acceptable acid addition salt, a racemic mixture, an enantiomer, an optical isomer, and/or stereoisomer thereof.

Examples of compounds of formula I-A1 are the following:

3-(3-fluoro-5-phenylethynyl-pyridin-2-yl)-5,5-dimethyl-oxazolidin-2-one;

(5RS)-5-methoxymethyl-3-(5-phenylethynyl-pyridin-2-yl)-oxazolidin-2-one;

(5R or 5S)-5-methoxymethyl-3-(5-phenylethynyl-pyridin-2-yl)-oxazolidin-2-one;

(5S or 5R)-5-methoxymethyl-3-(5-phenylethynyl-pyridin-2-yl)-oxazolidin-2-one;

5,5-dimethyl-3-(5-phenylethynyl-pyridin-2-yl)-oxazolidin-2-one;

3-[5-(3-fluoro-phenylethynyl)-pyridin-2-yl]-5,5-dimethyl-oxazolidin-2-one;

5,5-dimethyl-3-(5-pyridin-3-ylethynyl-pyridin-2-yl)-oxazolidin-2-one;
(5RS)-5-tert-butyl-3-(5-phenylethynyl-pyridin-2-yl)-oxazolidin-2-one;
6-(5-phenylethynyl-pyridin-2-yl)-4-oxa-6-aza-spiro[2.4]heptan-5-one;
7-(5-phenylethynyl-pyridin-2-yl)-5-oxa-7-aza-spiro[3.4]octan-6-one;
3-(5-phenylethynyl-pyridin-2-yl)-1-oxa-3-aza-spiro[4.4]nonan-2-one;
3-(5-phenylethynyl-pyridin-2-yl)-1-oxa-3-aza-spiro[4.5]decan-2-one;
(5RS)-5-tert-butyl-5-methyl-3-(5-phenylethynyl-pyridin-2-yl)-oxazolidin-2-one;
(3aRS,6aSR)-3-(5-phenylethynyl-pyridin-2-yl)-hexahydro-cyclopentaoxazol-2-one;
(3aRS,6aSR)-3-(5-pyridin-3-ylethynyl-pyridin-2-yl)-hexahydro-cyclopentaoxazol-2-one;
(3aRS,6aSR)-3-[5-(5-fluoro-pyridin-3-ylethynyl)-pyridin-2-yl]-hexahydro-cyclopentaoxazol-2-one;
(RS)-4,5,5-trimethyl-3-(5-phenylethynyl-pyridin-2-yl)-oxazolidin-2-one;
4,4,5,5-tetramethyl-3-(5-phenylethynyl-pyridin-2-yl)-oxazolidin-2-one;
3-[5-(5-fluoro-pyridin-3-ylethynyl)-pyridin-2-yl]-5,5-dimethyl-oxazolidin-2-one;
5,5-dimethyl-3-(5-pyrimidin-5-ylethynyl-pyridin-2-yl)-oxazolidin-2-one;
5,5-dimethyl-3-[5-(1-methyl-1H-pyrazol-4-ylethynyl)-pyridin-2-yl]-oxazolidin-2-one;
3-[5-(4-fluoro-phenylethynyl)-pyridin-2-yl]-5,5-dimethyl-oxazolidin-2-one;
3-[5-(3,4-difluoro-phenylethynyl)-pyridin-2-yl]-5,5-dimethyl-oxazolidin-2-one;
3-[5-(2,5-difluoro-phenylethynyl)-pyridin-2-yl]-5,5-dimethyl-oxazolidin-2-one;
3-[5-(6-fluoro-pyridin-3-ylethynyl)-pyridin-2-yl]-5,5-dimethyl-oxazolidin-2-one;
6-(5-pyridin-3-ylethynyl-pyridin-2-yl)-4-oxa-6-aza-spiro[2.4]heptan-5-one;
(6SR,7RS)-3-(5-phenylethynyl-pyridin-2-yl)-hexahydro-benzooxazol-2-one;
(3aSR,7aRS)-(3aRS,7RS)-1-(5-phenylethynyl-pyridin-2-yl)-hexahydro-pyrano[4,3-d]oxazol-2-one; and
5,5-dimethyl-3-(6-(phenylethynyl)pyridazin-3-yl)oxazolidin-2-one.

A further embodiment of the invention provides compounds of formula I-B1

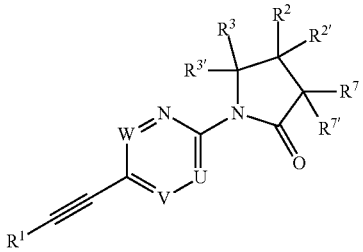

I-B1 wherein
U is =N— or =C(R$^5$)—;
V is —CH= or —N=;
W is =CH— or =N—;
with the proviso that only one of U, V or W is nitrogen.
R$^5$ is hydrogen, methyl or halogen;
R$^1$ is phenyl or heteroaryl, each of which is optionally substituted by one or two substituents, selected from halogen, lower alkyl and lower alkoxy;
R$^2$ and R$^{2'}$ are each independently hydrogen, lower alkyl, hydroxy, lower alkoxy, C$_3$-C$_6$-cycloalkyl, or CH$_2$-lower alkoxy, or together with the carbon atom to which they are attached form a C$_3$-C$_6$-cycloalkyl group or a ring containing —CH$_2$OCH$_2$—;
R$^3$ and R$^{3'}$ are each independently hydrogen, lower alkyl, or CH$_2$-lower alkoxy or together with the carbon atom to which they are attached form a C$_3$-C$_6$-cycloalkyl group; or R$^3$ and R$^2$ together with the carbon atom to which they are attached form a C$_{3-6}$-cycloalkyl group or a ring containing —(CH$_2$)$_2$OCH$_2$—; and
R$^7$ and R$^{7'}$ are each independently hydrogen, hydroxy, lower alkyl or lower alkoxy;
or a pharmaceutically acceptable acid addition salt, a racemic mixture, an enantiomer, an optical isomer, and/or stereoisomer thereof.

Specific examples of compounds of formula I-B1 are the following:
4,4-dimethyl-1-(5-phenylethynyl-pyridin-2-yl)-pyrrolidin-2-one;
(3RS)-3-hydroxy-4,4-dimethyl-1-(5-phenylethynyl-pyridin-2-yl)-pyrrolidin-2-one;
1-(3-fluoro-5-phenylethynyl-pyridin-2-yl)-4,4-dimethyl-pyrrolidin-2-one;
1-[5-(5-fluoro-pyridin-3-ylethynyl)-pyridin-2-yl]-4,4-dimethyl-pyrrolidin-2-one;
4,4-dimethyl-1-(5-pyridin-3-ylethynyl-pyridin-2-yl)-pyrrolidin-2-one;
1-[5-(5-chloro-pyridin-3-ylethynyl)-pyridin-2-yl]-4,4-dimethyl-pyrrolidin-2-one;
1-[5-(3-fluoro-phenylethynyl)-pyridin-2-yl]-4,4-dimethyl-pyrrolidin-2-one;
4,4-dimethyl-1-(3-methyl-5-phenylethynyl-pyridin-2-yl)-pyrrolidin-2-one;
2-(5-phenylethynyl-pyridin-2-yl)-2-aza-spiro[4.4]nonan-3-one;
(RS)-3-methoxy-4,4-dimethyl-1-(5-phenylethynyl-pyridin-2-yl)-pyrrolidin-2-one;
(5R or 5S)-5-methoxymethyl-3-(5-phenylethynyl-pyridin-2-yl)-oxazolidin-2-one;
(5S or 5R)-5-methoxymethyl-3-(5-phenylethynyl-pyridin-2-yl)-oxazolidin-2-one;
(RS)-1-[5-(5-chloro-pyridin-3-ylethynyl)-pyridin-2-yl]-3-methoxy-4,4-dimethyl-pyrrolidin-2-one;
(RS)-3-methoxy-4,4-dimethyl-1-(5-m-tolylethynyl-pyridin-2-yl)-pyrrolidin-2-one;
(RS)-1-[5-(3-fluoro-phenylethynyl)-pyridin-2-yl]-3-methoxy-4,4-dimethyl-pyrrolidin-2-one;
(RS)-1-[5-(4-fluoro-phenylethynyl)-pyridin-2-yl]-3-methoxy-4,4-dimethyl-pyrrolidin-2-one;
6-(5-phenylethynyl-pyridin-2-yl)-2-oxa-6-aza-spiro[3.4]octan-7-one;
4,4-dimethyl-5'-phenylethynyl-3,4,5,6-tetrahydro-[1,2]bipyridinyl-2-one;
5'-(3-fluoro-phenylethynyl)-4,4-dimethyl-3,4,5,6-tetrahydro-[1,2']bipyridinyl-2-one;
5'-(3-chloro-phenylethynyl)-4,4-dimethyl-3,4,5,6-tetrahydro-[1,2]bipyridinyl-2-one;
5'-(5-chloro-pyridin-3-ylethynyl)-4,4-dimethyl-3,4,5,6-tetrahydro-[1,2]bipyridinyl-2-one;
5'-(4-fluoro-phenylethynyl)-4,4-dimethyl-3,4,5,6-tetrahydro-[1,2]bipyridinyl-2-one;
5'-(2,5-difluoro-phenylethynyl)-4,4-dimethyl-3,4,5,6-tetrahydro-[1,2]bipyridinyl-2-one;
4,4-dimethyl-1-(5-phenylethynyl-pyrimidin-2-yl)-pyrrolidin-2-one;

2-(5-phenylethynyl-pyrimidin-2-yl)-2-aza-spiro[4.4]nonan-3-one;
1-[5-(3-fluoro-phenylethynyl)-pyrimidin-2-yl]-4,4-dimethyl-pyrrolidin-2-one;
1-[5-(3-chloro-phenylethynyl)-pyrimidin-2-yl]-4,4-dimethyl-pyrrolidin-2-one;
1-[5-(4-fluoro-phenylethynyl)-pyrimidin-2-yl]-4,4-dimethyl-pyrrolidin-2-one;
1-[5-(2,5-difluoro-phenylethynyl)-pyrimidin-2-yl]-4,4-dimethyl-pyrrolidin-2-one;
(RS)-3-methoxy-4,4-dimethyl-1-(5-phenylethynyl-pyrimidin-2-yl)-pyrrolidin-2-one;
(5R or 5S)-5-methoxymethyl-3-(5-phenylethynyl-pyrimidin-2-yl)-oxazolidin-2-one;
(5S or 5R)-5-methoxymethyl-3-(5-phenylethynyl-pyrimidin-2-yl)-oxazolidin-2-one;
(RS)-1-[5-(3-fluoro-phenylethynyl)-pyrimidin-2-yl]-3-methoxy-4,4-dimethyl-pyrrolidin-2-one;
(R or S)-1-[5-(3-fluoro-phenylethynyl)-pyrimidin-2-yl]-3-methoxy-4,4-dimethyl-pyrrolidin-2-one;
(S or R)-1-[5-(3-fluoro-phenylethynyl)-pyrimidin-2-yl]-3-methoxy-4,4-dimethyl-pyrrolidin-2-one;
(R or S)-1-[5-(2,5-difluoro-phenylethynyl)-pyrimidin-2-yl]-3-methoxy-4,4-dimethyl-pyrrolidin-2-one;
4,4-dimethyl-1-(6-(phenylethynyl)pyridazin-3-yl)pyrrolidin-2-one; and
4,4-dimethyl-1-(5-(pyridin-3-ylethynyl)pyrazin-2-yl)pyrrolidin-2-one.

A further embodiment of the invention provides compounds of formula I-C1

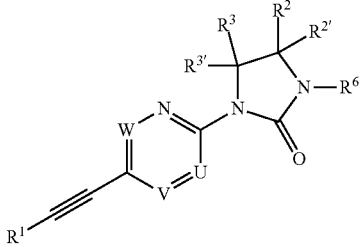

I-C1 wherein
U is =N— or =C($R^5$)—;
V is —CH= or —N=;
W is =CH— or =N—;
with the proviso that only one of U, V or W is nitrogen.
$R^5$ is hydrogen, methyl or halogen;
$R^6$ is hydrogen or lower alkyl;
$R^1$ is phenyl or heteroaryl, each of which is optionally substituted by one or two substituents, selected from halogen, lower alkyl and lower alkoxy;
$R^2$ and $R^{2'}$ are each independently hydrogen, lower alkyl, hydroxy, lower alkoxy, $C_3$-$C_6$-cycloalkyl, or $CH_2$-lower alkoxy, or together with the carbon atom to which they are attached form a $C_3$-$C_6$-cycloalkyl group or a ring containing —$CH_2OCH_2$—; and
$R^3$ and $R^{3'}$ are each independently hydrogen, lower alkyl, or $CH_2$-lower alkoxy or together with the carbon atom to which they are attached form a $C_3$-$C_6$-cycloalkyl group; or $R^3$ and $R^2$ together with the carbon atom to which they are attached form a $C_{3-6}$-cycloalkyl group or a ring containing —$(CH_2)_2OCH_2$—;
or $R^6$ and $R^2$ together with the carbon atom and the nitrogen atom to which they are attached form a $C_{3-6}$-cycloalkyl;

or a pharmaceutically acceptable acid addition salt, a racemic mixture, an enantiomer, an optical isomer and/or stereoisomer thereof.
Examples of compounds of formula I-C1 are the following:
4,4-dimethyl-1-(5-phenylethynyl-pyridin-2-yl)-imidazolidin-2-one;
3,4,4-trimethyl-1-(5-phenylethynyl-pyridin-2-yl)-imidazolidin-2-one;
3-ethyl-4,4-dimethyl-1-(5-phenylethynyl-pyridin-2-yl)-imidazolidin-2-one;
3-isopropyl-4,4-dimethyl-1-(5-phenylethynyl-pyridin-2-yl)-imidazolidin-2-one;
1-methyl-3-(5-phenylethynyl-pyridin-2-yl)-1,3-diaza-spiro[4.4]nonan-2-one;
(RS)-4-cyclopentyl-3-methyl-1-(5-phenylethynyl-pyridin-2-yl)-imidazolidin-2-one;
3,4,4-trimethyl-1-(5-pyridin-3-ylethynyl-pyridin-2-yl)-imidazolidin-2-one;
1-[5-(5-fluoro-pyridin-3-ylethynyl)-pyridin-2-yl]-3,4,4-trimethyl-imidazolidin-2-one;
3,4,4-trimethyl-1-[5-(1-methyl-1H-pyrazol-4-ylethynyl)-pyridin-2-yl]-imidazolidin-2-one;
1-[5-(5-chloro-pyridin-3-ylethynyl)-pyridin-2-yl]-3,4,4-trimethyl-imidazolidin-2-one;
3,4,4-trimethyl-1-(5-pyridazin-4-ylethynyl-pyridin-2-yl)-imidazolidin-2-one;
1-[5-(3-fluoro-phenylethynyl)-pyridin-2-yl]-3,4,4-trimethyl-imidazolidin-2-one;
1-[5-(3-chloro-phenylethynyl)-pyridin-2-yl]-3,4,4-trimethyl-imidazolidin-2-one;
3,4,4-trimethyl-1-(5-pyrimidin-5-ylethynyl-pyridin-2-yl)-imidazolidin-2-one;
3,4,4-trimethyl-1-(5-m-tolylethynyl-pyridin-2-yl)-imidazolidin-2-one;
1-[5-(4-fluoro-phenylethynyl)-pyridin-2-yl]-3,4,4-trimethyl-imidazolidin-2-one;
(RS)-2-(5-phenylethynyl-pyridin-2-yl)-hexahydro-imidazo[1,5-a]pyridin-3-one;
(RS)-2-(5-pyridin-3-ylethynyl-pyridin-2-yl)-hexahydro-imidazo[1,5-a]pyridin-3-one;
(RS)-2-[5-(3-fluoro-phenylethynyl)-pyridin-2-yl]-hexahydro-imidazo[1,5-a]pyridin-3-one;
(RS)-4-cyclopropyl-3-methyl-1-(5-phenylethynyl-pyridin-2-yl)-imidazolidin-2-one;
(3aSR,7aRS)-(3aRS,7RS)-1-methyl-3-(5-phenylethynyl-pyridin-2-yl)-octahydro-benzoimidazol-2-one;
(3aSR,7aRS)-(3aRS,7RS)-1-methyl-3-(5-pyridin-3-ylethynyl-pyridin-2-yl)-octahydro-benzoimidazol-2-one;
(3aSR,7aRS)-(3aRS,7RS)-1-[5-(5-fluoro-pyridin-3-ylethynyl)-pyridin-2-yl]-3-methyl-octahydro-benzoimidazol-2-one;
4-methyl-6-(5-phenylethynyl-pyridin-2-yl)-4,6-diaza-spiro[2 4]heptan-5-one;
(3aSR,7aRS)-(3aRS,7RS)-1-ethyl-3-(5-phenylethynyl-pyridin-2-yl)-octahydro-benzoimidazol-2-one;
(3aSR,7aRS)-(3aRS,7RS)-1-ethyl-3-(5-pyridin-3-ylethynyl-pyridin-2-yl)-octahydro-benzoimidazol-2-one;
(3aSR,7aRS)-(3aRS,7RS)-1-isopropyl-3-(5-phenylethynyl-pyridin-2-yl)-octahydro-benzoimidazol-2-one;
(3aRS, 6aSR)-1-methyl-3-(5-(phenylethynyl)pyridin-2-yl)hexahydrocyclopenta[d]imidazol-2(1H)-one;
(RS)-4-tert-butyl-3-methyl-1-(5-phenylethynyl-pyridin-2-yl)-imidazolidin-2-one;
1-[5-(3-fluoro-phenylethynyl)-3-methyl-pyridin-2-yl]-3,4,4-trimethyl-imidazolidin-2-one;
(3aSR,6aRS)-1-[5-(3-fluoro-phenylethynyl)-pyridin-2-yl]-3-methyl-hexahydro-cyclopenta-imidazol-2-one;

1-[3-fluoro-5-(4-fluoro-phenylethynyl)-pyridin-2-yl]-3,4,4-trimethyl-imidazolidin-2-one;
1-[3-fluoro-5-(3-fluoro-phenylethynyl)-pyridin-2-yl]-3,4,4-trimethyl-imidazolidin-2-one;
6-[5-(4-fluoro-phenylethynyl)-pyridin-2-yl]-4-methyl-4,6-diaza-spiro[2.4]heptan-5-one;
6-[5-(3-fluoro-phenylethynyl)-pyridin-2-yl]-4-methyl-4,6-diaza-spiro[2.4]heptan-5-one;
3,4,4-trimethyl-1-(5-phenylethynyl-pyrimidin-2-yl)-imidazolidin-2-one;
1-[5-(3-fluoro-phenylethynyl)-pyrimidin-2-yl]-3,4,4-trimethyl-imidazolidin-2-one;
1-[5-(2,5-difluoro-phenylethynyl)-pyrimidin-2-yl]-3,4,4-trimethyl-imidazolidin-2-one;
1-[5-(4-fluoro-phenylethynyl)-pyrimidin-2-yl]-3,4,4-trimethyl-imidazolidin-2-one;
1-[5-(3,4-di-fluoro-phenylethynyl)-pyrimidin-2-yl]-3,4,4-trimethyl-imidazolidin-2-one;
3-isopropyl-4,4-dimethyl-1-(5-phenylethynyl-pyrimidin-2-yl)-imidazolidin-2-one;
1-[5-(3-fluoro-phenylethynyl)-pyrimidin-2-yl]-3-isopropyl-4,4-dimethyl-imidazolidin-2-one;
1-[5-(4-fluoro-phenylethynyl)-pyrimidin-2-yl]-3-isopropyl-4,4-dimethyl-imidazolidin-2-one;
1-[5-(4-fluoro-phenylethynyl)-pyrimidin-2-yl]-3-ethyl-4,4-dimethyl-imidazolidin-2-one;
1-[5-(3-fluoro-phenylethynyl)-pyrimidin-2-yl]-3-ethyl-4,4-dimethyl-imidazolidin-2-one;
4-methyl-6-(5-phenylethynyl-pyrimidin-2-yl)-4,6-diaza-spiro[2.4]heptan-5-one;
3,4,4-trimethyl-1-(6-(m-tolylethynyl)pyridazin-3-yl)imidazolidin-2-one;
1-(6-((3-chlorophenyl)ethynyl)pyridazin-3-yl)-3,4,4-trimethylimidazolidin-2-one;
3,4,4-trimethyl-1-(5-(phenylethynyl)pyrazin-2-yl)imidazolidin-2-one;
3,4,4-trimethyl-1-(5-(pyridin-3-ylethynyl)pyrazin-2-yl)imidazolidin-2-one;
1-(5-((3-fluorophenyl)ethynyl)pyrazin-2-yl)-3,4,4-trimethylimidazolidin-2-one;
1-(5-((4-fluorophenyl)ethynyl)pyrazin-2-yl)-3,4,4-trimethylimidazolidin-2-one;
(3aRS,6aSR)-1-methyl-3-(6-phenylethynyl-pyridazin-3-yl)-hexahydro-cyclopentaimidazol-2-one; and
(3aSR,6aRS)-1-[6-(3-fluoro-phenylethynyl)-pyridazin-3-yl]-3-methyl-hexahydro-cyclopentaimidazol-2-one.

A further embodiment of the invention provides compounds of formula I-D1

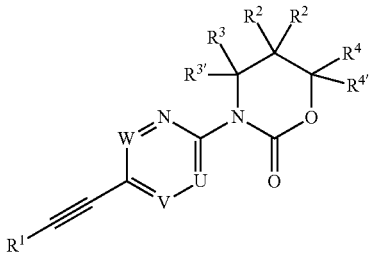

I-D1 wherein
U is =N— or =C($R^5$)—;
V is —CH= or —N=;
W is =CH— or =N—;
with the proviso that only one of U, V or W is nitrogen.
$R^5$ is hydrogen, methyl or halogen.
$R^1$ is phenyl or heteroaryl, each of which is optionally substituted by one or two substituents, selected from halogen, lower alkyl and lower alkoxy;
$R^2$ and $R^{2'}$ are each independently hydrogen, lower alkyl, hydroxy, lower alkoxy, $C_3$-$C_6$-cycloalkyl, or $CH_2$-lower alkoxy, or together with the carbon atom to which they are attached form a $C_3$-$C_6$-cycloalkyl group or a ring containing —$CH_2OCH_2$—;
$R^3$ and $R^{3'}$ are each independently hydrogen, lower alkyl, or $CH_2$-lower alkoxy or together with the carbon atom to which they are attached form a $C_3$-$C_6$-cycloalkyl group; or
$R^3$ and $R^2$ together with the carbon atom to which they are attached form a $C_{3-6}$-cycloalkyl group or a ring containing —$(CH_2)_2OCH_2$—; and
$R^4$ and $R^{4'}$ are each independently hydrogen, lower alkyl, or $CH_2$-lower alkoxy or together with the carbon atom to which they are attached from a $C_3$-$C_6$-cycloalkyl;
$R^4$ and $R^2$ together with the carbon atom to which they are attached form a $C_{3-6}$-cycloalkyl;
or a pharmaceutically acceptable acid addition salt, a racemic mixture, an enantiomer, an optical isomer and/or stereoisomer thereof.

Examples of compounds of formula I-D1 are the following:
5,5-dimethyl-3-(5-phenylethynyl-pyridin-2-yl)-[1,3]oxazinan-2-one;
6,6-dimethyl-3-(5-phenylethynyl-pyridin-2-yl)-[1,3]oxazinan-2-one;
6,6-dimethyl-3-(5-pyridin-3-ylethynyl-pyridin-2-yl)-[1,3]oxazinan-2-one;
3-[5-(5-fluoro-pyridin-3-ylethynyl)-pyridin-2-yl]-6,6-dimethyl-[1,3]oxazinan-2-one;
3-[5-(5-chloro-pyridin-3-ylethynyl)-pyridin-2-yl]-6,6-dimethyl-[1,3]oxazinan-2-one;
3-[5-(3-fluoro-phenylethynyl)-pyridin-2-yl]-6,6-dimethyl-[1,3]oxazinan-2-one;
3-[5-(3-chloro-phenylethynyl)-pyridin-2-yl]-6,6-dimethyl-[1,3]oxazinan-2-one;
6,6-dimethyl-3-(5-m-tolylethynyl-pyridin-2-yl)-[1,3]oxazinan-2-one;
3-[5-(4-fluoro-phenylethynyl)-pyridin-2-yl]-6,6-dimethyl-[1,3]oxazinan-2-one;
3-[5-(3,4-difluoro-phenylethynyl)-pyridin-2-yl]-6,6-dimethyl-[1,3]oxazinan-2-one;
3-[5-(2,5-difluoro-phenylethynyl)-pyridin-2-yl]-6,6-dimethyl-[1,3]oxazinan-2-one;
7,7-dimethyl-3-(5-phenylethynyl-pyridin-2-yl)-[1,3]oxazepan-2-one;
(RS)-5-hydroxy-6,6-dimethyl-3-(5-phenylethynyl-pyridin-2-yl)-[1,3]oxazinan-2-one;
(4aRS,7aSR)-3-(5-phenylethynyl-pyridin-2-yl)-hexahydro-cyclopenta[e][1,3]oxazin-2-one;
(4aRS,7aRS)-3-(5-phenylethynyl-pyridin-2-yl)-hexahydro-cyclopenta[e][1,3]oxazin-2-one;
(RS)-5,6,6-trimethyl-3-(5-phenylethynyl-pyridin-2-yl)-[1,3]oxazinan-2-one;
(RS)-6-methoxymethyl-3-(5-phenylethynyl-pyridin-2-yl)-[1,3]oxazinan-2-one;
(RS)-5-methoxy-6,6-dimethyl-3-(5-phenylethynyl-pyridin-2-yl)-[1,3]oxazinan-2-one;
(RS)-5,6,6-trimethyl-3-(5-phenylethynyl-pyrimidin-2-yl)-[1,3]oxazinan-2-one;
(RS)-3-[5-(2,5-difluoro-phenylethynyl)-pyrimidin-2-yl]-5,6,6-trimethyl-[1,3]oxazinan-2-one;
(RS)-3-[5-(3-fluoro-phenylethynyl)-pyrimidin-2-yl]-5,6,6-trimethyl-[1,3]oxazinan-2-one;
(RS)-3-[5-(4-fluoro-phenylethynyl)-pyrimidin-2-yl]-5,6,6-trimethyl-[1,3]oxazinan-2-one;
6,6-dimethyl-3-(6-(phenylethynyl)pyridazin-3-yl)-1,3-oxazinan-2-one;

6,6-dimethyl-3-(5-(phenylethynyl)pyrazin-2-yl)-1,3-oxazinan-2-one; and
(RS)-3-[5-(3-fluoro-phenylethynyl)-pyridin-2-yl]-5-methoxy-6,6-dimethyl-[1,3]oxazinan-2-one.

A further embodiment of the invention provides compounds of formula I-E1

I-E1 wherein
U is =N— or =C($R^5$)—;
V is —CH= or —N=;
W is =CH— or =N—;
with the proviso that only one of U, V or W is nitrogen.
$R^5$ is hydrogen, methyl or halogen;
$R^7$ and $R^{7'}$ are each independently hydrogen, hydroxy, lower alkyl or lower alkoxy;
$R^1$ is phenyl or heteroaryl, each of which is optionally substituted by one or two substituents, selected from halogen, lower alkyl and lower alkoxy;
$R^2$ and $R^{2'}$ are each independently hydrogen, lower alkyl, hydroxy, lower alkoxy, $C_3$-$C_6$-cycloalkyl, or $CH_2$-lower alkoxy, or together with the carbon atom to which they are attached form a $C_3$-$C_6$-cycloalkyl group or a ring containing —$CH_2OCH_2$—;
$R^3$ and $R^{3'}$ are each independently hydrogen, lower alkyl, or $CH_2$-lower alkoxy or together with the carbon atom to which they are attached form a $C_3$-$C_6$-cycloalkyl group; or $R^3$ and $R^2$ together with the carbon atom to which they are attached form a $C_{3-6}$-cycloalkyl group or a ring containing —$(CH_2)_2OCH_2$—; and
$R^4$ and $R^{4'}$ are each independently hydrogen, lower alkyl, or $CH_2$-lower alkoxy or together with the carbon atom to which they are attached form a $C_3$-$C_6$-cycloalkyl group;
$R^4$ and $R^2$ together with the carbon atom to which they are attached form a $C_{3-6}$-cycloalkyl group;
or a pharmaceutically acceptable acid addition salt, a racemic mixture, an enantiomer, an optical isomer and/or stereoisomer thereof.

Specific examples of compounds of formula I-E1 are the following:
5,5-dimethyl-5'-phenylethynyl-3,4,5,6-tetrahydro-[1,2]bipyridinyl-2-one;
5'-(3-fluoro-phenylethynyl)-5,5-dimethyl-3,4,5,6-tetrahydro-[1,2]bipyridinyl-2-one;
5,5-dimethyl-1-(5-phenylethynyl-pyrimidin-2-yl)-piperidin-2-one;
4,4-dimethyl-1-(5-phenylethynyl-pyrimidin-2-yl)-piperidin-2-one;
1-[5-(3-fluoro-phenylethynyl)-pyrimidin-2-yl]-4,4-dimethyl-piperidin-2-one;
1-[5-(2,5-difluoro-phenylethynyl)-pyrimidin-2-yl]-4,4-dimethyl-piperidin-2-one;
4,4-dimethyl-1-(6-(phenylethynyl)pyridazin-3-yl)piperidin-2-one;
1-(5-((3-fluorophenyl)ethynyl)pyrazin-2-yl)-4,4-dimethylpiperidin-2-one;
4,4-dimethyl-1-(5-(pyridin-3-ylethynyl)pyrazin-2-yl)piperidin-2-one; and
4,4-dimethyl-1-(5-(phenylethynyl)pyrazin-2-yl)piperidin-2-one.

A further embodiment of the invention provides compounds of formula I-F1

I-F1 wherein
U is =N— or =C($R^5$)—;
V is —CH= or —N=;
W is =CH— or =N—;
with the proviso that only one of U, V or W is nitrogen.
$R^5$ is hydrogen, methyl or halogen;
$R^6$ is hydrogen or lower alkyl;
$R^1$ is phenyl or heteroaryl, each of which is optionally substituted by one or two substituents, selected from halogen, lower alkyl and lower alkoxy;
$R^2$ and $R^{2'}$ are each independently hydrogen, lower alkyl, hydroxy, lower alkoxy, $C_3$-$C_6$-cycloalkyl, or $CH_2$-lower alkoxy, or together with the carbon atom to which they are attached form a $C_3$-$C_6$-cycloalkyl group or a ring containing —$CH_2OCH_2$—;
$R^3$ and $R^{3'}$ are each independently hydrogen, lower alkyl, or $CH_2$-lower alkoxy or together with the carbon atom to which they are attached form a $C_3$-$C_6$-cycloalkyl group; or $R^3$ and $R^2$ together with the carbon atom to which they are attached form a $C_{3-6}$-cycloalkyl group or a ring containing —$(CH_2)_2OCH_2$—; and
$R^4$ and $R^{4'}$ are each independently hydrogen, lower alkyl, or $CH_2$-lower alkoxy or together with the carbon atom to which they are attached form a $C_3$-$C_6$-cycloalkyl group; or
$R^4$ and $R^2$ together with the carbon atom to which they are attached form a $C_{3-6}$-cycloalkyl;
or a pharmaceutically acceptable acid addition salt, a racemic mixture, an enantiomer, an optical isomer and/or stereoisomer thereof.

Examples of compounds of formula I-F1 are the following:
5,5-dimethyl-1-(5-phenylethynyl-pyridin-2-yl)-tetrahydro-pyrimidin-2-one;
1,5,5-trimethyl-3-(5-phenylethynyl-pyridin-2-yl)-tetrahydro-pyrimidin-2-one;
3,4,4-trimethyl-1-(5-phenylethynyl-pyridin-2-yl)-tetrahydro-pyrimidin-2-one;
1-[5-(2,5-difluoro-phenylethynyl)-pyridin-2-yl]-3,4,4-trimethyl-tetrahydro-pyrimidin-2-one;
1-[5-(4-fluoro-phenylethynyl)-pyridin-2-yl]-3,4,4-trimethyl-tetrahydro-pyrimidin-2-one;
3,4,4-trimethyl-5'-phenylethynyl-3,4,5,6-tetrahydro-[1,2']bipyrimidinyl-2-one;
5'-(3-fluoro-phenylethynyl)-3,4,4-trimethyl-3,4,5,6-tetrahydro-[1,2']bipyrimidinyl-2-one;

5'-(2,5-difluoro-phenylethynyl)-3,4,4-trimethyl-3,4,5,6-tetrahydro-[1,2']bipyrimidinyl-2-one;
4,4-dimethyl-1-(5-(phenylethynyl)pyrazin-2-yl)tetrahydropyrimidin-2(1H)-one;
3,4,4-trimethyl-1-(5-(phenylethynyl)pyrazin-2-yl)tetrahydropyrimidin-2(1H)-one;
1-(5-((3-fluorophenyl)ethynyl)pyrazin-2-yl)-4,4-dimethyltetrahydropyrimidin-2(1H)-one; and
1-(5-((3-fluorophenyl)ethynyl)pyrazin-2-yl)-3,4,4-trimethyltetrahydropyrimidin-2(1H)-one.

A further embodiment of the invention provides compounds of formula I-G1

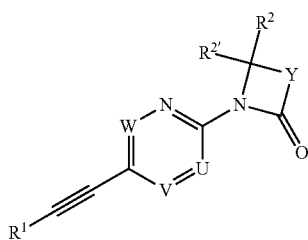

I-G1 wherein
U is =N— or =C(R⁵)—;
V is —CH= or —N=;
W is =CH— or =N—;
with the proviso that only one of U, V or W is nitrogen.
R⁵ is hydrogen, methyl or halogen;
Y is —N(R⁶)—, —O—, —C(R⁷)(R⁷')—, —CH₂O— or —CH₂S(O)₂—;
wherein R⁶ is hydrogen or lower alkyl and R⁷ and R⁷' are each independently hydrogen, hydroxy, lower alkyl and lower alkoxy;
R¹ is phenyl or heteroaryl, each of which is optionally substituted by one or two substituents, selected from halogen, lower alkyl and lower alkoxy; and
R² and R²' are each independently hydrogen, lower alkyl, hydroxy, lower alkoxy, C₃-C₆-cycloalkyl, or CH₂-lower alkoxy, or together with the carbon atom to which they are attached form a C₃-C₆-cycloalkyl group or a ring containing —CH₂OCH₂—;
or R⁶ and R² together with the carbon atom and the nitrogen atom to which they are attached form a C₃₋₆-cycloalkyl group;
or R² and R⁷ together with the carbon atoms to which they are attached form a C₃₋₆-cycloalkyl group;
or a pharmaceutically acceptable acid addition salt, a racemic mixture, an enantiomer, an optical isomer and/or stereoisomer thereof.

Examples of compounds of formula I-G1 are the following:
(1 RS,5 SR)-6-(5-phenylethynyl-pyridin-2-yl)-6-aza-bicyclo[3.2.0]heptan-7-one; 3,3-dimethyl-1-(5-phenylethynyl-pyridin-2-yl)-azetidin-2-one; and
(1 RS,5 SR)-6-(5-pyridin-3-ylethynyl-pyridin-2-yl)-6-azabicyclo[3.2.0]heptan-7-one.

The invention further provides compounds of formula I, wherein Y is —CH₂O—, for example
(RS)-6-methyl-4-(5-phenylethynyl-pyridin-2-yl)-morpholin-3-one and 6,6-dimethyl-4-(5-phenylethynyl-pyridin-2-yl)-morpholin-3-one.

The invention further provides compounds of formula I, wherein Y is —CH₂S(O)₂—, for example 1,1-dioxo-4-(5-phenylethynyl-pyridin-2-yl)-thiomorpholin-3-one.

The invention also provides compounds of formula I, wherein m is 2, for example 7,7-dimethyl-3-(5-phenylethynyl-pyridin-2-yl)-[1,3]oxazepan-2-one.

The invention provides ethynyl compounds of formula Ia

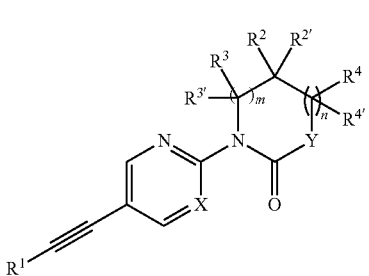

Ia wherein
X is N or C—R⁵,
wherein R⁵ is hydrogen or halogen;
Y is N—R⁶, O or CHR⁷,
wherein R⁶ is hydrogen or lower alkyl and R⁷ is hydrogen, hydroxy, lower alkyl or lower alkoxy;
R¹ is phenyl or heteroaryl, each of which is optionally substituted by halogen, lower alkyl or lower alkoxy;
R² and R²' are each independently hydrogen, lower alkyl, or CH₂-lower alkoxy or together with the carbon atom to which they are attached form a C₃-C₆-cycloalkyl group;
m is 0 or 1; when m is 1,
R³ and R³' are each independently hydrogen, lower alkyl, or CH₂-lower alkoxy or together with the carbon atom to which they are attached form a C₃-C₆-cycloalkyl group; and
n is 0 or 1; when n is 1,
R⁴ and R⁴' are each independently hydrogen, lower alkyl, or CH₂-lower alkoxy or together with the carbon atom to which they are attached form a C₃-C₆-cycloalkyl group;
or when m is 1 and n is 0, R³ and R² together with the carbon atoms to which they are attached form a C₃₋₆-cycloalkyl group;
or when m is 0 and m is 1, R⁴ and R² together with the carbon atoms to which they are attached form a C₃₋₆-cycloalkyl group;
or a pharmaceutically acceptable acid addition salt, racemic mixture, an enantiomer, an optical isomer, and/or stereoisomer thereof.

The preparation of compounds of formula I of the present invention can be carried out in sequential or convergent synthetic routes. Syntheses of the compounds of the invention are shown in the following schemes 1 to 3. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process variant described below, which process comprises reacting a compound of formula

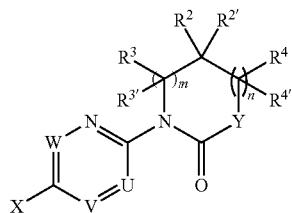

wherein X is a suitable leaving group which can be substituted by an acetylene moiety such as, for example a bromine or iodine atom, a trialkylstannyl group, a boronic acid or boronic ester group with a suitable aryl-acetylene of formula

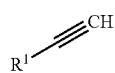

to obtain a compound of formula

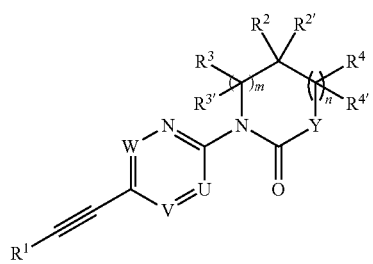

wherein the substituents are described above, or
if desired, converting the compounds obtained into pharmaceutically acceptable acid addition salts.

The preparation of compounds of formula I is further described in more detail in schemes 1 to 6 and in examples 1-174.

Scheme 1

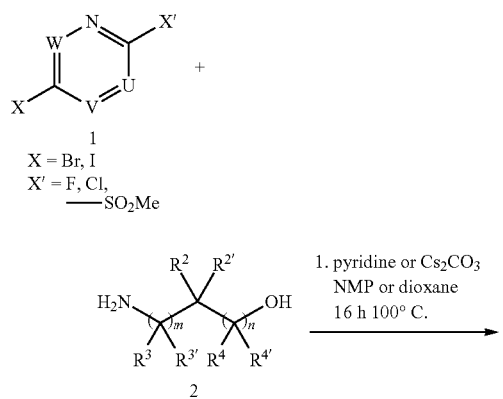

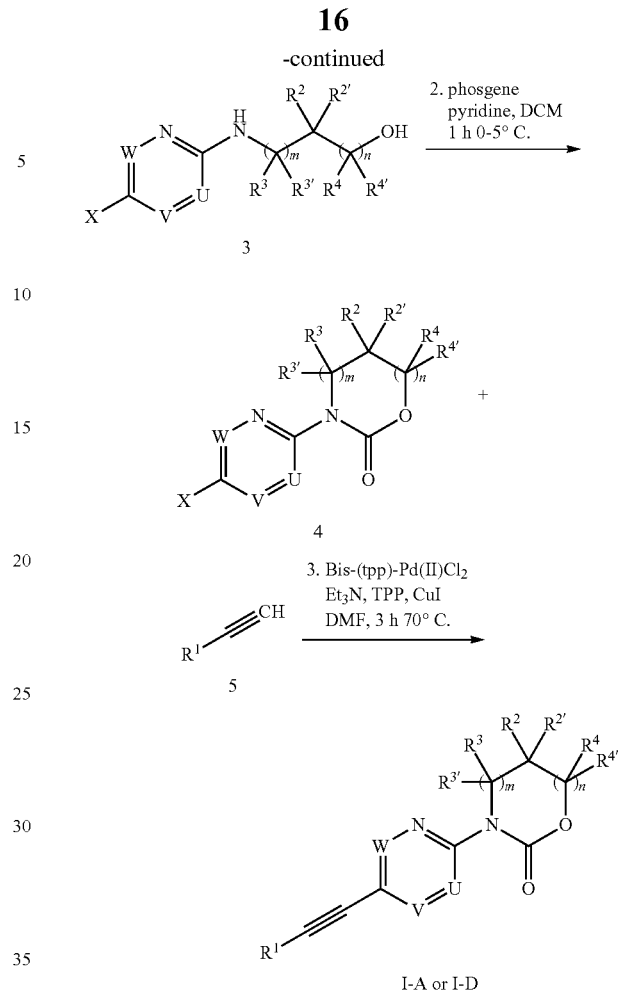

A ethynyl-pyridine, ethynyl-pyrimidine, ethynyl-pyrazine or ethynyl-pyridazine compound of formula I-A can be obtained by substitution of an appropriate 5-iodo-2-fluoro-pyridine, 5-iodo-2-fluoro-pyrimidine, 2-chloro-5-iodopyridazine or 2-bromo-5-iodopyrazine 1 or the like and an appropriate aminoalcohol 2 with a base such as pyridine, triethylamine, or cesium carbonate in a solvent such as NMP, pyridine, or dioxane to yield the corresponding 5-iodo-2-aminoalkoxy-adducts of formula 3, which are treated with phosgene or a phosgene equivalent such as triphosgene in presence of base such as pyridine in a solvent like dichloromethane to give the corresponding cyclized urethane- or urea-derivatives 4. Sonogashira coupling of the iodo-heteroaryl derivatives 4 with an appropriately substituted arylacetylene 5 yield the desired ethynyl compounds of general formula I-A or I-D (scheme 1).

Scheme 2

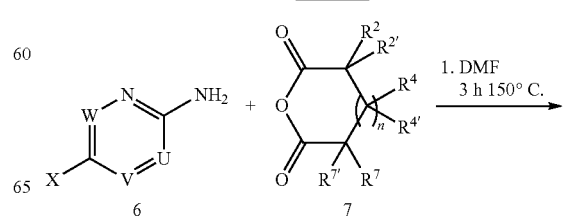

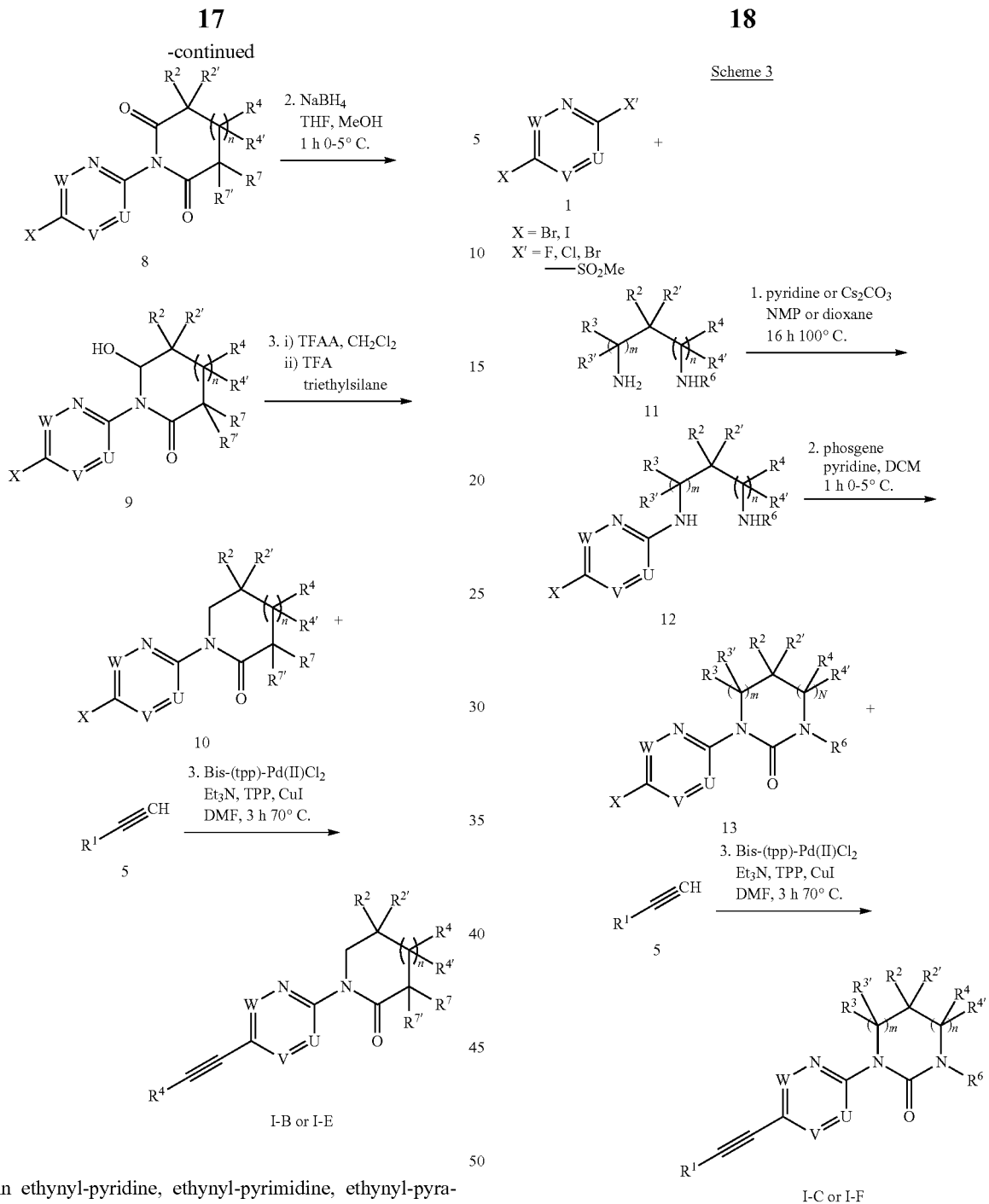

An ethynyl-pyridine, ethynyl-pyrimidine, ethynyl-pyrazine or ethynyl-pyridazine compound of formula I-B can be obtained by reacting an appropriate 5-iodo-2-amino-pyridine- or 5-iodo-2-amino-pyrimidine-, 5-iodo-2-amino-pyrazine, or 5-iodo-2-amino-pyridazine derivative 6 or the like with an appropriately substituted anhydride 7 in a solvent such as DMF to yield the corresponding imide derivative 8, which is reduced with a reducing agent such as sodium borohydride in a solvent such as THF and/or MeOH to give the corresponding alcohol derivative 9. Reacting compound 9 with trifluoroacetic anhydride in a solvent like dichloromethane followed by reduction with triethylsilane in a solvent like TFA yields the desired amide 10. Sonogashira coupling of the amide 10 with an appropriately substituted aryl-acetylene 5 yields the desired ethynyl-compounds of formula I-B or I-E (scheme 2).

An ethynyl-pyridine, ethynyl-pyrimidine, ethynyl-pyrazine or ethynyl-pyridazine compound of formula I-C can be obtained by substitution of an appropriate 5-iodo-2-fluoro-pyridine, 5-iodo-2-fluoro-pyrimidine, 2-chloro-5-iodopyridazine or 2-bromo-5-iodopyrazine 1 or the like (1) wherein Y is a suitable leaving group which can be displaced via nucleophillic substitution by an amine such as a fluorine, chlorine, or bromine atom or an alkysulfonyl group with an appropriate diaminoalkyl derivative 11 in presence of a base such as pyridine or cesium carbonate in a solvent like NMP, pyridine, or dioxane to yield the corresponding N-heteroaryl derivative 12, which is cyclized with phosgene or a phosgene equivalent in presence of a base such as pyridine or triethylamine in a solvent like dichloromethane or THF to give the corresponding urea derivative 13 which is then coupled with an appropriately substituted aryl-acetylene 5 to yield the desired ethynyl-compound of formula I-C or I-F (scheme 3).

with in-situ desilylation of 18 in presence of fluoride and an appropriately substituted aryl-halogenide 19 yields the desired arylethynyl-compounds of formula I (scheme 4).

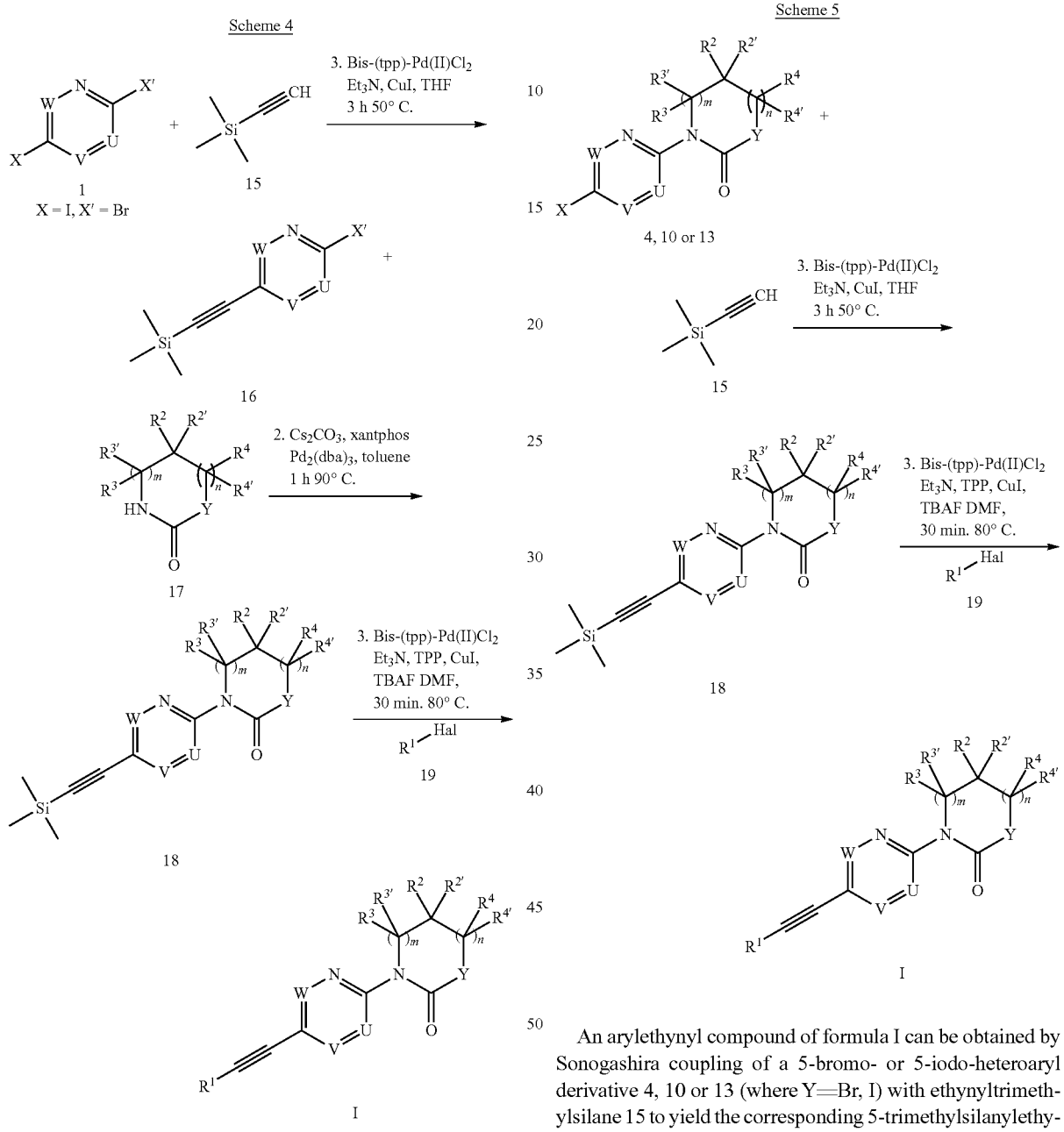

An ethynyl-pyridine or ethynyl-pyrimidine compound of formula I can be obtained for example by Sonogashira coupling of a 2-bromo-5-iodo-pyridine, 2-bromo-5-iodo-pyrimidine, 2-bromo-5-iodopyridazine or 2-bromo-5-iodopyrazine 1 or the like with ethynyltrimethylsilane 15 to yield the 2-bromo-5-trimethylsilanylethynyl-substituted heteroaryl derivatives 16. Substitution of 16 with an appropriate lactam, cyclic carbamate or cyclic urea derivative 17 in presence of a base such as cesium carbonate, or using xantphos and $Pd_2(dba)_3$ in a solvent like toluene yields the corresponding 5-trimethylsilanylethynyl derivatives 18. Sonogashira coupling An arylethynyl compound of formula I can be obtained by Sonogashira coupling of a 5-bromo- or 5-iodo-heteroaryl derivative 4, 10 or 13 (where Y=Br, I) with ethynyltrimethylsilane 15 to yield the corresponding 5-trimethylsilanylethynyl-derivatives 18. Sonogashira coupling with in-situ desilylation of 18 and an appropriately substituted aryl-halogenide 19 yields the desired ethynyl-pyridine or ethynyl-pyrimidine compounds of formula I (scheme 5).

Generally speaking, the sequence of steps used to synthesize the compounds of formula I can also be modified in certain cases, for example by first running the Sonogashira coupling with an appropriately substituted aryl- or heteroaryl-ethynyl derivative followed by the introduction of a lactam-, cyclic carbamate- or cyclic urea using procedures similar to those described in schemes 1 to 4. (scheme 6)

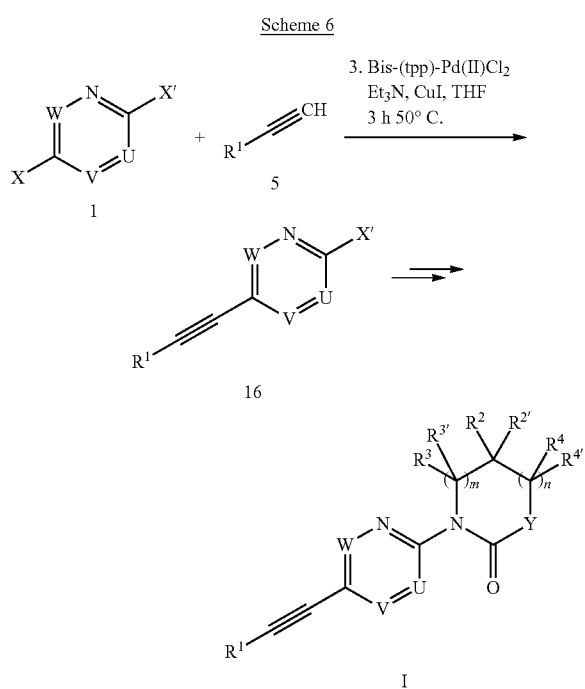

The compound of formula I as described herein as well as its pharmaceutically acceptable salt is used in the treatment or prevention of psychosis, epilepsy, schizophrenia, Alzheimer's disease, cognitive disorders and memory deficits, chronic and acute pain, restricted brain function caused by bypass operations or transplants, poor blood supply to the brain, spinal cord injuries, head injuries, hypoxia caused by pregnancy, cardiac arrest and hypoglycaemia, ischemia, Huntington's chorea, amyotrophic lateral sclerosis (ALS), dementia caused by AIDS, eye injuries, retinopathy, idiopathic parkinsonism or parkinsonism caused by medicaments, muscle spasms, convulsions, migraine, urinary incontinence, gastrointestinal reflux disorder, liver damage or failure whether drug or disease induced, Fragile-X syndrom, Down syndrom, autism, nicotine addiction, opiate addiction, anxiety, vomiting, dyskinesia, eating disorders, in particular bulimia or anorexia nervosa, and depressions, particularly for the treatment and prevention of acute and/or chronic neurological disorders, anxiety, the treatment of chronic and acute pain, urinary incontinence and obesity.

The preferred indications are schizophrenia and cognitive disorders.

Present invention further relates to the use of a compound of formula I as described herein, as well as its pharmaceutically acceptable salt, for the manufacture of a medicament, preferably for the treatment and prevention of the above-mentioned disorders.

Biological Assay and Data

Intracellular $Ca^{2+}$ Mobilization Assay

A monoclonal HEK-293 cell line stably transfected with a cDNA encoding for the human mGlu5a receptor was generated; for the work with mGlu5 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 μg/ml hygromycin and 15 μg/ml blasticidin (all cell culture reagents and antibiotics from Invitrogen, Basel, Switzerland).

About 24 hrs before an experiment, $5\times10^4$ cells/well were seeded in poly-D-lysine coated, black/clear-bottomed 96-well plates. The cells were loaded with 2.5 μM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist L-glutamate was added to the cells at a concentration corresponding to $EC_{20}$ (typically around 80 μM) with on-line recording of fluorescence; in order to account for day-to-day variations in the responsiveness of cells, the $EC_{20}$ of glutamate was determined immediately ahead of each experiment by recording of a full dose-response curve of glutamate.

Responses were measured as peak increase in fluorescence minus basal (i.e. fluorescence without addition of L-glutamate), normalized to the maximal stimulatory effect obtained with saturating concentrations of L-glutamate. Graphs were plotted with the % maximal stimulatory using XLfit, a curve fitting program that iteratively plots the data using Levenburg Marquardt algorithm. The single site competition analysis equation used was $y=A+((B-A)/(1+((x/C)D)))$, where y is the % maximal stimulatory effect, A is the minimum y, B is the maximum y, C is the $EC_{50}$, x is the log10 of the concentration of the competing compound and D is the slope of the curve (the Hill Coefficient). From these curves the $EC_{50}$ (concentration at which half maximal stimulation was achieved), the Hill coefficient as well as the maximal response in % of the maximal stimulatory effect obtained with saturating concentrations of L-glutamate were calculated.

Positive signals obtained during the pre-incubation with the PAM test compounds (i.e. before application of an $EC_{20}$ concentration of L-glutamate) were indicative of an agonistic activity, the absence of such signals were demonstrating the lack of agonistic activities. A depression of the signal observed after addition of the $EC_{20}$ concentration of L-glutamate was indicative of an inhibitory activity of the test compound.

In the list of examples below are shown the corresponding results for compounds which all have $EC_{50}<300$ nM.

The compounds of formula (I) and pharmaceutically acceptable salts thereof can be used as medicaments, e.g. in the form of pharmaceutical compositions. The pharmaceutical compositions can be administered orally, e.g. in the form of tablets, coated tablets, dragées, hard and soft gelatin capsules, solutions, emulsions or suspensions. However, the administration can also be effected rectally, e.g. in the form of suppositories, or parenterally, e.g. in the form of injectable solutions.

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. lactose, corn starch or derivatives thereof, talc, stearic acid or its salts and the like, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such compositions which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of pharmaceutical compositions useful in the prevention and/or the treatment of the above-recited diseases is also an aspect of the present invention.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention:

Tablets of the following composition are produced in a conventional manner:

|  | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

LIST OF EXAMPLES

| Ex. | Structure | Name | $EC_{50}$ (nM) mGlu5PAM | Eff. (%) |
|---|---|---|---|---|
| 1 | 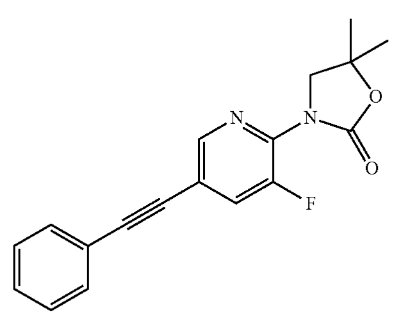 [SMILES: CC1(C)CN(c2ncc(C#Cc3ccccc3)cc2F)C(=O)O1] | 3-(3-Fluoro-5-phenylethynyl-pyridin-2-yl)-5,5-dimethyl-oxazolidin-2-one | 30 | 68 |
| 2 | 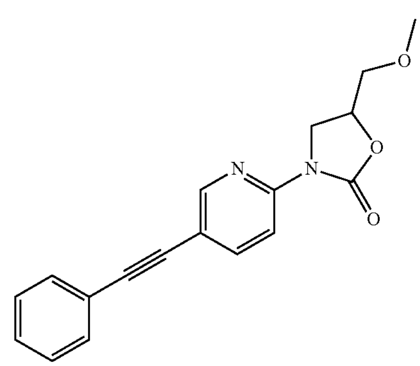 [SMILES: COCC1CN(c2ccc(C#Cc3ccccc3)cn2)C(=O)O1] | (5R5)-5-Methoxymethyl-3-(5-phenylethynyl-pyridin-2-yl)-oxazolidin-2-one | 47 | 34 |

| Ex. | Structure | Name | EC$_{50}$ (nM) mGlu5PAM | Eff. (%) |
|---|---|---|---|---|
| 3 | 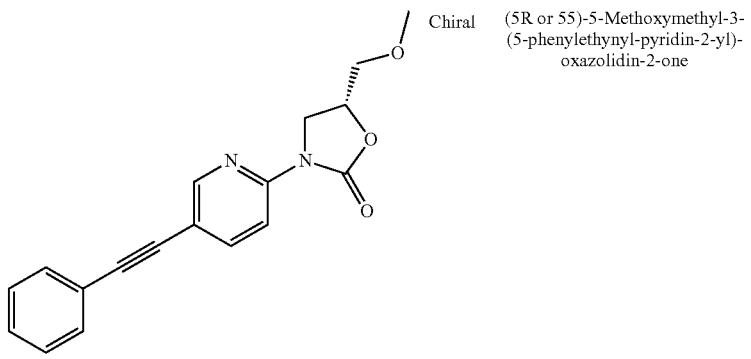<br>OR<br>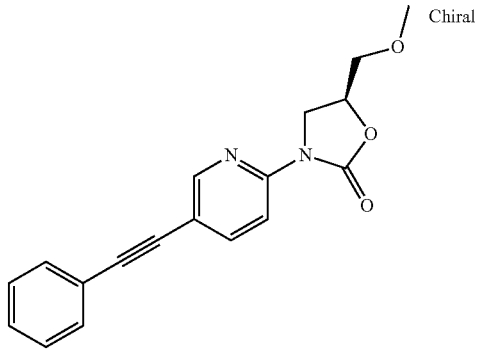 [SMILES: COC[C@@H]1CN(c2ccc(C#Cc3ccccc3)cn2)C(=O)O1] | (5R or 5S)-5-Methoxymethyl-3-(5-phenylethynyl-pyridin-2-yl)-oxazolidin-2-one | 18 | 46 |
| 4 | 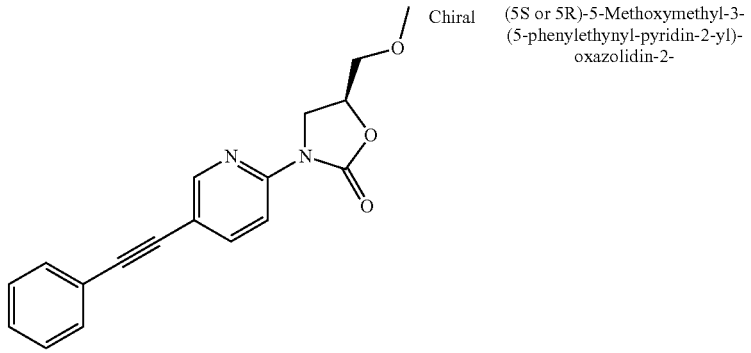<br>OR<br>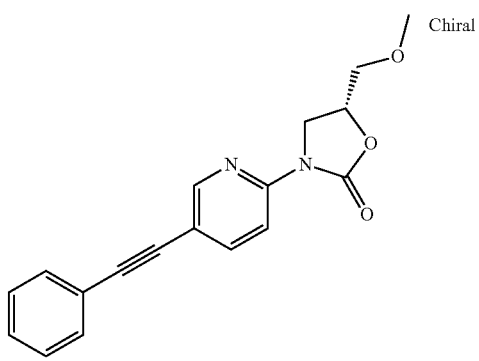 [SMILES: COC[C@H]1CN(c2ccc(C#Cc3ccccc3)cn2)C(=O)O1] | (5S or 5R)-5-Methoxymethyl-3-(5-phenylethynyl-pyridin-2-yl)-oxazolidin-2- | 278 | 98 |

-continued

| Ex. | Structure | Name | EC$_{50}$ (nM) mGlu5PAM | Eff. (%) |
|---|---|---|---|---|
| 5 | 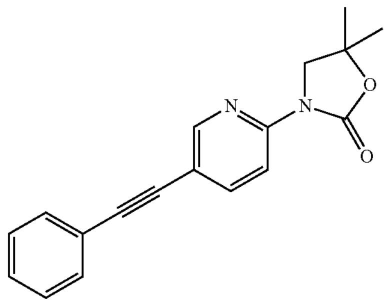 [SMILES: CC1(C)CN(c2ccc(C#Cc3ccccc3)cn2)C(=O)O1] | 5,5-Dimethyl-3-(5-phenylethynyl-pyridin-2-yl)-oxazolidin-2-one | 7 | 77 |
| 6 | 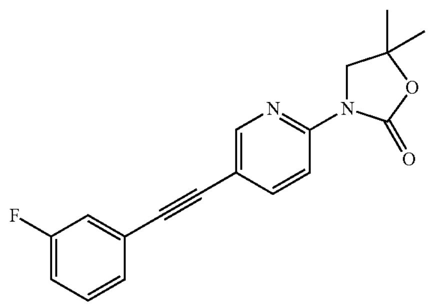 [SMILES: CC1(C)CN(c2ccc(C#Cc3cccc(F)c3)cn2)C(=O)O1] | 3-[5-(3-Fluoro-phenylethynyl)-pyridin-2-yl]-5,5-dimethyl-oxazolidin-2-one | 9 | 46 |
| 7 | 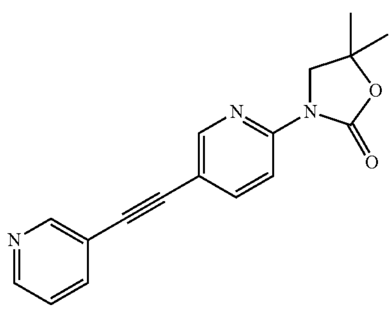 [SMILES: CC1(C)CN(c2ccc(C#Cc3cccnc3)cn2)C(=O)O1] | 5,5-Dimethyl-3-(5-pyridin-3-ylethynyl-pyridin-2-yl)-oxazolidin-2-one | 33 | 39 |
| 8 | 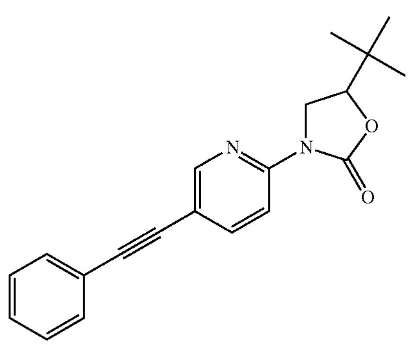 [SMILES: CC(C)(C)C1CN(c2ccc(C#Cc3ccccc3)cn2)C(=O)O1] | (5RS)-5-tert-Butyl-3-(5-phenylethynyl-pyridin-2-yl)-oxazolidin-2-one | 17 | 62 |
| 9 | 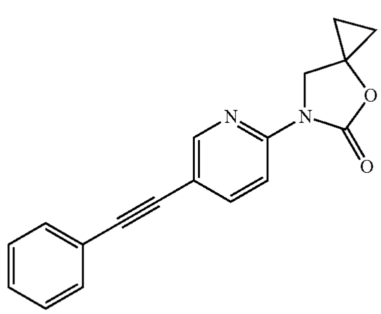 [SMILES: O=C1OC2(CC2)CN1c1ccc(C#Cc2ccccc2)cn1] | 6-(5-Phenylethynyl-pyridin-2-yl)-4-oxa-6-aza-spiro[2.4]heptan-5-one | 15 | 83 |

-continued

| Ex. | Structure | Name | EC$_{50}$ (nM) mGlu5PAM | Eff. (%) |
|---|---|---|---|---|
| 10 | 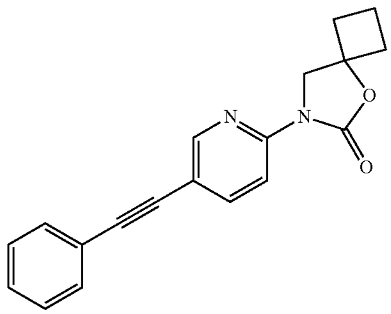 [SMILES: O=C1OC2(CCC2)CN1c1ccc(C#Cc2ccccc2)cn1] | 7-(5-Phenylethynyl-pyridin-2-yl)-5-oxa-7-aza-spiro[3.4]octan-6-one | 25 | 109 |
| 11 | 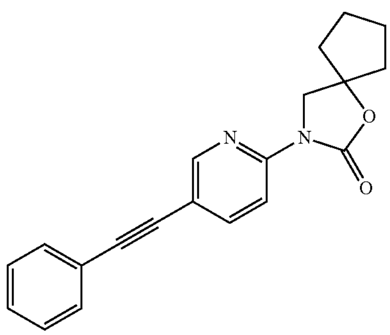 [SMILES: O=C1OC2(CCCC2)CN1c1ccc(C#Cc2ccccc2)cn1] | 3-(5-Phenylethynyl-pyridin-2-yl)-1-oxa-3-aza-spiro[4.4]nonan-2-one | 39 | 52 |
| 12 | 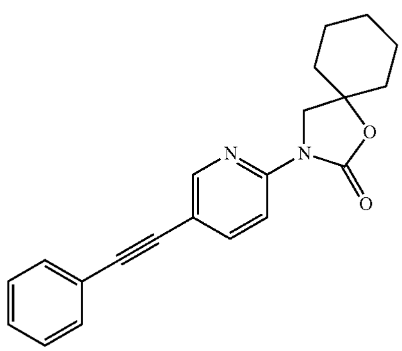 [SMILES: O=C1OC2(CCCCC2)CN1c1ccc(C#Cc2ccccc2)cn1] | 3-(5-Phenylethynyl-pyridin-2-yl)-1-oxa-3-aza-spiro[4.5]decan-2-one | 67 | 80 |
| 13 | 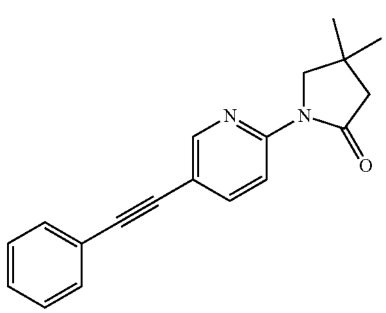 [SMILES: CC1(C)CC(=O)N(c2ccc(C#Cc3ccccc3)cn2)C1] | 4,4-Dimethyl-1-(5-phenylethynyl-pyridin-2-yl)-pyrrolidin-2-one | 37 | 129 |

-continued

| Ex. | Structure | Name | EC$_{50}$ (nM) mGlu5PAM | Eff. (%) |
|---|---|---|---|---|
| 14 | 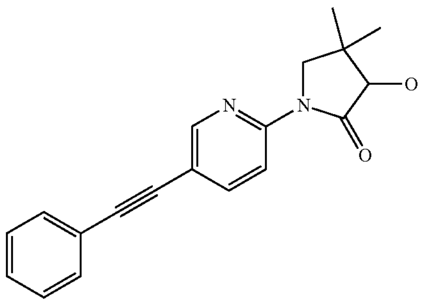 [SMILES: CC1(C)CN(c2ccc(C#Cc3ccccc3)cn2)C(=O)C1O] | (3RS)-3-Hydroxy-4,4-dimethyl-1-(5-phenylethynyl-pyridin-2-yl)-pyrrolidin-2-one | 388 | 114 |
| 15 | 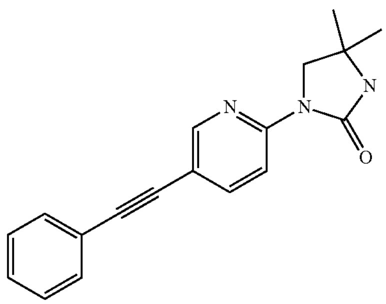 [SMILES: CC1(C)CN(c2ccc(C#Cc3ccccc3)cn2)C(=O)N1] | 4,4-Dimethyl-1-(5-phenylethynyl-pyridin-2-yl)-imidazolidin-2-one | 130 | 101 |
| 16 | 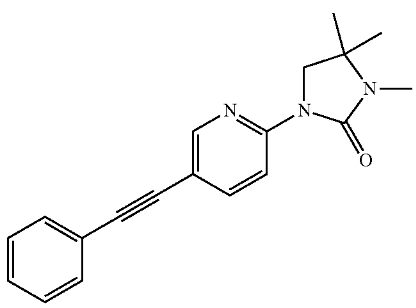 [SMILES: CN1C(=O)N(c2ccc(C#Cc3ccccc3)cn2)CC1(C)C] | 3,4,4-Trimethyl-1-(5-phenylethynyl-pyridin-2-yl)-imidazolidin-2-one | 35 | 103 |
| 17 | 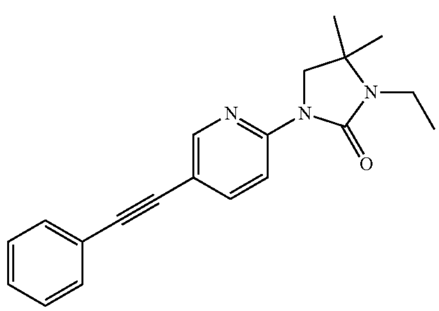 [SMILES: CCN1C(=O)N(c2ccc(C#Cc3ccccc3)cn2)CC1(C)C] | 3-Ethyl-4,4-dimethyl-1-(5-phenylethynyl-pyridin-2-yl)-imidazolidin-2-one | 66 | 103 |
| 18 | 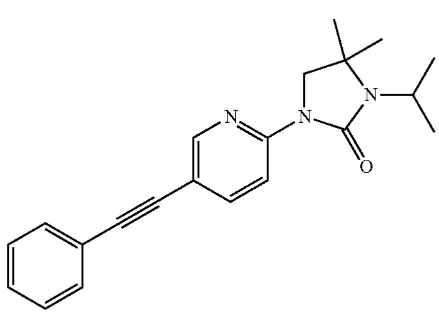 [SMILES: CC(C)N1C(=O)N(c2ccc(C#Cc3ccccc3)cn2)CC1(C)C] | 3-Isopropyl-4,4-dimethyl-1-(5-phenylethynyl-pyridin-2-yl)-imidazolidin-2-one | 39 | 133 |

-continued

| Ex. | Structure | Name | EC$_{50}$ (nM) mGlu5PAM | Eff. (%) |
|---|---|---|---|---|
| 19 | 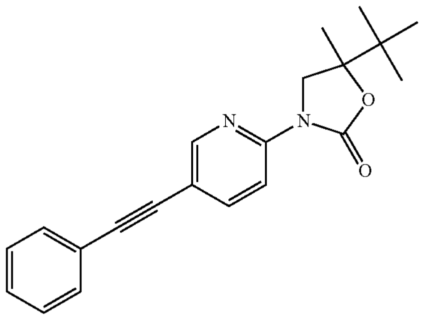 [SMILES: CC(C)(C)C1(C)CN(c2ccc(C#Cc3ccccc3)cn2)C(=O)O1] | (5RS)-5-tert-Butyl-5-methyl-3-(5-phenylethynyl-pyridin-2-yl)-oxazolidin-2-one | 27 | 85 |
| 20 | 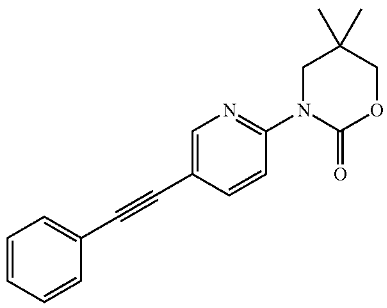 [SMILES: CC1(C)COC(=O)N(c2ccc(C#Cc3ccccc3)cn2)C1] | 5,5-Dimethyl-3-(5-phenylethynyl-pyridin-2-yl)-[1,3]oxazinan-2-one | 27 | 135 |
| 21 | 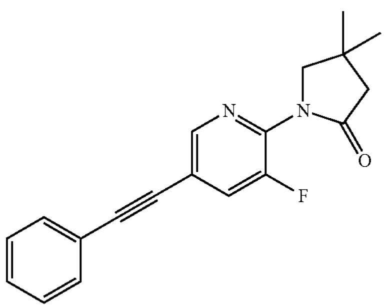 [SMILES: CC1(C)CC(=O)N(c2ncc(C#Cc3ccccc3)cc2F)C1] | 1-(3-Fluoro-5-phenylethynyl-pyridin-2-yl)-4,4-dimethyl-pyrrolidin-2-one | 30 | 128 |
| 22 | 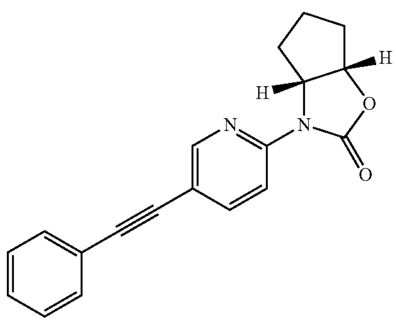 [SMILES: O=C1O[C@H]2CCC[C@H]2N1c1ccc(C#Cc2ccccc2)cn1] | (3aRS,6aSR)-3-(5-Phenylethynyl-pyridin-2-yl)-hexahydro-cyclopentaoxazol-2-one | 14 | 74 |
| 23 | 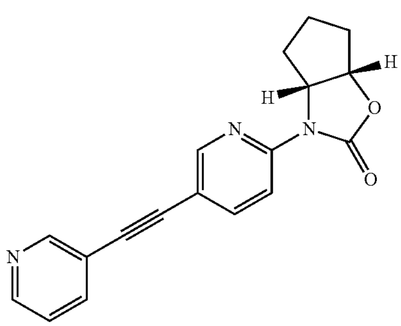 [SMILES: O=C1O[C@H]2CCC[C@H]2N1c1ccc(C#Cc2cccnc2)cn1] | (3aRS,6aSR)-3-(5-Pyridin-3-ylethynyl-pyridin-2-yl)-hexahydro-cyclopentaoxazol-2-one | 12 | 92 |

-continued

| Ex. | Structure | Name | EC$_{50}$ (nM) mGlu5PAM | Eff. (%) |
|---|---|---|---|---|
| 24 | 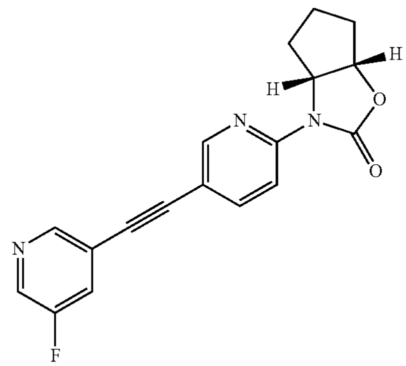 [SMILES: O=C1O[C@H]2CCC[C@H]2N1c1ccc(C#Cc2cncc(F)c2)cn1] | (3aRS,6aSR)-3-[5-(5-Fluoro-pyridin-3-ylethynyl)-pyridin-2-yl]-hexahydro-cyclopentaoxazol-2-one | 35 | 73 |
| 25 | 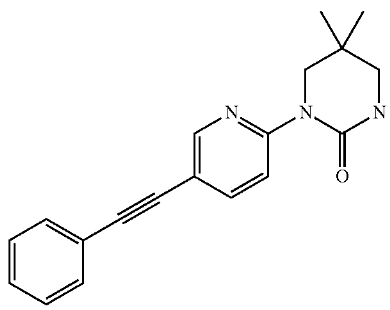 [SMILES: CC1(C)CNC(=O)N(c2ccc(C#Cc3ccccc3)cn2)C1] | 5,5-Dimethyl-1-(5-phenylethynyl-pyridin-2-yl)-tetrahydro-pyrimidin-2-one | 69 | 148 |
| 26 | 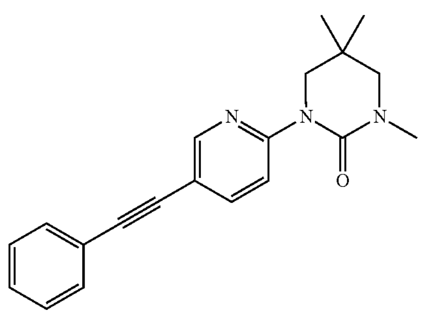 [SMILES: CN1CC(C)(C)CN(c2ccc(C#Cc3ccccc3)cn2)C1=O] | 1,5,5-Trimethyl-3-(5-phenylethynyl-pyridin-2-yl)-tetrahydro-pyrimidin-2-one | 33 | 131 |
| 27 | 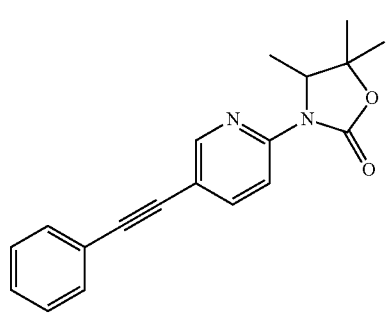 [SMILES: CC1N(c2ccc(C#Cc3ccccc3)cn2)C(=O)OC1(C)C] | (RS)-4,5,5-Trimethyl-3-(5-phenylethynyl-pyridin-2-yl)-oxazolidin-2-one | 15 | 61 |

-continued

| Ex. | Structure | Name | EC$_{50}$ (nM) mGlu5PAM | Eff. (%) |
|---|---|---|---|---|
| 28 | 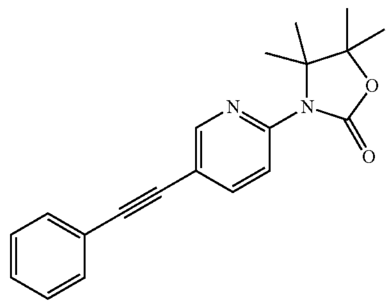 [SMILES: CC1(C)OC(=O)N(c2ccc(C#Cc3ccccc3)cn2)C1(C)C] | 4,4,5,5-Tetramethyl-3-(5-phenylethynyl-pyridin-2-yl)-oxazolidin-2-one | 48 | 31 |
| 29 | 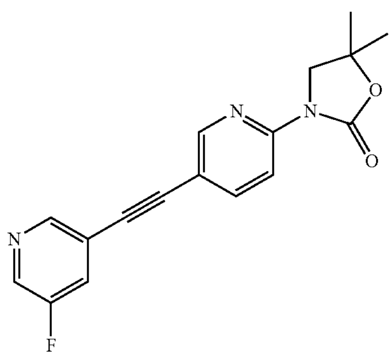 [SMILES: CC1(C)CN(c2ccc(C#Cc3cncc(F)c3)cn2)C(=O)O1] | 3-[5-(5-Fluoro-pyridin-3-ylethynyl)-pyridin-2-yl]-5,5-dimethyl-oxazolidin-2-one | 15 | 45 |
| 30 | 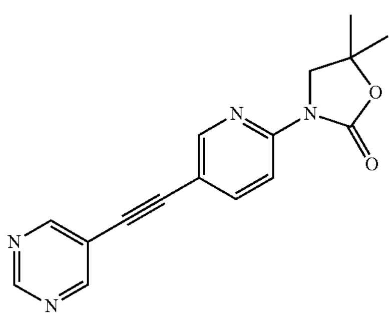 [SMILES: CC1(C)CN(c2ccc(C#Cc3cncnc3)cn2)C(=O)O1] | 5,5-Dimethyl-3-(5-pyrimidin-5-ylethynyl-pyridin-2-yl)-oxazolidin-2-one | 80 | 43 |
| 31 | 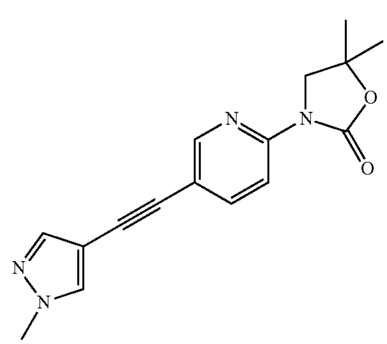 [SMILES: Cn1cc(C#Cc2ccc(N3CC(C)(C)OC3=O)nc2)cn1] | 5,5-Dimethyl-3-[5-(1-methyl-1H-pyrazol-4-ylethynyl)-pyridin-2-yl]-oxazolidin-2-one | 26 | 55 |

-continued

| Ex. | Structure | Name | EC$_{50}$ (nM) mGlu5PAM | Eff. (%) |
|---|---|---|---|---|
| 32 | 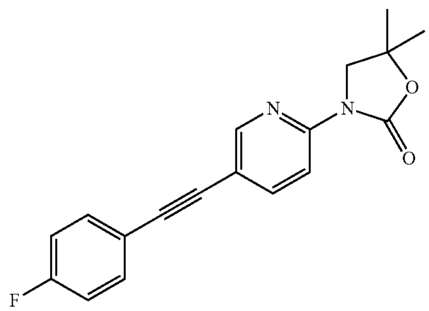 [SMILES: CC1(C)CN(c2ccc(C#Cc3ccc(F)cc3)cn2)C(=O)O1] | 3-[5-(4-Fluoro-phenylethynyl)-pyridin-2-yl]-5,5-dimethyl-oxazolidin-2-one | 19 | 60 |
| 33 | 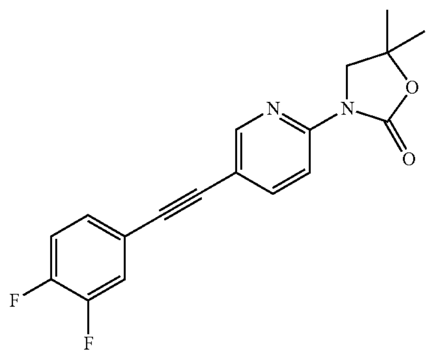 [SMILES: CC1(C)CN(c2ccc(C#Cc3ccc(F)c(F)c3)cn2)C(=O)O1] | 3-[5-(3,4-Difluoro-phenylethynyl)-pyridin-2-yl]-5,5-dimethyl-oxazolidin-2-one | 32 | 44 |
| 34 | 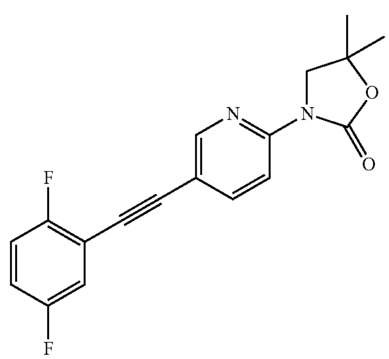 [SMILES: CC1(C)CN(c2ccc(C#Cc3cc(F)ccc3F)cn2)C(=O)O1] | 3-[5-(2,5-Difluoro-phenylethynyl)-pyridin-2-yl]-5,5-dimethyl-oxazolidin-2-one | 11 | 38 |
| 35 | 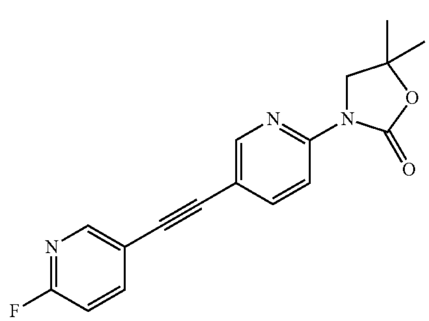 [SMILES: CC1(C)CN(c2ccc(C#Cc3ccc(F)nc3)cn2)C(=O)O1] | 3-[5-(6-Fluoro-pyridin-3-ylethynyl)-pyridin-2-yl]-5,5-dimethyl-oxazolidin-2-one | 54 | 52 |

| Ex. | Structure | Name | EC$_{50}$ (nM) mGlu5PAM | Eff. (%) |
|---|---|---|---|---|
| 36 | 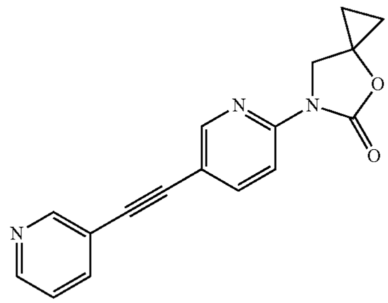 [SMILES: O=C1OC2(CC2)CN1c1ccc(C#Cc2cccnc2)cn1] | 6-(5-Pyridin-3-ylethynyl-pyridin-2-yl)-4-oxa-6-aza-spiro[2.4]heptan-5-one | 58 | 80 |
| 37 | 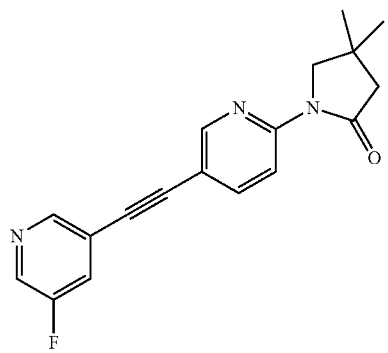 [SMILES: CC1(C)CC(=O)N(c2ccc(C#Cc3cncc(F)c3)cn2)C1] | 1-[5-(5-Fluoro-pyridin-3-ylethynyl)-pyridin-2-yl]-4,4-dimethyl-pyrrolidin-2-one | 22 | 96 |
| 38 | 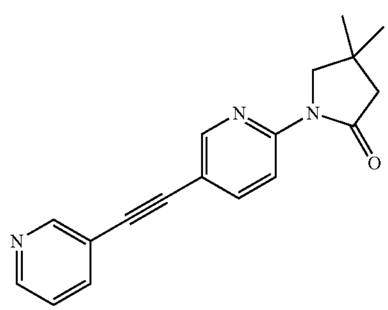 [SMILES: CC1(C)CC(=O)N(c2ccc(C#Cc3cccnc3)cn2)C1] | 4,4-Dimethyl-1-(5-pyridin-3-ylethynyl-pyridin-2-yl)-pyrrolidin-2-one | 33 | 147 |
| 39 | 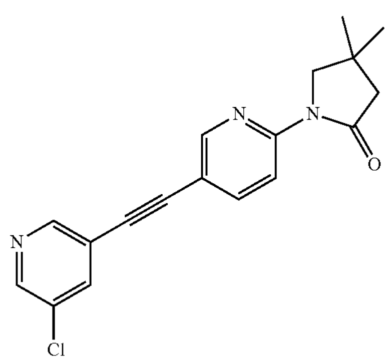 [SMILES: CC1(C)CC(=O)N(c2ccc(C#Cc3cncc(Cl)c3)cn2)C1] | 1-[5-(5-Chloro-pyridin-3-ylethynyl)-pyridin-2-yl]-4,4-dimethyl-pyrrolidin-2-one | 48 | 98 |

-continued

| Ex. | Structure | Name | EC$_{50}$ (nM) mGlu5PAM | Eff. (%) |
|---|---|---|---|---|
| 40 | 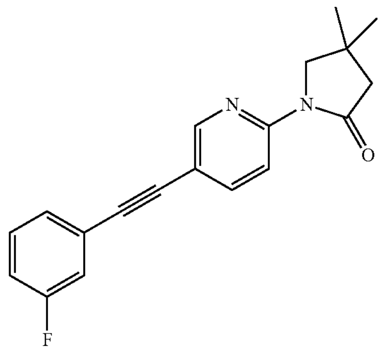 [SMILES: CC1(C)CC(=O)N(c2ccc(C#Cc3cccc(F)c3)cn2)C1] | 1-[5-(3-Fluoro-phenylethynyl)-pyridin-2-yl]-4,4-dimethyl-pyrrolidin-2-one | 15 | 100 |
| 41 | 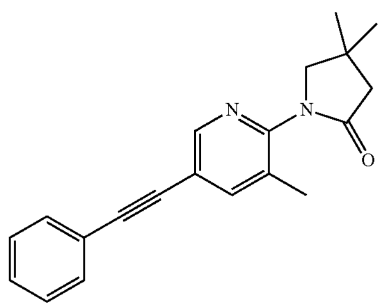 [SMILES: Cc1cc(C#Cc2ccccc2)cnc1N1CC(C)(C)CC1=O] | 4,4-Dimethyl-1-(3-methyl-5-phenylethynyl-pyridin-2-yl)-pyrrolidin-2-one | 58 | 89 |
| 42 | 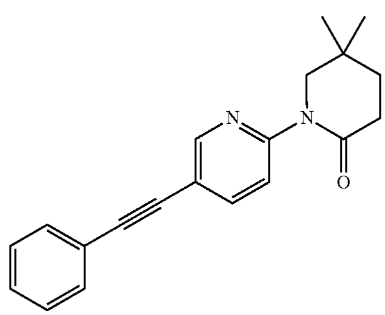 | 5,5-Dimethyl-5'-phenylethynyl-3,4,5,6-tetrahydro-[1,2']bipyridinyl-2-one | 16 | 139 |
| 43 | 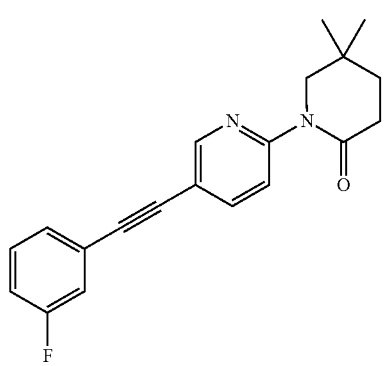 [SMILES: CC1(C)CCC(=O)N(c2ccc(C#Cc3cccc(F)c3)cn2)C1] | 5'-(3-Fluoro-phenylethynyl)-5,5-dimethyl-3,4,5,6-tetrahydro-[1,2']bipyridinyl-2-one | 12 | 100 |

-continued

| Ex. | Structure | Name | EC$_{50}$ (nM) mGlu5PAM | Eff. (%) |
|---|---|---|---|---|
| 44 | 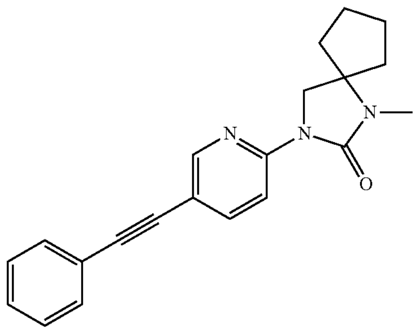 [SMILES: CN1C(=O)N(c2ccc(C#Cc3ccccc3)cn2)CC12CCCC2] | 1-Methyl-3-(5-phenylethynyl-pyridin-2-yl)-1,3-diaza-spiro[4.4]nonan-2-one | 29 | 92 |
| 45 | 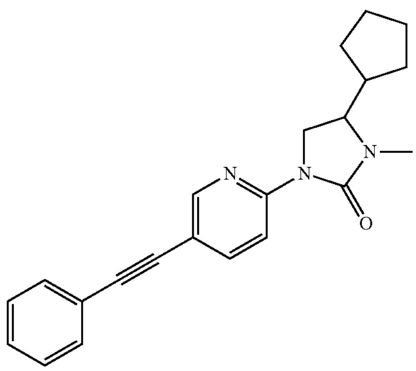 [SMILES: CN1C(=O)N(c2ccc(C#Cc3ccccc3)cn2)CC1C1CCCC1] | (RS)-4-Cyclopentyl-3-methyl-1-(5-phenylethynyl-pyridin-2-yl)-imidazolidin-2-one | 57 | 97 |
| 46 | 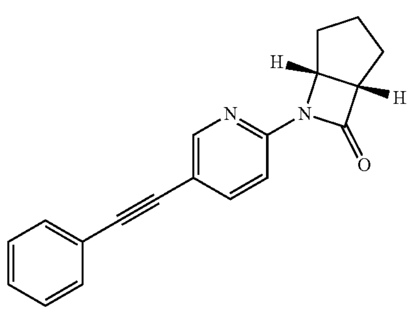 [SMILES: O=C1[C@H]2CCC[C@H]2N1c1ccc(C#Cc2ccccc2)cn1] | (1RS,5SR)-6-(5-Phenylethynyl-pyridin-2-yl)-6-aza-bicyclo[3.2.0]heptan-7-one | 26 | 27 |
| 47 | 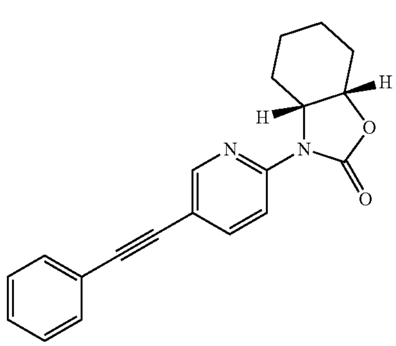 [SMILES: O=C1O[C@H]2CCCC[C@H]2N1c1ccc(C#Cc2ccccc2)cn1] | (6SR,7RS)-3-(5-Phenylethynyl-pyridin-2-yl)-hexahydro-benzooxazol-2-one | 36 | 109 |

-continued

| Ex. | Structure | Name | EC$_{50}$ (nM) mGlu5PAM | Eff. (%) |
|---|---|---|---|---|
| 48 | 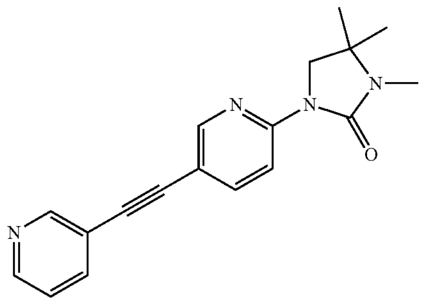 [SMILES: CN1C(=O)N(c2ccc(C#Cc3cccnc3)cn2)CC1(C)C] | 3,4,4-Trimethyl-1-(5-pyridin-3-ylethynyl-pyridin-2-yl)-imidazolidin-2-one | 14 | 89 |
| 49 | 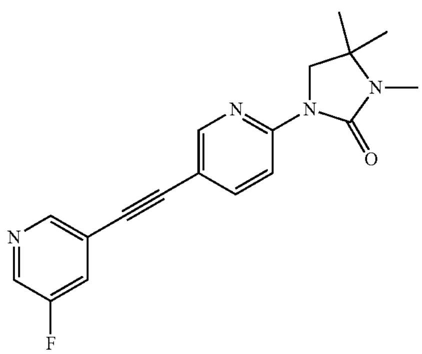 [SMILES: CN1C(=O)N(c2ccc(C#Cc3cncc(F)c3)cn2)CC1(C)C] | 1-[5-(5-Fluoro-pyridin-3-ylethynyl)-pyridin-2-yl]-3,4,4-trimethyl-imidazolidin-2-one | 37 | 91 |
| 50 | 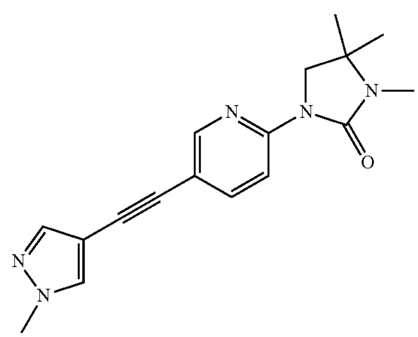 [SMILES: CN1C(=O)N(c2ccc(C#Cc3cnn(C)c3)cn2)CC1(C)C] | 3,4,4-Trimethyl-1-[5-(1-methyl-1H-pyrazol-4-ylethynyl)-pyridin-2-yl]-imidazolidin-2-one | 27 | 41 |
| 51 | 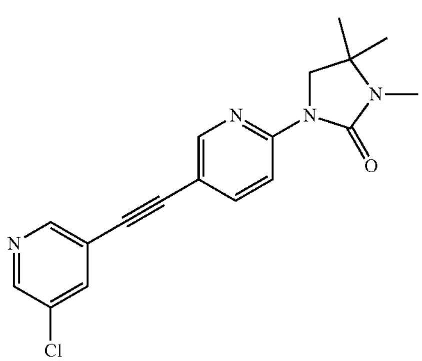 [SMILES: CN1C(=O)N(c2ccc(C#Cc3cncc(Cl)c3)cn2)CC1(C)C] | 1-[5-(5-Chloro-pyridin-3-ylethynyl)-pyridin-2-yl]-3,4,4-trimethyl-imidazolidin-2-one | 29 | 45 |

-continued

| Ex. | Structure | Name | EC$_{50}$ (nM) mGlu5PAM | Eff. (%) |
|---|---|---|---|---|
| 52 | 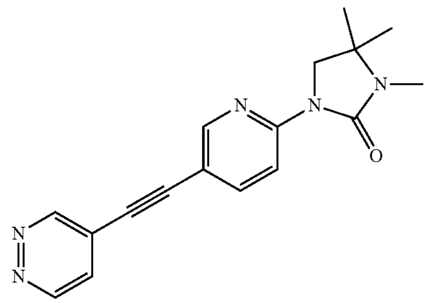 [SMILES: CN1C(=O)N(c2ccc(C#Cc3ccnnc3)cn2)CC1(C)C] | 3,4,4-Trimethyl-1-(5-pyridazin-4-ylethynyl-pyridin-2-yl)-imidazolidin-2-one | 34 | 32 |
| 53 | 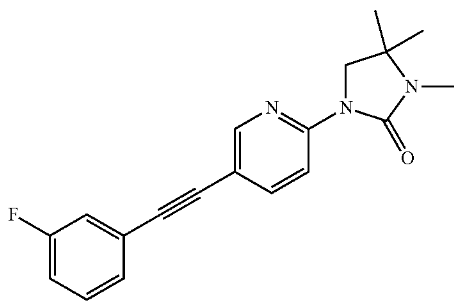 [SMILES: CN1C(=O)N(c2ccc(C#Cc3cccc(F)c3)cn2)CC1(C)C] | 1-[5-(3-Fluoro-phenylethynyl)-pyridin-2-yl]-3,4,4-trimethyl-imidazolidin-2-one | 29 | 103 |
| 54 | 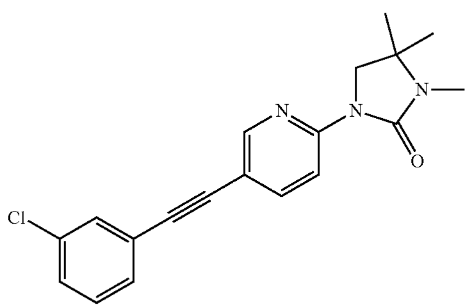 [SMILES: CN1C(=O)N(c2ccc(C#Cc3cccc(Cl)c3)cn2)CC1(C)C] | 1-[5-(3-Chloro-phenylethynyl)-pyridin-2-yl]-3,4,4-trimethyl-imidazolidin-2-one | 32 | 47 |
| 55 | 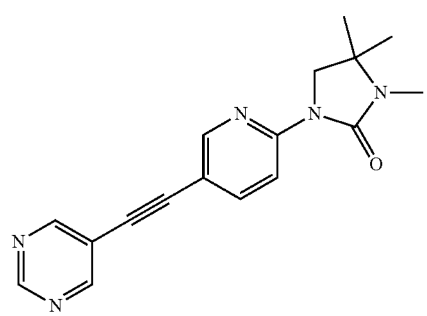 [SMILES: CN1C(=O)N(c2ccc(C#Cc3cncnc3)cn2)CC1(C)C] | 3,4,4-Trimethyl-1-(5-pyrimidin-5-ylethynyl-pyridin-2-yl)-imidazolidin-2-one | 54 | 110 |
| 56 | 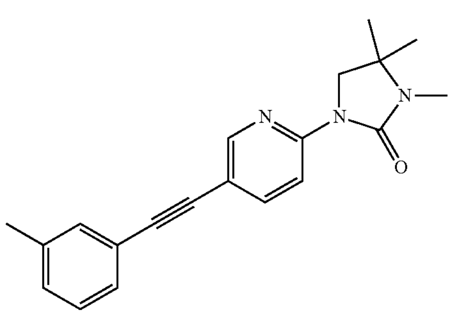 | 3,4,4-Trimethyl-1-(5-m-tolylethynyl-pyridin-2-yl)-imidazolidin-2-one | 87 | 56 |

-continued

| Ex. | Structure | Name | EC$_{50}$ (nM) mGlu5PAM | Eff. (%) |
|---|---|---|---|---|
| 57 | 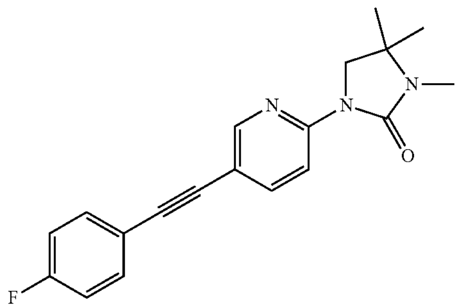 [SMILES: CN1C(=O)N(c2ccc(C#Cc3ccc(F)cc3)cn2)CC1(C)C] | 1-[5-(4-Fluoro-phenylethynyl)-pyridin-2-yl]-3,4,4-trimethyl-imidazolidin-2-one | 35 | 78 |
| 58 | 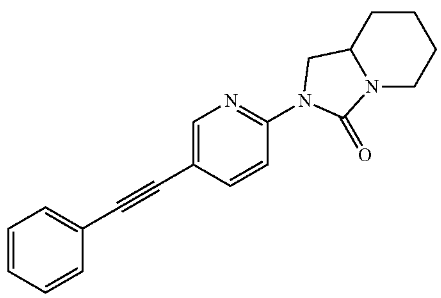 [SMILES: O=C1N(c2ccc(C#Cc3ccccc3)cn2)CC2CCCCN12] | (RS)-2-(5-Phenylethynyl-pyridin-2-yl)-hexahydro-imidazo[1,5-a]pyridin-3-one | 33 | 43 |
| 59 | 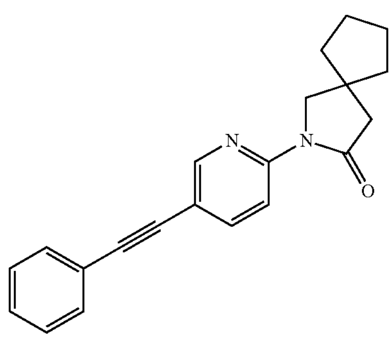 [SMILES: O=C1CC2(CCCC2)CN1c1ccc(C#Cc2ccccc2)cn1] | 2-(5-Phenylethynyl-pyridin-2-yl)-2-aza-spiro[4.4]nonan-3-one | 16 | 81 |
| 60 | 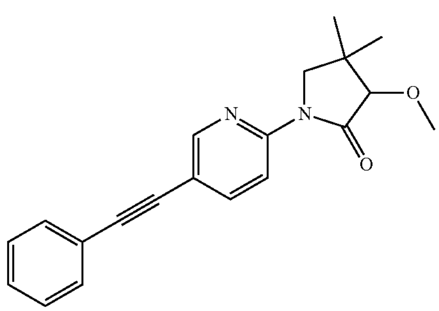 [SMILES: COC1C(=O)N(c2ccc(C#Cc3ccccc3)cn2)CC1(C)C] | (RS)-3-Methoxy-4,4-dimethyl-1-(5-phenylethynyl-pyridin-2-yl)-pyrrolidin-2-one | 35 | 89 |
| 61 | 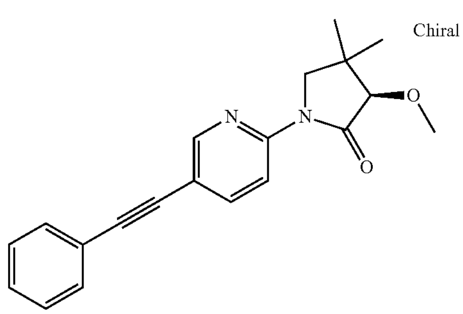 [SMILES: CO[C@H]1C(=O)N(c2ccc(C#Cc3ccccc3)cn2)CC1(C)C] | (R or S)-3-Methoxy-4,4-dimethyl-1-(5-phenylethynyl-pyridin-2-yl)-pyrrolidin-2-one | 75 | 70 |

| Ex. | Structure | Name | EC$_{50}$ (nM) mGlu5PAM | Eff. (%) |
|---|---|---|---|---|
| 62 | 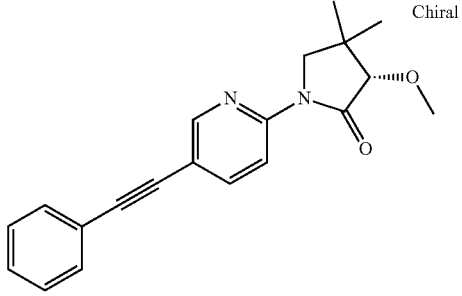 OR 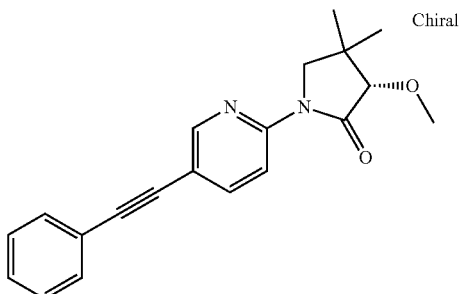 | (S or R)-3-Methoxy-4,4-dimethyl-1-(5-phenylethynyl-pyridin-2-yl)-pyrrolidin-2-one | 12 | 86 |
| 63 | 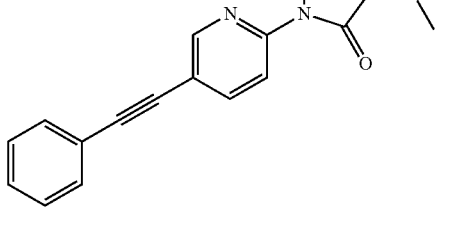 | (RS)-1-[5-(5-Chloro-pyridin-3-ylethynyl)-pyridin-2-yl]-3-methoxy-4,4-dimethyl-pyrrolidin-2-one | 70 | 99 |

-continued

| Ex. | Structure | Name | EC$_{50}$ (nM) mGlu5PAM | Eff. (%) |
|---|---|---|---|---|
| 64 | 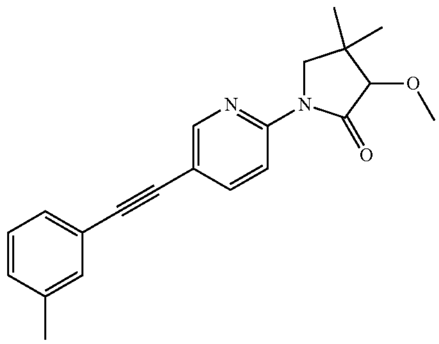 [SMILES: COC1C(=O)N(c2ccc(C#Cc3cccc(C)c3)cn2)CC1(C)C] | (RS)-3-Methoxy-4,4-dimethyl-1-(5-m-tolylethynyl-pyridin-2-yl)-pyrrolidin-2-one | 87 | 56 |
| 65 | 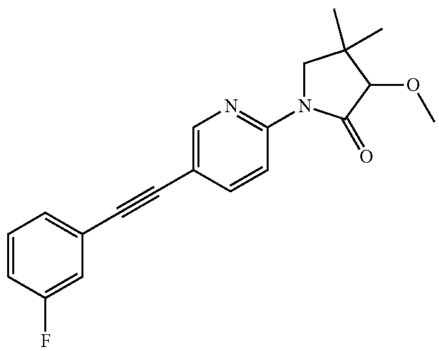 [SMILES: COC1C(=O)N(c2ccc(C#Cc3cccc(F)c3)cn2)CC1(C)C] | (RS)-1-[5-(3-Fluoro-phenylethynyl)-pyridin-2-yl]-3-methoxy-4,4-dimethyl-pyrrolidin-2-one | 43 | 91 |
| 66 | 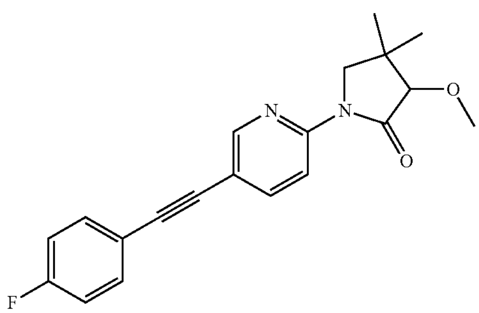 [SMILES: COC1C(=O)N(c2ccc(C#Cc3ccc(F)cc3)cn2)CC1(C)C] | (RS)-1-[5-(4-Fluoro-phenylethynyl)-pyridin-2-yl]-3-methoxy-4,4-dimethyl-pyrrolidin-2-one | 75 | 87 |
| 67 | 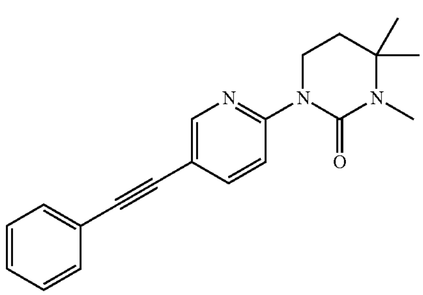 [SMILES: CN1C(=O)N(c2ccc(C#Cc3ccccc3)cn2)CCC1(C)C] | 3,4,4-Trimethyl-1-(5-phenylethynyl-pyridin-2-yl)-tetrahydro-pyrimidin-2-one | 15 | 81 |

-continued

| Ex. | Structure | Name | EC$_{50}$ (nM) mGlu5PAM | Eff. (%) |
|---|---|---|---|---|
| 68 | 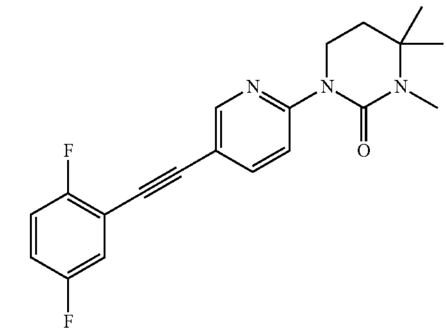 [SMILES: CN1C(=O)N(c2ccc(C#Cc3cc(F)ccc3F)cn2)CCC1(C)C] | 1-[5-(2,5-Difluoro-phenylethynyl)-pyridin-2-yl]-3,4,4-trimethyl-tetrahydro-pyrimidin-2-one | 41 | 79 |
| 69 | 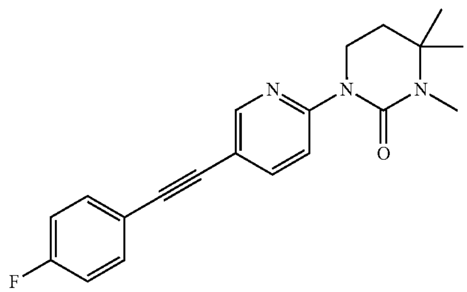 [SMILES: CN1C(=O)N(c2ccc(C#Cc3ccc(F)cc3)cn2)CCC1(C)C] | 1-[5-(4-Fluoro-phenylethynyl)-pyridin-2-yl]-3,4,4-trimethyl-tetrahydro-pyrimidin-2-one | 49 | 107 |
| 70 | 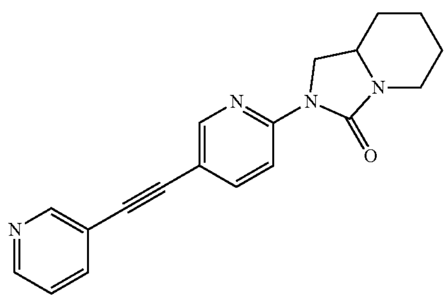 [SMILES: O=C1N(c2ccc(C#Cc3cccnc3)cn2)CC2CCCCN12] | (RS)-2-(5-Pyridin-3-ylethynyl-pyridin-2-yl)-hexahydro-imidazo[1,5-a]pyridin-3-one | 74 | 51 |
| 71 | 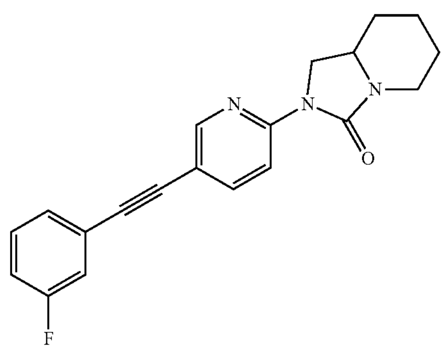 [SMILES: O=C1N(c2ccc(C#Cc3cccc(F)c3)cn2)CC2CCCCN12] | (RS)-2-[5-(3-Fluoro-phenylethynyl)-pyridin-2-yl]-hexahydro-imidazo[1,5-a]pyridin-3-one | 17 | 41 |
| 72 | 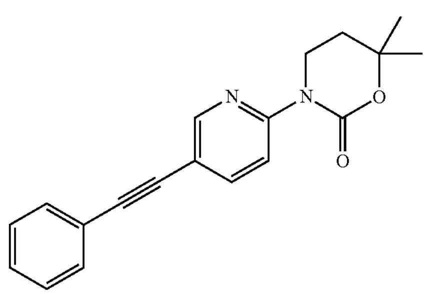 [SMILES: CC1(C)CCN(c2ccc(C#Cc3ccccc3)cn2)C(=O)O1] | 6,6-Dimethyl-3-(5-phenylethynyl-pyridin-2-yl)-[1,3]oxazinan-2-one | 10 | 86 |

| Ex. | Structure | Name | EC$_{50}$ (nM) mGlu5PAM | Eff. (%) |
|---|---|---|---|---|
| 73 | 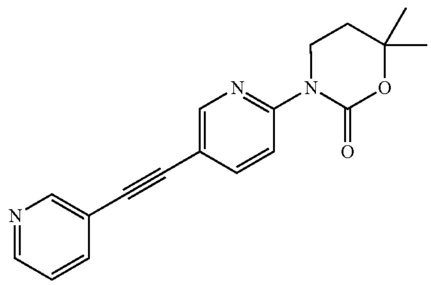 [SMILES: CC1(C)CCN(c2ccc(C#Cc3cccnc3)cn2)C(=O)O1] | 6,6-Dimethyl-3-(5-pyridin-3-ylethynyl-pyridin-2-yl)-[1,3]oxazinan-2-one | 59 | 98 |
| 74 | 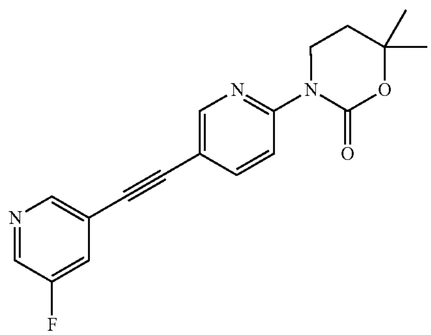 [SMILES: CC1(C)CCN(c2ccc(C#Cc3cncc(F)c3)cn2)C(=O)O1] | 3-[5-(5-Fluoro-pyridin-3-ylethynyl)-pyridin-2-yl]-6,6-dimethyl-[1,3]oxazinan-2-one | 59 | 108 |
| 75 | 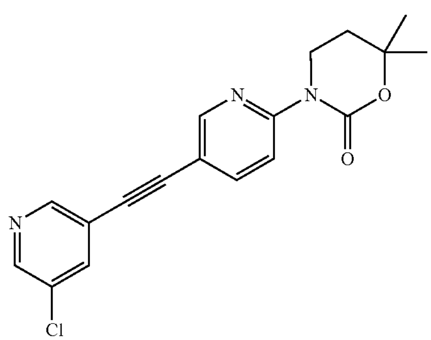 [SMILES: CC1(C)CCN(c2ccc(C#Cc3cncc(Cl)c3)cn2)C(=O)O1] | 3-[5-(5-Chloro-pyridin-3-ylethynyl)-pyridin-2-yl]-6,6-dimethyl-[1,3]oxazinan-2-one | 27 | 87 |
| 76 | 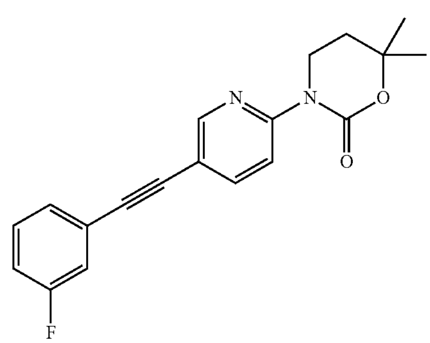 [SMILES: CC1(C)CCN(c2ccc(C#Cc3cccc(F)c3)cn2)C(=O)O1] | 3-[5-(3-Fluoro-phenylethynyl)-pyridin-2-yl]-6,6-dimethyl-[1,3]oxazinan-2-one | 13 | 124 |

-continued

| Ex. | Structure | Name | EC$_{50}$ (nM) mGlu5PAM | Eff. (%) |
|---|---|---|---|---|
| 77 | 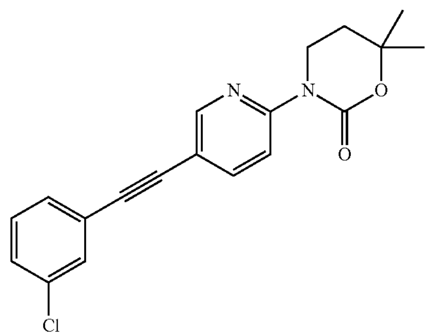 [SMILES: CC1(C)CCN(c2ccc(C#Cc3cccc(Cl)c3)cn2)C(=O)O1] | 3-[5-(3-Chloro-phenylethynyl)-pyridin-2-yl]-6,6-dimethyl-[1,3]oxazinan-2-one | 12 | 72 |
| 78 | 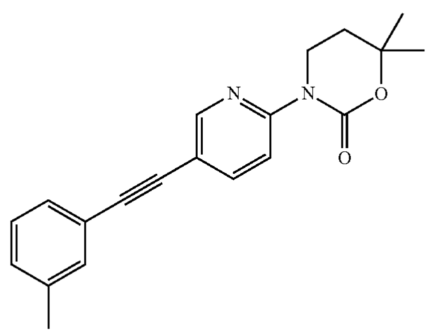 [SMILES: Cc1cccc(C#Cc2ccc(N3CCC(C)(C)OC3=O)nc2)c1] | 6,6-Dimethyl-3-(5-m-tolylethynyl-pyridin-2-yl)-[1,3]oxazinan-2-one | 24 | 72 |
| 79 | 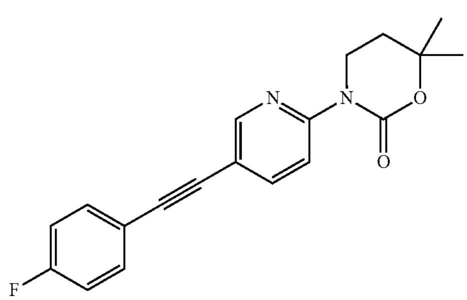 [SMILES: CC1(C)CCN(c2ccc(C#Cc3ccc(F)cc3)cn2)C(=O)O1] | 3-[5-(4-Fluoro-phenylethynyl)-pyridin-2-yl]-6,6-dimethyl-[1,3]oxazinan-2-one | 22 | 85 |
| 80 | 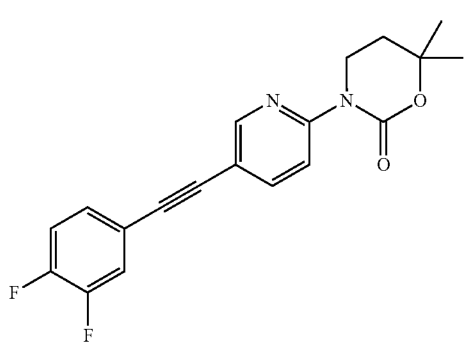 [SMILES: CC1(C)CCN(c2ccc(C#Cc3ccc(F)c(F)c3)cn2)C(=O)O1] | 3-[5-(3,4-Difluoro-phenylethynyl)-pyridin-2-yl]-6,6-dimethyl-[1,3]oxazinan-2-one | 37 | 69 |

-continued

| Ex. | Structure | Name | EC$_{50}$ (nM) mGlu5PAM | Eff. (%) |
|---|---|---|---|---|
| 81 | 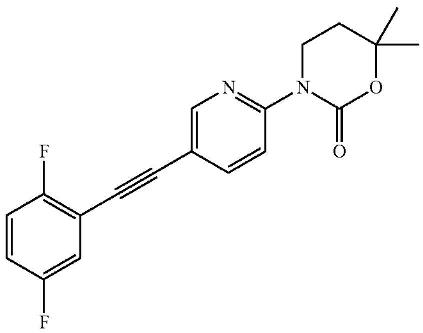 [SMILES: CC1(C)CCN(c2ccc(C#Cc3cc(F)ccc3F)cn2)C(=O)O1] | 3-[5-(2,5-Difluoro-phenylethynyl)-pyridin-2-yl]-6,6-dimethyl-[1,3]oxazinan-2-one | 12 | 95 |
| 82 | 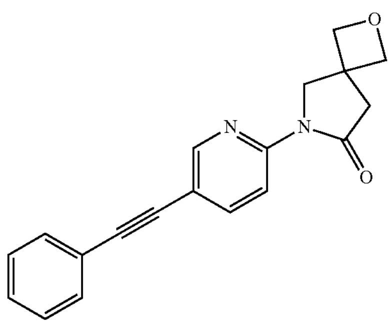 [SMILES: O=C1CC2(COC2)CN1c1ccc(C#Cc2ccccc2)cn1] | 6-(5-Phenylethynyl-pyridin-2-yl)-2-oxa-6-aza-spiro[3.4]octan-7-one | 57 | 72 |
| 83 | 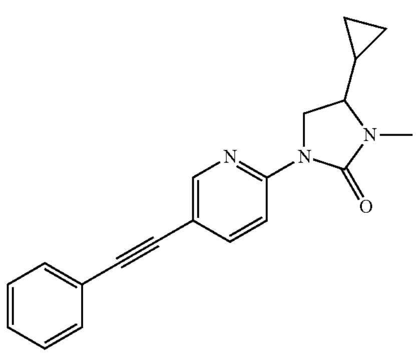 [SMILES: CN1C(=O)N(c2ccc(C#Cc3ccccc3)cn2)CC1C1CC1] | (RS)-4-Cyclopropyl-3-methyl-1-(5-phenylethynyl-pyridin-2-yl)-imidazolidin-2-one | 53 | 86 |
| 84 | 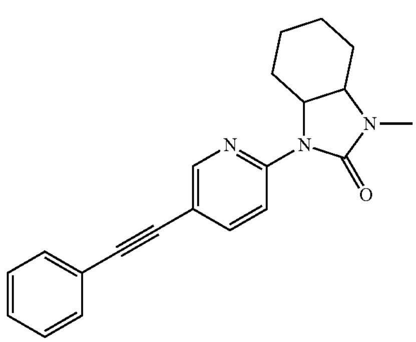 [SMILES: CN1C(=O)N(c2ccc(C#Cc3ccccc3)cn2)C2CCCCC21] | (3aSR,7aRS)-(3aRS,7RS)-1-Methyl-3-(5-phenylethynyl-pyridin-2-yl)-octahydro-benzoimidazol-2-one | 11 | 64 |

-continued

| Ex. | Structure | Name | EC$_{50}$ (nM) mGlu5PAM | Eff. (%) |
|---|---|---|---|---|
| 85 | 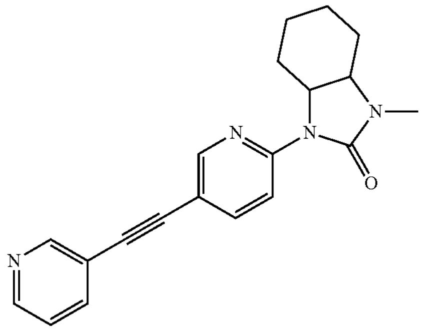 [SMILES: CN1C(=O)N(c2ccc(C#Cc3cccnc3)cn2)C2CCCCC21] | (3aSR,7aRS)-(3aRS,7RS)-1-Methyl-3-(5-pyridin-3-ylethynyl-pyridin-2-yl)-octahydro-benzoimidazol-2-one | 27 | 49 |
| 86 | 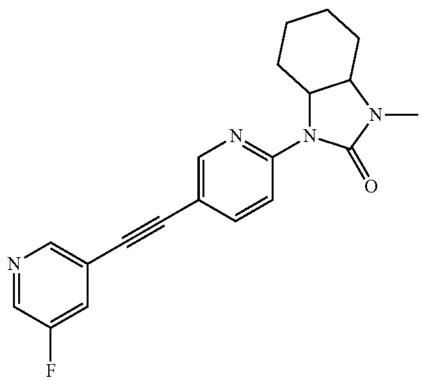 [SMILES: CN1C(=O)N(c2ccc(C#Cc3cncc(F)c3)cn2)C2CCCCC21] | (3aSR,7aRS)-(3aRS,7RS)-1-[5-(5-Fluoro-pyridin-3-ylethynyl)-pyridin-2-yl]-3-methyl-octahydro-benzoimidazol-2-one | 32 | 52 |
| 87 | 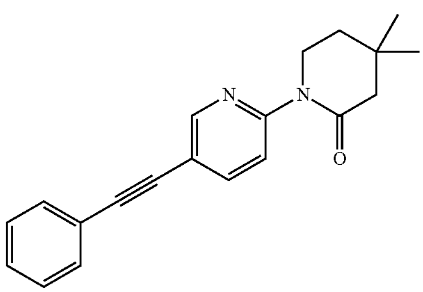 [SMILES: CC1(C)CCN(c2ccc(C#Cc3ccccc3)cn2)C(=O)C1] | 4,4-Dimethyl-5'-phenylethynyl-3,4,5,6-tetrahydro-[1,2']bipyridinyl-2-one | 12 | 89 |
| 88 | 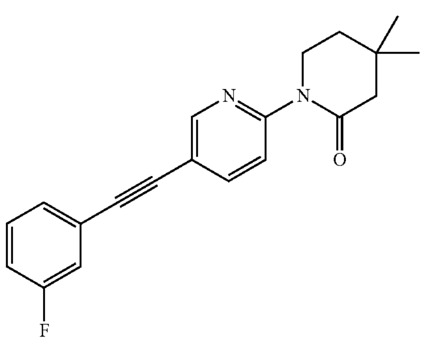 [SMILES: CC1(C)CCN(c2ccc(C#Cc3cccc(F)c3)cn2)C(=O)C1] | 5'-(3-Fluoro-phenylethynyl)-4,4-dimethyl-3,4,5,6-tetrahydro-[1,2']bipyridinyl-2-one | 19 | 110 |

| Ex. | Structure | Name | EC$_{50}$ (nM) mGlu5PAM | Eff. (%) |
|---|---|---|---|---|
| 89 | 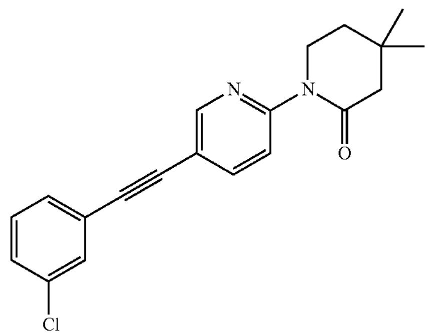 | 5'-(3-Chloro-phenylethynyl)-4,4-dimethyl-3,4,5,6-tetrahydro-[1,2']bipyridinyl-2-one | 25 | 78 |
| 90 | 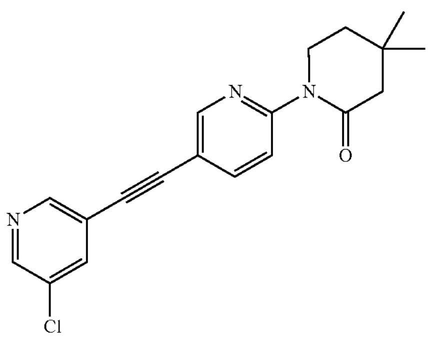 [SMILES: CC1(C)CCN(c2ccc(C#Cc3cncc(Cl)c3)cn2)C(=O)C1] | 5'-(5-Chloro-pyridin-3-ylethynyl)-4,4-dimethyl-3,4,5,6-tetrahydro-[1,2']bipyridinyl-2-one | 66 | 90 |
| 91 | 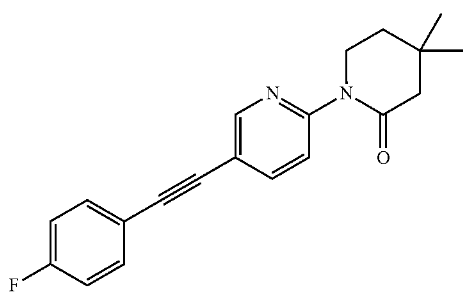 | 5'-(4-Fluoro-phenylethynyl)-4,4-dimethyl-3,4,5,6-tetrahydro-[1,2']bipyridinyl-2-one | 67 | 89 |
| 92 | 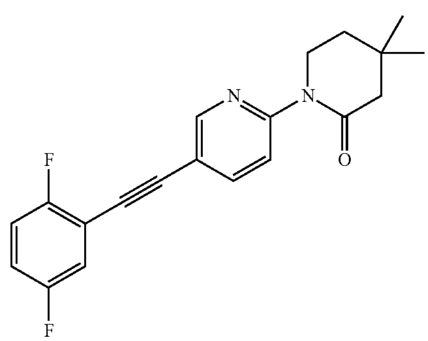 [SMILES: CC1(C)CCN(c2ccc(C#Cc3cc(F)ccc3F)cn2)C(=O)C1] | 5'-(2,5-Difluoro-phenylethynyl)-4,4-dimethyl-3,4,5,6-tetrahydro-[1,2']bipyridinyl-2-one | 32 | 84 |
| 93 | 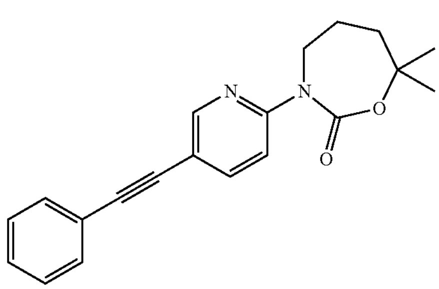 [SMILES: CC1(C)CCCN(c2ccc(C#Cc3ccccc3)cn2)C(=O)O1] | 7,7-Dimethyl-3-(5-phenylethynyl-pyridin-2-yl)-[1,3]oxazepan-2-one | 36 | 104 |

-continued

| Ex. | Structure | Name | EC$_{50}$ (nM) mGlu5PAM | Eff. (%) |
|---|---|---|---|---|
| 94 | 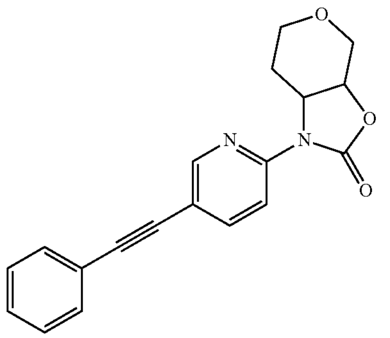 [SMILES: O=C1OC2COCCC2N1c1ccc(C#Cc2ccccc2)cn1] | (3aSR,7aRS)-(3aRS,7RS)-1-(5-Phenylethynyl-pyridin-2-yl)-hexahydro-pyrano[4,3-d]oxazol-2-one | 60 | 84 |
| 95 | 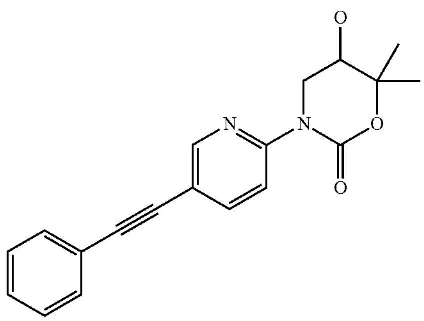 [SMILES: CC1(C)OC(=O)N(c2ccc(C#Cc3ccccc3)cn2)CC1O] | (RS)-5-Hydroxy-6,6-dimethyl-3-(5-phenylethynyl-pyridin-2-yl)-[1,3]oxazinan-2-one | 47 | 118 |
| 96 | 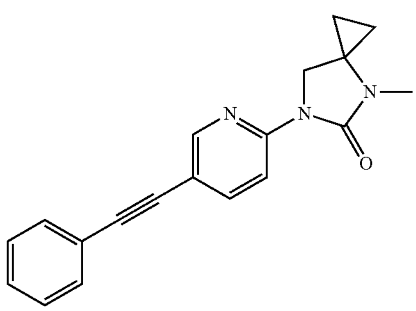 [SMILES: CN1C(=O)N(c2ccc(C#Cc3ccccc3)cn2)CC12CC2] | 4-Methyl-6-(5-phenylethynyl-pyridin-2-yl)-4,6-diaza-spiro[2.4]heptan-5-one | 35 | 98 |
| 97 | 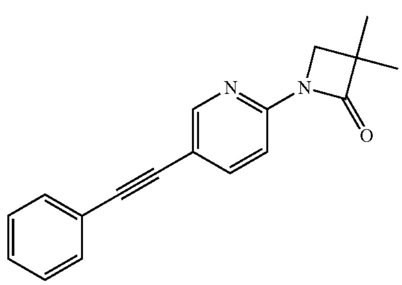 [SMILES: CC1(C)CN(c2ccc(C#Cc3ccccc3)cn2)C1=O] | 3,3-Dimethyl-1-(5-phenylethynyl-pyridin-2-yl)-azetidin-2-one | 36 | 71 |
| 98 | 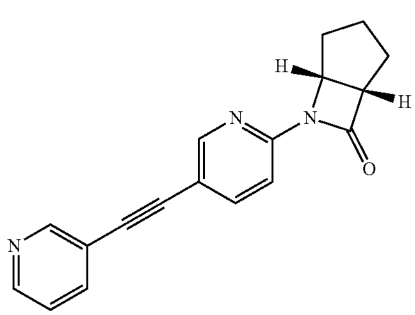 [SMILES: O=C1[C@H]2CCC[C@H]2N1c1ccc(C#Cc2cccnc2)cn1] | (1RS,5SR)-6-(5-Pyridin-3-ylethynyl-pyridin-2-yl)-6-aza-bicyclo[3.2.0]heptan-7-one | 39 | 73 |

-continued

| Ex. | Structure | Name | EC₅₀ (nM) mGlu5PAM | Eff. (%) |
|---|---|---|---|---|
| 99 | 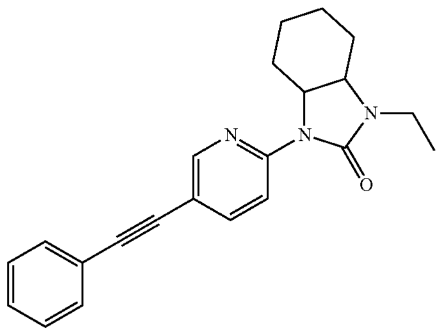 [SMILES: CCN1C(=O)N(c2ccc(C#Cc3ccccc3)cn2)C2CCCCC21] | (3aSR,7aRS)-(3aRS,7RS)-1-Ethyl-3-(5-phenylethynyl-pyridin-2-yl)-octahydro-benzoimidazol-2-one | 18 | 90 |
| 100 | 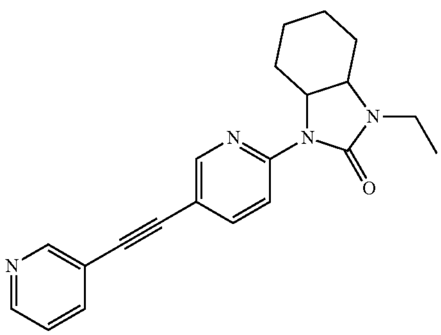 [SMILES: CCN1C(=O)N(c2ccc(C#Cc3cccnc3)cn2)C2CCCCC21] | (3aSR,7aRS)-(3aRS,7RS)-1-Ethyl-3-(5-pyridin-3-ylethynyl-pyridin-2-yl)-octahydro-benzoimidazol-2-one | 69 | 64 |
| 101 | 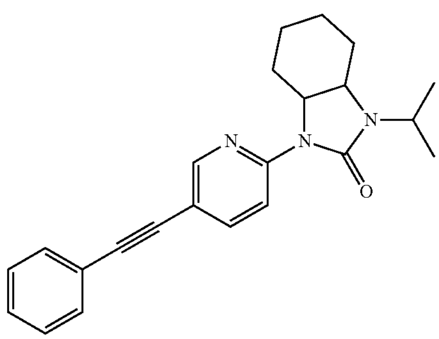 [SMILES: CC(C)N1C(=O)N(c2ccc(C#Cc3ccccc3)cn2)C2CCCCC21] | (3aSR,7aRS)-(3aRS,7RS)-1-Isopropyl-3-(5-phenylethynyl-pyridin-2-yl)-octahydro-benzoimidazol-2-one | 39 | 77 |
| 102 | 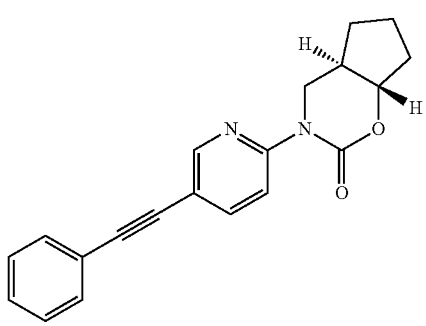 [SMILES: O=C1O[C@H]2CCC[C@@H]2CN1c1ccc(C#Cc2ccccc2)cn1] | (4aRS,7aSR)-3-(5-Phenylethynyl-pyridin-2-yl)-hexahydro-cyclopenta[e][1,3]oxazin-2-one | 43 | 115 |

-continued

| Ex. | Structure | Name | EC$_{50}$ (nM) mGlu5PAM | Eff. (%) |
|---|---|---|---|---|
| 103 | 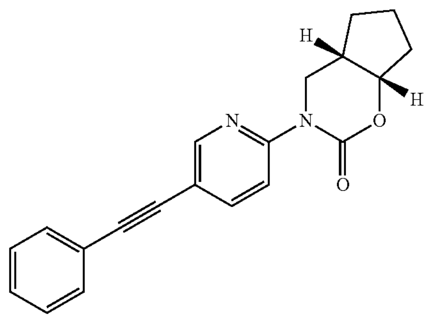 [SMILES: O=C1O[C@H]2CCC[C@H]2CN1c1ccc(C#Cc2ccccc2)cn1] | (4aRS,7aRS)-3-(5-Phenylethynyl-pyridin-2-yl)-hexahydro-cyclopenta[e][1,3]oxazin-2-one | 27 | 123 |
| 104 | 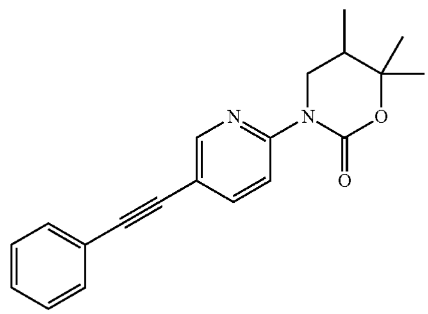 [SMILES: CC1CN(c2ccc(C#Cc3ccccc3)cn2)C(=O)OC1(C)C] | (RS)-5,6,6-Trimethyl-3-(5-phenylethynyl-pyridin-2-yl)-[1,3]oxazinan-2-one | 42 | 109 |
| 105 | 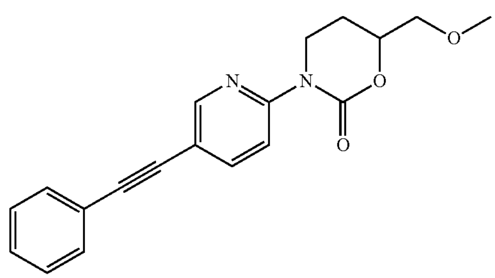 [SMILES: COCC1CCN(c2ccc(C#Cc3ccccc3)cn2)C(=O)O1] | (RS)-6-Methoxymethyl-3-(5-phenylethynyl-pyridin-2-yl)-[1,3]oxazinan-2-one | 68 | 51 |
| 106 | 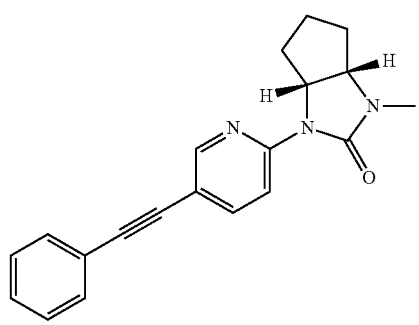 [SMILES: CN1C(=O)N(c2ccc(C#Cc3ccccc3)cn2)[C@@H]2CCC[C@@H]21] | (3aRS,6aSR)-1-Methyl-3-(5-(phenylethynyl)pyridin-2-yl)hexa-hydrocyclopenta[d]imidazol-2(1H)-one | 30 | 42 |
| 107 | 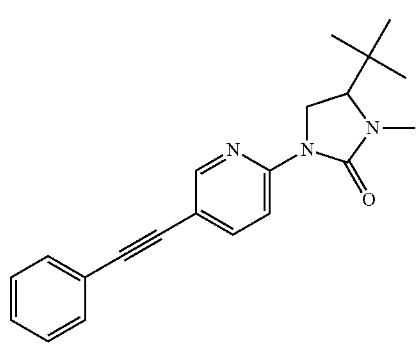 [SMILES: CN1C(=O)N(c2ccc(C#Cc3ccccc3)cn2)CC1C(C)(C)C] | (RS)-4-tert-Butyl-3-methyl-1-(5-phenylethynyl-pyridin-2-yl)-imidazolidin-2-one | 59 | 106 |

-continued

| Ex. | Structure | Name | EC$_{50}$ (nM) mGlu5PAM | Eff. (%) |
|---|---|---|---|---|
| 108 | 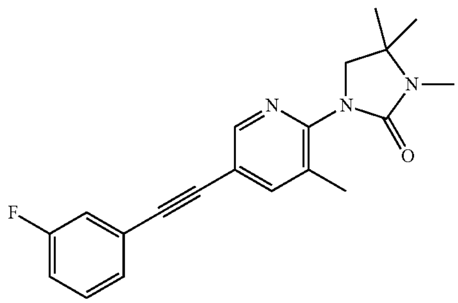 [SMILES: Cc1cc(C#Cc2cccc(F)c2)cnc1N1CC(C)(C)N(C)C1=O] | 1-[5-(3-Fluoro-phenylethynyl)-3-methyl-pyridin-2-yl]-3,4,4-trimethyl-imidazolidin-2-one | 102 | 115 |
| 109 | 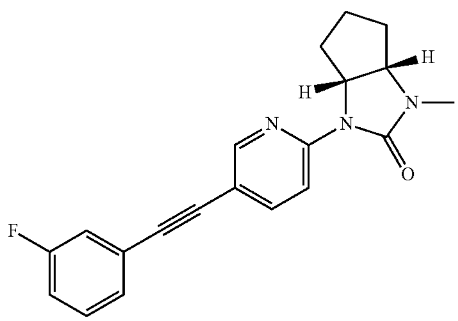 [SMILES: CN1C(=O)N(c2ccc(C#Cc3cccc(F)c3)cn2)[C@@H]2CCC[C@@H]21] | (3aRS,6aSR)-1-[5-(3-Fluoro-phenylethynyl)-pyridin-2-yl]-3-methyl-hexahydro-cyclopenta-imidazol-2-one | 18 | 37 |
| 110 | 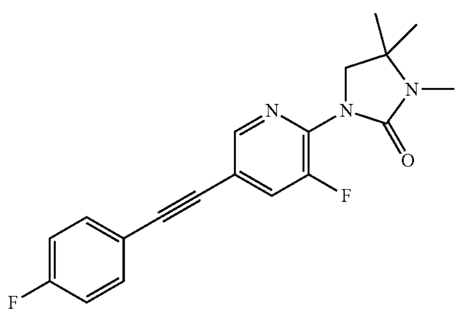 [SMILES: CN1C(=O)N(c2ncc(C#Cc3ccc(F)cc3)cc2F)CC1(C)C] | 1-[3-Fluoro-5-(4-fluoro-phenylethynyl)-pyridin-2-yl]-3,4,4-trimethyl-imidazolidin-2-one | 96 | 117 |
| 111 | 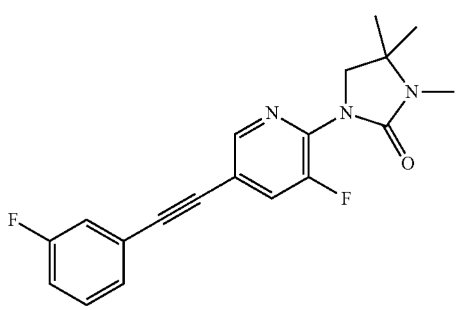 | 1-[3-Fluoro-5-(3-fluoro-phenylethynyl)-pyridin-2-yl]-3,4,4-trimethyl-imidazolidin-2-one | 32 | 107 |
| 112 | 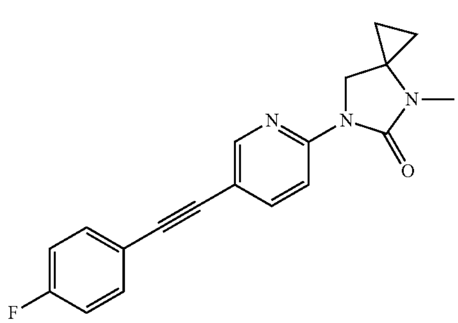 [SMILES: CN1C(=O)N(c2ccc(C#Cc3ccc(F)cc3)cn2)CC12CC2] | 6-[5-(4-Fluoro-phenylethynyl)-pyridin-2-yl]-4-methyl-4,6-diaza-spiro[2.4]heptan-5-one | 80 | 89 |

-continued

| Ex. | Structure | Name | EC₅₀ (nM) mGlu5PAM | Eff. (%) |
|---|---|---|---|---|
| 113 | 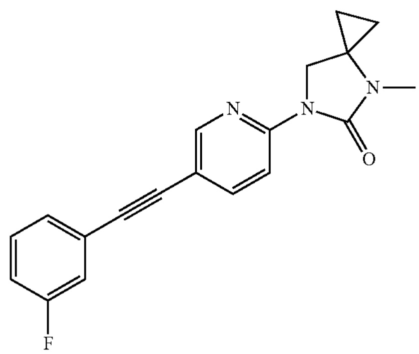 [SMILES: CN1C(=O)N(c2ccc(C#Cc3cccc(F)c3)cn2)CC12CC2] | 6-[5-(3-Fluoro-phenylethynyl)-pyridin-2-yl]-4-methyl-4,6-diaza-spiro[2.4]heptan-5-one | 51 | 75 |
| 114 | 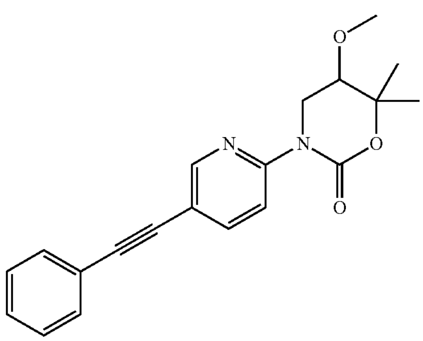 [SMILES: COC1CN(c2ccc(C#Cc3ccccc3)cn2)C(=O)OC1(C)C] | (RS)-5-Methoxy-6,6-dimethyl-3-(5-phenylethynyl-pyridin-2-yl)-[1,3]oxazinan-2-one | 22 | 57 |
| 115 | 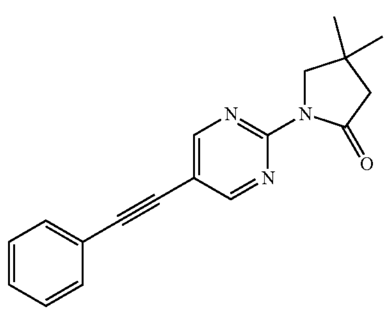 [SMILES: CC1(C)CC(=O)N(c2ncc(C#Cc3ccccc3)cn2)C1] | 4,4-Dimethyl-1-(5-phenylethynyl-pyrimidin-2-yl)-pyrrolidin-2-one | 13 | 109 |
| 116 | 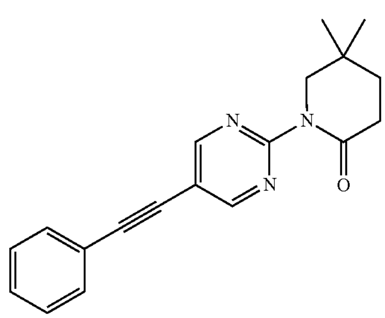 | 5,5-Dimethyl-1-(5-phenylethynyl-pyrimidin-2-yl)-piperidin-2-one | 41 | 101 |

| Ex. | Structure | Name | EC$_{50}$ (nM) mGlu5PAM | Eff. (%) |
|---|---|---|---|---|
| 117 | 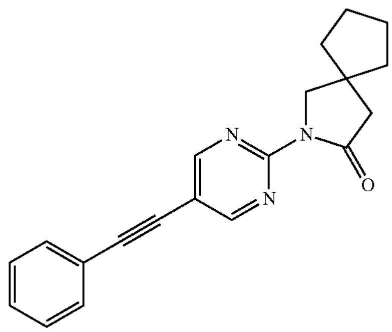 [SMILES: O=C1CC2(CCCC2)CN1c1ncc(C#Cc2ccccc2)cn1] | 2-[5-Phenylethynyl-pyrimidin-2-yl)-2-aza-spiro[4.4]nonan-3-one | 44 | 84 |
| 118 | 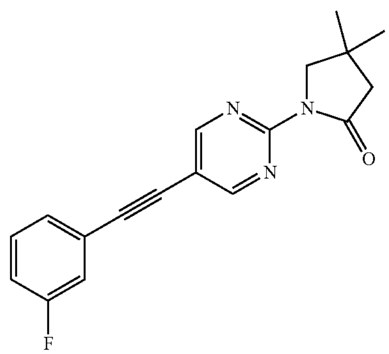 [SMILES: CC1(C)CC(=O)N(c2ncc(C#Cc3cccc(F)c3)cn2)C1] | 1-[5-(3-Fluoro-phenylethynyl)-pyrimidin-2-yl]-4,4-dimethyl-pyrrolidin-2-one | 13 | 78 |
| 119 | 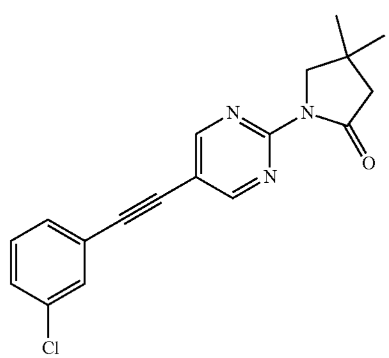 [SMILES: CC1(C)CC(=O)N(c2ncc(C#Cc3cccc(Cl)c3)cn2)C1] | 1-[5-(3-Chloro-phenylethynyl)-pyrimidin-2-yl]-4,4-dimethyl-pyrrolidin-2-one | 11 | 26 |
| 120 | 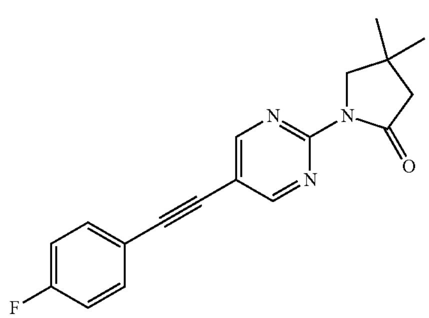 [SMILES: CC1(C)CC(=O)N(c2ncc(C#Cc3ccc(F)cc3)cn2)C1] | 1-[5-(4-Fluoro-phenylethynyl)-pyrimidin-2-yl]-4,4-dimethyl-pyrrolidin-2-one | 92 | 81 |

| Ex. | Structure | Name | EC$_{50}$ (nM) mGlu5PAM | Eff. (%) |
|---|---|---|---|---|
| 121 | 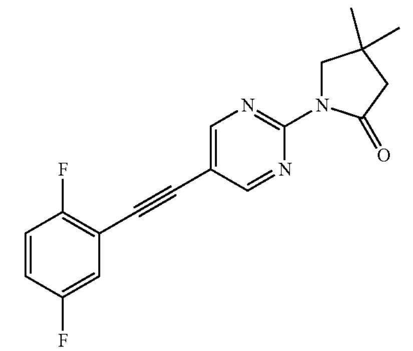 [SMILES: CC1(C)CC(=O)N(c2ncc(C#Cc3cc(F)ccc3F)cn2)C1] | 1-[5-(2,5-Difluoro-phenylethynyl)-pyrimidin-2-yl]-4,4-dimethyl-pyrrolidin-2-one | 41 | 70 |
| 122 | 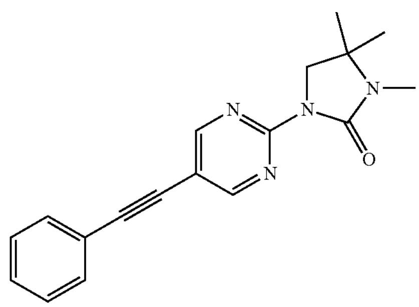 [SMILES: CN1C(=O)N(c2ncc(C#Cc3ccccc3)cn2)CC1(C)C] | 3,4,4-Trimethyl-1-(5-phenylethynyl-pyrimidin-2-yl)-imidazolidin-2-one | 11 | 36 |
| 123 | 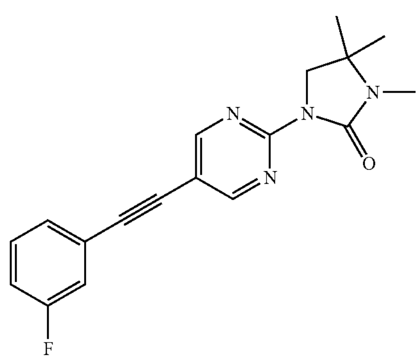 [SMILES: CN1C(=O)N(c2ncc(C#Cc3cccc(F)c3)cn2)CC1(C)C] | 1-[5-(3-Fluoro-phenylethynyl)-pyrimidin-2-yl]-3,4,4-trimethyl-imidazolidin-2-one | 18 | 30 |
| 124 | 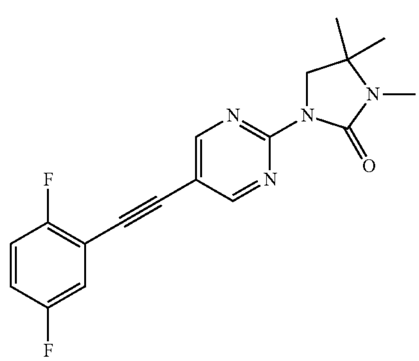 [SMILES: CN1C(=O)N(c2ncc(C#Cc3cc(F)ccc3F)cn2)CC1(C)C] | 1-[5-(2,5-Difluoro-phenylethynyl)-pyrimidin-2-yl]-3,4,4-trimethyl-imidazolidin-2-one | 7 | 43 |

| Ex. | Structure | Name | EC$_{50}$ (nM) mGlu5PAM | Eff. (%) |
|---|---|---|---|---|
| 125 | 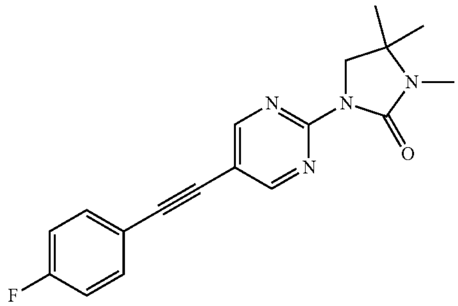 [SMILES: CN1C(=O)N(c2ncc(C#Cc3ccc(F)cc3)cn2)CC1(C)C] | 1-[5-(4-Fluoro-phenylethynyl)-pyrimidin-2-yl]-3,4,4-trimethyl-imidazolidin-2-one | 13 | 44 |
| 126 | 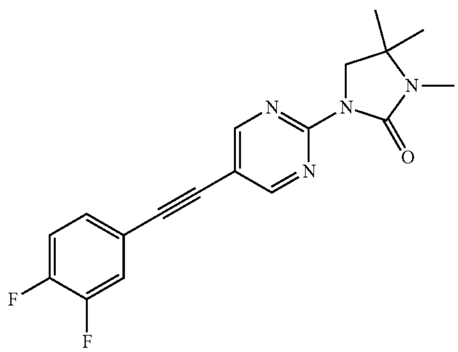 [SMILES: CN1C(=O)N(c2ncc(C#Cc3ccc(F)c(F)c3)cn2)CC1(C)C] | 1-[5-(3,4-Difluoro-phenylethynyl)-pyrimidin-2-yl]-3,4,4-trimethyl-imidazolidin-2-one | 23 | 36 |
| 127 | 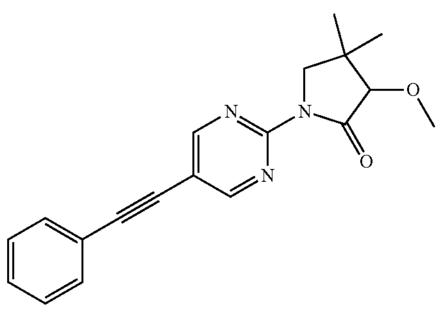 [SMILES: COC1C(=O)N(c2ncc(C#Cc3ccccc3)cn2)CC1(C)C] | (RS)-3-Methoxy-4,4-dimethyl-1-(5-phenylethynyl-pyrimidin-2-yl)-pyrrolidin-2-one | 29 | 94 |
| 128 | Chiral OR | (R or S)-3-Methoxy-4,4-dimethyl-1-(5-phenylethynyl-pyrimidin-2-yl)-pyrrolidin-2-one | 46 | 54 |

| Ex. | Structure | Name | EC$_{50}$ (nM) mGlu5PAM | Eff. (%) |
|---|---|---|---|---|
| 129 | (S or R)-3-Methoxy-4,4-dimethyl-1-(5-phenylethynyl-pyrimidin-2-yl)-pyrrolidin-2-one | 18 | 90 |
| | OR | | | |
| 130 | 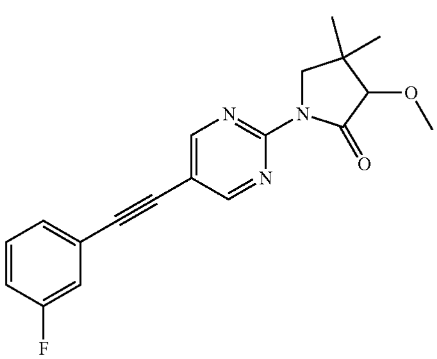 | (RS)-1-[5-(3-Fluoro-phenylethynyl)-pyrimidin-2-yl]-3-methoxy-4,4-dimethyl-pyrrolidin-2-one | 41 | 74 |

-continued
| Ex. | Structure | Name | EC$_{50}$ (nM) mGlu5PAM | Eff. (%) |
|---|---|---|---|---|
| 131 | 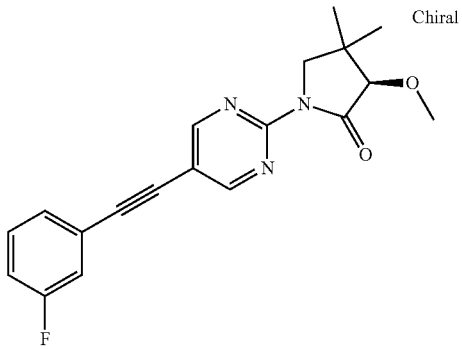<br>OR<br>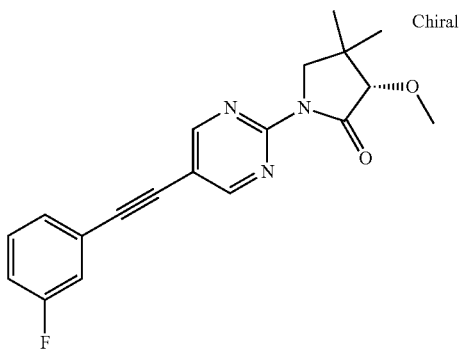 | (R or S)-1-[5-(3-Fluoro-phenylethynyl)-pyrimidin-2-yl]-3-methoxy-4,4-dimethyl-pyrrolidin-2-one | 35 | 48 |
| 132 | 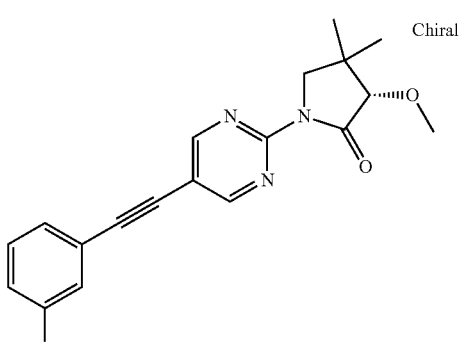<br>OR<br>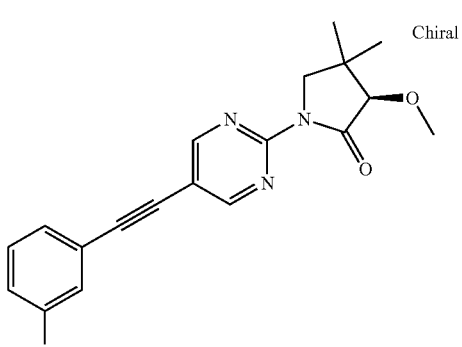 [SMILES: CO[C@H]1C(=O)N(c2ncc(C#Cc3ccccc3)cn2)CC1(C)C] | (S or R)-1-[5-(3-Fluoro-phenylethynyl)-pyrimidin-2-yl]-3-methoxy-4,4-dimethyl-pyrrolidin-2-one | 21 | 69 |

| Ex. | Structure | Name | EC$_{50}$ (nM) mGlu5PAM | Eff. (%) |
|---|---|---|---|---|
| 133 | 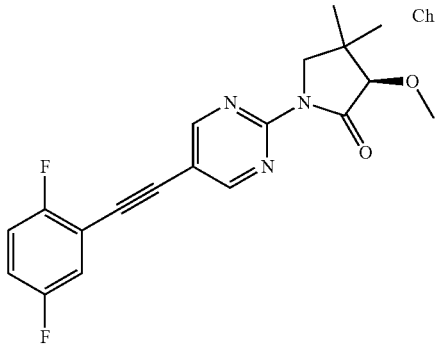<br>OR<br>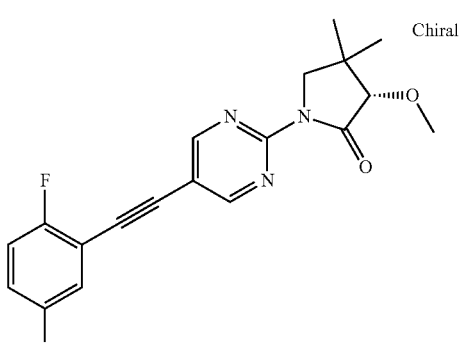 [SMILES: CO[C@@H]1C(=O)N(c2ncc(C#Cc3ccccc3)cn2)CC1(C)C] | (R or S)-1-[5-(2,5-Difluoro-phenylethynyl)-pyrimidin-2-yl]-3-methoxy-4,4-dimethyl-pyrrolidin-2-one | 57 | 49 |
| 134 | 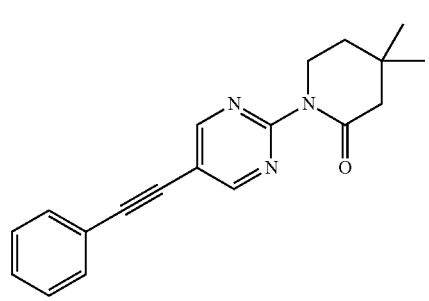 [SMILES: CC1(C)CCN(c2ncc(C#Cc3ccccc3)cn2)C(=O)C1] | 4,4-Dimethyl-1-(5-phenylethynyl-pyrimidin-2-yl)-piperidin-2-one | 42 | 90 |
| 135 | 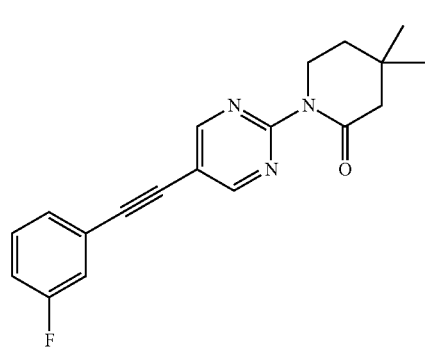 [SMILES: CC1(C)CCN(c2ncc(C#Cc3cccc(F)c3)cn2)C(=O)C1] | 1-[5-(3-Fluoro-phenylethynyl)-pyrimidin-2-yl]-4,4-dimethyl-piperidin-2-one | 35 | 47 |

| Ex. | Structure | Name | EC$_{50}$ (nM) mGlu5PAM | Eff. (%) |
|---|---|---|---|---|
| 136 | 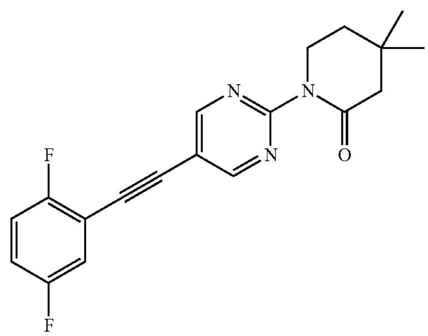 [SMILES: CC1(C)CCN(c2ncc(C#Cc3cc(F)ccc3F)cn2)C(=O)C1] | 1-[5-(2,5-Difluoro-phenylethynyl)-pyrimidin-2-yl]-4,4-dimethyl-piperidin-2-one | 31 | 49 |
| 137 | 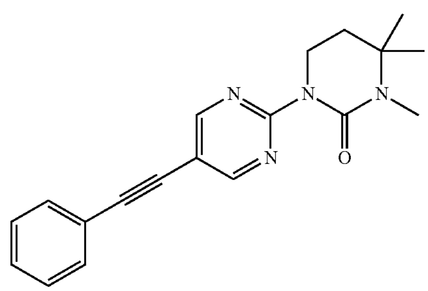 [SMILES: CN1C(=O)N(c2ncc(C#Cc3ccccc3)cn2)CCC1(C)C] | 3,4,4-Trimethyl-5'-phenylethynyl-3,4,5,6-tetrahydro-[1,2']bipyrimidinyl-2-one | 66 | 74 |
| 138 | 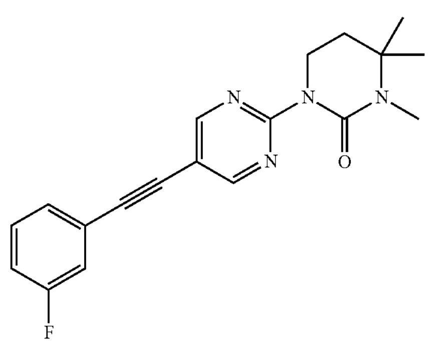 [SMILES: CN1C(=O)N(c2ncc(C#Cc3cccc(F)c3)cn2)CCC1(C)C] | 5'-(3-Fluoro-phenylethynyl)-3,4,4-trimethyl-3,4,5,6-tetrahydro-[1,2']bipyrimidinyl-2-one | 60 | 67 |
| 139 | 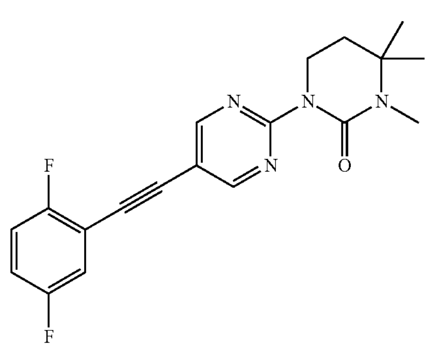 [SMILES: CN1C(=O)N(c2ncc(C#Cc3cc(F)ccc3F)cn2)CCC1(C)C] | 5'-(2,5-Difluoro-phenylethynyl)-3,4,4-trimethyl-3,4,5,6-tetrahydro-[1,2']bipyrimidinyl-2-one | 57 | 54 |

-continued

| Ex. | Structure | Name | EC$_{50}$ (nM) mGlu5PAM | Eff. (%) |
|---|---|---|---|---|
| 140 | 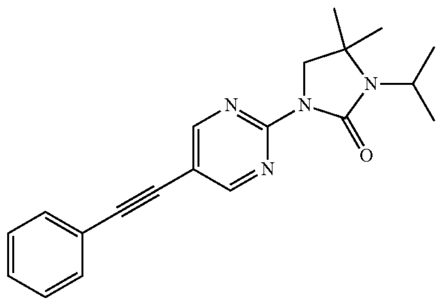 [SMILES: CC(C)N1C(=O)N(c2ncc(C#Cc3ccccc3)cn2)CC1(C)C] | 3-Isopropyl-4,4-dimethyl-1-(5-phenylethynyl-pyrimidin-2-yl)-imidazolidin-2-one | 28 | 58 |
| 141 | 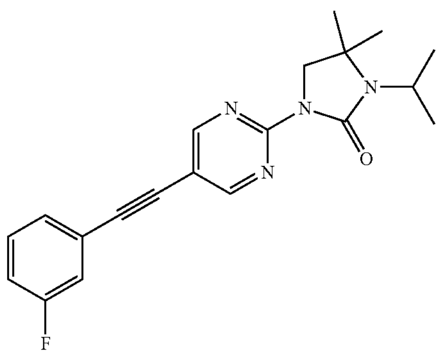 [SMILES: CC(C)N1C(=O)N(c2ncc(C#Cc3cccc(F)c3)cn2)CC1(C)C] | 1-[5-(3-Fluoro-phenylethynyl)-pyrimidin-2-yl]-3-isopropyl-4,4-dimethyl-imidazolidin-2-one | 28 | 39 |
| 142 | 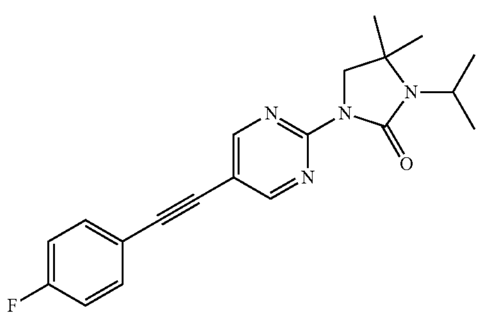 [SMILES: CC(C)N1C(=O)N(c2ncc(C#Cc3ccc(F)cc3)cn2)CC1(C)C] | 1-[5-(4-Fluoro-phenylethynyl)-pyrimidin-2-yl]-3-isopropyl-4,4-dimethyl-imidazolidin-2-one | 78 | 74 |
| 143 | 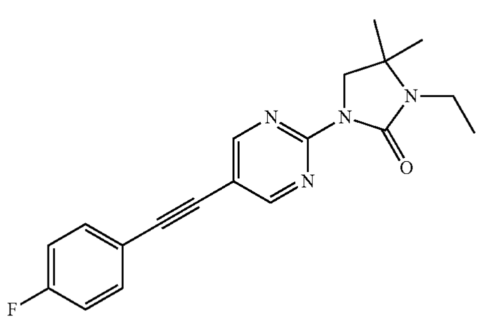 [SMILES: CCN1C(=O)N(c2ncc(C#Cc3ccc(F)cc3)cn2)CC1(C)C] | 1-[5-(4-Fluoro-phenylethynyl)-pyrimidin-2-yl]-3-ethyl-4,4-dimethyl-imidazolidin-2-one | 47 | 68 |

-continued

| Ex. | Structure | Name | EC$_{50}$ (nM) mGlu5PAM | Eff. (%) |
|---|---|---|---|---|
| 144 | 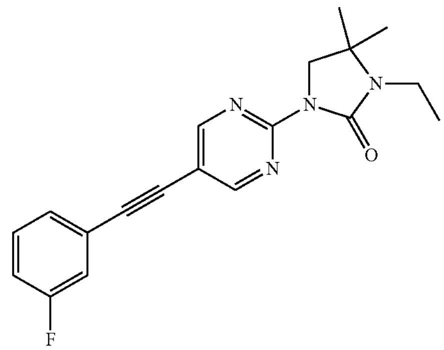 [SMILES: CCN1C(=O)N(c2ncc(C#Cc3cccc(F)c3)cn2)CC1(C)C] | 1-[5-(3-Fluoro-phenylethynyl)-pyrimidin-2-yl]-3-ethyl-4,4-dimethyl-imidazolidin-2-one | 31 | 58 |
| 145 | 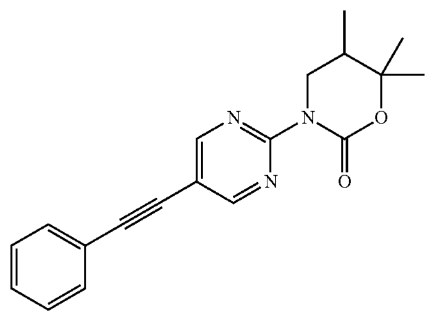 [SMILES: CC1CN(c2ncc(C#Cc3ccccc3)cn2)C(=O)OC1(C)C] | (RS)-5,6,6-Trimethyl-3-(5-phenylethynyl-pyrimidin-2-yl)-[1,3]oxazinan-2-one | 38 | 93 |
| 146 | 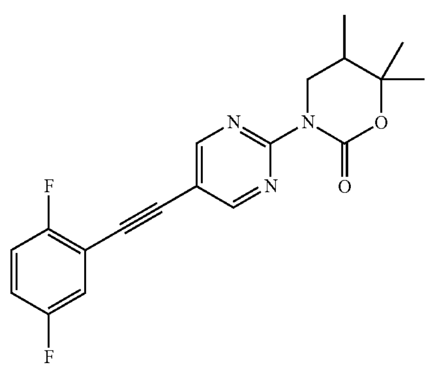 [SMILES: CC1CN(c2ncc(C#Cc3cc(F)ccc3F)cn2)C(=O)OC1(C)C] | (RS)-3-[5-(2,5-Difluoro-phenylethynyl)-pyrimidin-2-yl]-5,6,6-trimethyl-[1,3]oxazinan-2-one | 69 | 64 |
| 147 | 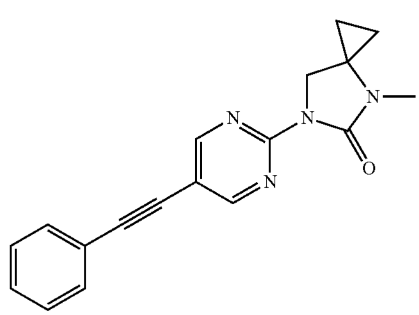 [SMILES: CN1C(=O)N(c2ncc(C#Cc3ccccc3)cn2)CC12CC2] | 4-Methyl-6-(5-phenylethynyl-pyrimidin-2-yl)-4,6-diaza-spiro[2.4]heptan-5-one | 25 | 36 |

-continued

| Ex. | Structure | Name | EC$_{50}$ (nM) mGlu5PAM | Eff. (%) |
|---|---|---|---|---|
| 148 | 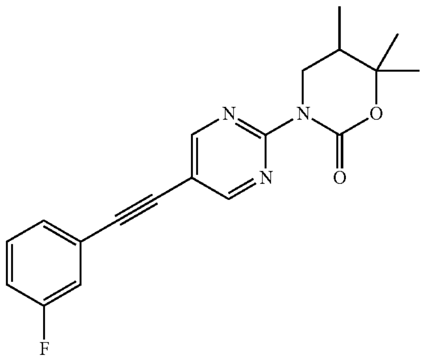 [SMILES: CC1CN(c2ncc(C#Cc3cccc(F)c3)cn2)C(=O)OC1(C)C] | (RS)-3-[5-(3-Fluoro-phenylethynyl)-pyrimidin-2-yl]-5,6,6-trimethyl-[1,3]oxazinan-2-one | 39 | 75 |
| 149 | 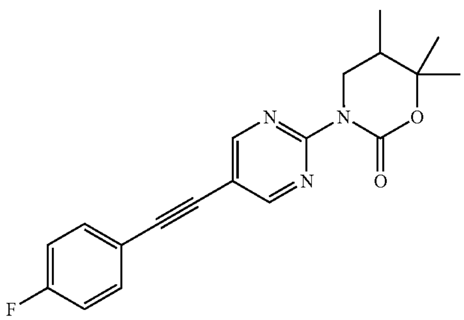 [SMILES: CC1CN(c2ncc(C#Cc3ccc(F)cc3)cn2)C(=O)OC1(C)C] | (RS)-3-[5-(4-Fluoro-phenylethynyl)-pyrimidin-2-yl]-5,6,6-trimethyl-[1,3]oxazinan-2-one | 114 | 78 |
| 150 | 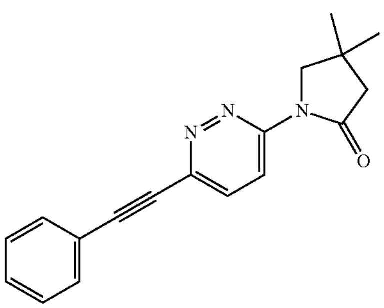 [SMILES: CC1(C)CC(=O)N(c2ccc(C#Cc3ccccc3)nn2)C1] | 4,4-dimethyl-1-(6-(phenylethynyl)pyridazin-3-yl)pyrrolidin-2-one | 21 | 113 |
| 151 | 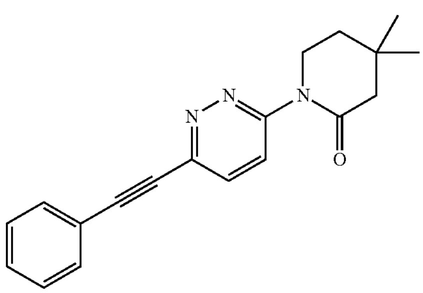 [SMILES: CC1(C)CCN(c2ccc(C#Cc3ccccc3)nn2)C(=O)C1] | 4,4-dimethyl-1-(6-(phenylethynyl)pyridazin-3-yl)piperidin-2-one | 19 | 130 |
| 152 | 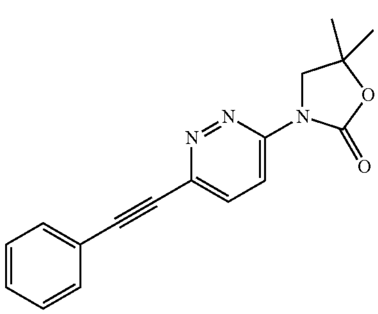 [SMILES: CC1(C)CN(c2ccc(C#Cc3ccccc3)nn2)C(=O)O1] | 5,5-dimethyl-3-(6-(phenylethynyl)pyridazin-3-yl)oxazolidin-2-one | 15 | 112 |

| Ex. | Structure | Name | EC$_{50}$ (nM) mGlu5PAM | Eff. (%) |
|---|---|---|---|---|
| 153 | 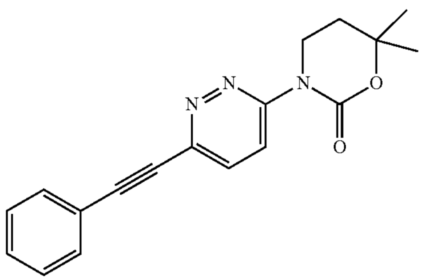 [SMILES: CC1(C)CCN(c2ccc(C#Cc3ccccc3)nn2)C(=O)O1] | 6,6-dimethyl-3-(6-(phenylethynyl)pyridazin-3-yl)-1,3-oxazinan-2-one | 14 | 86 |
| 154 | 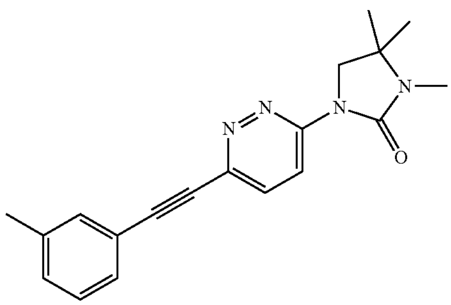 | 3,4,4-trimethyl-1-(6-(m-tolylethynyl)pyridazin-3-yl)imidazolidin-2-one | 61 | 108 |
| 155 | 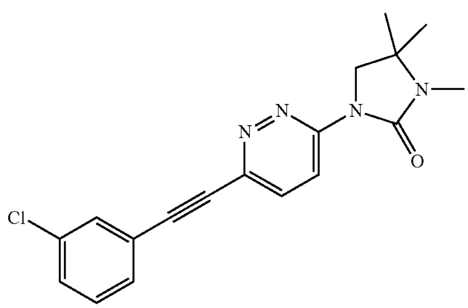 [SMILES: CN1C(=O)N(c2ccc(C#Cc3cccc(Cl)c3)nn2)CC1(C)C] | 1-[6-((3-chlorophenyl)ethynyl)pyridazin-3-yl)-3,4,4-trimethylimidazolidin-2-one | 73 | 95 |
| 156 | 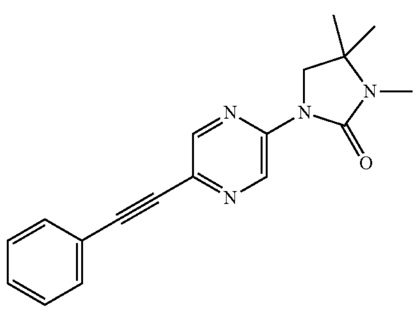 [SMILES: CN1C(=O)N(c2cnc(C#Cc3ccccc3)cn2)CC1(C)C] | 3,4,4-trimethyl-1-(5-(phenylethynyl)pyrazin-2-yl)imidazolidin-2-one | 24 | 58 |
| 157 | 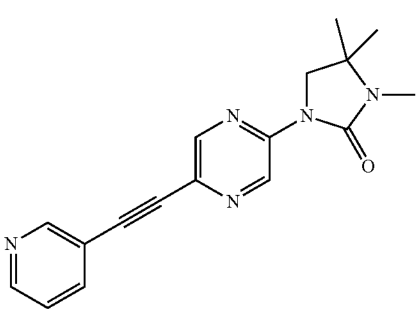 [SMILES: CN1C(=O)N(c2cnc(C#Cc3cccnc3)cn2)CC1(C)C] | 3,4,4-trimethyl-1-(5-(pyridin-3-ylethynyl)pyrazin-2-yl)imidazolidin-2-one | 206 | 34 |

-continued

| Ex. | Structure | Name | EC₅₀ (nM) mGlu5PAM | Eff. (%) |
|---|---|---|---|---|
| 158 | 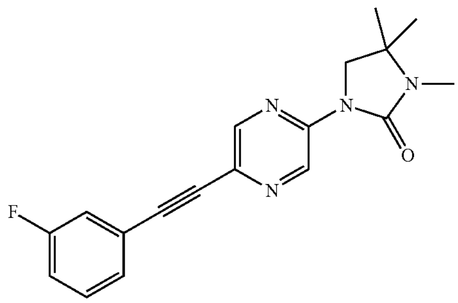 [SMILES: CN1C(=O)N(c2cnc(C#Cc3cccc(F)c3)cn2)CC1(C)C] | 1-(5-((3-fluorophenyl)ethynyl)pyrazin-2-yl)-3,4,4-trimethylimidazolidin-2-one | 46 | 36 |
| 159 | 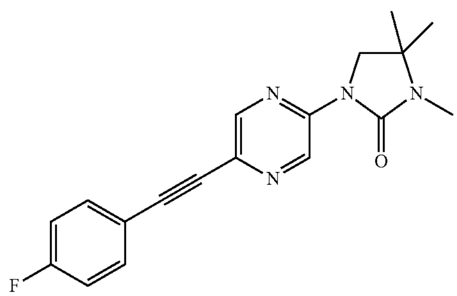 [SMILES: CN1C(=O)N(c2cnc(C#Cc3ccc(F)cc3)cn2)CC1(C)C] | 1-[5-(4-Fluoro-phenylethynyl)-pyrazin-2-yl]-3,4,4-trimethyl-imidazolidin-2-one | 49 | 49 |
| 160 | 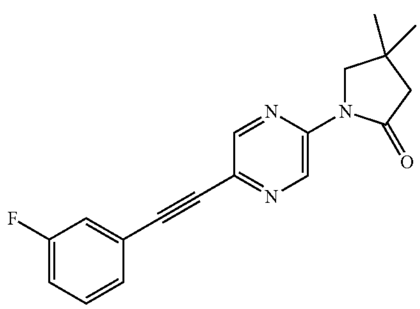 [SMILES: CC1(C)CC(=O)N(c2cnc(C#Cc3cccc(F)c3)cn2)C1] | 1-(5-((3-fluorophenyl)ethynyl)pyrazin-2-yl)-4,4-dimethylpyrrolidin-2-one | 29 | 39 |
| 161 | 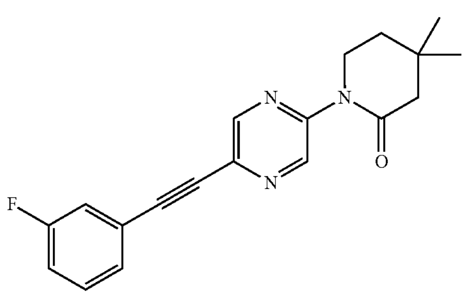 [SMILES: CC1(C)CCN(c2cnc(C#Cc3cccc(F)c3)cn2)C(=O)C1] | 1-(5-((3-fluorophenyl)ethynyl)pyrazin-2-yl)-4,4-dimethylpiperidin-2-one | 29 | 68 |
| 162 | 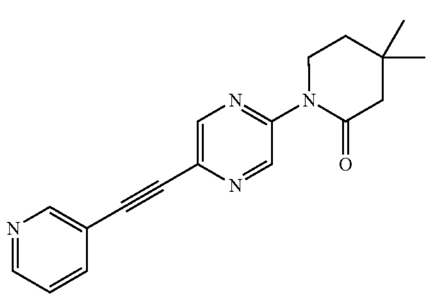 [SMILES: CC1(C)CCN(c2cnc(C#Cc3cccnc3)cn2)C(=O)C1] | 4,4-dimethyl-1-(5-(pyridin-3-ylethynyl)pyrazin-2-yl)piperidin-2-one | 681 | 76 |

-continued

| Ex. | Structure | Name | EC$_{50}$ (nM) mGlu5PAM | Eff. (%) |
|---|---|---|---|---|
| 163 | 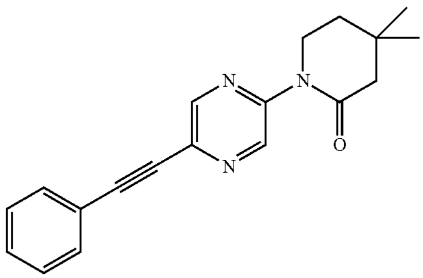 | 4,4-dimethyl-1-(5-(phenylethynyl)pyrazin-2-yl)piperidin-2-one | 69 | 74 |
| 164 | 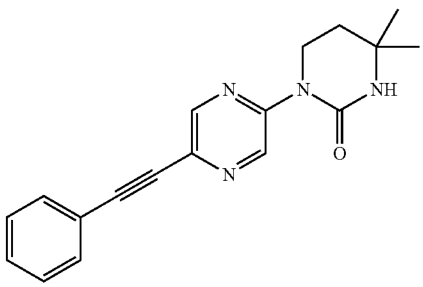 [SMILES: CC1(C)CCN(c2cnc(C#Cc3ccccc3)cn2)C(=O)N1] | 4,4-dimethyl-1-(5-(phenylethynyl)pyrazin-2-yl)tetrahydro-pyrimidin-2(1H)-one | 329 | 89 |
| 165 | 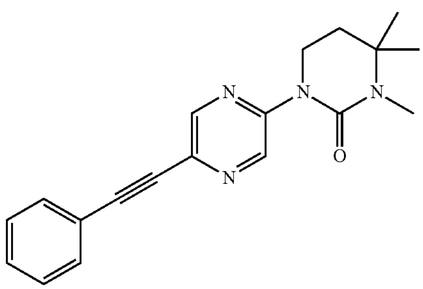 [SMILES: CN1C(=O)N(c2cnc(C#Cc3ccccc3)cn2)CCC1(C)C] | 3,4,4-trimethyl-1-(5-(phenylethynyl)pyrazin-2-yl)tetrahydro-pyrimidin-2(1H)-one | 36 | 55 |
| 166 | 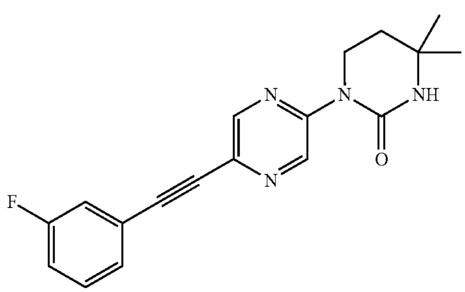 [SMILES: CC1(C)CCN(c2cnc(C#Cc3cccc(F)c3)cn2)C(=O)N1] | 1-[5-((3-fluorophenyl)ethynyl)pyrazin-2-yl]-4,4-dimethyltetrahydro-pyrimidin-2(1H)-one | 140 | 56 |
| 167 | 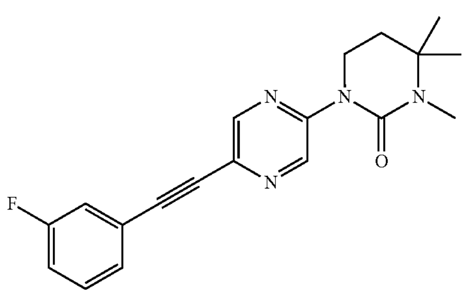 [SMILES: CN1C(=O)N(c2cnc(C#Cc3cccc(F)c3)cn2)CCC1(C)C] | 1-[5-((3-fluorophenyl)ethynyl)pyrazin-2-yl]-3,4,4-trimethyltetrahydro-pyrimidin-2(1H)-one | 26 | 54 |

| Ex. | Structure | Name | EC$_{50}$ (nM) mGlu5PAM | Eff. (%) |
|---|---|---|---|---|
| 168 | 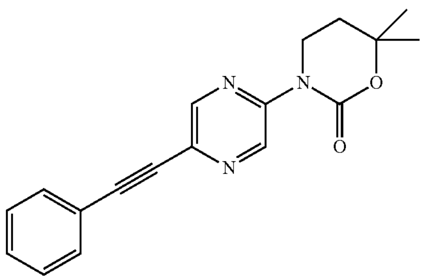 [SMILES: CC1(C)CCN(c2cnc(C#Cc3ccccc3)cn2)C(=O)O1] | 6,6-dimethyl-3-(5-(phenylethynyl)pyrazin-2-yl)-1,3-oxazinan-2-one | 15 | 41 |
| 169 | 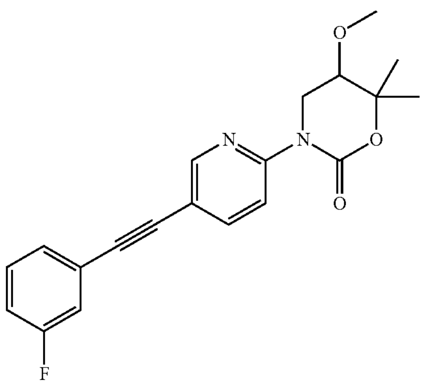 [SMILES: COC1CN(c2ccc(C#Cc3cccc(F)c3)cn2)C(=O)OC1(C)C] | (RS)-3-[5-(3-Fluoro-phenylethynyl)-pyridin-2-yl]-5-methoxy-6,6-dimethyl-[1,3]oxazinan-2-one | 13 | 52 |
| 170 | 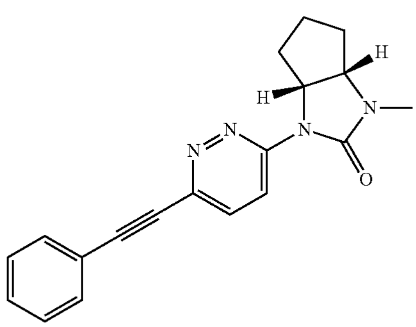 [SMILES: CN1C(=O)N(c2ccc(C#Cc3ccccc3)nn2)[C@@H]2CCC[C@@H]21] | (3aRS,6aSR)-1-Methyl-3-(6-phenylethynyl-pyridazin-3-yl)-hexahydro-cyclopentaimidazol-2-one | 13 | 105 |
| 171 | 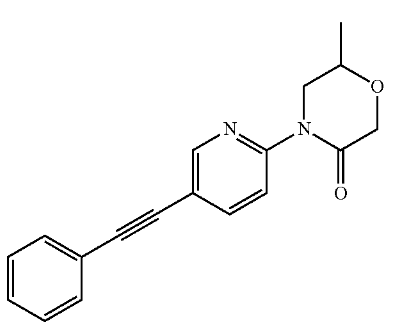 [SMILES: CC1CN(c2ccc(C#Cc3ccccc3)cn2)C(=O)CO1] | (RS)-6-Methyl-4-(5-phenylethynyl-pyridin-2-yl)-morpholin-3-one | 88 | 73 |

| Ex. | Structure | Name | EC$_{50}$ (nM) mGlu5PAM | Eff. (%) |
|---|---|---|---|---|
| 172 | 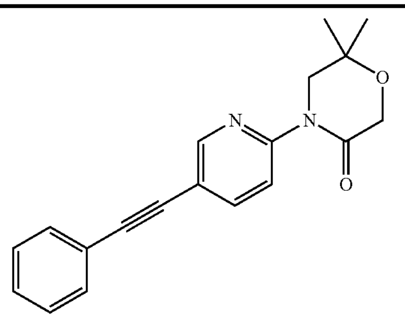 | 6,6-Dimethyl-4-(5-phenylethynyl-pyridin-2-yl)-morpholin-3-one | 29 | 82 |
| 173 | 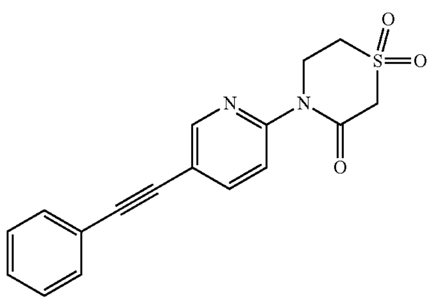 [SMILES: O=C1CS(=O)(=O)CCN1c1ccc(C#Cc2ccccc2)cn1] | 1,1-Dioxo-4-(5-phenylethynyl-pyridin-2-yl)-thiomorpholin-3-one | 29 | 82 |
| 174 | 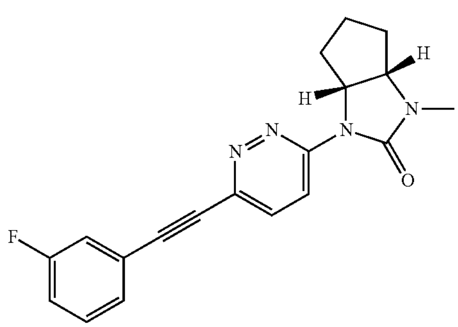 [SMILES: CN1C(=O)N(c2ccc(C#Cc3cccc(F)c3)nn2)[C@@H]2CCC[C@@H]21] | (3aRS,6aSR)-1-[6-(3-Fluoro-phenylethynyl)-pyridazin-3-yl]-3-methyl-hexahydro-cyclopentaimidazol-2-one | 12 | 56 |

EXPERIMENTAL SECTION

Example 1

3-(3-Fluoro-5-phenylethynyl-pyridin-2-yl)-5,5-dimethyl-oxazolidin-2-one

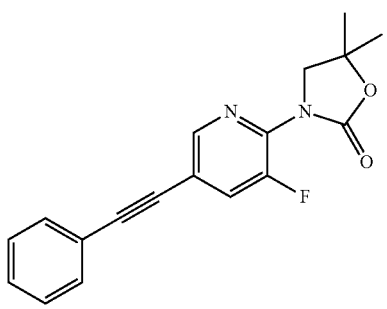 [SMILES: CC1(C)CN(c2ncc(C#Cc3ccccc3)cc2F)C(=O)O1]

Step 1: 1-(3-Fluoro-5-iodo-pyridin-2-ylamino)-2-methyl-propan-2-ol

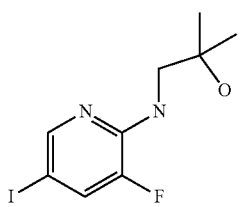

2,3-Difluoro-5-iodopyridine (500 mg, 2.07 mmol) was dissolved in NMP (500 μL) and pyridine (201 μl, 2.49 mmol, 1.2 equiv.) and 1-amino-2-methylpropan-2-ol (555 mg, 6.22 mmol, 3 equiv.) were added at room temperature. The mixture was stirred for 16 hours at 100° C. The reaction mixture was cooled and extracted with saturated NaHCO$_3$ solution and two times with a small volume of dichloromethane. The crude product was purified by flash chromatography by directly loading the dichloromethane layers onto a silica gel column and eluting with an ethyl acetate:heptane gradient 0:100 to 100:0. The desired 1-(3-fluoro-5-iodopyridin-2-ylamino)-2-methylpropan-2-ol (590 mg, 1.9 mmol, 91.7% yield) was obtained as a colorless oil, MS: m/e=311.0 (M+H$^+$).

Step 2: 3-(3-Fluoro-5-iodopyridin-2-yl)-5,5-dimethyloxazolidin-2-one

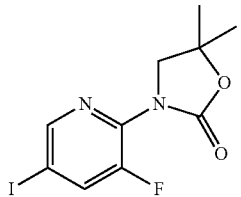 [SMILES: CC1(C)CN(c2ncc(I)cc2F)C(=O)O1]

(580 mg, 1.87 mmol) 1-(3-Fluoro-5-iodopyridin-2-ylamino)-2-methylpropan-2-ol (Example 1, step 1) was dissolved in dichloromethane (10 ml) and pyridine (300 µl, 3.74 mmol, 2 equiv.) was added at room temperature. The mixture was cooled to 0-5° C. and phosgene (20% in toluene) (1.19 ml, 2.24 mmol, 1.2 equiv.) was added dropwise over a period of 15 min at 0-5° C. The mixture was stirred for 1 hour at 0-5° C. The reaction mixture was extracted with saturated NaHCO$_3$ solution and two times with a small volume of dichloromethane. The crude product was purified by flash chromatography by directly loading the dichloromethane layers onto a silica gel column and eluting with a heptane:ethyl acetate gradient 100:0 to 50:50. The desired 3-(3-fluoro-5-iodopyridin-2-yl)-5,5-dimethyloxazolidin-2-one (500 mg, 1.49 mmol, 79.5% yield) was obtained as a white solid, MS: m/e=337.0 (M+H$^+$).

Step 3: 3-(3-Fluoro-5-phenylethynyl-pyridin-2-yl)-5,5-dimethyl-oxazolidin-2-one

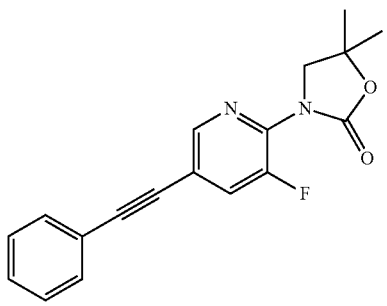 [SMILES: CC1(C)CN(c2ncc(C#Cc3ccccc3)cc2F)C(=O)O1]

Bis-(triphenylphosphine)-palladium(II)dichloride (12.5 mg, 17.9 µmol, 0.05 equiv.) was dissolved in 1 ml DMF. (120 mg, 357 µmol) 3-(3-Fluoro-5-iodopyridin-2-yl)-5,5-dimethyloxazolidin-2-one (Example 1, step 2) and phenylacetylene (72.9 mg, 78.4 µL, 714 µmol, 2 equiv.) were added at room temperature. Triethylamine (108 mg, 149 µl, 1.07 mmol, 3 equiv.), triphenylphosphine (2.81 mg, 10.7 µmol, 0.03 equiv.) and copper(I)iodide (2.04 mg, 10.7 µmol, 0.03 equiv.) were added and the mixture was stirred for 3 hours at 70° C. The reaction mixture was cooled and extracted with saturated NaHCO$_3$ solution and two times with a small volume of dichloromethane. The crude product was purified by flash chromatography by directly loading the dichloromethane layers onto a silica gel column and eluting with an ethyl acetate:heptane gradient 0:100 to 40:60. The desired 3-(3-fluoro-5-(phenylethynyl)pyridin-2-yl)-5,5-dimethyloxazolidin-2-one (96 mg, 309 µmol, 86.6% yield) was obtained as a yellow solid, MS: m/e=311.2 (M+H$^+$).

Example 2

(5RS)-5-Methoxymethyl-3-(5-phenylethynyl-pyridin-2-yl)-oxazolidin-2-one

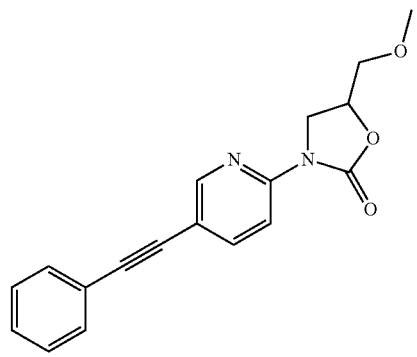 [SMILES: COCC1CN(c2ccc(C#Cc3ccccc3)cn2)C(=O)O1]

The title compound, a light brown solid, MS: m/e=309.1 (M+H$^+$), was prepared using a procedure similar to that described in Example 1, step 3 from 3-(5-bromo-pyridin-2-yl)-5-methoxymethyl-oxazolidin-2-one (CAS 170011-45-7) and phenylacetylene.

Example 3

(5R or 5S)-5-Methoxymethyl-3-(5-phenylethynyl-pyridin-2-yl)-oxazolidin-2-one

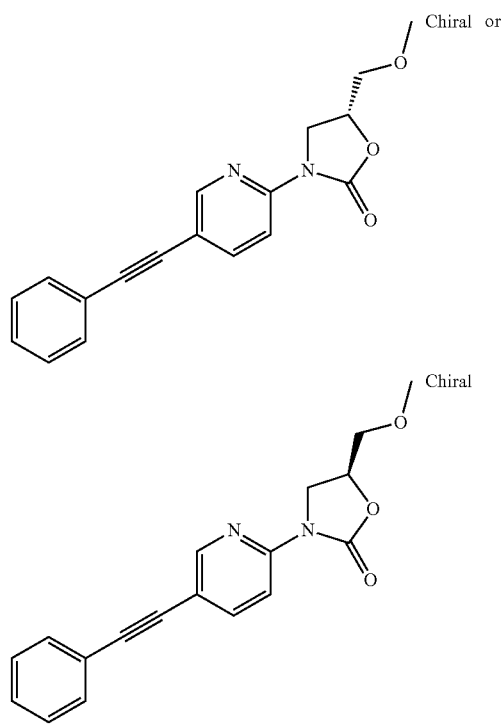

The title compound, a white solid, MS: m/e=309.1 (M+H$^+$), was prepared by separation of (5RS)-5-methoxymethyl-3-(5-phenylethynyl-pyridin-2-yl)-oxazolidin-2-one (Example 2) using a chiral column (chiralpak AD with heptane:isopropanol 80:20 as solvent).

Example 4

(5S or 5R)-5-Methoxymethyl-3-(5-phenylethynyl-pyridin-2-yl)-oxazolidin-2-one

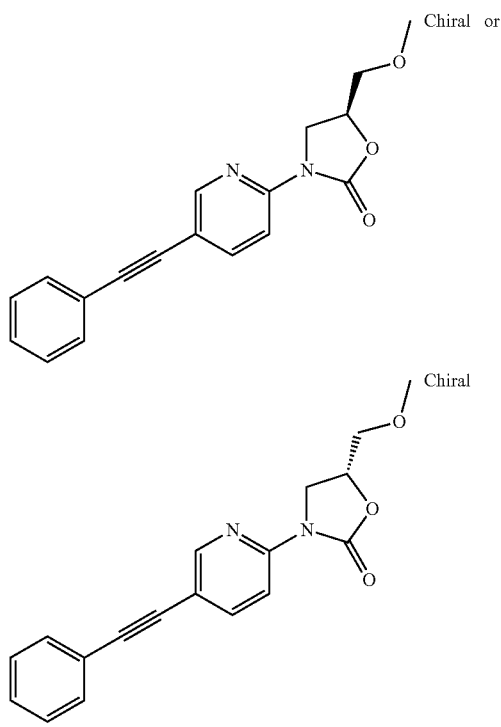

The title compound, a white solid, MS: m/e=309.1 (M+H⁺), was prepared by separation of (5RS)-5-methoxymethyl-3-(5-phenylethynyl-pyridin-2-yl)-oxazolidin-2-one (Example 2) using a chiral column (chiralpak AD with heptane:isopropanol 80:20 as solvent).

Example 5

5,5-Dimethyl-3-(5-phenylethynyl-pyridin-2-yl)-oxazolidin-2-one

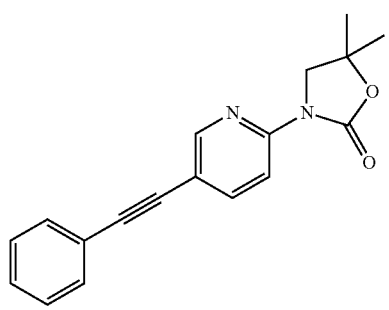 [SMILES: CC1(C)CN(c2ccc(C#Cc3ccccc3)cn2)C(=O)O1]

Step 1: 3-(5-Iodo-pyridin-2-yl)-5,5-dimethyl-oxazolidin-2-one

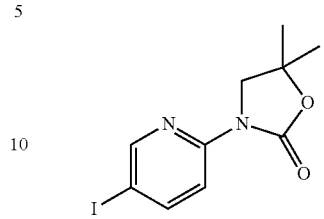

The title compound was obtained as a white solid, MS: m/e=292.9 (M+H⁺), using procedures similar to those described in Example 1, step 1 and step 2 from 2-fluoro-5-iodopyridine and 1-amino-2-methylpropan-2-ol.

Step 2: 5,5-Dimethyl-3-(5-phenylethynyl-pyridin-2-yl)-oxazolidin-2-one

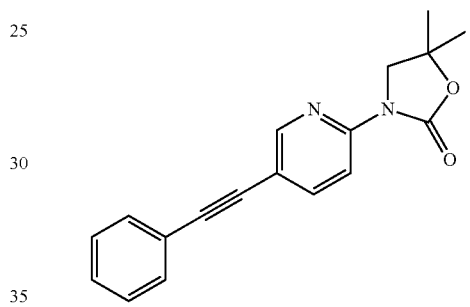

The title compound was obtained as a white solid, MS: m/e=293.0 (M+H⁺), using chemistry similar to that described in Example 1, step 3 from 3-(5-iodo-pyridin-2-yl)-5,5-dimethyl-oxazolidin-2-one (Example 5, step 1) and phenylacetylene.

Example 6

3-[5-(3-Fluoro-phenylethynyl)-pyridin-2-yl]-5,5-dimethyl-oxazolidin-2-one

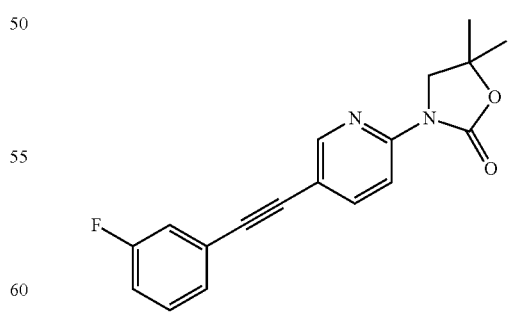

The title compound was obtained as a white solid, MS: m/e=311.2 (M+H⁺), using chemistry similar to that described in Example 1, step 3 from 3-(5-iodo-pyridin-2-yl)-5,5-dimethyl-oxazolidin-2-one (Example 5, step 1) and 3-fluorophenylacetylene.

Example 7

5,5-Dimethyl-3-(5-pyridin-3-ylethynyl-pyridin-2-yl)-oxazolidin-2-one

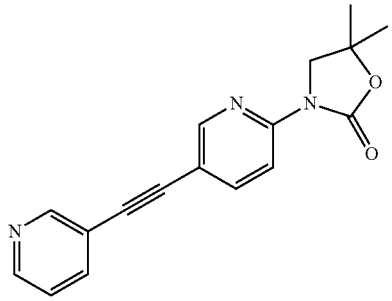 [SMILES: CC1(C)CN(c2ccc(C#Cc3cccnc3)cn2)C(=O)O1]

The title compound was obtained as a white solid, MS: m/e=294.1 (M+H⁺), using chemistry similar to that described in Example 1, step 3 from 3-(5-iodo-pyridin-2-yl)-5,5-dimethyl-oxazolidin-2-one (Example 5, step 1) and 3-ethynyl-pyridine.

Example 8

(5RS)-5-tert-Butyl-3-(5-phenylethynyl-pyridin-2-yl)-oxazolidin-2-one

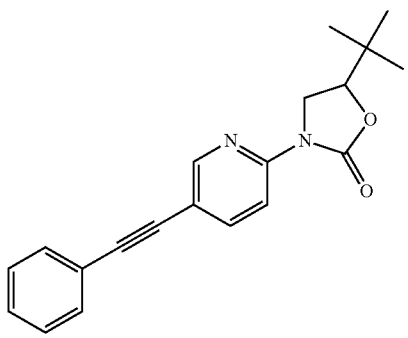 [SMILES: CC(C)(C)C1CN(c2ccc(C#Cc3ccccc3)cn2)C(=O)O1]

Step 1: (5RS)-5-tert-Butyl-3-(5-iodo-pyridin-2-yl)-oxazolidin-2-one

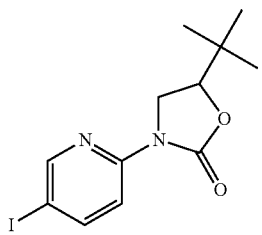 [SMILES: CC(C)(C)C1CN(c2ccc(I)cn2)C(=O)O1]

The title compound was obtained as a white solid, MS: m/e=346.9 (M+H⁺), using procedures similar to those described in Example 1, step 1 and step 2 from 2-fluoro-5-iodopyridine and (rac)-1-amino-3,3-dimethylbutan-2-ol hydrochloride.

Step 2: (5RS)-5-tert-Butyl-3-(5-phenylethynyl-pyridin-2-yl)-oxazolidin-2-one

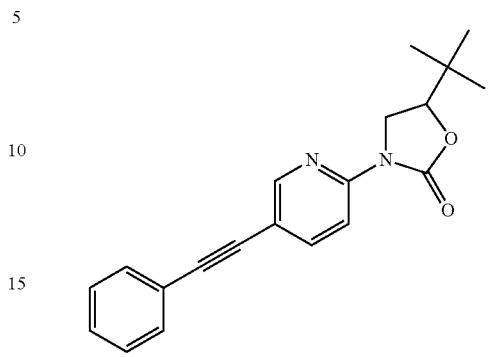

The title compound was obtained as a white solid, MS: m/e=321.2 (M+H⁺), using chemistry similar to that described in Example 1, step 3 from (5RS)-5-tert-butyl-3-(5-iodo-pyridin-2-yl)-oxazolidin-2-one (Example 8, step 1) and phenylacetylene.

Example 9

6-(5-Phenylethynyl-pyridin-2-yl)-4-oxa-6-aza-spiro[2.4]heptan-5-one

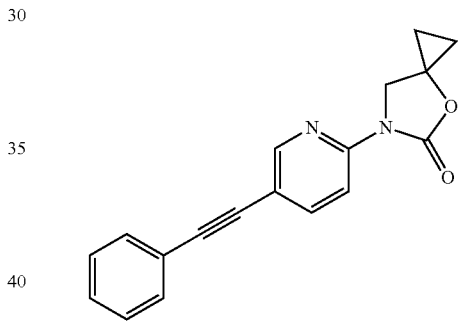

The title compound was obtained as a colourless solid, MS: m/e=291.2 (M+H⁺), using procedures similar to those described in Example 1 starting from 2-fluoro-5-bromopyridine, 1-aminomethyl-cyclopropanol (*Russian J. Org. Chem.* 2001, 37, 1238) and phenylacetylene.

Example 10

7-(5-Phenylethynyl-pyridin-2-yl)-5-oxa-7-aza-spiro[3.4]octan-6-one

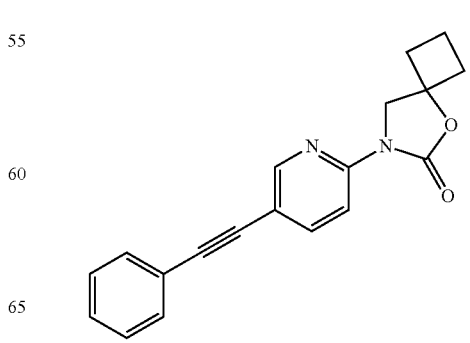

The title compound was obtained as a light yellow solid, MS: m/e=305.2 (M+H$^+$), using procedures similar to those described in Example 1 starting from 2-fluoro-5-bromopyridine, 1-aminomethyl-cyclobutanol (WO2006/29115 A2) and phenylacetylene.

Example 11

3-(5-Phenylethynyl-pyridin-2-yl)-1-oxa-3-aza-spiro[4.4]nonan-2-one

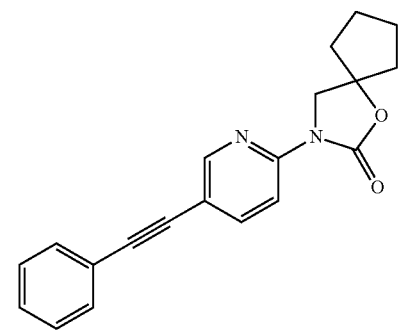 [SMILES: O=C1OC2(CCCC2)CN1c1ccc(C#Cc2ccccc2)cn1]

The title compound was obtained as a light yellow solid, MS: m/e=319.2 (M+H$^+$), using procedures similar to those described in Example 1 starting from 2-fluoro-5-bromopyridine, 1-aminomethyl-cyclopentanol and phenylacetylene.

Example 12

3-(5-Phenylethynyl-pyridin-2-yl)-1-oxa-3-aza-spiro[4.5]decan-2-one

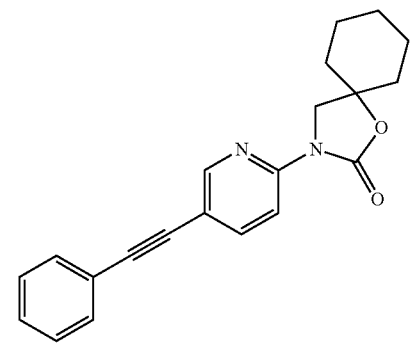 [SMILES: O=C1OC2(CCCCC2)CN1c1ccc(C#Cc2ccccc2)cn1]

The title compound was obtained as a light yellow solid, MS: m/e=333.2 (M+H$^+$), using procedures similar to those described in Example 1 starting from 2-fluoro-6-bromopyridine, 1-aminomethyl-cyclohexanol and phenylacetylene.

Example 13

4,4-Dimethyl-1-(5-phenylethynyl-pyridin-2-yl)-pyrrolidin-2-one

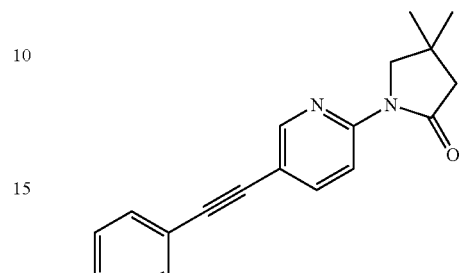

Step 1: 1-(5-Iodo-pyridin-2-yl)-3,3-dimethyl-pyrrolidine-2,5-dione

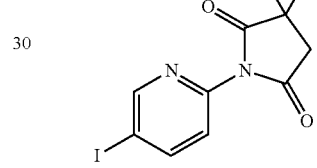

5-iodopyridin-2-amine (1 g, 4.55 mmol) was dissolved in DMF (5 ml) and 3,3-dimethyldihydrofuran-2,5-dione (1.28 g, 10.0 mmol, 2.2 equiv.) was added at room temperature. The mixture was stirred for 3 hr at 150° C. The reaction mixture was evaporated to dryness and loaded directly to a silica gel column. The crude material was purified by flash chromatography on silica gel (20 gr, ethyl acetate/heptane gradient, 0:100 to 100:0). The desired 1-(5-iodopyridin-2-yl)-3,3-dimethylpyrrolidine-2,5-dione (1.3 g, 3.94 mmol, 86.6% yield) was obtained as a yellow solid, MS: m/e=331.0 (M+H$^+$).

Step 2: (5RS)-5-Hydroxy-1-(5-iodo-pyridin-2-yl)-4,4-dimethyl-pyrrolidin-2-one

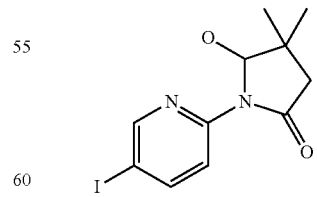

(800 mg, 2.42 mmol) 145-Iodopyridin-2-yl)-3,3-dimethylpyrrolidine-2,5-dione (Example 13, step 1) was dissolved in THF (6 ml) and MeOH (2 ml) and the solution was cooled to 0-5° C. NaBH$_4$ (101 mg, 2.67 mmol, 1.1 equiv.) was added at 0-5° C. and the mixture was stirred for 1 hr at 0-5° C. The reaction mixture was extracted with sat. NaHCO₃ solution and two times with a small volume of dichloromethane. The crude product was purified by flash chromatography by directly loading the dichloromethane layers onto a amino-silica gel column and eluting with a ethyl acetate/heptane gradient, 0:100 to 100:0. The desired (5-RS)-5-hydroxy-1-(5-iodo-pyridin-2-yl)-4,4-dimethyl-pyrrolidin-2-one (370 mg, 46% yield) was obtained as a white solid, MS: m/e=333.0 (M+H⁺).

Step 3: 1-(5-Iodo-pyridin-2-yl)-4,4-dimethyl-pyrrolidin-2-one

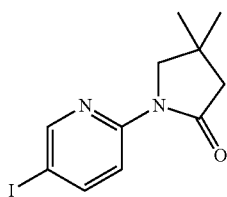

(275 mg, 828 µmol) (5RS)-5-Hydroxy-1-(5-iodopyridin-2-yl)-4,4-dimethylpyrrolidin-2-one (Example 13, step 2) was dissolved in CH₂Cl₂ (2 ml) and trifluoroacetic anhydride (140 µl, 994 µmol, 1.2 equiv.) was added at room temperature. The mixture was stirred for 1 hr at 20-25° C. The solution was evaporated to dryness and the residue was dissolved in trifluoroacetic acid (957 µl, 12.4 mmol, 15 equiv.) and triethylsilane (159 µl, 994 µmol, 1.2 equiv.) was added at room temperature. The mixture was stirred 1 h at room temperature. The reaction mixture was evaporated and extracted with sat. NaHCO₃ solution and two times with a small volume of dichloromethane. The crude product was purified by flash chromatography by directly loading the dichloromethane layers onto a silica gel column (20 gr, ethyl acetate/heptane gradient, 0:100 to 100:0). The desired 1-(5-iodopyridin-2-yl)-4,4-dimethylpyrrolidin-2-one (209 mg, 80% yield) was obtained as a white solid, MS: m/e=317.0 (M+H⁺).

Step 4: 4,4-Dimethyl-1-(5-phenylethynyl-pyridin-2-yl)-pyrrolidin-2-one

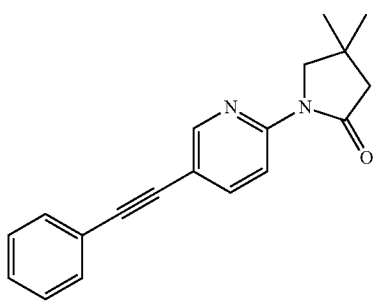 [SMILES: CC1(C)CC(=O)N(c2ccc(C#Cc3ccccc3)cn2)C1]

The title compound was obtained as a yellow oil, MS: m/e=291.1 (M+H⁺), using chemistry that is described in Example 1, step 3 from 1-(5-iodo-pyridin-2-yl)-4,4-dimethyl-pyrrolidin-2-one (Example 13, step 3) and phenylacetylene.

Example 14

(3RS)-3-Hydroxy-4,4-dimethyl-1-(5-phenylethynyl-pyridin-2-yl)-pyrrolidin-2-one

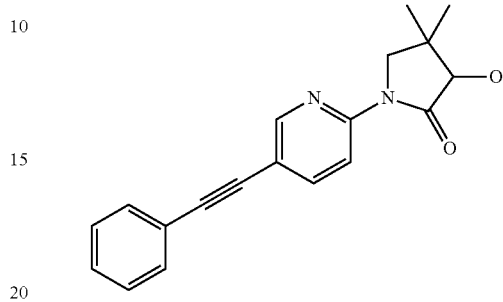

Step 1: (4RS)-4-Hydroxy-3,3-dimethyl-dihydro-furan-2,5-dione

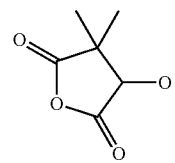

(3RS)-3-Hydroxy-2,2-dimethyl-succinic acid [Tetrahedron Letters (2002), 43(52), 9513-9515] (120 mg, 0.74 mmol) was suspended in CH₂Cl₂ (2 ml) and cooled to 0-5° C. Trifluoroacetic anhydride (260 µl, 1.85 mmol) was added and the reaction mixture stirred for 2 hours at room temperature. The reaction mixture was evaporated to dryness and used without any further purification in the next step.

Step 2: (4RS)-4-Hydroxy-1-(5-iodo-pyridin-2-yl)-3,3-dimethyl-pyrrolidine-2,5-dione

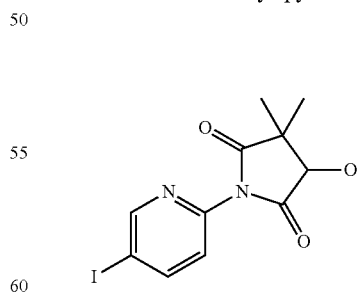

The title compound was obtained as a light yellow solid, MS: m/e=346.8 (M+H⁺), using chemistry similar to that described in Example 12, step 1 from 5-iodopyridin-2-amine and (4RS)-4-hydroxy-3,3-dimethyl-dihydro-furan-2,5-dione (Example 14, step 1).

Step 3: (4RS)-4-(tert-Butyl-diphenyl-silanyloxy)-1-(5-iodo-pyridin-2-yl)-3,3-dimethyl-pyrrolidine-2,5-dione

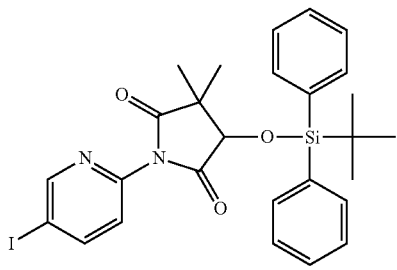 [SMILES: CC1(C)C(=O)N(c2ccc(I)cn2)C(=O)C1O[Si](c1ccccc1)(c1ccccc1)C(C)(C)C]

(2.4 g, 3.47 mmol, 50%) (4RS)-4-Hydroxy-1-(5-iodo-pyridin-2-yl)-3,3-dimethyl-pyrrolidine-2,5-dione (Example 14, step 2) was dissolved in dichloromethane (20 ml). Imidazole (520 mg, 7.63 mmol) and tert-butyldiphenylchlorosilane (1.0 g, 3.64 mmol) were added at room temperature and the mixture was stirred for 3 hours at room temperature. Sat. NaHCO$_3$ solution was added and the mixture was extracted with dichloromethane. The organic extracts were dried with sodium sulfate, filtered and evaporated. The crude product was purified by flash chromatography on silica gel (ethyl acetate/heptane gradient 0:100 to 30:70). The desired compound was obtained as a white solid (1.5 g, 74% yield), MS: m/e=585.1 (M+H$^+$).

Step 4: (3RS,5RS)-3-(tert-Butyl-diphenyl-silanyloxy)-5-hydroxy-1-(5-iodo-pyridin-2-yl)-4,4-dimethyl-pyrrolidin-2-one

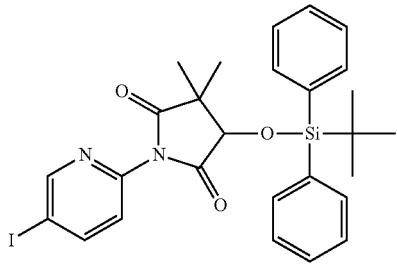 [SMILES: CC1(C)C(=O)N(c2ccc(I)cn2)C(=O)C1O[Si](c1ccccc1)(c1ccccc1)C(C)(C)C]

The title compound was obtained as a light yellow solid, MS: m/e=587.0 (M+H$^+$), using chemistry similar to that described in Example 12, step 2 from (4RS)-4-(tert-butyl-diphenyl-silanyloxy)-1-(5-iodo-pyridin-2-yl)-3,3-dimethyl-pyrrolidine-2,5-dione (Example 14, step 3).

Step 5: (3RS)-3-(tert-Butyl-diphenyl-silanyloxy)-1-(5-iodo-pyridin-2-yl)-4,4-dimethyl-pyrrolidin-2-one

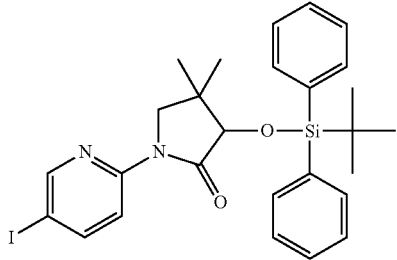 [SMILES: CC1(C)CN(c2ccc(I)cn2)C(=O)C1O[Si](c1ccccc1)(c1ccccc1)C(C)(C)C]

The title compound was obtained as a colorless oil, MS: m/e=571.1 (M+H$^+$), using chemistry similar to that described in Example 12, step 3 from (3RS,5RS)-3-(tert-butyl-diphenyl-silanyloxy)-5-hydroxy-1-(5-iodo-pyridin-2-yl)-4,4-dimethyl-pyrrolidin-2-one (Example 14, step 4).

Step 6: (3RS)-3-(tert-Butyl-diphenyl-silanyloxy)-4,4-dimethyl-1-(5-phenylethynyl-pyridin-2-yl)-pyrrolidin-2-one

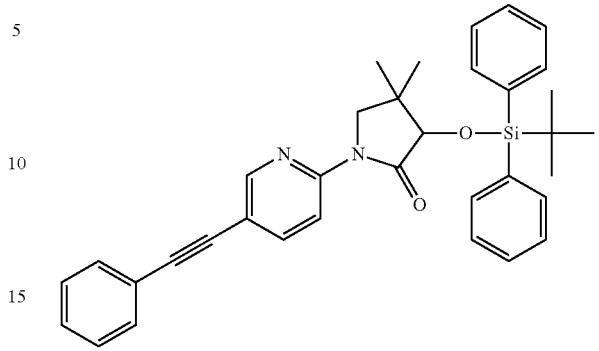

The title compound was obtained as a brown oil, MS: m/e=545.3 (M+H$^+$), using chemistry similar to that described in Example 1, step 3 from (3RS)-3-(tert-butyl-diphenyl-silanyloxy)-1-(5-iodo-pyridin-2-yl)-4,4-dimethyl-pyrrolidin-2-one (Example 14, step 5) and phenylacetylene.

Step 7: (3RS)-3-Hydroxy-4,4-dimethyl-1-(5-phenylethynyl-pyridin-2-yl)-pyrrolidin-2-one

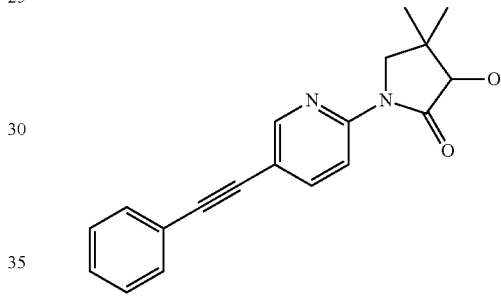

(100 mg, 0.18 mmol) (3RS)-3-(tert-Butyl-diphenyl-silanyloxy)-4,4-dimethyl-1-(5-phenylethynyl-pyridin-2-yl)-pyrrolidin-2-one (Example 14, step 6) was dissolved in THF (1 ml) and TBAF (1M in THF) (184 µl, 0.184) was added drop wise at room temperature. The mixture was stirred for 1 hr at 60° C. The reaction mixture was extracted with sat. NaHCO$_3$-solution and two times EtOAc. The organic layers were extracted with water, dryed over Na$_2$SO$_4$, filtered and evaporated to dryness. The crude material was purified by flash chromatography on silica gel (20 gr, ethyl acetate/heptane gradient, 0:100 to 100:0). The desired (3RS)-3-hydroxy-4,4-dimethyl-1-(5-phenylethynyl-pyridin-2-yl)-pyrrolidin-2-one (44 mg, 78% yield) was obtained as a white solid, MS: m/e=307.3 (M+H$^+$).

Example 15

4,4-Dimethyl-1-(5-phenylethynyl-pyridin-2-yl)-imidazolidin-2-one

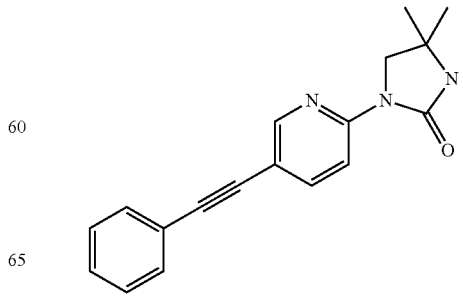

Step 1: N-1-(5-Iodo-pyridin-2-yl)-2-methyl-propane-1,2-diamine

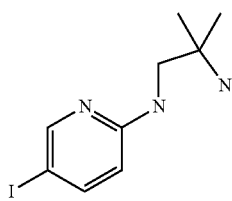

The title compound was obtained as a colorless oil, MS: m/e=292.0 (M+H⁺), using chemistry similar to that described in Example 1, step 1 from 2-fluoro-5-iodopyridine and 2-methylpropane-1,2-diamine.

Step 2: 1-(5-Iodo-pyridin-2-yl)-4,4-dimethyl-imidazolidin-2-one

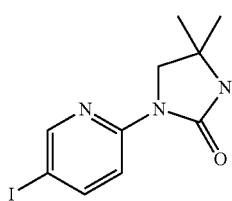

The title compound was obtained as a light yellow solid, MS: m/e=318.0 (M+H⁺), using chemistry similar to that described in Example 1, step 2 from N-1-(5-iodo-pyridin-2-yl)-2-methyl-propane-1,2-diamine (Example 15, step 1).

Step 3: 4,4-Dimethyl-1-(5-phenylethynyl-pyridin-2-yl)-imidazolidin-2-one

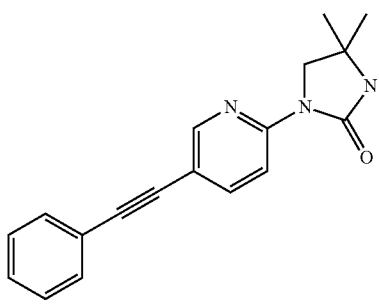 [SMILES: CC1(C)CN(c2ccc(C#Cc3ccccc3)cn2)C(=O)N1]

The title compound was obtained as a yellow solid, MS: m/e=292.1 (M+H⁺), using chemistry similar to that described in Example 1, step 3 from 1-(5-iodo-pyridin-2-yl)-4,4-dimethyl-imidazolidin-2-one (Example 15, step 2) and phenylacetylene.

Example 16

3,4,4-Trimethyl-1-(5-phenylethynyl-pyridin-2-yl)-imidazolidin-2-one

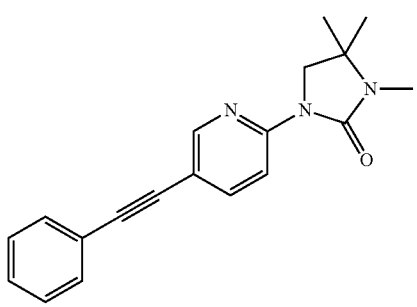 [SMILES: CN1C(=O)N(c2ccc(C#Cc3ccccc3)cn2)CC1(C)C]

(110 mg, 378 μmol) 4,4-Dimethyl-1-(5-(phenylethynyl)pyridin-2-yl)imidazolidin-2-one (Example 15, step 3) was dissolved in DMF (0.5 ml) and cooled to 0-5° C. NaH (55%) (19.8 mg, 453 μmol, 1.2 equiv.) was added and the mixture was stirred for 30 min at 0-5° C. Iodomethane (35.3 μl, 566 μmol, 1.5 equiv.) was added and the mixture was stirred for 30 min at 0-5° C. The reaction mixture was treated with sat. NaHCO₃ solution and extracted twice with a small volume of CH₂Cl₂. The organic layers were loaded directly to silica gel column and the crude material was purified by flash chromatography on silica gel (20 gr, ethyl acetate/heptane gradient, 0:100 to 100:0). The desired 3,4,4-trimethyl-1-(5-phenylethynyl-pyridin-2-yl)-imidazolidin-2-one (93 mg, 81% yield) was obtained as a yellow solid, MS: m/e=306.2 (M+H⁺).

Example 17

3-Ethyl-4,4-dimethyl-1-(5-phenylethynyl-pyridin-2-yl)-imidazolidin-2-one

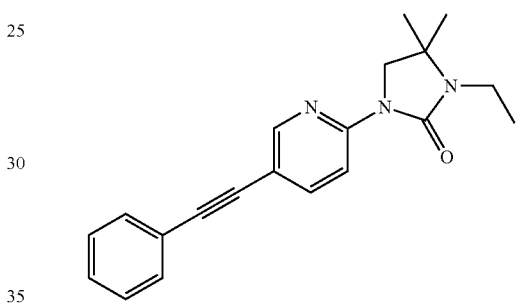

The title compound was obtained as a yellow oil, MS: m/e=320.2 (M+H⁺), using chemistry similar to that described in Example 16 starting from 4,4-dimethyl-1-(5-(phenylethynyl)pyridin-2-yl)imidazolidin-2-one (Example 15, step 3) and iodoethane.

Example 18

3-Isopropyl-4,4-dimethyl-1-(5-phenylethynyl-pyridin-2-yl)-imidazolidin-2-one

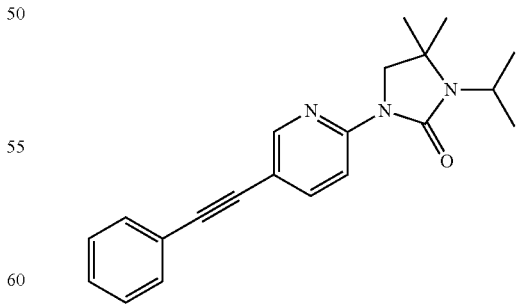

The title compound was obtained as a yellow oil, MS: m/e=334.3 (M+H⁺), using chemistry similar to that described in Example 16 starting from 4,4-dimethyl-1-(5-(phenylethynyl)pyridin-2-yl)imidazolidin-2-one (Example 15, step 3) and 2-bromopropane.

Example 19

(5RS)-5-tert-Butyl-5-methyl-3-(5-phenylethynyl-pyridin-2-yl)-oxazolidin-2-one

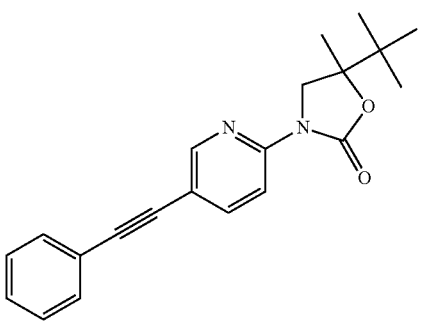 [SMILES: CC(C)(C)C1(C)CN(c2ccc(C#Cc3ccccc3)cn2)C(=O)O1]

Step 1: 1-Dibenzylamino-3,3-dimethyl-butan-2-one

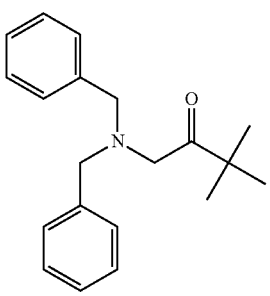 [SMILES: CC(C)(C)C(=O)CN(Cc1ccccc1)Cc1ccccc1]

(2.15 ml, 16.8 mmol) Dibenzylamine was dissolved in acetonitrile (30 ml). Potassium carbonate (2.3 g, 16.8 mmol, 1.5 equiv.) and 1-bromo-3,3-dimethylbutan-2-one (1.5 ml, 11.2 mmol, 1.0 equiv.) were added and the mixture was stirred for 16 hours at 90° C. The reaction mixture was extracted with sat. NaHCO₃-solution and two times EtOAc. The organic layers were extracted with water, dryed over Na₂SO₄, filtered and evaporated to dryness. The crude material was purified by flash chromatography on silica gel (70 gr, ethyl acetate/heptane gradient, 0:100 to 100:0). The desired 1-(dibenzylamino)-3,3-dimethylbutan-2-one (1.6 g, 48.5% yield) was obtained as a yellow oil, MS: m/e=296.3 (M+H⁺).

Step 2: (RS)-1-Dibenzylamino-2,3,3-trimethyl-butan-2-ol

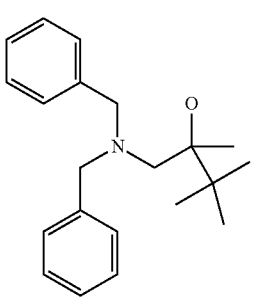 [SMILES: CC(C)(C)C(C)(O)CN(Cc1ccccc1)Cc1ccccc1]

(1.6 g, 5.4 mmol) 1-Dibenzylamino-3,3-dimethyl-butan-2-one (Example 19, step 1) was dissolved in diethylether (20 ml) and cooled to 0-5° C. Methylmagnesium bromide (3M in diethylether) (2.2 ml, 6.5 mmol, 1.2 equiv.) was added dropwise at 0-5° C. and the mixture was stirred for 72 hours at room temperature. The reaction mixture was extracted with sat. NH₄Cl-solution and two times EtOAc. The organic layers were extracted with water, dryed over Na₂SO₄, filtered and evaporated to dryness. The crude material was purified by flash chromatography on silica gel (50 gr, ethyl acetate/heptane gradient, 0:100 to 100:0). The desired (RS)-1-dibenzylamino-2,3,3-trimethyl-butan-2-ol (1.2 g, 71% yield) was obtained as a yellow oil, MS: m/e=312.4 (M+H⁺).

Step 3: (RS)-1-Amino-2,3,3-trimethyl-butan-2-ol

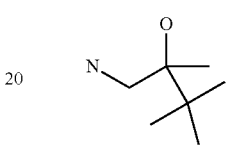

The title compound was obtained as a white solid, MS: m/e=132.1 (M+H⁺), was prepared from (RS)-1-dibenzylamino-2,3,3-trimethyl-butan-2-ol (Example 19, step 2) by hydrogenation 16 hours at room temperature using Pd/C (10%) in ethyl acetate.

Step 4: (RS)-1-(5-Iodo-pyridin-2-ylamino)-2,3,3-trimethyl-butan-2-ol

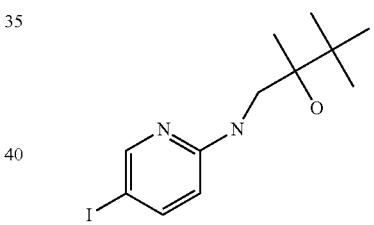

The title compound was obtained as a yellow solid, MS: m/e=335.1 (M+H⁺), using chemistry similar to that described in Example 1, step 1 from 2-fluoro-5-iodopyridine and (RS)-1-amino-2,3,3-trimethyl-butan-2-ol (Example 19, step 3).

Step 5: (5RS)-5-tert-Butyl-3-(5-iodo-pyridin-2-yl)-5-methyl-oxazolidin-2-one

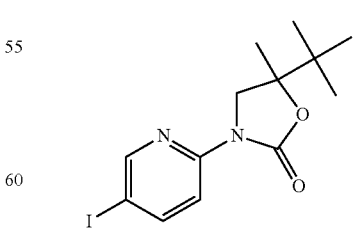

The title compound was obtained as a yellow oil, MS: m/e=361.1 (M+H⁺), using chemistry similar to that described in Example 1, step 2 from (RS)-1-(5-iodo-pyridin-2-ylamino)-2,3,3-trimethyl-butan-2-ol (Example 19, step 4).

Step 6: (5RS)-5-tert-Butyl-5-methyl-3-(5-phenyl-ethynyl-pyridin-2-yl)-oxazolidin-2-one

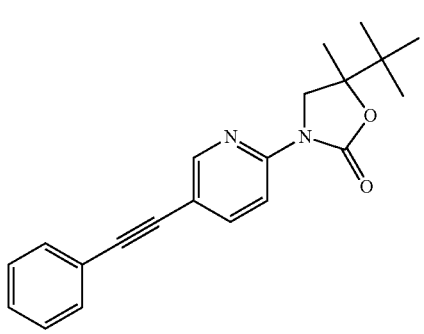 [SMILES: CC(C)(C)C1(C)CN(c2ccc(C#Cc3ccccc3)cn2)C(=O)O1]

The title compound was obtained as a light brown solid, MS: m/e=335.2 (M+H⁺), using chemistry similar to that described in Example 1, step 3 from (5RS)-5-tert-butyl-3-(5-iodo-pyridin-2-yl)-5-methyl-oxazolidin-2-one (Example 19, step 5) and phenylacetylene.

Example 20

5,5-Dimethyl-3-(5-phenylethynyl-pyridin-2-yl)-[1,3]oxazinan-2-one

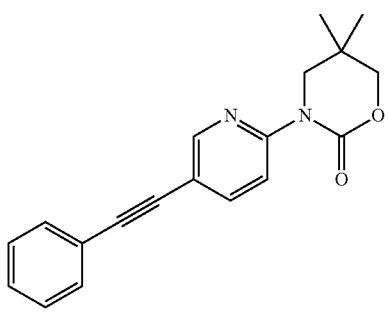

Step 1: 3-(5-Iodo-pyridin-2-yl)-5,5-dimethyl-[1,3]oxazinan-2-one

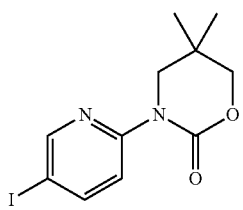 [SMILES: CC1(C)COC(=O)N(c2ccc(I)cn2)C1]

The title compound was obtained as a colorless oil, MS: m/e=333.1 (M+H⁺), using procedures similar to those described in Example 1, step 1 and step 2 from 2-fluoro-5-iodopyridine and 3-amino-2,2-dimethylpropan-1-ol.

Step 2: 5,5-Dimethyl-3-(5-phenylethynyl-pyridin-2-yl)-[1,3]oxazinan-2-one

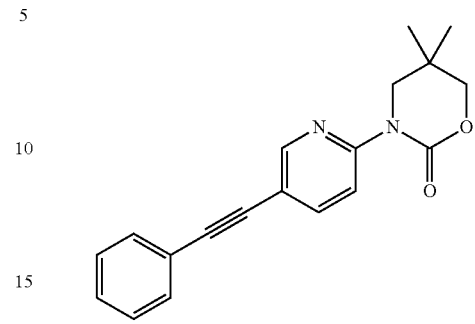

The title compound was obtained as a light brown oil, MS: m/e=307.3 (M+H⁺), using chemistry similar to that described in Example 1, step 3 from 3-(5-iodo-pyridin-2-yl)-5,5-dimethyl-[1,3]oxazinan-2-one (Example 20, step 1) and phenylacetylene.

Example 21

1-(3-Fluoro-5-phenylethynyl-pyridin-2-yl)-4,4-dimethyl-pyrrolidin-2-one

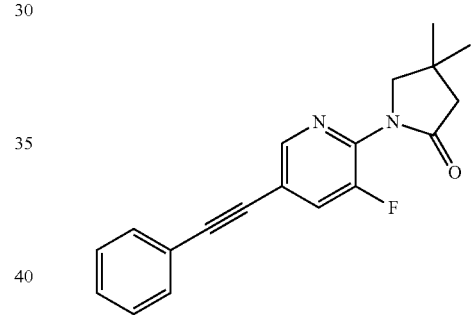

The title compound was obtained as a orange solid, MS: m/e=309.2 (M+H⁺), using procedures similar to those described in Example 13 by using 2-amino-3-fluoro-5-iodopyridine instead of 5-iodopyridin-2-amine.

Example 22

(3aRS,6aSR)-3-(5-Phenylethynyl-pyridin-2-yl)-hexahydro-cyclopentaoxazol-2-one

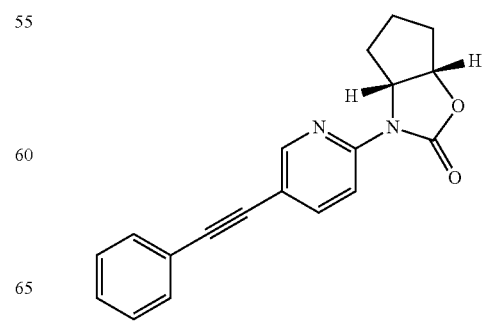

Step 1: (3aRS,6aSR)-3-(5-Iodo-pyridin-2-yl)-hexahydro-cyclopentaoxazol-2-one

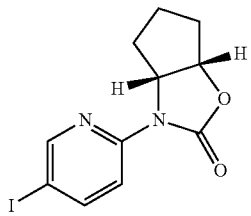 [SMILES: O=C1O[C@H]2CCC[C@H]2N1c1ccc(I)cn1]

The title compound was obtained as a light brown solid, MS: m/e=331.1 (M+H⁺), using procedures similar to those described in Example 1, step 1 and step 2 from 2-fluoro-5-iodopyridine and (1SR,2RS)-2-aminocyclopentanol hydrochloride.

Step 2: (3aRS,6aSR)-3-(5-Phenylethynyl-pyridin-2-yl)-hexahydro-cyclopentaoxazol-2-one

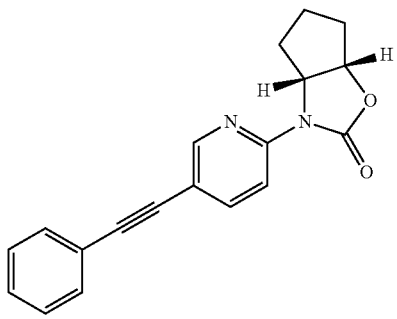 [SMILES: O=C1O[C@H]2CCC[C@H]2N1c1ccc(C#Cc2ccccc2)cn1]

The title compound was obtained as a light yellow solid, MS: m/e=305.2 (M+H⁺), using chemistry similar to that described in Example 1, step 3 from (3aRS,6aSR)-3-(5-iodo-pyridin-2-yl)-hexahydro-cyclopentaoxazol-2-one (Example 13, step 1) and phenylacetylene.

Example 23

(3aRS,6aSR)-3-(5-Pyridin-3-ylethynyl-pyridin-2-yl)-hexahydro-cyclopentaoxazol-2-one

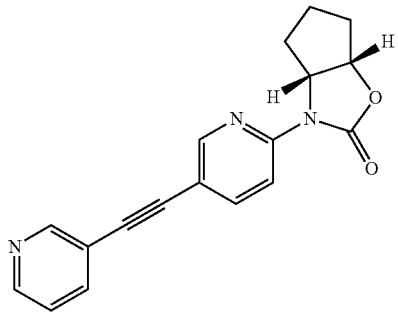 [SMILES: O=C1O[C@H]2CCC[C@H]2N1c1ccc(C#Cc2cccnc2)cn1]

The title compound was obtained as a colorless oil, MS: m/e=306.2 (M+H⁺), using chemistry similar to that described in Example 1, step 3 from (3aRS,6aSR)-3-(5-iodo-pyridin-2-yl)-hexahydro-cyclopentaoxazol-2-one (Example 13, step 1) and 3-ethynyl-pyridine.

Example 24

(3aRS,6aSR)-3-[5-(5-Fluoro-pyridin-3-ylethynyl)-pyridin-2-yl]-hexahydro-cyclopentaoxazol-2-one

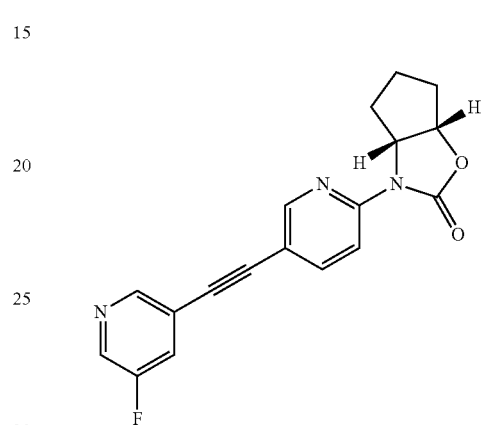

The title compound was obtained as a light brown solid, MS: m/e=324.2 (M+H⁺), using chemistry similar to that described in Example 1, step 3 from (3aRS,6aSR)-3-(5-iodo-pyridin-2-yl)-hexahydro-cyclopentaoxazol-2-one (Example 13, step 1) and 3-ethynyl-5-fluoro-pyridine (CAS 872122-54-8).

Example 25

5,5-Dimethyl-1-(5-phenylethynyl-pyridin-2-yl)-tetrahydro-pyrimidin-2-one

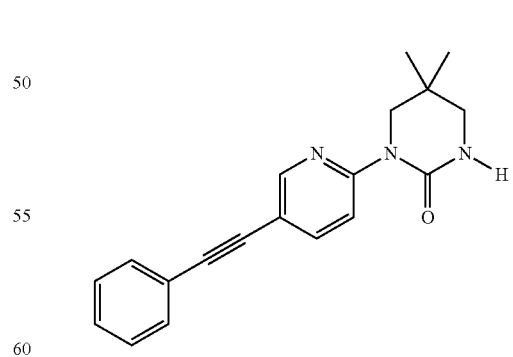

The title compound was obtained as a light brown solid, MS: m/e=306.2 (M+H⁺), using procedures similar to those described in Example 15 starting from 2-fluoro-5-iodopyridine and by using 2,2-dimethylpropane-1,3-diamine instead of 2-methylpropane-1,2-diamine.

Example 26

1,5,5-Trimethyl-3-(5-phenylethynyl-pyridin-2-yl)-tetrahydro-pyrimidin-2-one

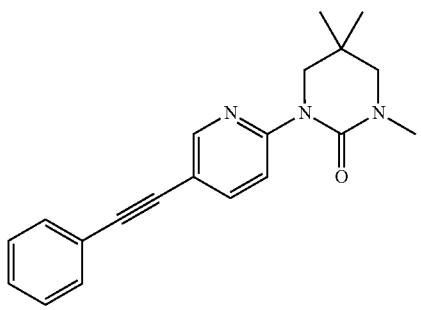 [SMILES: CN1CC(C)(C)CN(c2ccc(C#Cc3ccccc3)cn2)C1=O]

The title compound was obtained as a light brown solid, MS: m/e=306.2 (M+H⁺), using procedures similar to those described in Example 16 from 5,5-dimethyl-1-(5-phenyl-ethynyl-pyridin-2-yl)-tetrahydro-pyrimidin-2-one (Example 25) and iodomethane.

Example 27

(RS)-4,5,5-Trimethyl-3-(5-phenylethynyl-pyridin-2-yl)-oxazolidin-2-one

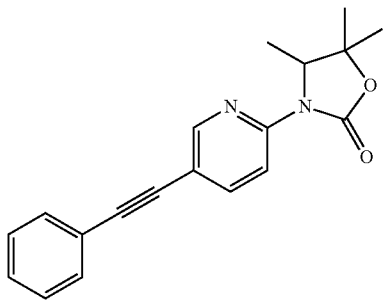 [SMILES: CC1N(c2ccc(C#Cc3ccccc3)cn2)C(=O)OC1(C)C]

The title compound was obtained as a yellow solid, MS: m/e=307.2 (M+H⁺), using procedures similar to those described in Example 1 from 2-fluoro-5-iodopyridine and by using (RS)-3-amino-2-methyl-butan-2-ol (CAS 6291-17-4) instead of 1-amino-2-methylpropan-2-ol.

Example 28

4,4,5,5-Tetramethyl-3-(5-phenylethynyl-pyridin-2-yl)-oxazolidin-2-one

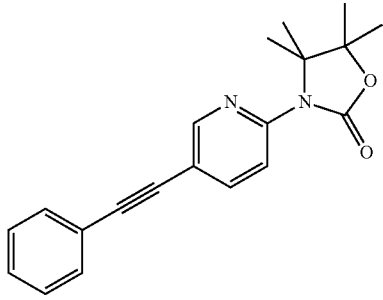 [SMILES: CC1(C)OC(=O)N(c2ccc(C#Cc3ccccc3)cn2)C1(C)C]

The title compound was obtained as a light yellow solid, MS: m/e=321.2 (M+H⁺), using procedures similar to those described in Example 1 from 2-fluoro-5-iodopyridine and by using 3-amino-2,3-dimethyl-butan-2-ol (CAS 89585-13-7) instead of 1-amino-2-methylpropan-2-ol.

Example 29

3-[5-(5-Fluoro-pyridin-3-ylethynyl)-pyridin-2-yl]-5,5-dimethyl-oxazolidin-2-one

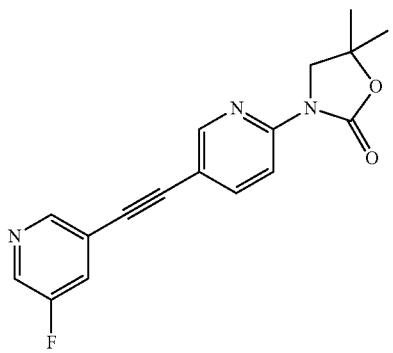 [SMILES: CC1(C)CN(c2ccc(C#Cc3cncc(F)c3)cn2)C(=O)O1]

Step 1: 5,5-Dimethyl-3-(5-trimethylsilanylethynyl-pyridin-2-yl)-oxazolidin-2-one

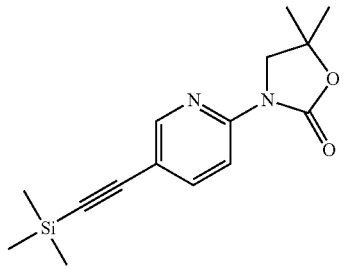 [SMILES: CC1(C)CN(c2ccc(C#C[Si](C)(C)C)cn2)C(=O)O1]

The title compound was obtained as a brown solid, MS: m/e=289.0 (M+H⁺), using chemistry similar to that described in Example 1, step 3 from 3-(5-iodo-pyridin-2-yl)-5,5-dimethyl-oxazolidin-2-one (Example 5, step 1) and ethynyltrimethylsilane.

Step 2: 3-[5-(5-Fluoro-pyridin-3-ylethynyl)-pyridin-2-yl]-5,5-dimethyl-oxazolidin-2-one

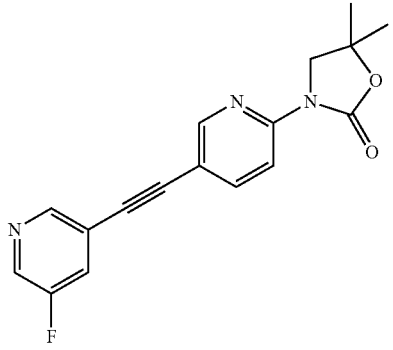 [SMILES: CC1(C)CN(c2ccc(C#Cc3cncc(F)c3)cn2)C(=O)O1]

5,5-Dimethyl-3-(5-trimethylsilanylethynyl-pyridin-2-yl)-oxazolidin-2-one (Example 29, step 1) (100 mg, 0.35 mmol)

was dissolved in THF (3 ml). 3-Fluoro-5-iodopyridine (100 mg, 0.45 mmol, 1.3 equiv.), Et$_3$N (145 µl, 1.04 mmol, 3 equiv.), Bis-(triphenylphosphine)-palladium(II)dichloride (10 mg, 14 µmol, 0.05 equiv.), triphenylphosphine (11 mg, 17 µmol, 0.05 equiv.), triphenylphosphine (3 mg, 10 µmol, 0.03 equiv.) and copper(I)iodide (1 mg, 3.5 µmol, 0.01 equiv.) were added under nitrogen and the mixture was heated to 60° C. TBAF 1M in THF (520 µl, 0.52 mmol, 1.5 equiv.) was added dropwise in 20 minutes at 60° C. The reaction mixture was stirred for 3 hours at 60° C. Sat. NaHCO$_3$ solution was added and the mixture was extracted with dichloromethane. The organic extracts were dried with sodium sulfate, filtered and evaporated. The crude product was purified by flash chromatography on silica gel (dichloromethane/methanol gradient 100:0 to 90:10). The desired 3-[5-(5-fluoro-pyridin-3-ylethynyl)-pyridin-2-yl]-5,5-dimethyl-oxazolidin-2-one was obtained as a white solid (55 mg, 51% yield), MS: m/e=312.3 (M+H$^+$).

Example 30

5,5-Dimethyl-3-(5-pyrimidin-5-ylethynyl-pyridin-2-yl)-oxazolidin-2-one

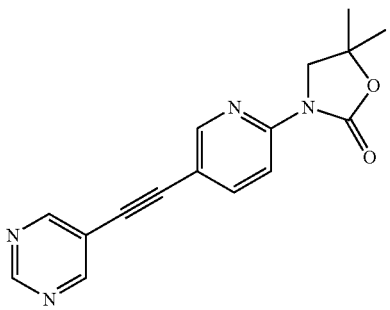

The title compound was obtained as a light yellow solid, MS: m/e=295.2 (M+H$^+$), using chemistry similar to that described in Example 29, step 2 from 5,5-dimethyl-3-(5-trimethylsilanylethynyl-pyridin-2-yl)-oxazolidin-2-one (Example 29, step 1) and 5-bromopyrimidine.

Example 31

5,5-Dimethyl-3-[5-(1-methyl-1H-pyrazol-4-ylethynyl)-pyridin-2-yl]-oxazolidin-2-one

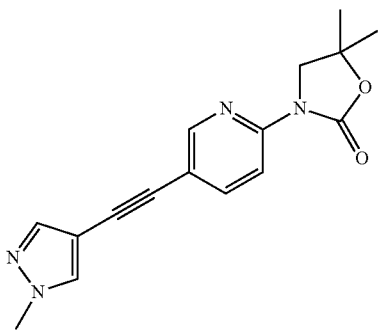 [SMILES: Cn1cc(C#Cc2ccc(N3CC(C)(C)OC3=O)nc2)cn1]

The title compound was obtained as a light yellow solid, MS: m/e=297.2 (M+H$^+$), using chemistry similar to that described in Example 29, step 2 from 5,5-dimethyl-3-(5-trimethylsilanylethynyl-pyridin-2-yl)-oxazolidin-2-one (Example 29, step 1) and 4-iodo-1-methyl-1H-pyrazole.

Example 32

3-[5-(4-Fluoro-phenylethynyl)-pyridin-2-yl]-5,5-dimethyl-oxazolidin-2-one

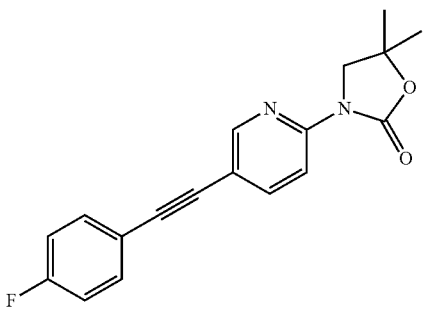

The title compound was obtained as a yellow solid, MS: m/e=311.2 (M+H$^+$), using chemistry similar to that described in Example 1, step 3 from 3-(5-iodo-pyridin-2-yl)-5,5-dimethyl-oxazolidin-2-one (Example 5, step 1) and 1-ethynyl-4-fluoro-benzene.

Example 33

3-[5-(3,4-Difluoro-phenylethynyl)-pyridin-2-yl]-5,5-dimethyl-oxazolidin-2-one

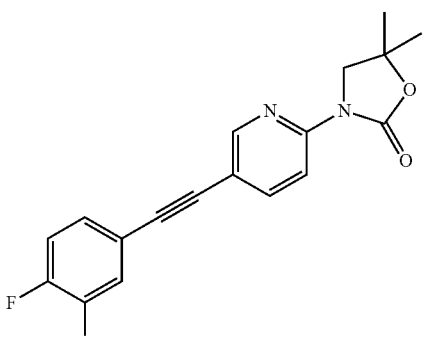

The title compound was obtained as a white solid, MS: m/e=329.2 (M+H$^+$), using chemistry similar to that described in Example 29, step 2 from 5,5-dimethyl-3-(5-trimethylsilanylethynyl-pyridin-2-yl)-oxazolidin-2-one (Example 29, step 1) and 1,2-difluoro-4-iodobenzene.

Example 34

3-[5-(2,5-Difluoro-phenylethynyl)-pyridin-2-yl]-5,5-dimethyl-oxazolidin-2-one

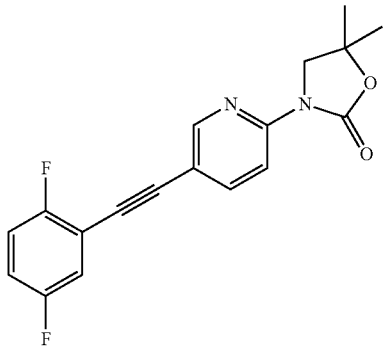 [SMILES: CC1(C)CN(c2ccc(C#Cc3cc(F)ccc3F)cn2)C(=O)O1]

The title compound was obtained as a white solid, MS: m/e=329.2 (M+H$^+$), using chemistry similar to that described in Example 29, step 2 from 5,5-dimethyl-3-(5-trimethylsilanylethynyl-pyridin-2-yl)-oxazolidin-2-one (Example 29, step 1) and 1,4-difluoro-2-iodobenzene.

Example 35

3-[5-(6-Fluoro-pyridin-3-ylethynyl)-pyridin-2-yl]-5,5-dimethyl-oxazolidin-2-one

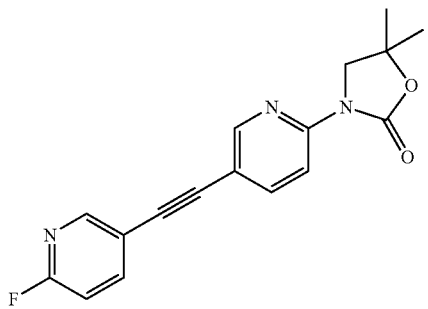

The title compound was obtained as a white solid, MS: m/e=312.2 (M+H$^+$), using chemistry similar to that described in Example 29, step 2 from 5,5-dimethyl-3-(5-trimethylsilanylethynyl-pyridin-2-yl)-oxazolidin-2-one (Example 29, step 1) and 2-fluoro-5-iodopyridine.

Example 36

6-(5-Pyridin-3-ylethynyl-pyridin-2-yl)-4-oxa-6-aza-spiro[2.4]heptan-5-one

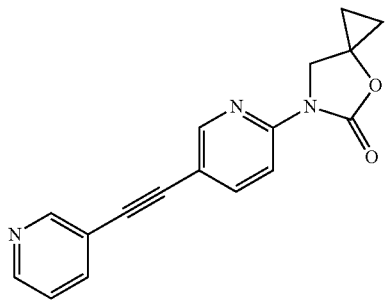 [SMILES: O=C1OC2(CC2)CN1c1ccc(C#Cc2cccnc2)cn1]

The title compound was obtained as a white solid, MS: m/e=292.2 (M+H$^+$), using procedures similar to those described in Example 1 starting from 2-fluoro-5-bromopyridine, 1-aminomethyl-cyclopropanol (*Russian J. Org. Chem.* 2001, 37, 1238) and 3-ethynyl-pyridine.

Example 37

1-[5-(5-Fluoro-pyridin-3-ylethynyl)-pyridin-2-yl]-4,4-dimethyl-pyrrolidin-2-one

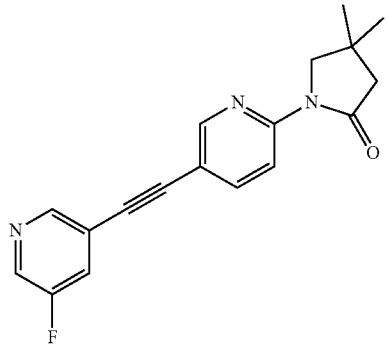 [SMILES: CC1(C)CC(=O)N(c2ccc(C#Cc3cncc(F)c3)cn2)C1]

Step 1: 2-Bromo-5-trimethylsilanylethynyl-pyridine

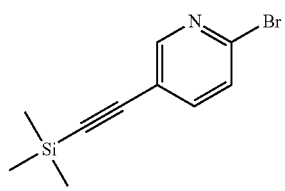

2-Bromo-5-iodopyridine (2.5 g, 8.8 mmol) was dissolved under nitrogen in 50 ml THF. Bis-(triphenylphosphine)-palladium(II)dichloride (618 mg, 880 µmol, 0.1 equiv.), ethynyl-trimethylsilane (950 mg, 1.34 ml, 9.6 mmol, 1.1 equiv.), triethylamine (1.78 g, 2.44 ml, 17.6 mmol, 3 equiv.) and copper(I)iodide (84 mg, 440 µmol, 0.05 equiv.) were added and the mixture was stirred for 3 hours at 50° C. The reaction mixture was cooled and evaporated to dryness. The crude product was purified by flash chromatography on silica gel, eluting with an ethyl acetate:heptane gradient 0:100 to 15:85. The desired 2-bromo-5-trimethylsilanylethynyl-pyridine (1.95 g, 7.7 mmol, 87% yield) was obtained as a white solid, MS: m/e=254.1/256.1 (M+H$^+$).

Step 2: 4,4-Dimethyl-1-(5-trimethylsilanylethynyl-pyridin-2-yl)-pyrrolidin-2-one

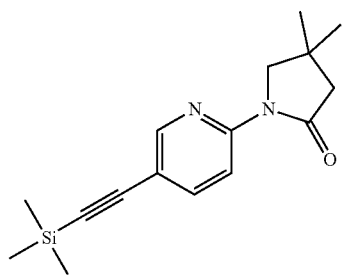

(260 mg, 1.0 mmol) 2-Bromo-5-trimethylsilanylethynyl-pyridine (Example 37, step 1) was dissolved in toluene (2 ml) and 4,4-dimethylpyrrolidin-2-one (115 mg, 1.0 mmol, 1.0 equiv.), cesium carbonate (660 mg, 2.05 mmol, 2.0 equiv.), xantphos (CAS 161265-03-8) (24 mg, 0.04 mmol, 0.04 equiv.) and Pd$_2$(dba)$_3$ (19 mg, 0.02 mmol, 0.02 equiv.) were added under nitrogen. The mixture was stirred for 1 hour at 90° C. The crude product was purified by flash chromatography by directly loading the toluene mixture onto a silica gel column and eluting with an ethyl acetate:heptane gradient 0:100 to 40:60. The desired 4,4-dimethyl-1-(5-trimethylsilanylethynyl-pyridin-2-yl)-pyrrolidin-2-one (230 mg, 0.81 mmol, 75% yield) was obtained as a yellow solid, MS: m/e=287.1 (M+H$^+$).

Step 3: 1-[5-(5-Fluoro-pyridin-3-ylethynyl)-pyridin-2-yl]-4,4-dimethyl-pyrrolidin-2-one

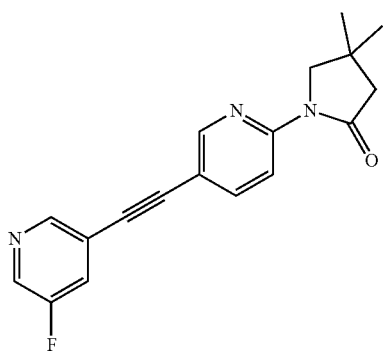 [SMILES: CC1(C)CC(=O)N(c2ccc(C#Cc3cncc(F)c3)cn2)C1]

4,4-Dimethyl-1-(5-trimethylsilanylethynyl-pyridin-2-yl)-pyrrolidin-2-one (Example 37, step 2) (80 mg, 0.28 mmol) was dissolved in DMF (1 ml). 3-Fluoro-5-iodopyridine (87 mg, 0.39 mmol, 1.4 equiv.), Et$_3$N (85 mg, 117 µl, 0.84 mmol, 3 equiv.), Bis-(triphenylphosphine)-palladium(II)dichloride (10 mg, 14 µmol, 0.05 equiv.), triphenylphosphine (2 mg, 8.4 µmol, 0.03 equiv.) and copper(I)iodide (2 mg, 8.4 µmol, 0.03 equiv.) were added under nitrogen and the mixture was heated to 70° C. TBAF 1M in THF (300 µl, 0.3 mmol, 1.1 equiv.) was added dropwise in 20 minutes at 70° C. The reaction mixture was stirred for 30 minutes at 70° C. and evaporated with isolute to dryness. The crude product was purified by flash chromatography with a 20 g silica gel column and eluting with heptane:ethyl acetate 100:0->0:100. The desired 1-[5-(5-fluoro-pyridin-3-ylethynyl)-pyridin-2-yl]-4,4-dimethyl-pyrrolidin-2-one (36 mg, 42% yield) was obtained as a white solid, MS: m/e=310.2 (M+H$^+$).

Example 38

4,4-Dimethyl-1-(5-pyridin-3-ylethynyl-pyridin-2-yl)-pyrrolidin-2-one

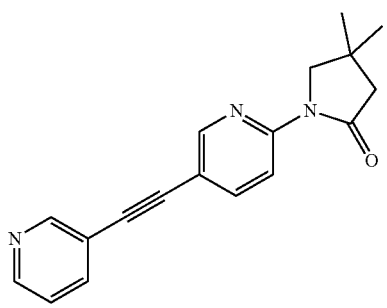 [SMILES: CC1(C)CC(=O)N(c2ccc(C#Cc3cccnc3)cn2)C1]

The title compound was obtained as a white solid, MS: m/e=292.1 (M+H$^+$), using chemistry similar to that described in Example 37, step 3 from 4,4-dimethyl-1-(5-trimethylsilanylethynyl-pyridin-2-yl)-pyrrolidin-2-one (Example 37, step 2) and 3-iodopyridine.

Example 39

1-[5-(5-Chloro-pyridin-3-ylethynyl)-pyridin-2-yl]-4,4-dimethyl-pyrrolidin-2-one

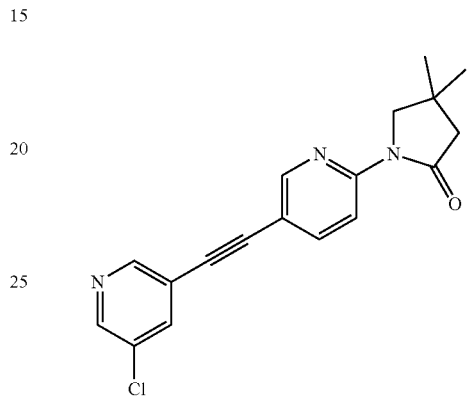

The title compound was obtained as a white solid, MS: m/e=326.2/328.2 (M+H$^+$), using chemistry similar to that described in Example 37, step 3 from 4,4-dimethyl-1-(5-trimethylsilanylethynyl-pyridin-2-yl)-pyrrolidin-2-one (Example 37, step 2) and 3-chloro-5-iodopyridine.

Example 40

1-[5-(3-Fluoro-phenylethynyl)-pyridin-2-yl]-4,4-dimethyl-pyrrolidin-2-one

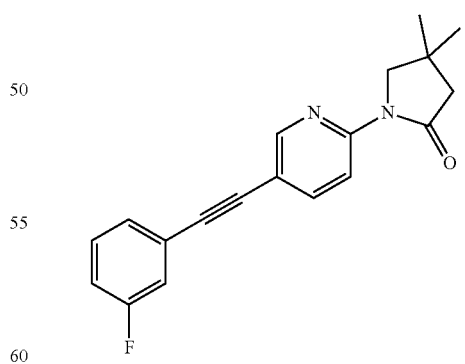

The title compound was obtained as a white solid, MS: m/e=309.2 (M+H$^+$), using chemistry similar to that described in Example 37, step 3 from 4,4-dimethyl-1-(5-trimethylsilanylethynyl-pyridin-2-yl)-pyrrolidin-2-one (Example 37, step 2) and 1-fluoro-3-iodobenzene.

Example 41

4,4-Dimethyl-1-(3-methyl-5-phenylethynyl-pyridin-2-yl)-pyrrolidin-2-one

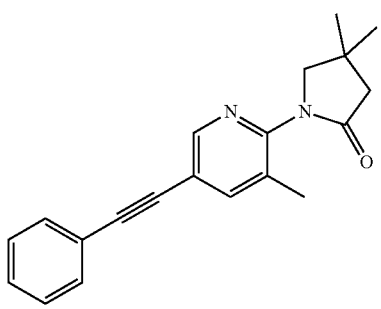 [SMILES: Cc1cc(C#Cc2ccccc2)cnc1N1CC(C)(C)CC1=O]

Step 1: 2-Bromo-3-methyl-5-trimethylsilanylethynyl-pyridine

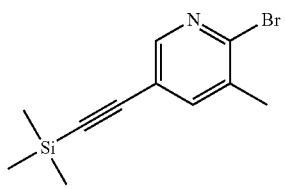

The title compound was obtained as a yellow oil, MS: m/e=268.1/270.1 (M+H$^+$), using chemistry similar to that described in Example 37, step 1 by using 2-bromo-5-iodo-3-methylpyridine instead of 2-bromo-5-iodopyridine.

Step 2: 4,4-Dimethyl-1-(3-methyl-5-trimethylsilanylethynyl-pyridin-2-yl)-pyrrolidin-2-one

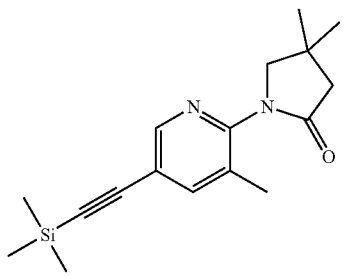

The title compound was obtained as a brown solid, MS: m/e=301.3 (M+H$^+$), using chemistry similar to that described in Example 37, step 2 from 2-bromo-3-methyl-5-trimethylsilanylethynyl-pyridine (Example 41, step 1) and 4,4-dimethylpyrrolidin-2-one.

Step 3: 4,4-Dimethyl-1-(3-methyl-5-phenylethynyl-pyridin-2-yl)-pyrrolidin-2-one

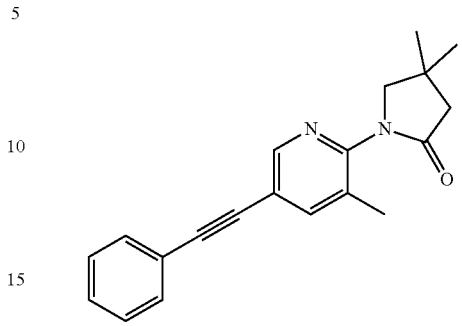

The title compound was obtained as a white solid, MS: m/e=305.3 (M+H$^+$), using chemistry similar to that described in Example 37, step 3 from 4,4-dimethyl-1-(3-methyl-5-trimethylsilanylethynyl-pyridin-2-yl)-pyrrolidin-2-one (Example 41, step 2) and iodobenzene.

Example 42

5,5-Dimethyl-5'-phenylethynyl-3,4,5,6-tetrahydro-[1,2']bipyridinyl-2-one

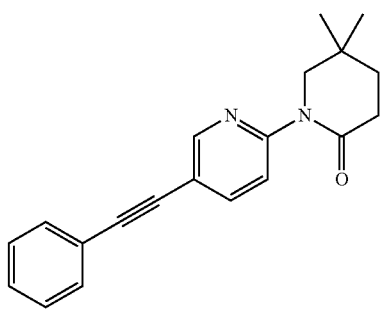 [SMILES: CC1(C)CCC(=O)N(c2ccc(C#Cc3ccccc3)cn2)C1]

Step 1: 5,5-Dimethyl-5'-trimethylsilanylethynyl-3,4,5,6-tetrahydro-[1,2']bipyridinyl-2-one

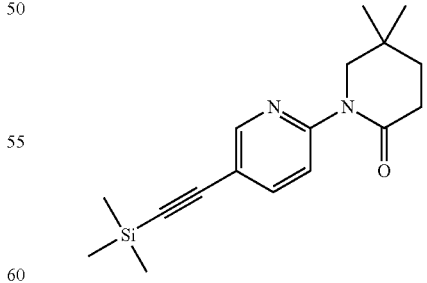

The title compound was obtained as a yellow solid, MS: m/e=301.3 (M+H$^+$), using chemistry similar to that described in Example 37, step 2 from 2-bromo-5-trimethylsilanylethynyl-pyridine (Example 37, step 1) and by using 5,5-dimethyl-piperidin-2-one (CAS 4007-79-8) instead of 4,4-dimethylpyrrolidin-2-one.

Step 2: 5,5-Dimethyl-5'-phenylethynyl-3,4,5,6-tetrahydro-[1,2']bipyridinyl-2-one

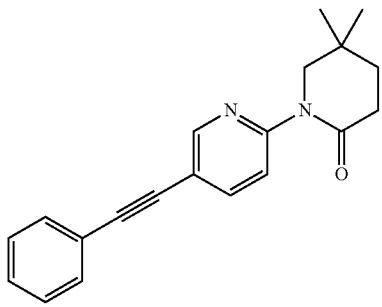 [SMILES: CC1(C)CCC(=O)N(c2ccc(C#Cc3ccccc3)cn2)C1]

The title compound was obtained as a yellow oil, MS: m/e=305.2 (M+H$^+$), using chemistry similar to that described in Example 37, step 3 from 5,5-dimethyl-5'-trimethylsilanyl-ethynyl-3,4,5,6-tetrahydro-[1,2']bipyridinyl-2-one (Example 42, step 1) and iodobenzene.

Example 43

5'-(3-Fluoro-phenylethynyl)-5,5-dimethyl-3,4,5,6-tetrahydro-[1,2']bipyridinyl-2-one

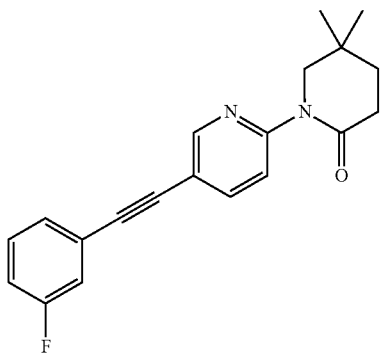 [SMILES: CC1(C)CCC(=O)N(c2ccc(C#Cc3cccc(F)c3)cn2)C1]

The title compound was obtained as a yellow oil, MS: m/e=323.2 (M+H$^+$), using chemistry similar to that described in Example 37, step 3 from 5,5-dimethyl-5'-trimethylsilanyl-ethynyl-3,4,5,6-tetrahydro-[1,2']bipyridinyl-2-one (Example 42, step 1) and 1-fluoro-3-iodobenzene.

Example 44

1-Methyl-3-(5-phenylethynyl-pyridin-2-yl)-1,3-diaza-spiro[4.4]nonan-2-one

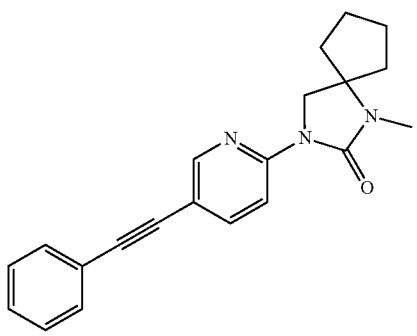 [SMILES: CN1C(=O)N(c2ccc(C#Cc3ccccc3)cn2)CC12CCCC2]

Step 1: {1-[(5-Iodo-pyridin-2-ylamino)-methyl]-cyclopentyl}-carbamic acid tert-butyl ester

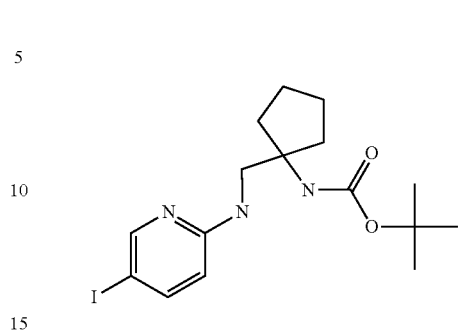

The title compound was obtained as a white solid, MS: m/e=418.2 (M+H$^+$), using chemistry similar to that described in Example 1, step 1 from 2-fluoro-5-iodopyridine and tert-butyl 1-(aminomethyl)cyclopentylcarbamate (CAS 889949-09-1) by using neat pyridine as solvent instead of NMP.

Step 2: (1-Amino-cyclopentylmethyl)-(5-iodo-pyridin-2-yl)-amine hydrochloride

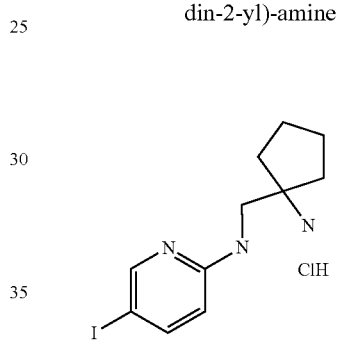

The BOC protecting group is removed by reacting {1-[(5-iodo-pyridin-2-ylamino)-methyl]-cyclopentyl}-carbamic acid tert-butyl ester (Example 44, step 1) with 4N HCl in dioxane for 1 hour at room temperature. The title compound was obtained by filtration of the hydrochloride salt as a light yellow solid, MS: m/e=318.1 (M+H$^+$).

Step 3: 3-(5-Iodo-pyridin-2-yl)-1,3-diaza-spiro[4.4]nonan-2-one

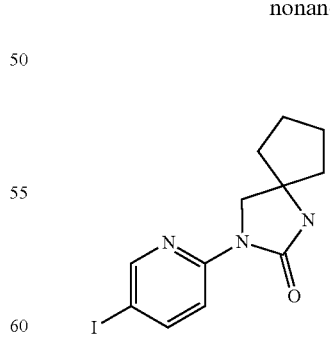

The title compound was obtained as a white solid, MS: m/e=344.1 (M+H$^+$), using chemistry similar to that described in Example 1, step 2 from (1-amino-cyclopentylmethyl)-(5-iodo-pyridin-2-yl)-amine hydrochloride (Example 44, step 2).

Step 4: 3-(5-Phenylethynyl-pyridin-2-yl)-1,3-diaza-spiro[4.4]nonan-2-one

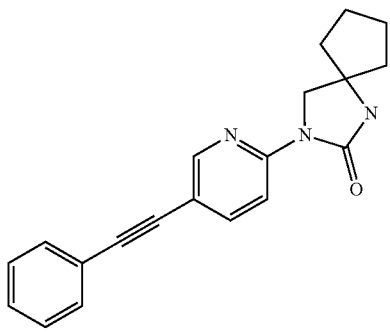 [SMILES: O=C1NC2(CCCC2)CN1c1ccc(C#Cc2ccccc2)cn1]

The title compound was obtained as a light yellow solid, MS: m/e=318.2 (M+H⁺), using chemistry similar to that described in Example 1, step 3 from 3-(5-iodo-pyridin-2-yl)-1,3-diaza-spiro[4.4]nonan-2-one (Example 44, step 3) and phenylacetylene.

Step 5: 1-Methyl-3-(5-phenylethynyl-pyridin-2-yl)-1,3-diaza-spiro[4.4]nonan-2-one

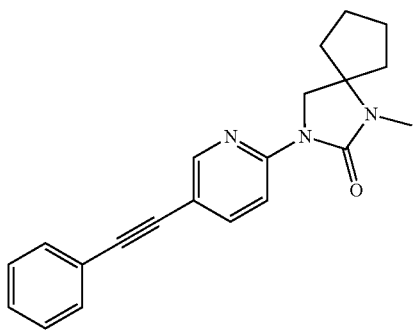 [SMILES: CN1C(=O)N(c2ccc(C#Cc3ccccc3)cn2)CC12CCCC2]

The title compound was obtained as a light yellow oil, MS: m/e=332.2 (M+H⁺), using chemistry similar to that described in Example 16 from 3-(5-phenylethynyl-pyridin-2-yl)-1,3-diaza-spiro[4.4]nonan-2-one (Example 44, step 4) and iodomethane.

Example 45

(RS)-4-Cyclopentyl-3-methyl-1-(5-phenylethynyl-pyridin-2-yl)-imidazolidin-2-one

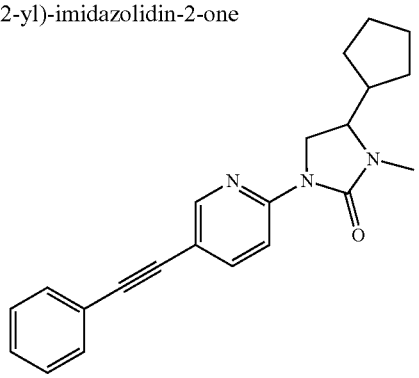

The title compound was obtained as a light yellow solid, MS: m/e=346.2 (M+H⁺), using procedures similar to those described in Example 44 from 2-fluoro-5-iodopyridine and by using (RS)-tert-butyl 2-amino-1-cyclopentylethylcarbamate (CAS 936497-76-6) instead of tert-butyl 1-(aminomethyl)cyclopentylcarbamate.

Example 46

(1RS,5SR)-6-(5-Phenylethynyl-pyridin-2-yl)-6-aza-bicyclo[3.2.0]heptan-7-one

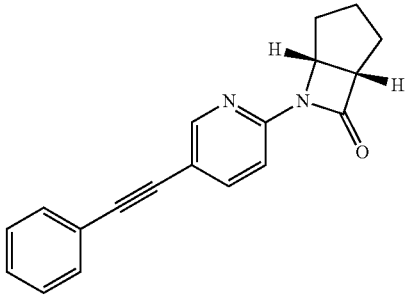 [SMILES: O=C1[C@H]2CCC[C@H]2N1c1ccc(C#Cc2ccccc2)cn1]

Step 1: (1RS,5SR)-6-(5-Bromo-pyridin-2-yl)-6-aza-bicyclo[3.2.0]heptan-7-one

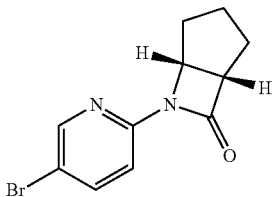 [SMILES: O=C1[C@H]2CCC[C@H]2N1c1ccc(Br)cn1]

The title compound was obtained as a white solid, MS: m/e=268.2 (M+H⁺), using chemistry similar to that described in Example 37, step 2 from 2,5-dibromopyridine and (1RS,5SR)-6-aza-bicyclo[3.2.0]heptan-7-one (CAS 22031-52-3).

Step 2: (1RS,5SR)-6-(5-Phenylethynyl-pyridin-2-yl)-6-aza-bicyclo[3.2.0]heptan-7-one

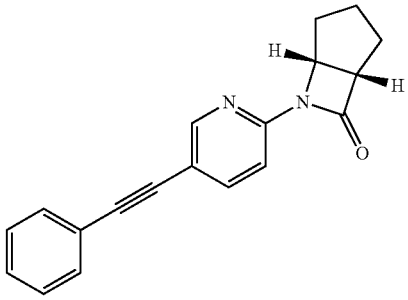 [SMILES: O=C1[C@H]2CCC[C@H]2N1c1ccc(C#Cc2ccccc2)cn1]

The title compound was obtained as a brown solid, MS: m/e=289.2 (M+H⁺), using chemistry similar to that described in Example 1, step 3 from (1RS,5SR)-6-(5-bromo-pyridin-2-yl)-6-aza-bicyclo[3.2.0]heptan-7-one (Example 46, step 1) with phenylacetylene.

Example 47

(6SR,7RS)-3-(5-Phenylethynyl-pyridin-2-yl)-hexahydro-benzooxazol-2-one

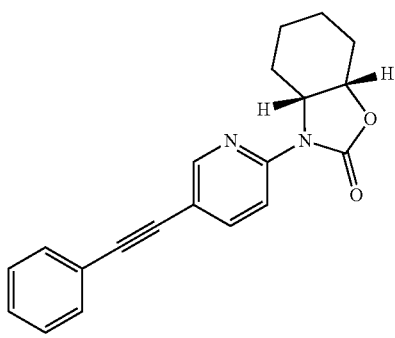 [SMILES: O=C1O[C@H]2CCCC[C@H]2N1c1ccc(C#Cc2ccccc2)cn1]

The title compound was obtained as a yellow solid, MS: m/e=319.2 (M+H⁺), using procedures similar to those described in Example 1 starting from 2-fluoro-5-bromopyridine, (5SR,6RS)-2-amino-cyclohexanol hydrochloride (CAS 190792-72-4) and phenylacetylene.

Example 48

3,4,4-Trimethyl-1-(5-pyridin-3-ylethynyl-pyridin-2-yl)-imidazolidin-2-one

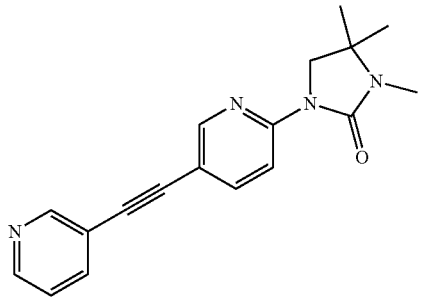 [SMILES: CN1C(=O)N(c2ccc(C#Cc3cccnc3)cn2)CC1(C)C]

Step 1: 1-(5-Iodo-pyridin-2-yl)-3,4,4-trimethyl-imidazolidin-2-one

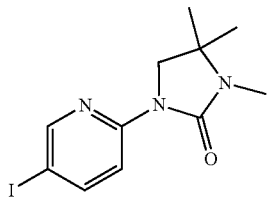 [SMILES: CN1C(=O)N(c2ccc(I)cn2)CC1(C)C]

The title compound was obtained as a light yellow solid, MS: m/e=332.1 (M+H⁺), using chemistry similar to that described in Example 16 from 1-(5-iodo-pyridin-2-yl)-4,4-dimethyl-imidazolidin-2-one (Example 15, step 2) and iodomethane.

Step 2: 3,4,4-Trimethyl-1-(5-pyridin-3-ylethynyl-pyridin-2-yl)-imidazolidin-2-one

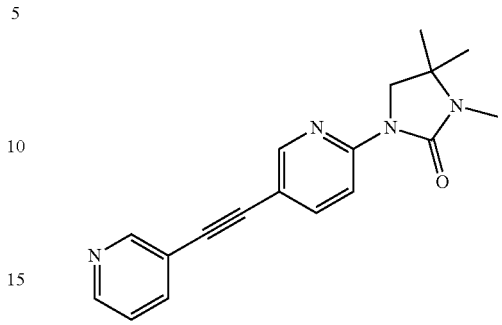

The title compound was obtained as a white solid, MS: m/e=307.3 (M+H⁺), using chemistry similar to that described in Example 1, step 3 from 1-(5-iodo-pyridin-2-yl)-3,4,4-trimethyl-imidazolidin-2-one (Example 48, step 1) and 3-ethynyl-pyridine.

Example 49

1-[5-(5-Fluoro-pyridin-3-ylethynyl)-pyridin-2-yl]-3,4,4-trimethyl-imidazolidin-2-one

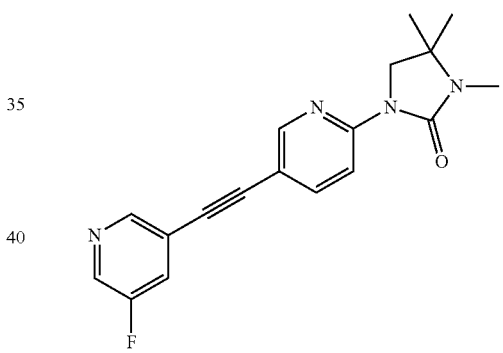

Step 1: 3,4,4-Trimethyl-1-(5-trimethylsilanylethynyl-pyridin-2-yl)-imidazolidin-2-one

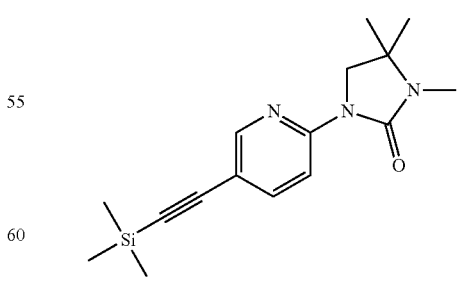

The title compound was obtained as a yellow solid, MS: m/e=302.3 (M+H⁺), using chemistry similar to that described in Example 37, step 1 from 1-(5-iodo-pyridin-2-yl)-3,4,4-trimethyl-imidazolidin-2-one (Example 48, step 1) and ethynyltrimethylsilane.

Step 2: 1-[5-(5-Fluoro-pyridin-3-ylethynyl)-pyridin-2-yl]-3,4,4-trimethyl-imidazolidin-2-one

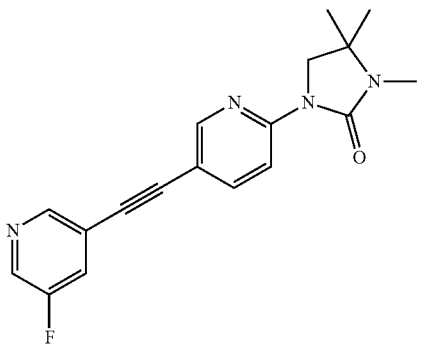 [SMILES: CN1C(=O)N(c2ccc(C#Cc3cncc(F)c3)cn2)CC1(C)C]

The title compound was obtained as a light yellow solid, MS: m/e=325.4 (M+H⁺), using chemistry similar to that described in Example 37, step 3 from 3,4,4-trimethyl-1-(5-trimethylsilanylethynyl-pyridin-2-yl)-imidazolidin-2-one (Example 49, step 1) and 3-fluoro-5-iodopyridine.

Example 50

3,4,4-Trimethyl-1-[5-(1-methyl-1H-pyrazol-4-yl-ethynyl)-pyridin-2-yl]-imidazolidin-2-one

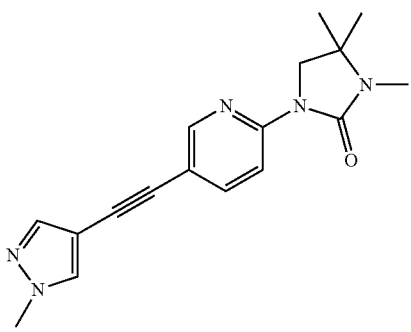 [SMILES: CN1C(=O)N(c2ccc(C#Cc3cnn(C)c3)cn2)CC1(C)C]

The title compound was obtained as a light yellow solid, MS: m/e=310.3 (M+H⁺), using chemistry similar to that described in Example 37, step 3 from 3,4,4-trimethyl-1-(5-trimethylsilanylethynyl-pyridin-2-yl)-imidazolidin-2-one (Example 49, step 1) and 4-iodo-1-methyl-1H-pyrazole.

Example 51

1-[5-(5-Chloro-pyridin-3-ylethynyl)-pyridin-2-yl]-3,4,4-trimethyl-imidazolidin-2-one

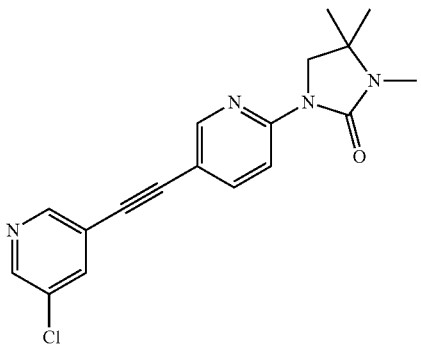 [SMILES: CN1C(=O)N(c2ccc(C#Cc3cncc(Cl)c3)cn2)CC1(C)C]

The title compound was obtained as a white solid, MS: m/e=341.1/343.3 (M+H⁺), using chemistry similar to that described in Example 37, step 3 from 3,4,4-trimethyl-1-(5-trimethylsilanylethynyl-pyridin-2-yl)-imidazolidin-2-one (Example 49, step 1) and 3-chloro-5-iodopyridine.

Example 52

3,4,4-Trimethyl-1-(5-pyridazin-4-ylethynyl-pyridin-2-yl)-imidazolidin-2-one

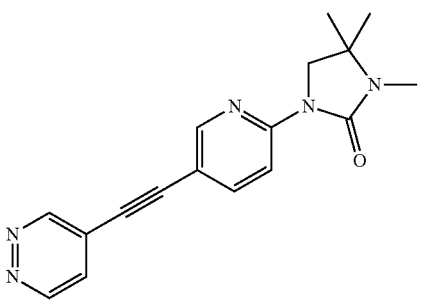 [SMILES: CN1C(=O)N(c2ccc(C#Cc3ccnnc3)cn2)CC1(C)C]

The title compound was obtained as a light yellow solid, MS: m/e=308.4 (M+H⁺), using chemistry similar to that described in Example 37, step 3 from 3,4,4-trimethyl-1-(5-trimethylsilanylethynyl-pyridin-2-yl)-imidazolidin-2-one (Example 49, step 1) and 4-bromo-pyridazine.

Example 53

1-[5-(3-Fluoro-phenylethynyl)-pyridin-2-yl]-3,4,4-trimethyl-imidazolidin-2-one

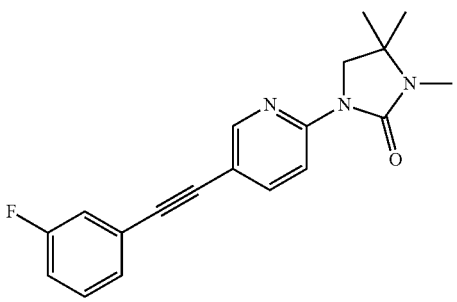 [SMILES: CN1C(=O)N(c2ccc(C#Cc3cccc(F)c3)cn2)CC1(C)C]

The title compound was obtained as a yellow solid, MS: m/e=324.3 (M+H⁺), using chemistry similar to that described in Example 1, step 3 from 1-(5-iodo-pyridin-2-yl)-3,4,4-trimethyl-imidazolidin-2-one (Example 48, step 1) and 1-ethynyl-3-fluoro-benzene.

Example 54

1-[5-(3-Chloro-phenylethynyl)-pyridin-2-yl]-3,4,4-trimethyl-imidazolidin-2-one

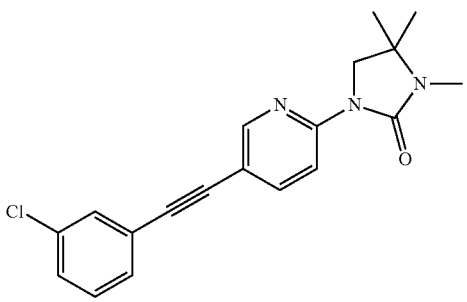 [SMILES: CN1C(=O)N(c2ccc(C#Cc3cccc(Cl)c3)cn2)CC1(C)C]

The title compound was obtained as a yellow solid, MS: m/e=340.1/342.2 (M+H⁺), using chemistry similar to that described in Example 1, step 3 from 1-(5-iodo-pyridin-2-yl)-3,4,4-trimethyl-imidazolidin-2-one (Example 48, step 1) and 1-ethynyl-3-chloro-benzene.

Example 55

3,4,4-Trimethyl-1-(5-pyrimidin-5-ylethynyl-pyridin-2-yl)-imidazolidin-2-one

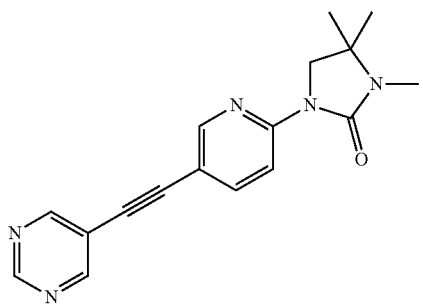 [SMILES: CN1C(=O)N(c2ccc(C#Cc3cncnc3)cn2)CC1(C)C]

The title compound was obtained as a light yellow solid, MS: m/e=308.2 (M+H$^+$), using chemistry similar to that described in Example 37, step 3 from 3,4,4-trimethyl-1-(5-trimethylsilanylethynyl-pyridin-2-yl)-imidazolidin-2-one (Example 49, step 1) and 5-bromo-pyrimidine.

Example 56

3,4,4-Trimethyl-1-(5-m-tolylethynyl-pyridin-2-yl)-imidazolidin-2-one

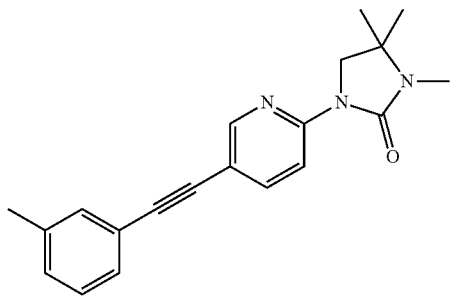

The title compound was obtained as a brown oil, MS: m/e=320.1 (M+H$^+$), using chemistry similar to that described in Example 1, step 3 from 1-(5-iodo-pyridin-2-yl)-3,4,4-trimethyl-imidazolidin-2-one (Example 48, step 1) and 1-ethynyl-3-methyl-benzene.

Example 57

1-[5-(4-Fluoro-phenylethynyl)-pyridin-2-yl]-3,4,4-trimethyl-imidazolidin-2-one

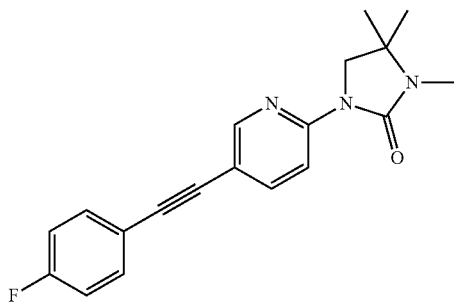 [SMILES: CN1C(=O)N(c2ccc(C#Cc3ccc(F)cc3)cn2)CC1(C)C]

The title compound was obtained as a light brown solid, MS: m/e=324.2 (M+H$^+$), using chemistry similar to that described in Example 1, step 3 from 1-(5-iodo-pyridin-2-yl)-3,4,4-trimethyl-imidazolidin-2-one (Example 48, step 1) and 1-ethynyl-4-fluoro-benzene.

Example 58

(RS)-2-(5-Phenylethynyl-pyridin-2-yl)-hexahydro-imidazo[1,5-a]pyridin-3-one

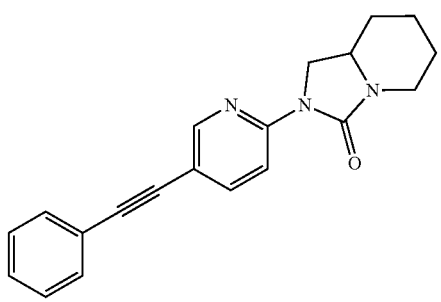 [SMILES: O=C1N(c2ccc(C#Cc3ccccc3)cn2)CC2CCCCN12]

Step 1: (RS)-2-(5-Iodo-pyridin-2-yl)-hexahydro-imidazo[1,5-a]pyridin-3-one

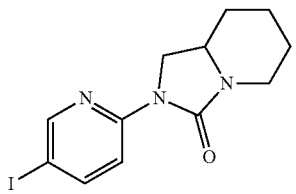 [SMILES: O=C1N(c2ccc(I)cn2)CC2CCCCN12]

The title compound was obtained as a white solid, MS: m/e=344.0 (M+H$^+$), using procedures similar to those described in Example 1, step 1 and step 2 from 2-fluoro-5-iodopyridine and (RS)-hexahydro-imidazo[1,5-a]pyridin-3-one (CAS 76561-92-7) by using neat pyridine as solvent instead of NMP.

Step 2: (RS)-2-(5-Phenylethynyl-pyridin-2-yl)-hexahydro-imidazo[1,5-a]pyridin-3-one

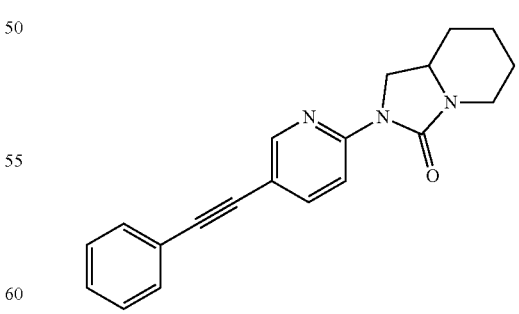

The title compound was obtained as a white solid, MS: m/e=318.2 (M+H$^+$), using chemistry similar to that described in Example 1, step 3 from (RS)-2-(5-iodo-pyridin-2-yl)-hexahydro-imidazo[1,5-a]pyridin-3-one (Example 58, step 1) and phenylacetylenen.

Example 59

2-(5-Phenylethynyl-pyridin-2-yl)-2-aza-spiro[4.4]nonan-3-one

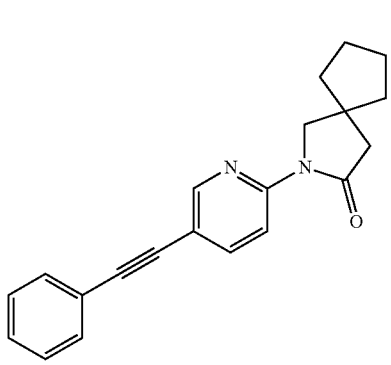 [SMILES: O=C1CC2(CCCC2)CN1c1ccc(C#Cc2ccccc2)cn1]

The title compound was obtained as a light yellow, MS: m/e=317.2 (M+H⁺), using chemistry similar to that described in Example 37, step 2 from 2-bromo-5-phenylethynyl-pyridine (Example 58, step 1) and 2-aza-spiro[4.4]nonan-3-one (CAS 75751-72-3).

Example 60

(RS)-3-Methoxy-4,4-dimethyl-1-(5-phenylethynyl-pyridin-2-yl)-pyrrolidin-2-one

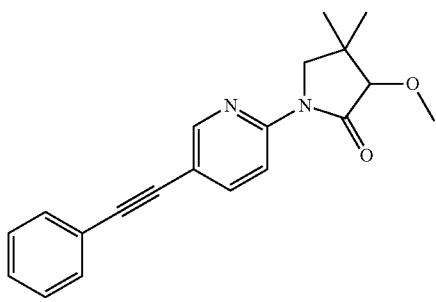 [SMILES: COC1C(=O)N(c2ccc(C#Cc3ccccc3)cn2)CC1(C)C]

Step 1: (RS)-4-Iodo-N-(5-iodo-pyridin-2-yl)-2-methoxy-3,3-dimethyl-butyramide

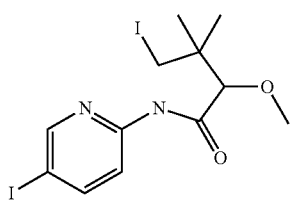 [SMILES: COC(C(=O)Nc1ccc(I)cn1)C(C)(C)CI]

The title compound was obtained as a white solid, MS: m/e=474.9 (M+H⁺), using chemistry similar to that described in patent WO9637466, page 17, step 2 starting from (RS)-3-methoxy-4,4-dimethyl-dihydro-furan-2-one (CAS 100101-82-4) instead of 3-t-butylcarbamoyloxy-tetrahydrofuran-2-one and by using 2-amino-5-iodopyridine instead of 2-amino-4-trifluoromethylpyridine.

Step 2: (RS)-1-(5-Iodo-pyridin-2-yl)-3-methoxy-4,4-dimethyl-pyrrolidin-2-one

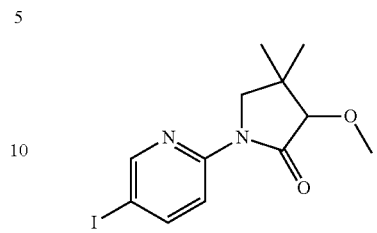

The title compound was obtained as a light yellow solid, MS: m/e=347.0 (M+H⁺), using chemistry similar to that described in patent WO9637466, page 17, step 3 from (RS)-4-iodo-N-(5-iodo-pyridin-2-yl)-2-methoxy-3,3-dimethyl-butyramide (Example 60, step 1).

Step 3: (RS)-3-Methoxy-4,4-dimethyl-1-(5-phenylethynyl-pyridin-2-yl)-pyrrolidin-2-one

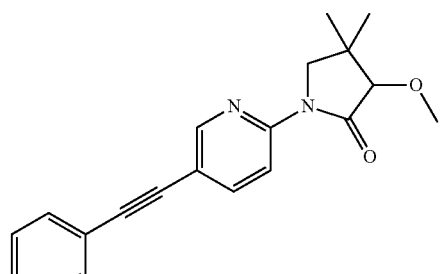

The title compound was obtained as a light yellow solid, MS: m/e=321.3 (M+H⁺), using chemistry similar to that described in Example 1, step 3 from (RS)-1-(5-iodo-pyridin-2-yl)-3-methoxy-4,4-dimethyl-pyrrolidin-2-one (Example 60, step 2) and phenylacetylene.

Example 61

(5R or 5S)-5-Methoxymethyl-3-(5-phenylethynyl-pyridin-2-yl)-oxazolidin-2-one Chiral or

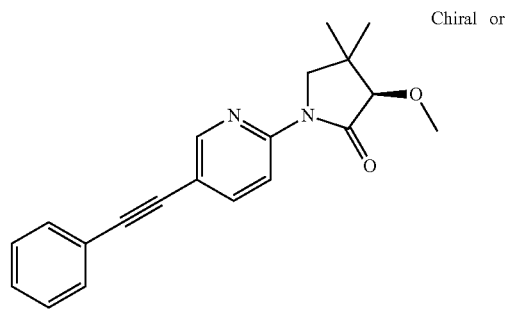

151
-continued

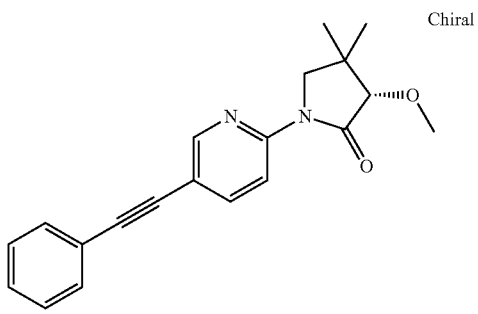

The title compound, a yellow oil, MS: m/e=321.3 (M+H$^+$), was prepared by separation of (RS)-3-methoxy-4,4-dimethyl-1-(5-phenylethynyl-pyridin-2-yl)-pyrrolidin-2-one (Example 60) using a chiral column (chiralpak AD with heptane:isopropanol 90:10 as solvent).

Example 62

(5S or 5R)-5-Methoxymethyl-3-(5-phenylethynyl-pyridin-2-yl)-oxazolidin-2-one

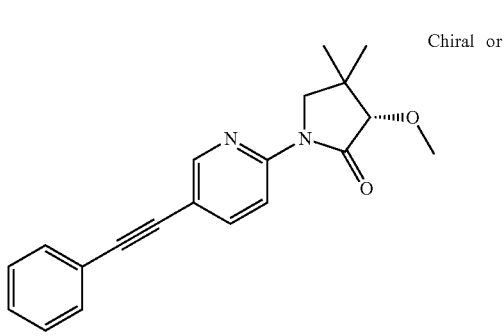

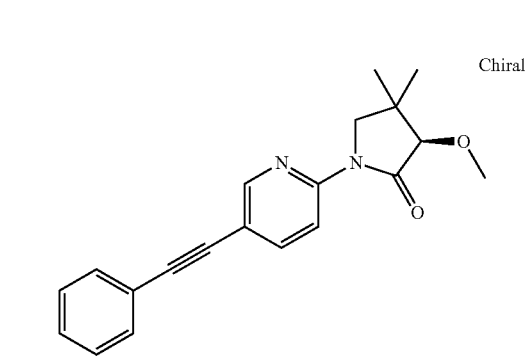

The title compound, a white solid, MS: m/e=321.3 (M+H$^+$), was prepared by separation of (RS)-3-methoxy-4,4-dimethyl-1-(5-phenylethynyl-pyridin-2-yl)-pyrrolidin-2-one (Example 60) using a chiral column (chiralpak AD with heptane:isopropanol 90:10 as solvent).

152

Example 63

(RS)-1-[5-(5-Chloro-pyridin-3-ylethynyl)-pyridin-2-yl]-3-methoxy-4,4-dimethyl-pyrrolidin-2-one

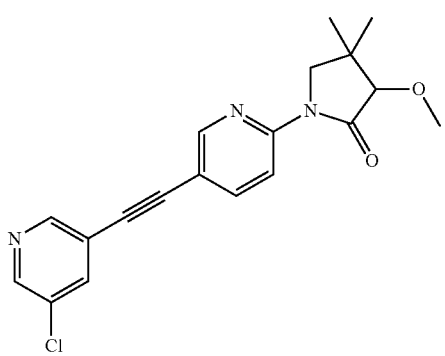 [SMILES: COC1C(=O)N(c2ccc(C#Cc3cncc(Cl)c3)cn2)CC1(C)C]

Step 1: (RS)-3-Methoxy-4,4-dimethyl-1-(5-trimethylsilanylethynyl-pyridin-2-yl)-pyrrolidin-2-one

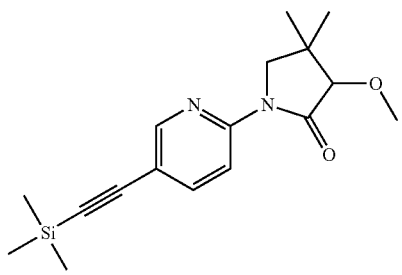

The title compound was obtained as a yellow solid, MS: m/e=317.2 (M+H$^+$), using chemistry similar to that described in Example 37, step 1 from (RS)-1-(5-iodo-pyridin-2-yl)-3-methoxy-4,4-dimethyl-pyrrolidin-2-one (Example 60, step 2) and ethynyltrimethylsilane.

Step 2: (RS)-1-[5-(5-Chloro-pyridin-3-ylethynyl)-pyridin-2-yl]-3-methoxy-4,4-dimethyl-pyrrolidin-2-one

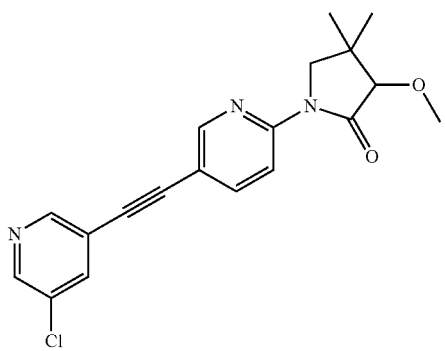 [SMILES: COC1C(=O)N(c2ccc(C#Cc3cncc(Cl)c3)cn2)CC1(C)C]

153

The title compound was obtained as a white solid, MS: m/e=356.1/358.2 (M+H⁺), using chemistry similar to that described in Example 37, step 3 from (RS)-3-methoxy-4,4-dimethyl-1-(5-trimethylsilanylethynyl-pyridin-2-yl)-pyrrolidin-2-one (Example 63, step 1) and 3-chloro-5-iodopyridine.

Example 64

(RS)-3-Methoxy-4,4-dimethyl-1-(5-m-tolylethynyl-pyridin-2-yl)-pyrrolidin-2-one

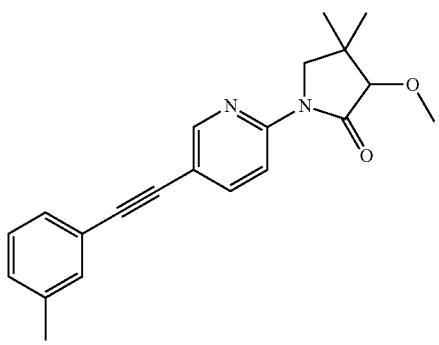 [SMILES: COC1C(=O)N(c2ccc(C#Cc3cccc(C)c3)cn2)CC1(C)C]

The title compound was obtained as an orange oil, MS: m/e=335.2 (M+H⁺), using chemistry similar to that described in Example 1, step 3 from (RS)-1-(5-iodo-pyridin-2-yl)-3-methoxy-4,4-dimethyl-pyrrolidin-2-one (Example 60, step 2) and 1-ethynyl-3-methyl-benzene.

Example 65

(RS)-1-[5-(3-Fluoro-phenylethynyl)-pyridin-2-yl]-3-methoxy-4,4-dimethyl-pyrrolidin-2-one

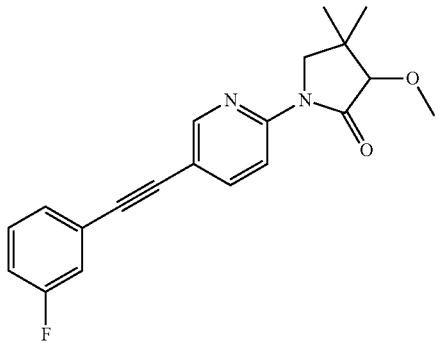

The title compound was obtained as a brown solid, MS: m/e=339.2 (M+H⁺), using chemistry similar to that described in Example 1, step 3 from (RS)-1-(5-iodo-pyridin-2-yl)-3-methoxy-4,4-dimethyl-pyrrolidin-2-one (Example 60, step 2) and 1-ethynyl-3-fluorobenzene.

154

Example 66

(RS)-1-[5-(4-Fluoro-phenylethynyl)-pyridin-2-yl]-3-methoxy-4,4-dimethyl-pyrrolidin-2-one

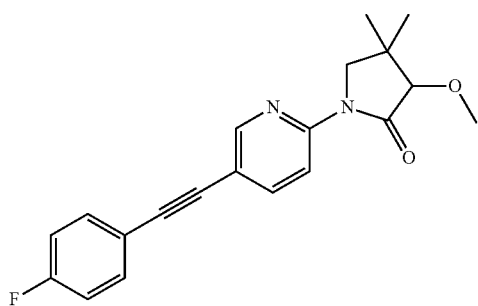 [SMILES: COC1C(=O)N(c2ccc(C#Cc3ccc(F)cc3)cn2)CC1(C)C]

The title compound was obtained as a brown solid, MS: m/e=339.2 (M+H⁺), using chemistry similar to that described in Example 1, step 3 from (RS)-1-(5-iodo-pyridin-2-yl)-3-methoxy-4,4-dimethyl-pyrrolidin-2-one (Example 60, step 2) and 1-ethynyl-4-fluorobenzene.

Example 67

3,4,4-Trimethyl-1-(5-phenylethynyl-pyridin-2-yl)-tetrahydro-pyrimidin-2-one

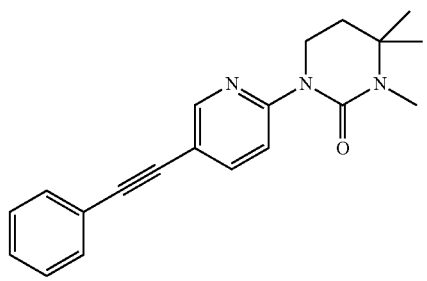 [SMILES: CN1C(=O)N(c2ccc(C#Cc3ccccc3)cn2)CCC1(C)C]

Step 1: [3-(5-Iodo-pyridin-2-ylamino)-1,1-dimethyl-propyl]-carbamic acid tert-butyl ester

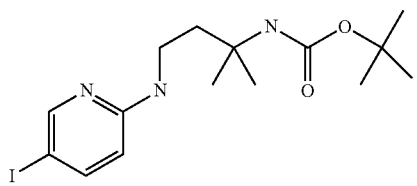 [SMILES: CC(C)(CCNc1ccc(I)cn1)NC(=O)OC(C)(C)C]

The title compound was obtained as a white solid, MS: m/e=406.3 (M+H⁺), using chemistry similar to that described in Example 1, step 1 from 2-fluoro-5-iodopyridine and tert-butyl 4-amino-2-methylbutan-2-ylcarbamate (CAS 880100-43-6).

Step 2: N-1-(5-Iodo-pyridin-2-yl)-3-methyl-butane-1,3-diamine hydrochloride

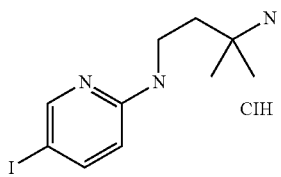

The BOC protecting group is removed by reacting [3-(5-iodo-pyridin-2-ylamino)-1,1-dimethyl-propyl]-carbamic acid tert-butyl ester (Example 67, step 1) with 4N HCl in dioxane for 4 hours at room temperature. The title compound was obtained by filtration of the hydrochloride salt as a pink solid, MS: m/e=306.1 (M+H$^+$).

Step 3: 1-(5-Iodo-pyridin-2-yl)-4,4-dimethyl-tetrahydro-pyrimidin-2-one

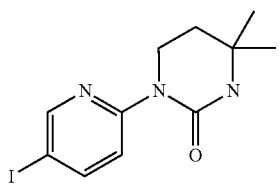 [SMILES: CC1(C)CCN(c2ccc(I)cn2)C(=O)N1]

The title compound was obtained as a yellow solid, MS: m/e=332.1 (M+H$^+$), using chemistry similar to that described in Example 1, step 2 from N-1-(5-iodo-pyridin-2-yl)-3-methyl-butane-1,3-diamine hydrochloride (Example 67, step 2).

Step 4: 1-(5-Iodo-pyridin-2-yl)-3,4,4-trimethyl-tetrahydro-pyrimidin-2-one

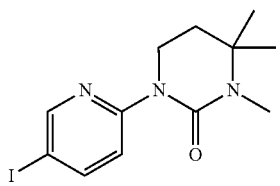 [SMILES: CN1C(=O)N(c2ccc(I)cn2)CCC1(C)C]

The title compound was obtained as a yellow solid, MS: m/e=346.0 (M+H$^+$), using chemistry similar to that described in Example 16 from 1-(5-iodo-pyridin-2-yl)-4,4-dimethyl-tetrahydro-pyrimidin-2-one (Example 67, step 3) and iodomethane.

Step 5: 3,4,4-Trimethyl-1-(5-phenylethynyl-pyridin-2-yl)-tetrahydro-pyrimidin-2-one

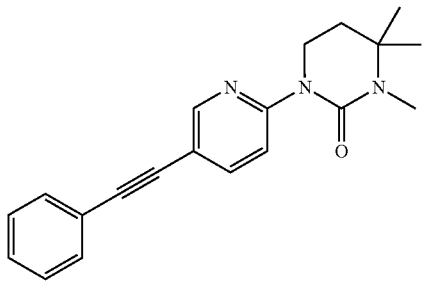 [SMILES: CN1C(=O)N(c2ccc(C#Cc3ccccc3)cn2)CCC1(C)C]

The title compound was obtained as a brown solid, MS: m/e=320.2 (M+H$^+$), using chemistry similar to that described in Example 1, step 3 from 1-(5-iodo-pyridin-2-yl)-3,4,4-trimethyl-tetrahydro-pyrimidin-2-one (Example 67, step 4) and phenylacetylene.

Example 68

1-[5-(2,5-Difluoro-phenylethynyl)-pyridin-2-yl]-3,4,4-trimethyl-tetrahydro-pyrimidin-2-one

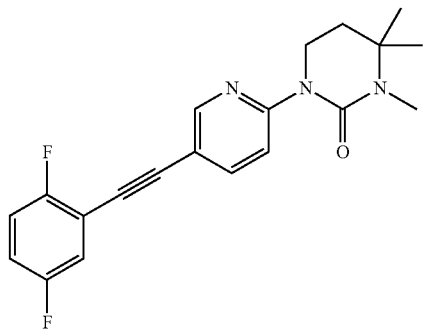

Step 1: 3,4,4-Trimethyl-1-(5-trimethylsilanylethynyl-pyridin-2-yl)-tetrahydro-pyrimidin-2-one

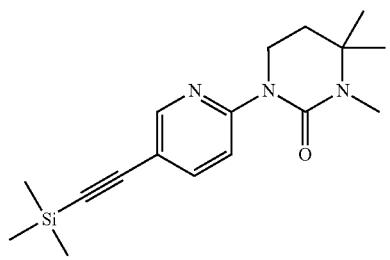

The title compound was obtained as a white solid, MS: m/e=316.2 (M+H$^+$), using chemistry similar to that described in Example 37, step 1 from 1-(5-iodo-pyridin-2-yl)-3,4,4-trimethyl-tetrahydro-pyrimidin-2-one (Example 67, step 4) and ethynyltrimethylsilane.

Step 2: 1-[5-(2,5-Difluoro-phenylethynyl)-pyridin-2-yl]-3,4,4-trimethyl-tetrahydro-pyrimidin-2-one

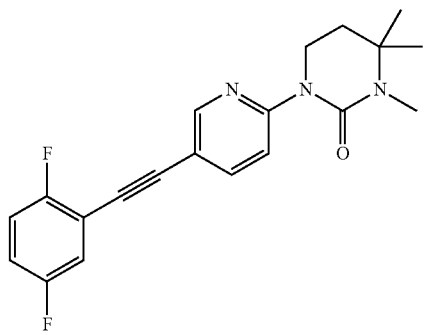

The title compound was obtained as a light yellow solid, MS: m/e=356.2 (M+H$^+$), using chemistry similar to that described in Example 37, step 3 from 3,4,4-trimethyl-1-(5- trimethylsilanylethynyl-pyridin-2-yl)-tetrahydro-pyrimidin-2-one (Example 68, step 1) and 1,4-difluoro-2-iodobenzene.

Example 69

1-[5-(4-Fluoro-phenylethynyl)-pyridin-2-yl]-3,4,4-trimethyl-tetrahydro-pyrimidin-2-one

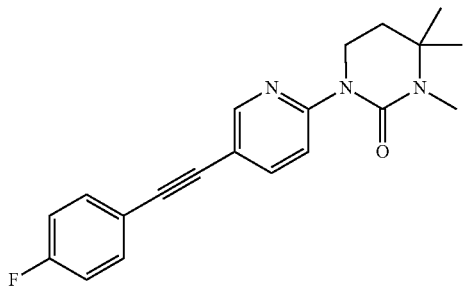 [SMILES: CN1C(=O)N(c2ccc(C#Cc3ccc(F)cc3)cn2)CCC1(C)C]

The title compound was obtained as a white solid, MS: m/e=338.3 (M+H$^+$), using chemistry similar to that described in Example 37, step 3 from 3,4,4-trimethyl-1-(5-trimethylsilanylethynyl-pyridin-2-yl)-tetrahydro-pyrimidin-2-one (Example 68, step 1) and 1-fluoro-4-iodobenzene.

Example 70

(RS)-2-(5-Pyridin-3-ylethynyl-pyridin-2-yl)-hexahydro-imidazo[1,5-a]pyridin-3-one

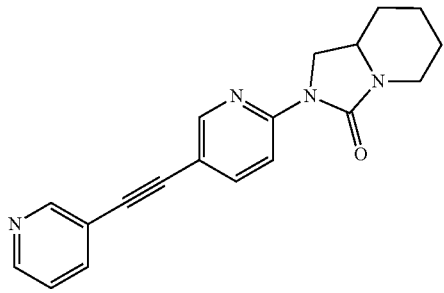 [SMILES: O=C1N(c2ccc(C#Cc3cccnc3)cn2)CC2CCCCN12]

The title compound was obtained as a light yellow solid, MS: m/e=319.1 (M+H$^+$), using chemistry similar to that described in Example 1, step 3 from (RS)-2-(5-iodo-pyridin-2-yl)-hexahydro-imidazo[1,5-a]pyridin-3-one (Example 58, step 1) and 3-ethynyl-pyridine.

Example 71

(RS)-2-[5-(3-Fluoro-phenylethynyl)-pyridin-2-yl]-hexahydro-imidazo[1,5-a]pyridin-3-one

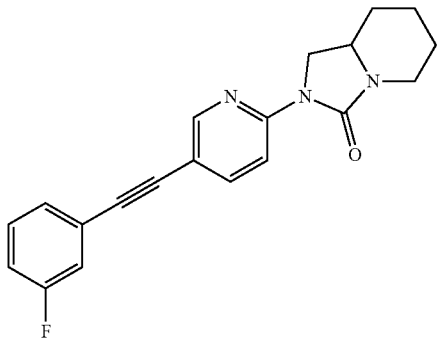 [SMILES: O=C1N(c2ccc(C#Cc3cccc(F)c3)cn2)CC2CCCCN12]

The title compound was obtained as a light brown solid, MS: m/e=336.2 (M+H$^+$), using chemistry similar to that described in Example 1, step 3 from (RS)-2-(5-iodo-pyridin-2-yl)-hexahydro-imidazo[1,5-a]pyridin-3-one (Example 58, step 1) and 1-ethynyl-3-fluorobenzene.

Example 72

6,6-Dimethyl-3-(5-phenylethynyl-pyridin-2-yl)-[1,3]oxazinan-2-one

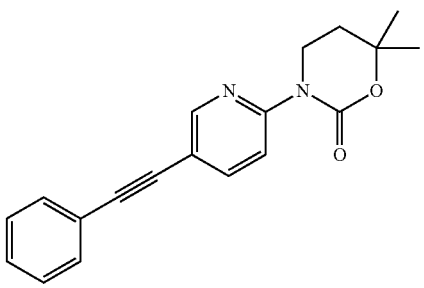

Step 1: (3-Hydroxy-3-methyl-butyl)-carbamic acid benzyl ester

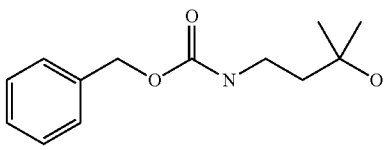 [SMILES: CC(C)(O)CCNC(=O)OCc1ccccc1]

(10 g, 42.1 mmol) Methyl 3-(benzyloxycarbonylamino)propanoate (CAS 54755-77-0) was dissolved in THF (150 ml) and cooled to 0-5° C. 3N Methylmagnesium bromide in THF (56.2 ml, 120 mmol, 4 equiv.) was added drop wise and the mixture stirred for 1 hour at 0-5° C. The reaction mixture was extracted with saturated NH$_4$Cl solution and two times with EtOAc. The organic layers were dried over Na$_2$SO$_4$ and evaporated to dryness. The desired (3-hydroxy-3-methyl-butyl)-carbamic acid benzyl ester (11.6 g, quant.) was obtained as a colorless oil, MS: m/e=238.1 (M+H$^+$) and used in the next step without further purification.

Step 2: 6,6-dimethyl-[1,3]oxazinan-2-one

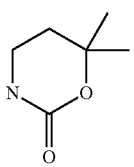

(11.6 g, 48.9 mmol) (3-Hydroxy-3-methyl-butyl)-carbamic acid benzyl ester (Example 72, step 1) was dissolved in THF (250 ml) and sodium hydride (60%, 5.2 g, 108 mmol, 2.2 equiv.) was added in portions. The mixture was stirred for 3 hours at room temperature. 5 ml saturated NaHCO$_3$ solution was added carefully and the mixture was evaporated with isolute to dryness. The crude product was purified by flash chromatography by directly loading the residue onto a silica gel column and eluting with an ethyl acetate:methanol gradient 100:0 to 90:10. The desired 6,6-dimethyl-[1,3]oxazinan-2-one (3.2 g, 51% yield) was obtained as a yellow solid, MS: m/e=130.1 (M+H$^+$).

Step 3: 6,6-Dimethyl-3-(5-trimethylsilanylethynyl-pyridin-2-yl)-[1,3]oxazinan-2-one

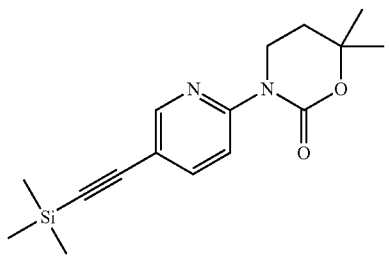

The title compound was obtained as an orange solid, MS: m/e=303.2 (M+H$^+$), using chemistry similar to that described in Example 37, step 2 from 2-bromo-5-trimethylsilanylethynyl-pyridine (Example 37, step 1) and by using 6,6-dimethyl-[1,3]oxazinan-2-one (Example 72, step 2) instead of 4,4-dimethylpyrrolidin-2-one.

Step 4: 6,6-Dimethyl-3-(5-phenylethynyl-pyridin-2-yl)-[1,3]oxazinan-2-one

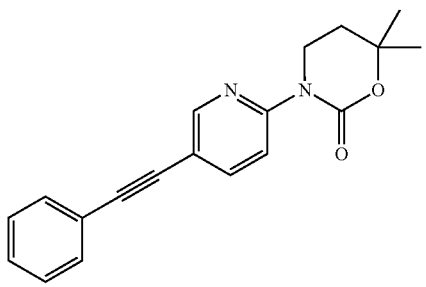 [SMILES: CC1(C)CCN(c2ccc(C#Cc3ccccc3)cn2)C(=O)O1]

The title compound was obtained as a yellow solid, MS: m/e=307.2 (M+H$^+$), using chemistry similar to that described in Example 37, step 3 from 6,6-dimethyl-3-(5-trimethylsilanylethynyl-pyridin-2-yl)-[1,3]oxazinan-2-one (Example 72, step 3) and iodobenzene.

Example 73

6,6-Dimethyl-3-(5-pyridin-3-ylethynyl-pyridin-2-yl)-[1,3]oxazinan-2-one

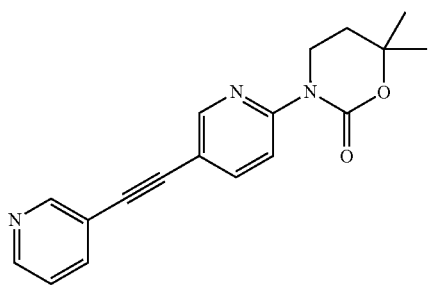 [SMILES: CC1(C)CCN(c2ccc(C#Cc3cccnc3)cn2)C(=O)O1]

Step 1: 3-(5-Iodo-pyridin-2-yl)-6,6-dimethyl-[1,3]oxazinan-2-one

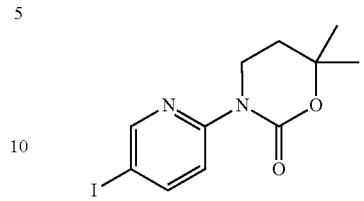

The title compound was obtained as a white solid, MS: m/e=333.1 (M+H$^+$), using procedures similar to those described in Example 1, step 1 and step 2 from 2-fluoro-5-iodopyridine and 4-amino-2-methyl-butan-2-ol hydrochloride.

Step 2: 6,6-Dimethyl-3-(5-pyridin-3-ylethynyl-pyridin-2-yl)-[1,3]oxazinan-2-one

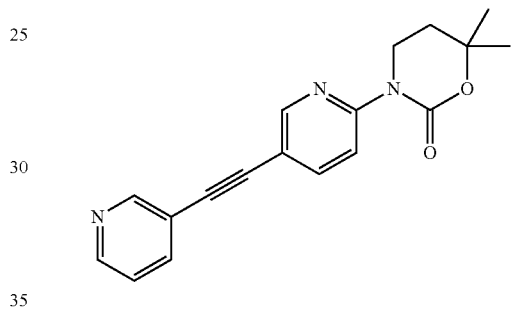

The title compound was obtained as a light yellow solid, MS: m/e=308.2 (M+H$^+$), using chemistry similar to that described in Example 1, step 3 from 3-(5-iodo-pyridin-2-yl)-6,6-dimethyl-[1,3]oxazinan-2-one (Example 73, step 1) and phenylacetylene.

Example 74

3-[5-(5-Fluoro-pyridin-3-ylethynyl)-pyridin-2-yl]-6,6-dimethyl-[1,3]oxazinan-2-one

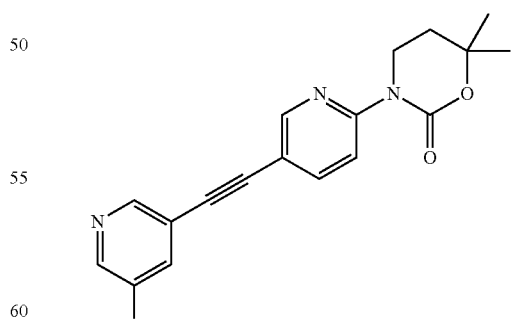

The title compound was obtained as a white solid, MS: m/e=326.3 (M+H$^+$), using chemistry similar to that described in Example 37, step 3 from 6,6-dimethyl-3-(5-trimethylsilanylethynyl-pyridin-2-yl)-[1,3]oxazinan-2-one (Example 72, step 3) and 3-fluoro-5-iodopyridine.

Example 75

3-[5-(5-Chloro-pyridin-3-ylethynyl)-pyridin-2-yl]-6,6-dimethyl-[1,3]oxazinan-2-one

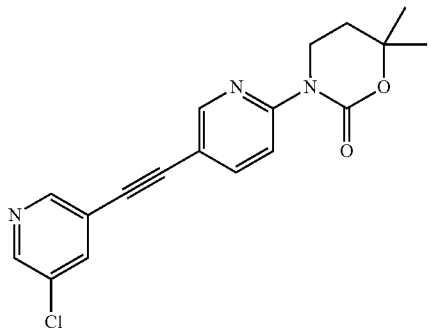

The title compound was obtained as a white solid, MS: m/e=342.1/344.2 (M+H$^+$), using chemistry similar to that described in Example 37, step 3 from 6,6-dimethyl-3-(5-trimethylsilanylethynyl-pyridin-2-yl)-[1,3]oxazinan-2-one (Example 72, step 3) and 3-chloro-5-iodopyridine.

Example 76

3-[5-(3-Fluoro-phenylethynyl)-pyridin-2-yl]-6,6-dimethyl-[1,3]oxazinan-2-one

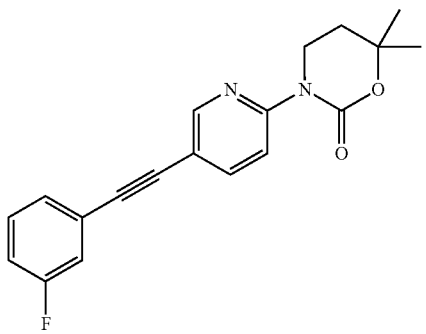 [SMILES: CC1(C)CCN(c2ccc(C#Cc3cccc(F)c3)cn2)C(=O)O1]

The title compound was obtained as a white solid, MS: m/e=325.4 (M+H$^+$), using chemistry similar to that described in Example 37, step 3 from 6,6-dimethyl-3-(5-trimethylsilanylethynyl-pyridin-2-yl)-[1,3]oxazinan-2-one (Example 72, step 3) and 1-fluoro-3-iodobenzene.

Example 77

3-[5-(3-Chloro-phenylethynyl)-pyridin-2-yl]-6,6-dimethyl-[1,3]oxazinan-2-one

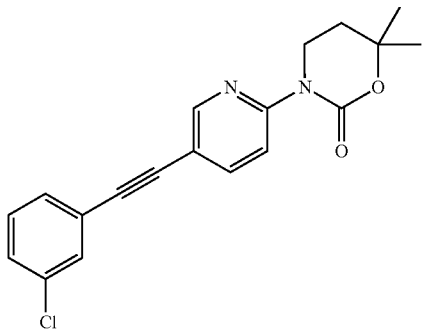 [SMILES: CC1(C)CCN(c2ccc(C#Cc3cccc(Cl)c3)cn2)C(=O)O1]

The title compound was obtained as a white solid, MS: m/e=341.2/343.2 (M+H$^+$), using chemistry similar to that described in Example 37, step 3 from 6,6-dimethyl-3-(5-trimethylsilanylethynyl-pyridin-2-yl)-[1,3]oxazinan-2-one (Example 72, step 3) and 1-chloro-3-iodobenzene.

Example 78

6,6-Dimethyl-3-(5-m-tolylethynyl-pyridin-2-yl)-[1,3]oxazinan-2-one

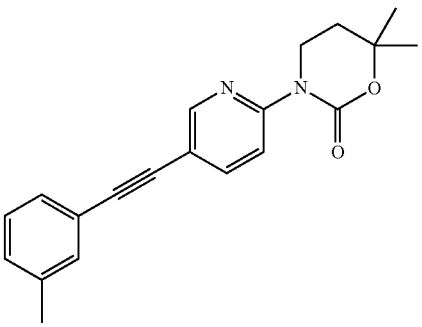 [SMILES: Cc1cccc(C#Cc2ccc(N3CCC(C)(C)OC3=O)nc2)c1]

The title compound was obtained as a light yellow solid, MS: m/e=321.4 (M+H$^+$), using chemistry similar to that described in Example 37, step 3 from 6,6-dimethyl-3-(5-trimethylsilanylethynyl-pyridin-2-yl)-[1,3]oxazinan-2-one (Example 72, step 3) and 1-iodo-3-methylbenzene.

Example 79

3-[5-(4-Fluoro-phenylethynyl)-pyridin-2-yl]-6,6-dimethyl-[1,3]oxazinan-2-one

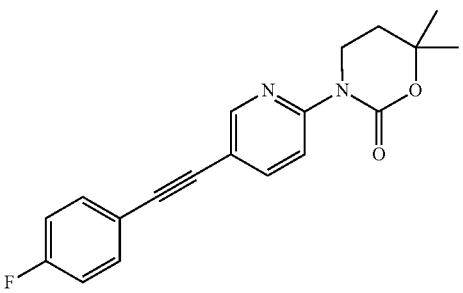 [SMILES: CC1(C)CCN(c2ccc(C#Cc3ccc(F)cc3)cn2)C(=O)O1]

The title compound was obtained as a light brown solid, MS: m/e=325.2 (M+H$^+$), using chemistry similar to that described in Example 1, step 3 from 3-(5-iodo-pyridin-2-yl)-6,6-dimethyl-[1,3]oxazinan-2-one (Example 73, step 1) and 1-ethynyl-4-fluorobenzene.

Example 80

3-[5-(3,4-Difluoro-phenylethynyl)-pyridin-2-yl]-6,6-dimethyl-[1,3]oxazinan-2-one

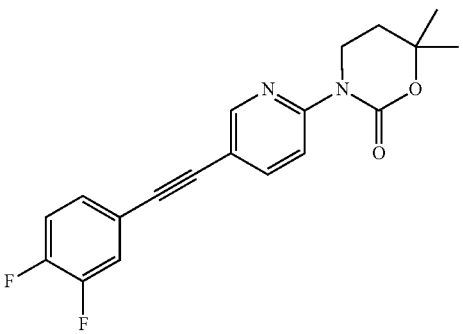 [SMILES: CC1(C)CCN(c2ccc(C#Cc3ccc(F)c(F)c3)cn2)C(=O)O1]

The title compound was obtained as a light yellow solid, MS: m/e=343.1 (M+H$^+$), using chemistry similar to that described in Example 1, step 3 from 3-(5-iodo-pyridin-2-yl)-6,6-dimethyl-[1,3]oxazinan-2-one (Example 73, step 1) and 4-ethynyl-1,2-difluorobenzene.

Example 81

3-[5-(2,5-Difluoro-phenylethynyl)-pyridin-2-yl]-6,6-dimethyl-[1,3]oxazinan-2-one

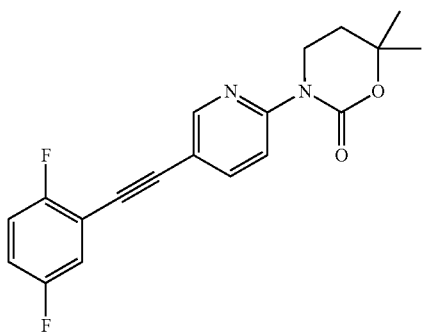 [SMILES: CC1(C)CCN(c2ccc(C#Cc3cc(F)ccc3F)cn2)C(=O)O1]

The title compound was obtained as a light yellow solid, MS: m/e=343.1 (M+H$^+$), using chemistry similar to that described in Example 37, step 3 from 6,6-dimethyl-3-(5-trimethylsilanylethynyl-pyridin-2-yl)-[1,3]oxazinan-2-one (Example 72, step 3) and 1,4-difluoro-2-iodobenzene.

Example 82

6-(5-Phenylethynyl-pyridin-2-yl)-2-oxa-6-aza-spiro[3.4]octan-7-one

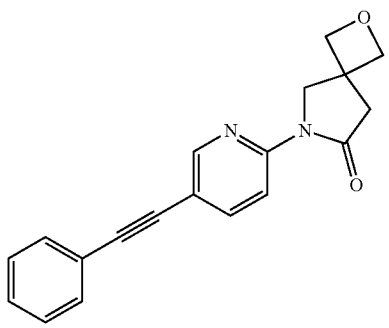 [SMILES: O=C1CC2(COC2)CN1c1ccc(C#Cc2ccccc2)cn1]

Step 1: 6-(5-Trimethylsilanylethynyl-pyridin-2-yl)-2-oxa-6-aza-spiro[3.4]octan-7-one

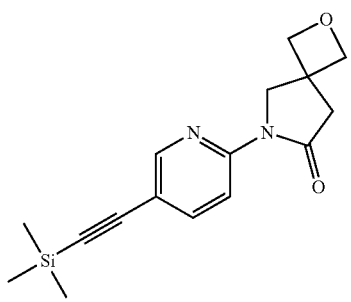 [SMILES: C[Si](C)(C)C#Cc1ccc(N2CC3(COC3)CC2=O)nc1]

The title compound was obtained as a white solid, MS: m/e=301.3 (M+H$^+$), using chemistry similar to that described in Example 37, step 2 from 2-bromo-5-trimethylsilanylethynyl-pyridine (Example 37, step 1) and 2-oxa-6-aza-spiro[3.4]octan-7-one (CAS 1207174-87-5).

Step 2: 6-(5-Phenylethynyl-pyridin-2-yl)-2-oxa-6-aza-spiro[3.4]octan-7-one

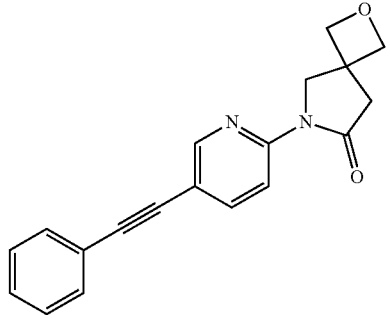 [SMILES: O=C1CC2(COC2)CN1c1ccc(C#Cc2ccccc2)cn1]

The title compound was obtained as a light yellow solid, MS: m/e=305.3 (M+H$^+$), using chemistry similar to that described in Example 37, step 3 from 6-(5-trimethylsilanyl-ethynyl-pyridin-2-yl)-2-oxa-6-aza-spiro[3.4]octan-7-one (Example 82, step 1) and iodobenzene.

Example 83

(RS)-4-Cyclopropyl-3-methyl-1-(5-phenylethynyl-pyridin-2-yl)-imidazolidin-2-one

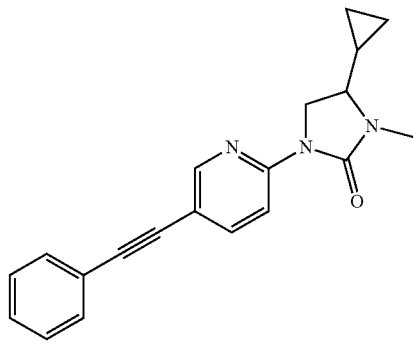 [SMILES: CN1C(=O)N(c2ccc(C#Cc3ccccc3)cn2)CC1C1CC1]

The title compound was obtained as an orange solid, MS: m/e=318.1 (M+H$^+$), using procedures similar to those described in Example 58 from 2-fluoro-5-iodopyridine and by using (RS)-1-cyclopropyl-ethane-1,2-diamine instead of (RS)-hexahydro-imidazo[1,5-a]pyridin-3-one.

Example 84

(3 aSR,7aRS)-(3aRS,7RS)-1-Methyl-3-(5-phenylethynyl-pyridin-2-yl)-octahydro-benzoimidazol-2-one

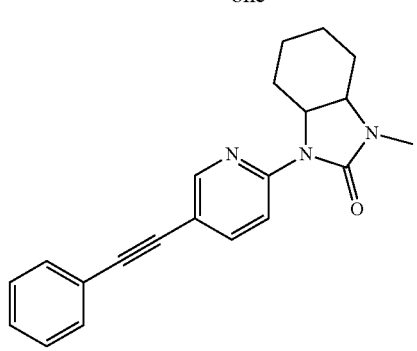

Step 1: (1SR,2RS)-(1RS,2RS)—N-(5-Iodo-pyridin-2-yl)-cyclohexane-1,2-diamine

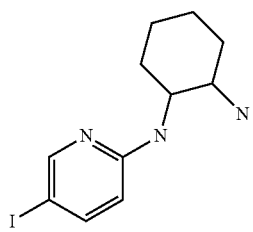 [SMILES: NC1CCCCC1Nc1ccc(I)cn1]

The title compound was obtained as a brown oil, MS: m/e=318.1 (M+H⁺), using chemistry similar to that described in Example 1, step 1 from 2-fluoro-5-iodopyridine and rac-cyclohexane-1,2-diamine.

Step 2: (3aSR,7aRS)-(3aRS,7aRS)-1-(5-Iodo-pyridin-2-yl)-octahydro-benzoimidazol-2-one

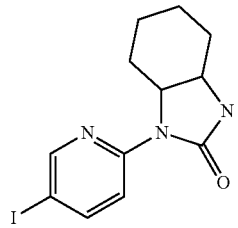 [SMILES: O=C1NC2CCCCC2N1c1ccc(I)cn1]

The title compound was obtained as a yellow solid, MS: m/e=344.1 (M+H⁺), using chemistry similar to that described in Example 1, step 2 from (1SR,2RS)-(1RS,2RS)-N-(5-iodo-pyridin-2-yl)-cyclohexane-1,2-diamine (Example 84, step 1).

Step 3: (3aSR,7aRS)-(3aRS,7aRS)-1-(5-Iodo-pyridin-2-yl)-3-methyl-octahydro-benzoimidazol-2-one

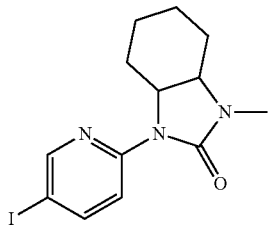 [SMILES: CN1C(=O)N(c2ccc(I)cn2)C2CCCCC21]

The title compound was obtained as a white solid, MS: m/e=358.0 (M+H⁺), using chemistry similar to that described in Example 16 from (3aSR,7aRS)-(3aRS,7aRS)-1-(5-iodo-pyridin-2-yl)-octahydro-benzoimidazol-2-one (Example 84, step 2) and iodomethane.

Step 4: (3aSR,7aRS)-(3aRS,7RS)-1-Methyl-3-(5-phenylethynyl-pyridin-2-yl)-octahydro-benzoimidazol-2-one

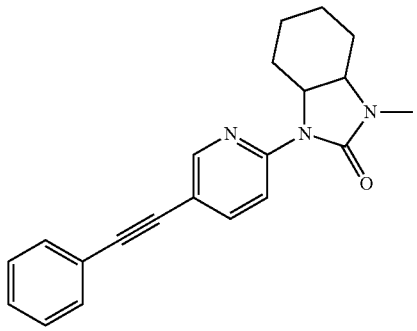 [SMILES: CN1C(=O)N(c2ccc(C#Cc3ccccc3)cn2)C2CCCCC21]

The title compound was obtained as a yellow solid, MS: m/e=332.3 (M+H⁺), using chemistry similar to that described in Example 1, step 3 from (3aSR,7aRS)-(3aRS,7aRS)-1-(5-iodo-pyridin-2-yl)-3-methyl-octahydro-benzoimidazol-2-one (Example 84, step 3) and phenylacetylene.

Example 85

(3aSR,7aRS)-(3aRS,7RS)-1-Methyl-3-(5-pyridin-3-ylethynyl-pyridin-2-yl)-octahydro-benzoimidazol-2-one

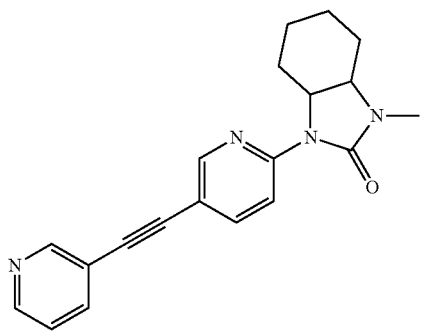 [SMILES: CN1C(=O)N(c2ccc(C#Cc3cccnc3)cn2)C2CCCCC21]

The title compound was obtained as a light yellow solid, MS: m/e=333.3 (M+H⁺), using chemistry similar to that described in Example 1, step 3 from (3aSR,7aRS)-(3aRS,7aRS)-1-(5-iodo-pyridin-2-yl)-3-methyl-octahydro-benzoimidazol-2-one (Example 84, step 3) and 3-ethynylpyridine.

Example 86

(3aSR,7aRS)-(3aRS,7RS)-1-[5-(5-Fluoro-pyridin-3-ylethynyl)-pyridin-2-yl]-3-methyl-octahydro-benzoimidazol-2-one

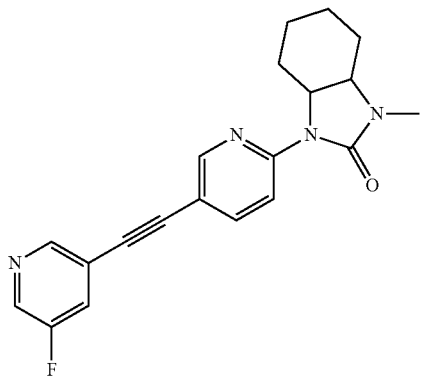 [SMILES: CN1C(=O)N(c2ccc(C#Cc3cncc(F)c3)cn2)C2CCCCC21]

The title compound was obtained as a light yellow solid, MS: m/e=351.3 (M+H⁺), using chemistry similar to that described in Example 1, step 3 from (3aSR,7aRS)-(3aRS,7aRS)-1-(5-iodo-pyridin-2-yl)-3-methyl-octahydro-benzoimidazol-2-one (Example 84, step 3) and 3-ethynyl-5-fluoro-pyridine (generated by in situ Sonogashira reaction of 3-fluoro-5-iodopyridine with ethynyltrimethylsilane and TBAF).

Example 87

4,4-Dimethyl-5'-phenylethynyl-3,4,5,6-tetrahydro-[1,2']bipyridinyl-2-one

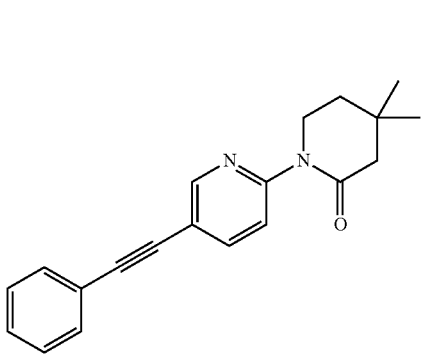

Step 1: 4,4-Dimethyl-5'-trimethylsilanylethynyl-3,4,5,6-tetrahydro-[1,2']bipyridinyl-2-one

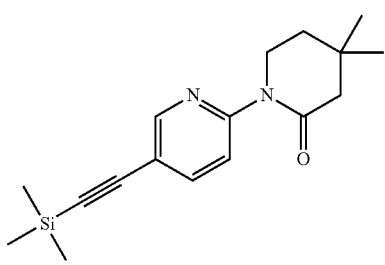

The title compound was obtained as a yellow solid, MS: m/e=301.3 (M+H$^+$), using chemistry similar to that described in Example 37, step 2 from 2-bromo-5-trimethylsilanylethynyl-pyridine (Example 37, step 1) and by using 4,4-dimethyl-piperidin-2-one (CAS 55047-81-9) instead of 4,4-dimethylpyrrolidin-2-one.

Step 2: 4,4-Dimethyl-5'-phenylethynyl-3,4,5,6-tetrahydro-[1,2']bipyridinyl-2-one

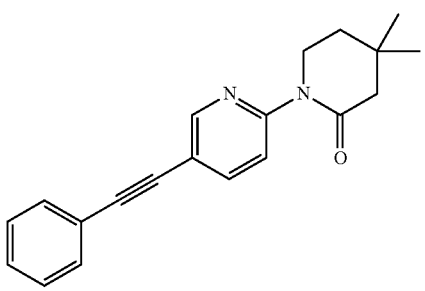

The title compound was obtained as a white solid, MS: m/e=305.2 (M+H$^+$), using chemistry similar to that described in Example 37, step 3 from 4,4-dimethyl-5'-trimethylsilanyl-ethynyl-3,4,5,6-tetrahydro-[1,2']bipyridinyl-2-one (Example 87, step 1) and iodobenzene.

Example 88

5'-(3-Fluoro-phenylethynyl)-4,4-dimethyl-3,4,5,6-tetrahydro-[1,2']bipyridinyl-2-one

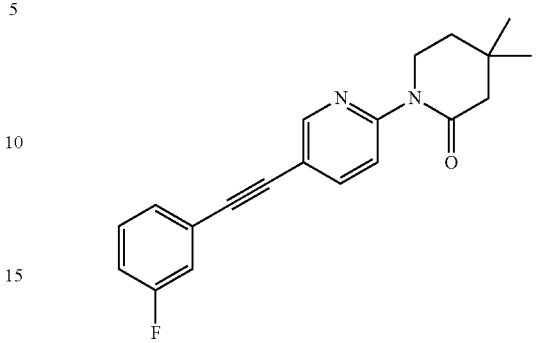

The title compound was obtained as a white solid, MS: m/e=323.2 (M+H$^+$), using chemistry similar to that described in Example 37, step 3 from 4,4-dimethyl-5'-trimethylsilanyl-ethynyl-3,4,5,6-tetrahydro-[1,2']bipyridinyl-2-one (Example 87, step 1) and 1-fluoro-3-iodobenzene.

Example 89

5'-(3-Chloro-phenylethynyl)-4,4-dimethyl-3,4,5,6-tetrahydro-[1,2']bipyridinyl-2-one

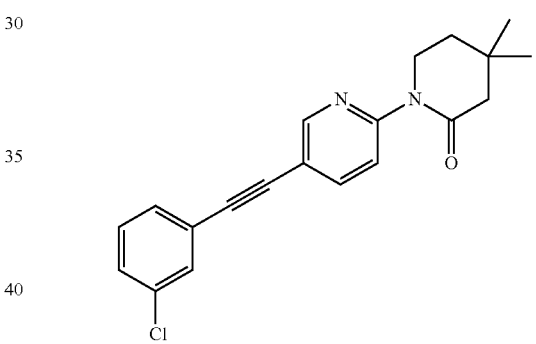

The title compound was obtained as a light yellow solid, MS: m/e=339.2/341.1 (M+H$^+$), using chemistry similar to that described in Example 37, step 3 from 4,4-dimethyl-5'-trimethylsilanylethynyl-3,4,5,6-tetrahydro-[1,2']bipyridinyl-2-one (Example 87, step 1) and 1-chloro-3-iodobenzene.

Example 90

5'-(5-Chloro-pyridin-3-ylethynyl)-4,4-dimethyl-3,4,5,6-tetrahydro-[1,2']bipyridinyl-2-one

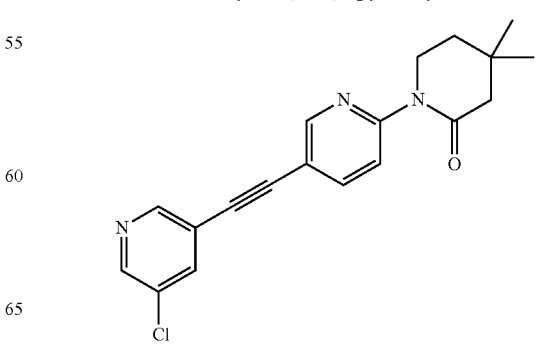

The title compound was obtained as a light yellow solid, MS: m/e=340.1/342.2 (M+H⁺), using chemistry similar to that described in Example 37, step 3 from 4,4-dimethyl-5'-trimethylsilanylethynyl-3,4,5,6-tetrahydro-[1,2']bipyridinyl-2-one (Example 87, step 1) and 1-chloro-3-iodopyridine.

Example 91

5'-(4-Fluoro-phenylethynyl)-4,4-dimethyl-3,4,5,6-tetrahydro-[1,2']bipyridinyl-2-one

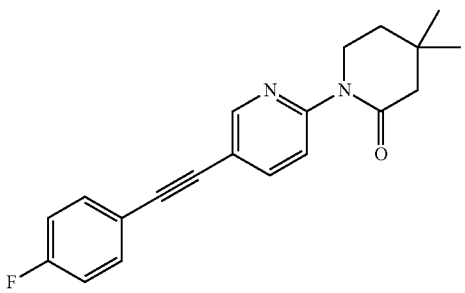

The title compound was obtained as a light yellow solid, MS: m/e=323.2 (M+H⁺), using chemistry similar to that described in Example 37, step 3 from 4,4-dimethyl-5'-trimethylsilanylethynyl-3,4,5,6-tetrahydro-[1,2']bipyridinyl-2-one (Example 87, step 1) and 1-fluoro-4-iodobenzene.

Example 92

5'-(2,5-Difluoro-phenylethynyl)-4,4-dimethyl-3,4,5,6-tetrahydro-[1,2']bipyridinyl-2-one

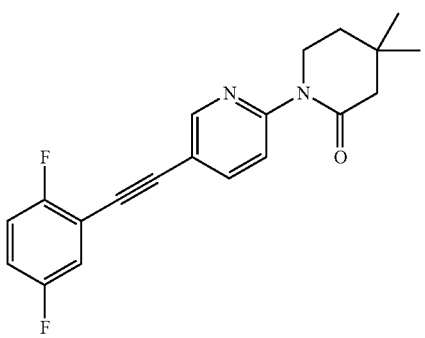 [SMILES: CC1(C)CCN(c2ccc(C#Cc3cc(F)ccc3F)cn2)C(=O)C1]

The title compound was obtained as a white solid, MS: m/e=341.1 (M+H⁺), using chemistry similar to that described in Example 37, step 3 from 4,4-dimethyl-5'-trimethylsilanylethynyl-3,4,5,6-tetrahydro-[1,2']bipyridinyl-2-one (Example 87, step 1) and 1,4-difluoro-2-iodobenzene.

Example 93

7,7-Dimethyl-3-(5-phenylethynyl-pyridin-2-yl)-[1,3]oxazepan-2-one

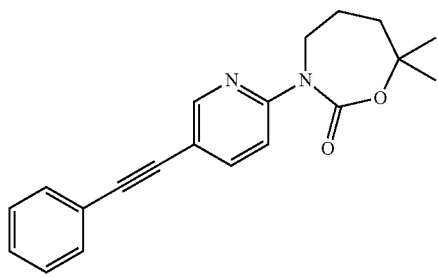 [SMILES: CC1(C)CCCN(c2ccc(C#Cc3ccccc3)cn2)C(=O)O1]

Step 1: 3-(5-Iodo-pyridin-2-yl)-7,7-dimethyl-[1,3]oxazepan-2-one

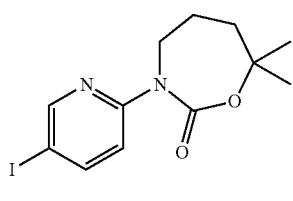 [SMILES: CC1(C)CCCN(c2ccc(I)cn2)C(=O)O1]

The title compound was obtained as a colorless oil, MS: m/e=346.9 (M+H⁺), using procedures similar to those described in Example 1, step 1 and step 2 from 2-fluoro-5-iodopyridine and 5-amino-2-methylpentan-2-ol (CAS 108262-66-4).

Step 2: 7,7-Dimethyl-3-(5-phenylethynyl-pyridin-2-yl)-[1,3]oxazepan-2-one

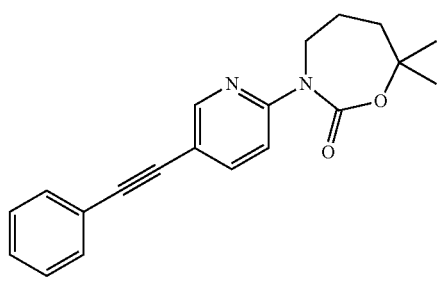 [SMILES: CC1(C)CCCN(c2ccc(C#Cc3ccccc3)cn2)C(=O)O1]

The title compound was obtained as an orange solid, MS: m/e=321.2 (M+H⁺), using chemistry similar to that described in Example 1, step 3 from 3-(5-iodo-pyridin-2-yl)-7,7-dimethyl-[1,3]oxazepan-2-one (Example 93, step 1) and phenylacetylene.

Example 94

(3aSR,7aRS)-(3aRS,7RS)-1-(5-Phenylethynyl-pyridin-2-yl)-hexahydro-pyrano[4,3-d]oxazol-2-one

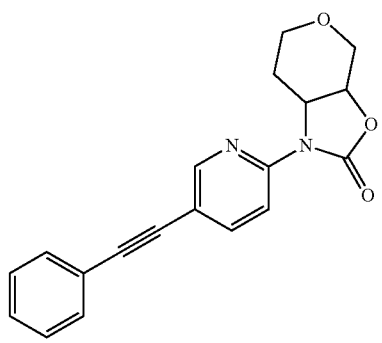 [SMILES: O=C1OC2COCCC2N1c1ccc(C#Cc2ccccc2)cn1]

Step 1: (3aSR,7aRS)-(3aRS,7RS)-1-(5-Iodo-pyridin-2-yl)-hexahydro-pyrano[4,3-d]oxazol-2-one

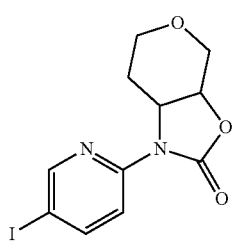 [SMILES: O=C1OC2COCCC2N1c1ccc(I)cn1]

The title compound was obtained as a white solid, MS: m/e=346.9 (M+H⁺), using procedures similar to those described in Example 1, step 1 and step 2 from 2-fluoro-5-iodopyridine and (3RS,4RS)-(3RS,4SR)-4-aminotetrahydro-2H-pyran-3-ol (CAS 33332-01-3).

Step 2: (3aSR,7aRS)-(3aRS,7RS)-1-(5-Phenylethynyl-pyridin-2-yl)-hexahydro-pyrano[4,3-d]oxazol-2-one

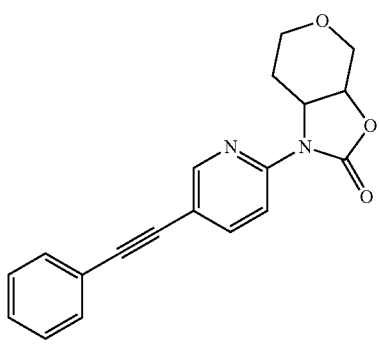 [SMILES: O=C1OC2COCCC2N1c1ccc(C#Cc2ccccc2)cn1]

The title compound was obtained as a brown solid, MS: m/e=321.1 (M+H⁺), using chemistry similar to that described in Example 1, step 3 from (3aSR,7aRS)-(3aRS,7RS)-1-(5-iodo-pyridin-2-yl)-hexahydro-pyrano[4,3-d]oxazol-2-one (Example 94, step 1) and phenylacetylene.

Example 95

(RS)-5-Hydroxy-6,6-dimethyl-3-(5-phenylethynyl-pyridin-2-yl)-[1,3]oxazinan-2-one

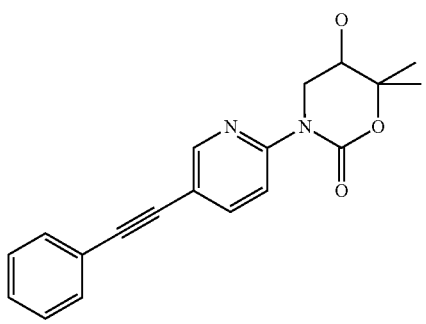 [SMILES: CC1(C)OC(=O)N(c2ccc(C#Cc3ccccc3)cn2)CC1O]

Step 1: (RS)-2-(tert-Butyl-diphenyl-silanyloxy)-3-dibenzylamino-propionic acid ethyl ester

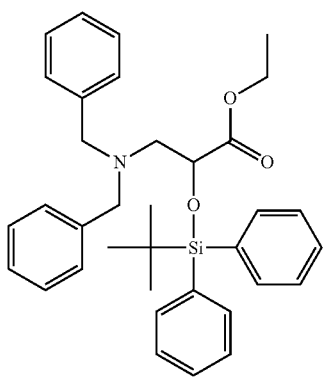 [SMILES: CCOC(=O)C(CN(Cc1ccccc1)Cc1ccccc1)O[Si](c1ccccc1)(c1ccccc1)C(C)(C)C]

(5.8 g, 18.6 mmol) (RS)-3-Dibenzylamino-2-hydroxy-propionic acid ethyl ester (CAS 93715-75-4) was dissolved in DMF (40 ml) and tert-butylchlorodiphenylsilane (6.76 ml, 26 mmol, 1.4 equiv.), Imidazole (1.9 g, 27.9 mmol, 1.5 equiv.) and DMAP (227 mg, 1.9 mmol, 0.1 equiv.) were added at room temperature. The mixture was stirred for 3 hours at 80° C. The reaction mixture was evaporated and extracted with saturated NaHCO₃ solution and two times with EtOAc. The organic layers were extracted with brine, dried over Na₂SO₄ and evaporated to dryness. The crude product was purified by flash chromatography on silica gel column and eluting with an ethyl acetate:heptane gradient 0:100 to 40:60. The desired (RS)-2-(tert-butyl-diphenyl-silanyloxy)-3-dibenzylamino-propionic acid ethyl ester (8.1 g, 79% yield) was obtained as a colorless oil, MS: m/e=552.5 (M+H⁺).

Step 2: (RS)-3-(tert-Butyl-diphenyl-silanyloxy)-4-dibenzylamino-2-methyl-butan-2-ol

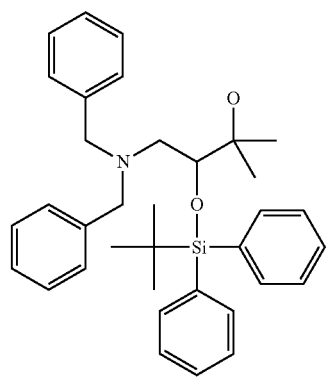 [SMILES: CC(C)(O)C(CN(Cc1ccccc1)Cc1ccccc1)O[Si](c1ccccc1)(c1ccccc1)C(C)(C)C]

(8.0 g, 14.5 mmol) (RS)-2-(tert-Butyl-diphenyl-silanyloxy)-3-dibenzylamino-propionic acid ethyl ester (Example 95, step 1) was dissolved in THF (100 ml) and methylmagnesium bromide (3M in diethylether) (19.3 ml, 58 mmol, 4 equiv.) was drop wise at room temperature. The mixture was stirred for 3.5 hours at room temperature. The reaction mixture was extracted with saturated NaHCO₃ solution and two times with EtOAc. The organic layers were extracted with brine, dried over Na₂SO₄ and evaporated to dryness. The desired (RS)-3-(tert-butyl-diphenyl-silanyloxy)-4-dibenzylamino-2-methyl-butan-2-ol (6.9 g, 84% yield) was obtained as a white solid, MS: m/e=538.5 (M+H⁺) and used in the next step without further purification.

Step 3: (RS)-4-Amino-3-(tert-butyl-diphenyl-silanyloxy)-2-methyl-butan-2-ol

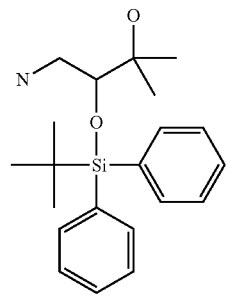 [SMILES: CC(C)(O)C(CN)O[Si](c1ccccc1)(c1ccccc1)C(C)(C)C]

(RS)-3-(tert-Butyl-diphenyl-silanyloxy)-4-dibenzylamino-2-methyl-butan-2-ol (Example 95, step 2) was hydrogenated in EtOH with Pd(OH)₂ for 16 hours at 60° C. The desired (RS)-4-amino-3-(tert-butyl-diphenyl-silanyloxy)-2- methyl-butan-2-ol (4.2 g, 92% yield) was obtained as a colorless oil, MS: m/e=358.2 (M+H⁺) and used in the next step without further purification.

Step 4: (RS)-5-(2,2-Dimethyl-1,1-diphenyl-propoxy)-6,6-dimethyl-[1,3]oxazinan-2-one

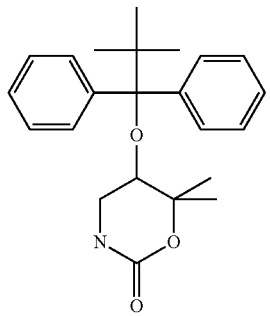 [SMILES: CC1(C)OC(=O)NCC1OC(c1ccccc1)(c1ccccc1)C(C)(C)C]

(1.83 mg, 5.1 mmol) (RS)-4-Amino-3-(tert-butyl-diphenyl-silanyloxy)-2-methyl-butan-2-ol (Example 95, step 3) was dissolved in THF (35 ml) and cooled to 0-5° C. Triethylamine (2.14 ml, 15.4 mmol, 3 equiv.) and triphosgene (1.67 g, 5.63 mmol, 1.1 equiv.) dissolved in 15 ml THF were added drop wise at 0-5° C. The mixture was stirred for 1 hour at 0-5° C. The reaction mixture was evaporated with isolute and the crude product was purified by flash chromatography by directly loading the residue onto a silica gel column and eluting with a heptane:ethyl acetate gradient 100:0 to 0:100. The desired (RS)-5-(2,2-dimethyl-1,1-diphenyl-propoxy)-6,6-dimethyl-[1,3]oxazinan-2-one (535 mg, 27% yield) was obtained as a white solid, MS: m/e=384.3 (M+H⁺).

Step 5: (RS)-5-(2,2-Dimethyl-1,1-diphenyl-propoxy)-6,6-dimethyl-3-(5-trimethylsilanylethynyl-pyridin-2-yl)-[1,3]oxazinan-2-one

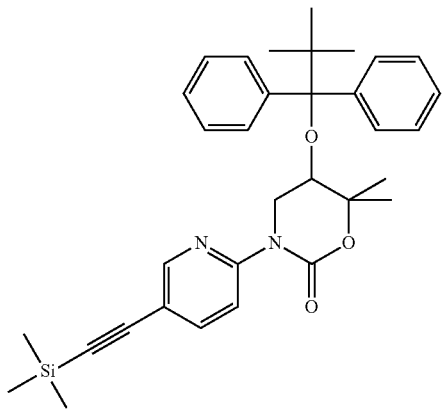 [SMILES: CC1(C)OC(=O)N(c2ccc(C#C[Si](C)(C)C)cn2)CC1OC(c1ccccc1)(c1ccccc1)C(C)(C)C]

The title compound was obtained as a yellow oil, MS: m/e=557.3 (M+H⁺), using chemistry similar to that described in Example 37, step 2 from 2-bromo-5-trimethylsilanylethynyl-pyridine (Example 37, step 1) and (RS)-5-(2,2-dimethyl-1,1-diphenyl-propoxy)-6,6-dimethyl-[1,3]oxazinan-2-one (Example 95, step 4).

Step 6: (RS)-5-Hydroxy-6,6-dimethyl-3-(5-phenyl-ethynyl-pyridin-2-yl)-[1,3]oxazinan-2-one

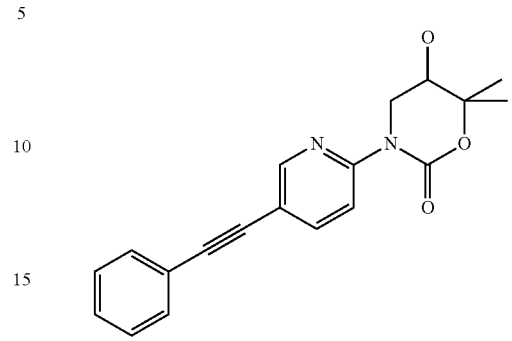

The title compound was obtained as a light yellow solid, MS: m/e=323.1 (M+H⁺), using chemistry similar to that described in Example 37, step 3 from (RS)-5-(2,2-dimethyl-1,1-diphenyl-propoxy)-6,6-dimethyl-3-(5-trimethylsilanyl-ethynyl-pyridin-2-yl)-[1,3]oxazinan-2-one (Example 95, step 5) and iodobenzene.

Example 96

4-Methyl-6-(5-phenylethynyl-pyridin-2-yl)-4,6-diaza-spiro[2.4]heptan-5-one

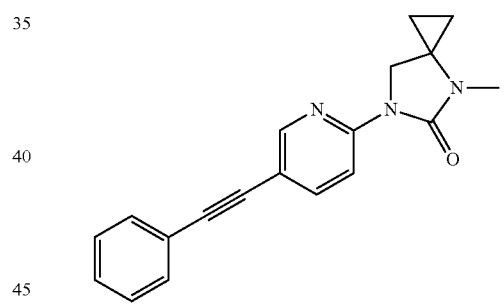

Step 1: 2-Bromo-5-phenylethynyl-pyridine

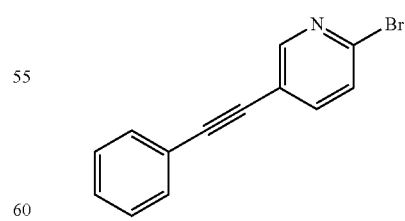

The title compound was obtained as a white solid, MS: m/e=258/260 (M+H⁺), using chemistry similar to that described in Example 37, step 1 from 2-bromo-5-iodopyridine and by using phenylacetylene instead of ethynyltrimethylsilane.

Step 2: 4,6-Diaza-spiro[2.4]heptan-5-one

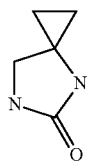

(0.88 g, 5.53 mmol) 1-(Aminomethyl)cyclopropanamine dihydrochloride (CAS 849149-67-3) was dissolved in THF (10 ml) and CDI (0.9 g, 5.53 mmol, 1.0 equiv.) was added at room temperature. The mixture was stirred for 16 hours at 70° C. The reaction mixture was evaporated and extracted with saturated NaHCO$_3$ solution and five times with dichloromethane. The organic layers were dried over Na$_2$SO$_4$ and evaporated to dryness. The desired 4,6-diaza-spiro[2.4]heptan-5-one (0.52 g, 50% purity, 42% yield) was obtained as a white solid, MS: m/e=113.0 (M+H$^+$) and was used without further purification in the next step.

Step 3: 6-(5-Phenylethynyl-pyridin-2-yl)-4,6-diaza-spiro[2.4]heptan-5-one

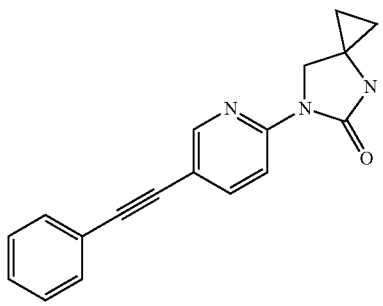 [SMILES: O=C1NC2(CC2)CN1c1ccc(C#Cc2ccccc2)cn1]

The title compound was obtained as a yellow solid, MS: m/e=290.1 (M+H$^+$), using chemistry similar to that described in Example 37, step 2 from 2-bromo-5-phenylethynyl-pyridine (Example 96, step 1) and 4,6-diaza-spiro[2.4]heptan-5-one (Example 96, step 2).

Step 4: 4-Methyl-6-(5-phenylethynyl-pyridin-2-yl)-4,6-diaza-spiro[2.4]heptan-5-one

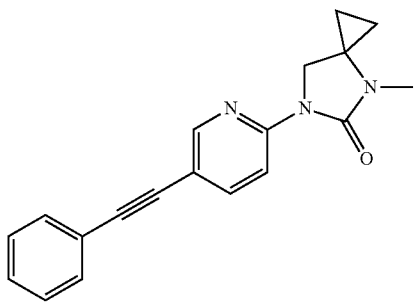

The title compound was obtained as a white solid, MS: m/e=304.1 (M+H$^+$), using chemistry similar to that described in Example 16 from 6-(5-phenylethynyl-pyridin-2-yl)-4,6-diaza-spiro[2.4]heptan-5-one (Example 96, step 3) and iodomethane.

Example 97

3,3-Dimethyl-1-(5-phenylethynyl-pyridin-2-yl)-azetidin-2-one

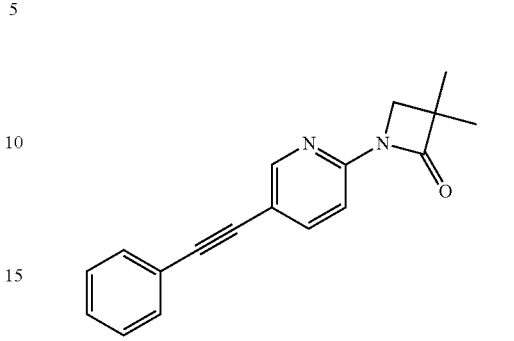

Step 1: N-(5-Bromo-pyridin-2-yl)-3-chloro-2,2-dimethyl-propionamide

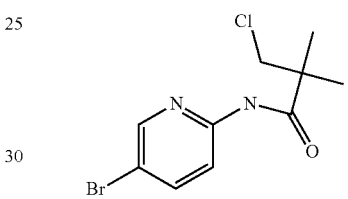

To a solution of 2-amino-5-bromopyridine (100 mg, 0.454 mmol) in dichloromethane (6 ml) were added triethylamine (0.19 ml, 1.364 mmol, 3 equiv.) and 3-chloro-2,2-dimethyl-propionyl chloride (CAS 4300-97-4) (140 mg, 0.909 mmol, 2 equiv.) at 0-5° C. The mixture was stirred for 16 hours at room temperature. The reaction mixture was evaporated and the crude product was purified by flash chromatography on silica gel column and eluting with an ethyl acetate:heptane gradient 5:95 to 10:90. The desired N-(5-bromo-pyridin-2-yl)-3-chloro-2,2-dimethyl-propionamide (154 mg, 74% yield) was obtained as a white solid.

Step 2: 1-(5-Bromo-pyridin-2-yl)-3,3-dimethyl-azetidin-2-one

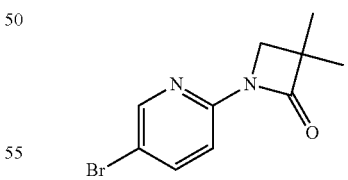

(250 mg, 0.738 mmol) N-(5-Bromo-pyridin-2-yl)-3-chloro-2,2-dimethyl-propionamide (Example 97, step 1) dissolved in DMF (3 ml) was added at room temperature to a solution of NaH (29.5 mg, 0.738 mmol, 1 equiv.) in 5 ml DMF. The mixture was stirred for 3 hours at 70° C. The reaction mixture was evaporated and the crude product was purified by flash chromatography on silica gel column and eluting with an ethyl acetate:heptane gradient 10:90 to 15:85. The desired 1-(5-bromo-pyridin-2-yl)-3,3-dimethyl-azetidin-2-one (160 mg, 72% yield) was obtained as a white solid.

Step 3: 3,3-Dimethyl-1-(5-phenylethynyl-pyridin-2-yl)-azetidin-2-one

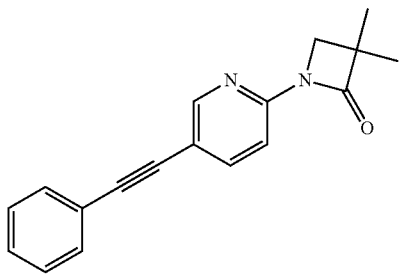 [SMILES: CC1(C)CN(c2ccc(C#Cc3ccccc3)cn2)C1=O]

The title compound was obtained as a brown solid, MS: m/e=277.0 (M+H$^+$), using chemistry similar to that described in Example 1, step 3 from 1-(5-bromo-pyridin-2-yl)-3,3-dimethyl-azetidin-2-one (Example 97, step 2) and phenylacetylene.

Example 98

(1RS,5SR)-6-(5-Pyridin-3-ylethynyl-pyridin-2-yl)-6-aza-bicyclo[3.2.0]heptan-7-one

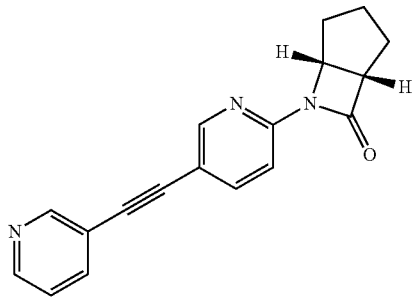 [SMILES: O=C1[C@H]2CCC[C@H]2N1c1ccc(C#Cc2cccnc2)cn1]

The title compound was obtained as a brown solid, MS: m/e=290.2 (M+H$^+$), using chemistry similar to that described in Example 1, step 3 from (1RS,5SR)-6-(5-bromo-pyridin-2-yl)-6-aza-bicyclo[3.2.0]heptan-7-one (Example 46, step 1) with 3-ethynyl-pyridine.

Example 99

(3aSR,7aRS)-(3aRS,7RS)-1-Ethyl-3-(5-phenylethynyl-pyridin-2-yl)-octahydro-benzoimidazol-2-one

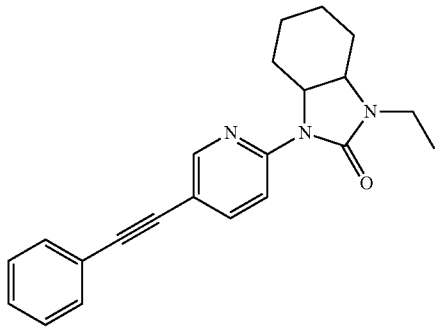 [SMILES: CCN1C(=O)N(c2ccc(C#Cc3ccccc3)cn2)C2CCCCC21]

Step 1: (3aSR,7aRS)-(3aRS,7aRS)-1-(5-Iodo-pyridin-2-yl)-3-ethyl-octahydro-benzoimidazol-2-one

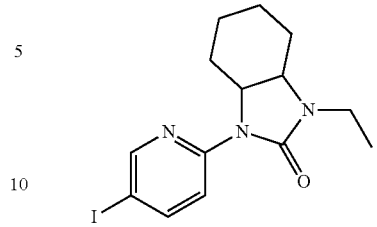

The title compound was obtained as a light yellow solid, MS: m/e=372.2 (M+H$^+$), using chemistry similar to that described in Example 16 from (3aSR,7aRS)-(3aRS,7aRS)-1-(5-iodo-pyridin-2-yl)-octahydro-benzoimidazol-2-one (Example 84, step 2) and iodoethane by stirring the reaction at 60° C. instead of 0-5° C.

Step 2: (3aSR,7aRS)-(3aRS,7RS)-1-Ethyl-3-(5-phenylethynyl-pyridin-2-yl)-octahydro-benzoimidazol-2-one

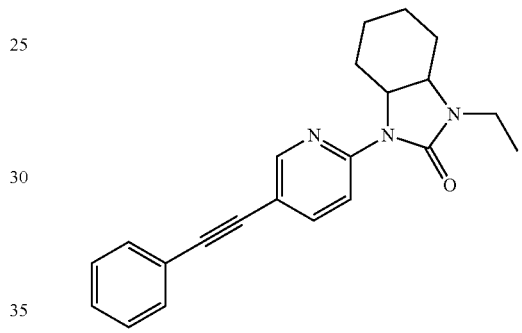

The title compound was obtained as a brown oil, MS: m/e=346.4 (M+H$^+$), using chemistry similar to that described in Example 1, step 3 from (3aSR,7aRS)-(3aRS,7aRS)-1-(5-iodo-pyridin-2-yl)-3-ethyl-octahydro-benzoimidazol-2-one (Example 99, step 1) and phenylacetylene.

Example 100

(3aSR,7aRS)-(3aRS,7RS)-1-Ethyl-3-(5-pyridin-3-ylethynyl-pyridin-2-yl)-octahydro-benzoimidazol-2-one

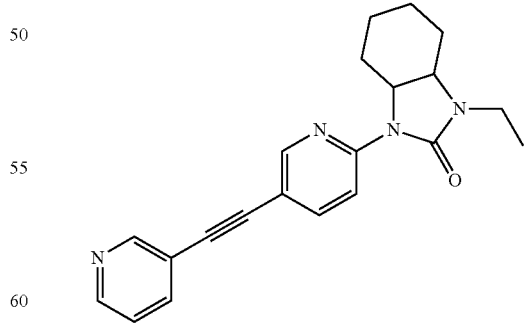

The title compound was obtained as a brown solid, MS: m/e=347.8 (M+H$^+$), using chemistry similar to that described in Example 1, step 3 from (3aSR,7aRS)-(3aRS,7aRS)-1-(5-iodo-pyridin-2-yl)-3-ethyl-octahydro-benzoimidazol-2-one (Example 99, step 1) and 3-ethynyl-pyridine.

Example 101

(3aSR,7aRS)-(3aRS,7RS)-1-Isopropyl-3-(5-phenyl-ethynyl-pyridin-2-yl)-octahydro-benzoimidazol-2-one

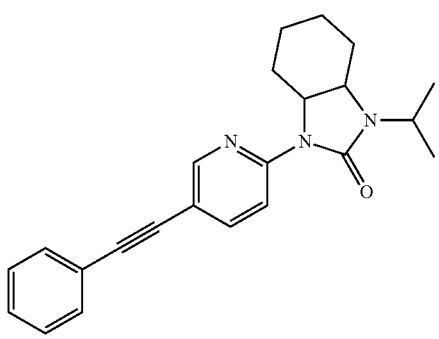 [SMILES: CC(C)N1C(=O)N(c2ccc(C#Cc3ccccc3)cn2)C2CCCCC21]

Step 1: (3aSR,7aRS)-(3aRS,7aRS)-1-(5-Iodo-pyridin-2-yl)-3-isopropyl-octahydro-benzoimidazol-2-one

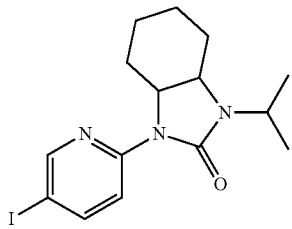 [SMILES: CC(C)N1C(=O)N(c2ccc(I)cn2)C2CCCCC21]

The title compound was obtained as a white solid using chemistry similar to that described in Example 16 from (3aSR,7aRS)-(3aRS,7aRS)-1-(5-iodo-pyridin-2-yl)-octahydro-benzoimidazol-2-one (Example 84, step 2) and isopropyl iodide by stirring the reaction at 60° C. instead of 0-5° C.

Step 2: (3aSR,7aRS)-(3aRS,7RS)-1-Isopropyl-3-(5-phenylethynyl-pyridin-2-yl)-octahydro-benzoimidazol-2-one

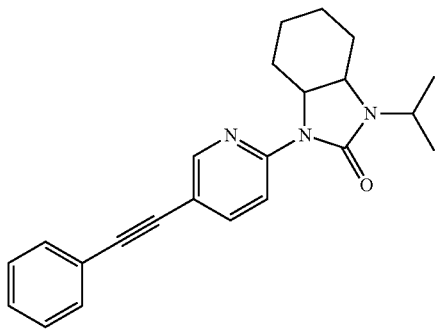 [SMILES: CC(C)N1C(=O)N(c2ccc(C#Cc3ccccc3)cn2)C2CCCCC21]

The title compound was obtained as a brown oil, MS: m/e=360.1 (M+H⁺), using chemistry similar to that described in Example 1, step 3 from (3aSR,7aRS)-(3aRS,7aRS)-1-(5-iodo-pyridin-2-yl)-3-isopropyl-octahydro-benzoimidazol-2-one (Example 101, step 1) and phenylacetylene.

Example 102

(4aRS,7aSR)-3-(5-Phenylethynyl-pyridin-2-yl)-hexahydro-cyclopenta[e][1,3]oxazin-2-one

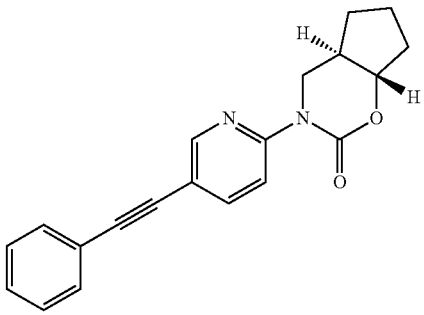 [SMILES: O=C1O[C@H]2CCC[C@@H]2CN1c1ccc(C#Cc2ccccc2)cn1]

Step 1: (4aRS,7aSR)-3-(5-Iodo-pyridin-2-yl)-hexahydro-cyclopenta[e][1,3]oxazin-2-one

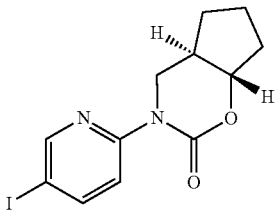 [SMILES: O=C1O[C@H]2CCC[C@@H]2CN1c1ccc(I)cn1]

The title compound was obtained as a white solid, MS: m/e=345.0 (M+H⁺), using procedures similar to those described in Example 1, step 1 and step 2 from 2-fluoro-5-iodopyridine and (1SR,2RS)-2-aminomethyl-cyclopentanol (CAS 40482-02-8) by using triphosgene and triethylamine in THF for 12 hours at room temperature instead of the conditions used in Example 1, step 2.

Step 2: (4aRS,7aSR)-3-(5-Phenylethynyl-pyridin-2-yl)-hexahydro-cyclopenta[e][1,3]oxazin-2-one

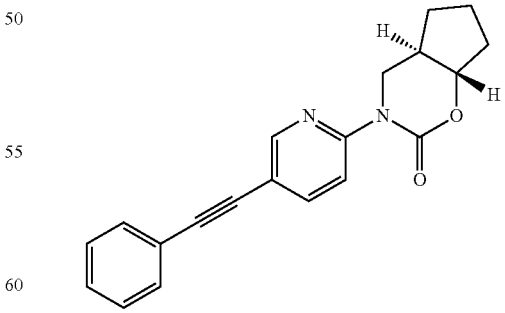

The title compound was obtained as a brown solid, MS: m/e=319.0 (M+H⁺), using chemistry similar to that described in Example 1, step 3 from (4aRS,7aSR)-3-(5-iodo-pyridin-2-yl)-hexahydro-cyclopenta[e][1,3]oxazin-2-one (Example 102, step 1) and phenylacetylene.

Example 103

(4aRS,7aRS)-3-(5-Phenylethynyl-pyridin-2-yl)-hexahydro-cyclopenta[e][1,3]oxazin-2-one

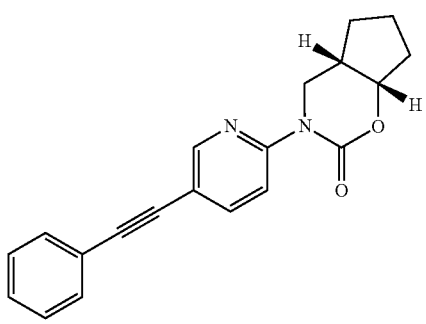 [SMILES: O=C1O[C@H]2CCC[C@H]2CN1c1ccc(C#Cc2ccccc2)cn1]

Step 1: (4aRS,7aRS)-3-(5-Iodo-pyridin-2-yl)-hexahydro-cyclopenta[e][1,3]oxazin-2-one

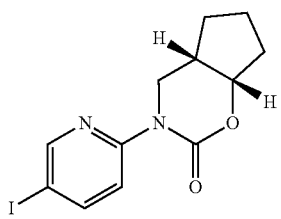 [SMILES: O=C1O[C@H]2CCC[C@H]2CN1c1ccc(I)cn1]

The title compound was obtained as a white solid, MS: m/e=345.0 (M+H$^+$), using procedures similar to those described in Example 1, step 1 and step 2 from 2-fluoro-5-iodopyridine and (1SR,2SR)-2-aminomethyl-cyclopentanol (CAS 40482-00-6) by using triphosgene and triethylamine in THF for 12 hours at room temperature instead of the conditions used in Example 1, step 2.

Step 2: (4aRS,7aRS)-3-(5-Phenylethynyl-pyridin-2-yl)-hexahydro-cyclopenta[e][1,3]oxazin-2-one

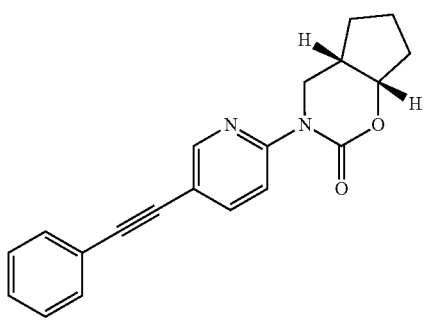

The title compound was obtained as a brown solid, MS: m/e=318.8 (M+H$^+$), using chemistry similar to that described in Example 1, step 3 from (4aRS,7aRS)-3-(5-iodo-pyridin-2-yl)-hexahydro-cyclopenta[e][1,3]oxazin-2-one (Example 103, step 1) and phenylacetylene.

Example 104

(RS)-5,6,6-Trimethyl-3-(5-phenylethynyl-pyridin-2-yl)-[1,3]oxazinan-2-one

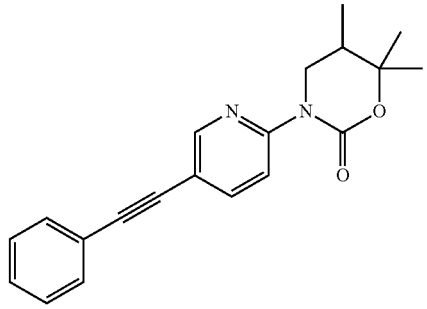

Step 1: (RS)-(3-Hydroxy-2,3-dimethyl-butyl)-carbamic acid tert-butyl ester

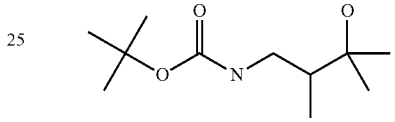

The title compound was obtained as a colorless oil, MS: m/e=218.3 (M+H$^+$), using chemistry similar to that described in Example 95, step 2 from methyl 3-(tert-butoxycarbonylamino)-2-methylpropanoate (CAS 182486-16-4).

Step 2: (RS)-5,6,6-Trimethyl-[1,3]oxazinan-2-one

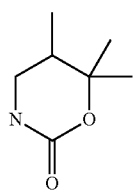

The title compound was obtained as a yellow solid, MS: m/e=144.0 (M+H$^+$), using chemistry similar to that described in Example 72, step 2 from (RS)-(3-hydroxy-2,3-dimethyl-butyl)-carbamic acid tert-butyl ester (Example 104, step 1).

Step 3: (RS)-5,6,6-Trimethyl-3-(5-phenylethynyl-pyridin-2-yl)-[1,3]oxazinan-2-one

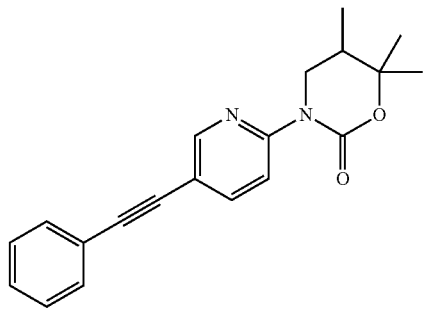

The title compound was obtained as a yellow oil, MS: m/e=321.1 (M+H⁺), using chemistry similar to that described in Example 37, step 2 from 2-bromo-5-phenylethynyl-pyridine (Example 96, step 1) and (RS)-5,6,6-trimethyl-[1,3]oxazinan-2-one (Example 104, step 2).

Example 105

(RS)-6-Methoxymethyl-3-(5-phenylethynyl-pyridin-2-yl)-[1,3]oxazinan-2-one

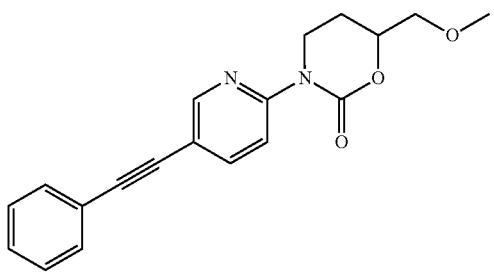 [SMILES: COCC1CCN(c2ccc(C#Cc3ccccc3)cn2)C(=O)O1]

The title compound was obtained as a light yellow solid, MS: m/e=323.1 (M+H⁺), using chemistry similar to that described in Example 37, step 2 from 2-bromo-5-phenylethynyl-pyridine (Example 96, step 1) and (RS)-6-methoxymethyl-[1,3]oxazinan-2-one (CAS 39754-63-7).

Example 106

(3aRS, 6aSR)-1-methyl-3-(5-(phenylethynyl)pyridin-2-yl)hexahydrocyclopenta[d]imidazol-2(1H)-one

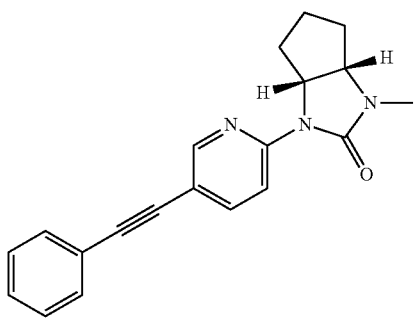 [SMILES: CN1C(=O)N(c2ccc(C#Cc3ccccc3)cn2)[C@@H]2CCC[C@@H]21]

Step 1: (3aSR, 6aRS)-2-oxo-hexahydro-cyclopentaimidazole-1-carboxylic acid tert-butyl ester

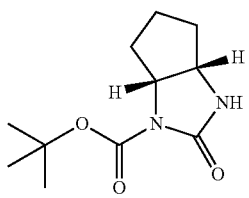 [SMILES: CC(C)(C)OC(=O)N1C(=O)N[C@H]2CCC[C@H]21]

A solution of (rac)-cis-2-(tert-butoxycarbonylamino)cyclopentanecarboxylic acid (2.28 g, 9.98 mmol) and N-methylmorpholine (1.1 g, 1.21 ml, 11.0 mmol, 1.1 equiv.) in 28 ml of dichloroethane was stirred at r.t. for 10 min. Then diphenylphosphoricacid azide (3.02 g, 2.37 ml, 11.0 mmol, 1.1 equiv.) was added dropwise at room temperature and the colorless solution was stirred for 45 min at room temperature during which the solution turned light yellow. The solution was then warmed to 75° C. and stirred overnight and allowed to cool. After workup with dichloromethane/water, the combined organic phases were evaporated to dryness. The orange solid was triturated with ethyl acetate and filtered to give 1.27 g of a white solid. The mother liquors were concentrated and the crystallized material was again filtered to yield an additional 0.55 g of product. One obtains a total yield of 1.82 g (81%) of the title compound as a crystalline white solid, MS: m/e=227.3 (M+H⁺).

Step 2: (3aSR, 6aRS)-3-Methyl-2-oxo-hexahydro-cyclopentaimidazole-1-carboxylic acid tert-butyl ester

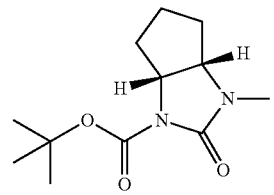 [SMILES: CN1C(=O)N(C(=O)OC(C)(C)C)[C@@H]2CCC[C@@H]21]

To a solution of (3aSR, 6aRS)-2-oxo-hexahydro-cyclopentaimidazole-1-carboxylic acid tert-butyl ester (Example 106, step 1) (1.82 g, 8.04 mmol) in 30 ml of DMF was added a 60% suspension of sodium hydride in mineral oil (386 mg, 9.65 mmol, 1.2 equiv.). The suspension was stirred for 45 minutes at room temperature (gas evolution), then iodomethane (0.604 ml, 9.65 mmol, 1.2 equiv.) was added and the mixture was stirred at room temperature overnight. After concentration in vaccuo and workup with ethyl acetate/water, 2.05 g of a yellow oil were obtained containing mineral-oil drops which was directly used in the next step without further characterisation.

Step 3: (3aRS, 6aSR)-1-Methyl-hexahydro-cyclopentaimidazol-2-one

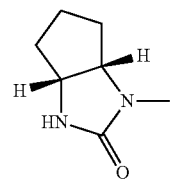

To a solution of (3aSR, 6aRS)-3-methyl-2-oxo-hexahydro-cyclopentaimidazole-1-carboxylic acid tert-butyl ester (Example 106, step 2) (1.99 g, 8.28 mmol) in 30 ml of dichloromethane was added trifluoroacetic acid (7.55 g, 5.1 ml, 66.3 mmol, 8 equiv.) and the yellow solution was stirred at for 5 h at room temperature. The reaction mixture was quenched by addition of saturated sodium bicarbonate solution and the pH of the aqueous phase was set to 9. After workup with dichloromethane/water, the organic phases were dried, filtered and concentrated in vaccuo to yield 1.07 g of an off-white solid, which was taken up in cold ethyl acetate and filtered to yield the title compound (822 mg, 71%) as a crystalline white solid which was directly used in the next step without further characterisation.

Step 4: (3aRS, 6aSR)-1-methyl-3-(5-(phenylethynyl)pyridin-2-yl)hexahydrocyclopenta [d]imidazol-2 (1H)-one

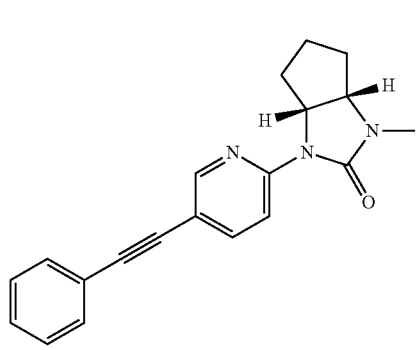 [SMILES: CN1C(=O)N(c2ccc(C#Cc3ccccc3)cn2)[C@@H]2CCC[C@@H]21]

To a suspension of 2-bromo-5-(phenylethynyl)pyridine (Example 96, step 1) (55.0 mg, 0.213 mmol), (3aR,6aS)-1-methylhexahydrocyclopenta[d]imidazol-2(1H)-one (Example 106, step 3) (35.8 mg, 0.256 mmol, 1.2 equiv.), 139 mg cesium carbonate (139 mg, 0.426 mmol, 2 equiv.), and 4,5-bis(diphenylphosphino)-9,9-dimethylxanthene (xantphos) (5 mg, 0.008 mmol, 0.04 equiv.) in 1 ml of toluene was added under argon atmosphere tris(dibenzylideneacetone)dipalladium(0) (Pd$_2$(dba)$_3$) (4 mg, 0.0046 mmol, 0.02 equiv.). The mixture was stirred overnight at 70° C. The mixture was directly loaded on a 20 g silicagel column and was eluted with a heptane to 33% ethylacetate in heptane gradient to yield the title compound (49 mg, 73%) as an amorphous light-yellow solid, MS: m/e=318.1 (M+H$^+$).

Example 107

(RS)-4-tert-Butyl-3-methyl-1-(5-phenylethynyl-pyridin-2-yl)-imidazolidin-2-one

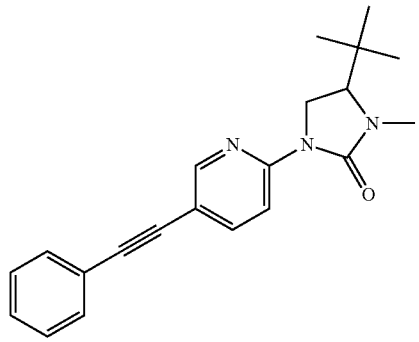 [SMILES: CN1C(=O)N(c2ccc(C#Cc3ccccc3)cn2)CC1C(C)(C)C]

The title compound was obtained as a light yellow solid, MS: m/e=334.1 (M+H$^+$), using procedures similar to those described in Example 106 starting from (rac)-2-(tert-butoxycarbonylamino-methyl)-3,3-dimethyl-butyric acid instead of (rac)-cis-2-(tert-butoxycarbonylamino)cyclopentanecarboxylic acid.

Examples 108

1-[5-(3-Fluoro-phenylethynyl)-3-methyl-pyridin-2-yl]-3,4,4-trimethyl-imidazolidin-2-one

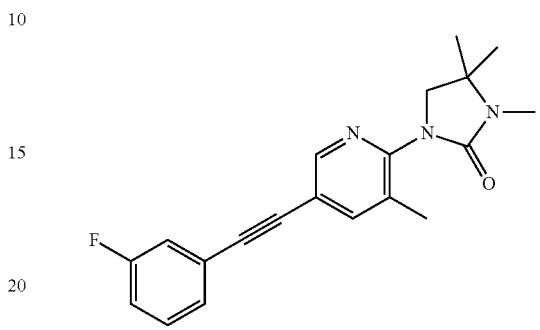

Step 1: 4,4-Dimethyl-1-(3-methyl-5-trimethylsilanylethynyl-pyridin-2-yl)-imidazolidin-2-one

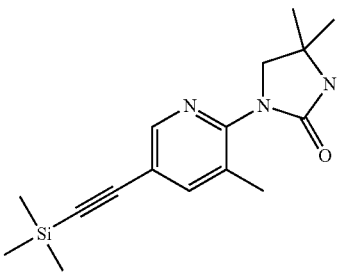

The title compound was obtained as a yellow solid, MS: m/e=302.1 (M+H$^+$), using chemistry similar to that described in Example 37, step 2 from 2-bromo-3-methyl-5-trimethylsilanylethynyl-pyridine (Example 41, step 1) and 4,4-dimethyl-imidazolidin-2-one (CAS 24572-33-6).

Step 2: 1-[5-(3-Fluoro-phenylethynyl)-3-methylpyridin-2-yl]-4,4-dimethyl-imidazolidin-2-one

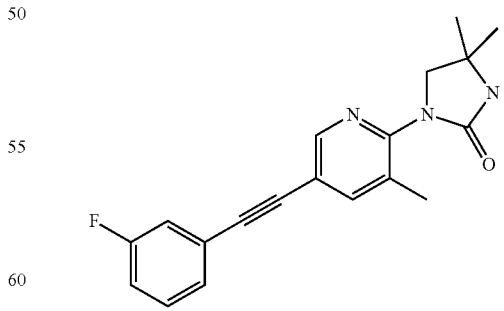

The title compound was obtained as a light yellow solid, MS: m/e=324.4 (M+H$^+$), using chemistry similar to that described in Example 37, step 3 from 4,4-dimethyl-1-(3-methyl-5-trimethylsilanylethynyl-pyridin-2-yl)-imidazolidin-2-one (Example 108, step 1) and 1-fluoro-3-iodobenzene.

Step 3: 1-[5-(3-Fluoro-phenylethynyl)-3-methyl-pyridin-2-yl]-3,4,4-trimethyl-imidazolidin-2-one

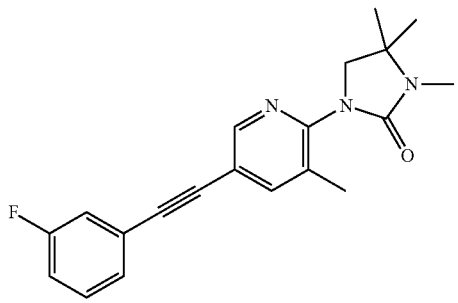 [SMILES: Cc1cc(C#Cc2cccc(F)c2)cnc1N1CC(C)(C)N(C)C1=O]

The title compound was obtained as a light yellow solid, MS: m/e=338.3 (M+H⁺), using chemistry similar to that described in Example 16 from 1-[5-(3-fluoro-phenylethynyl)-3-methyl-pyridin-2-yl]-4,4-dimethyl-imidazolidin-2-one (Example 108, step 2) and iodomethane.

Example 109

(3aSR,6aRS)-1-[5-(3-Fluoro-phenylethynyl)-pyridin-2-yl]-3-methyl-hexahydro-cyclopenta-imidazol-2-one

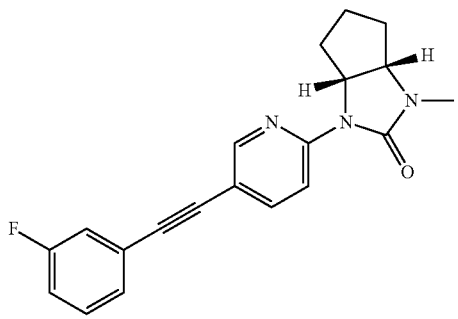 [SMILES: CN1C(=O)N(c2ccc(C#Cc3cccc(F)c3)cn2)[C@@H]2CCC[C@@H]21]

Step 1: (3aRS,6aSR)-1-Methyl-3-(5-trimethylsilanyl-ethynyl-pyridin-2-yl)-hexahydro-cyclopenta-imidazol-2-one

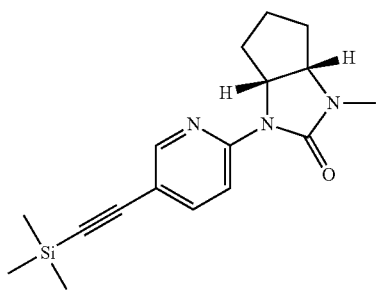

The title compound, an off-white solid, MS: m/e=314.1 (M+H⁺), was prepared in accordance with the general method of example 106, step 4 starting from 2-bromo-5-((trimethyl-silyl)ethynyl)-pyridine (Example 37, step 1) and (3aRS,6aSR)-1-methylhexahydrocyclopenta[d]imidazol-2(1H)-one (Example 106, step 3).

Step 2: (3aSR,6aRS)-1-[5-(3-Fluoro-phenylethynyl)-pyridin-2-yl]-3-methyl-hexahydro-cyclopenta-imidazol-2-one

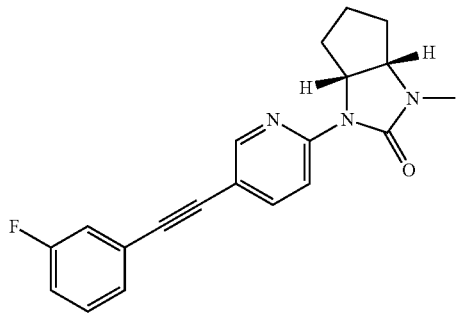 [SMILES: CN1C(=O)N(c2ccc(C#Cc3cccc(F)c3)cn2)[C@@H]2CCC[C@@H]21]

The title compound, a light yellow oil, MS: m/e=336.2 (M+H⁺), was prepared in accordance with the general method of Example 37, step 3 starting from (3aRS,6aSR)-1-methyl-3-(5-trimethylsilanylethynyl-pyridin-2-yl)-hexahydro-cyclopenta-imidazol-2-one (Example 109, step 1) and 1-fluoro-3-iodobenzene.

Example 110

1-[5-Fluoro-5-(4-fluoro-phenylethynyl)-pyridin-2-yl]-3,4,4-trimethyl-imidazolidin-2-one

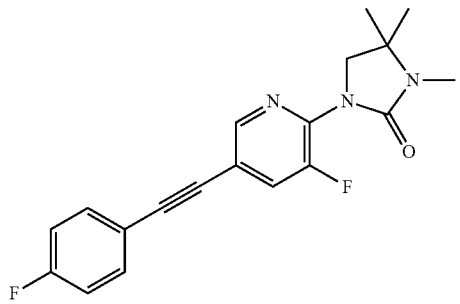 [SMILES: CN1C(=O)N(c2ncc(C#Cc3ccc(F)cc3)cc2F)CC1(C)C]

Step 1: 1-(3-Fluoro-5-iodo-pyridin-2-yl)-4,4-dimethyl-imidazolidin-2-one

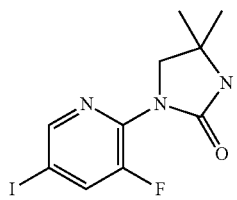 [SMILES: CC1(C)CN(c2ncc(I)cc2F)C(=O)N1]

2,3-Difluoro-5-iodopyridine (300 mg, 1.24 mmol) was dissolved in 2 ml toluene. (140 mg, 1.24 mmol, 1 equiv.) 4,4-Dimethylimidazolidin-2-one (CAS 24572-33-6) and cesium carbonate (650 mg, 1.99 mmol, 1.6 equiv.) were added and the mixture was heated to 100° C. for 4 hours. The reaction mixture was loaded directly onto a silica gel column and purified by flash chromatography eluting with an ethyl acetate:heptane gradient 0:100 to 100:0. The desired 1-(3-fluoro-5-iodo-pyridin-2-yl)-4,4-dimethyl-imidazolidin-2-one (205 mg, 49% yield) was obtained as a white solid, MS: m/e=336.1 (M+H⁺).

Step 2: 1-(3-Fluoro-5-iodo-pyridin-2-yl)-3,4,4-trimethyl-imidazolidin-2-one

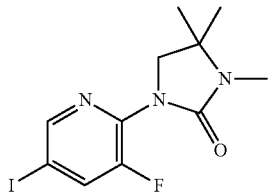 [SMILES: CN1C(=O)N(c2ncc(I)cc2F)CC1(C)C]

The title compound, a yellow oil, MS: m/e=350.0 (M+H⁺), was prepared in accordance with the general method of Example 16 from 1-(3-fluoro-5-iodo-pyridin-2-yl)-4,4-dimethyl-imidazolidin-2-one (Example 110, step 1) and iodomethane.

Step 3: 1-[3-Fluoro-5-(4-fluoro-phenylethynyl)-pyridin-2-yl]-3,4,4-trimethyl-imidazolidin-2-one

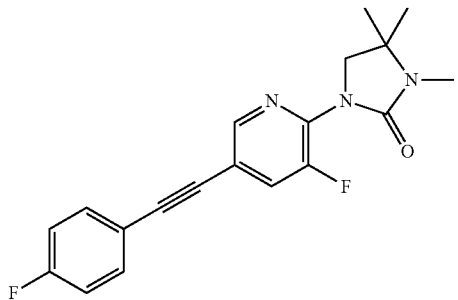 [SMILES: CN1C(=O)N(c2ncc(C#Cc3ccc(F)cc3)cc2F)CC1(C)C]

The title compound was obtained as a light yellow solid, MS: m/e=342.1 (M+H⁺), using chemistry similar to that described in Example 1, step 3 from 1-(3-fluoro-5-iodo-pyridin-2-yl)-3,4,4-trimethyl-imidazolidin-2-one (Example 110, step 2) and 1-ethynyl-4-fluorobenzene.

Example 111

1-[5-Fluoro-5-(3-fluoro-phenylethynyl)-pyridin-2-yl]-3,4,4-trimethyl-imidazolidin-2-one

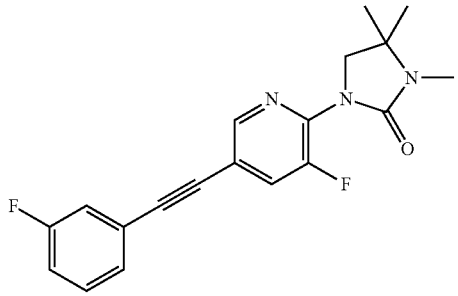 [SMILES: CN1C(=O)N(c2ncc(C#Cc3cccc(F)c3)cc2F)CC1(C)C]

The title compound was obtained as a light yellow solid, MS: m/e=342.1 (M+H⁺), using chemistry similar to that described in Example 1, step 3 from 1-(3-fluoro-5-iodo-pyridin-2-yl)-3,4,4-trimethyl-imidazolidin-2-one (Example 110, step 2) and 1-ethynyl-3-fluorobenzene.

Example 112

6-[5-(4-Fluoro-phenylethynyl)-pyridin-2-yl]-4-methyl-4,6-diaza-spiro[2.4]heptan-5-one

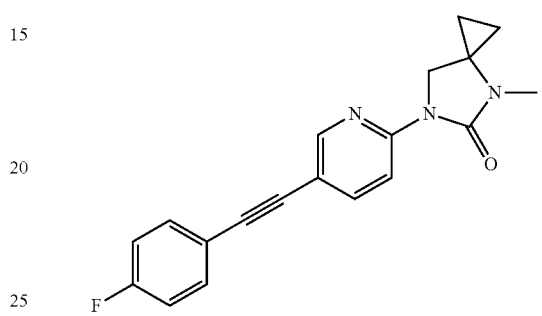

Step 1: 4-Methyl-4,6-diaza-spiro[2.4]heptan-5-one

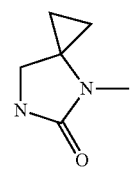

The title compound was obtained as a white solid using procedures similar to those described in Example 106, step 1 to 3 starting from 1-((tert-butoxycarbonylamino)methyl)cyclopropanecarboxylic acid instead of (rac)-cis-2-(tert-butoxycarbonylamino)cyclopentanecarboxylic acid.

Step 2: 4-Methyl-6-(5-trimethylsilanylethynyl-pyridin-2-yl)-4,6-diaza-spiro[2.4]heptan-5-one

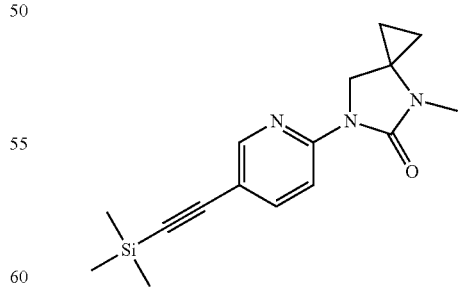

The title compound was obtained as a white solid, MS: m/e=300.2 (M+H⁺), using chemistry similar to that described in Example 37, step 2 from 2-bromo-5-trimethylsilanylethynyl-pyridine (Example 37, step 1) and 4-methyl-4,6-diaza-spiro[2.4]heptan-5-one (Example 112, step 1).

Step 3: 6-[5-(4-Fluoro-phenylethynyl)-pyridin-2-yl]-4-methyl-4,6-diaza-spiro[2.4]heptan-5-one

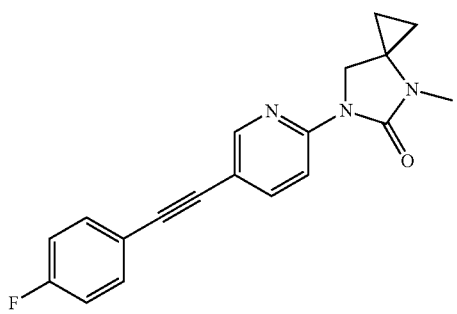 [SMILES: CN1C(=O)N(c2ccc(C#Cc3ccc(F)cc3)cn2)CC12CC2]

The title compound was obtained as a light yellow solid, MS: m/e=322.2 (M+H⁺), using chemistry similar to that described in Example 37, step 3 from 4-methyl-6-(5-trimethylsilanylethynyl-pyridin-2-yl)-4,6-diaza-spiro[2.4]heptan-5-one (Example 112, step 2) and 1-fluoro-4-iodobenzene.

Example 113

6-[5-(3-Fluoro-phenylethynyl)-pyridin-2-yl]-4-methyl-4,6-diaza-spiro[2.4]heptan-5-one

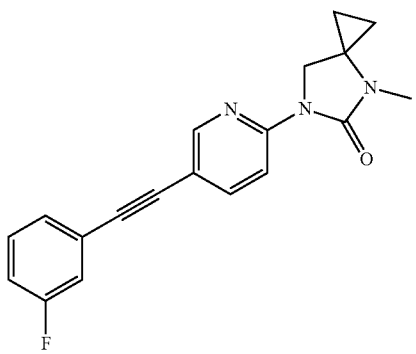 [SMILES: CN1C(=O)N(c2ccc(C#Cc3cccc(F)c3)cn2)CC12CC2]

The title compound was obtained as a light brown solid, MS: m/e=322.2 (M+H⁺), using chemistry similar to that described in Example 37, step 3 from 4-methyl-6-(5-trimethylsilanylethynyl-pyridin-2-yl)-4,6-diaza-spiro[2.4]heptan-5-one (Example 112, step 2) and 1-fluoro-3-iodobenzene.

Example 114

(RS)-5-Methoxy-6,6-dimethyl-3-(5-phenylethynyl-pyridin-2-yl)-[1,3]oxazinan-2-one

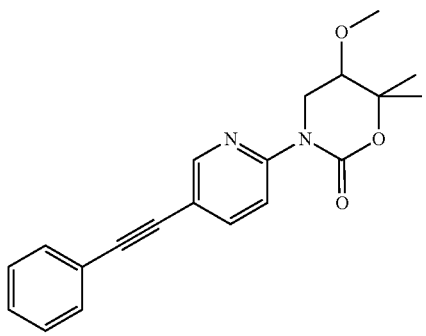 [SMILES: COC1CN(c2ccc(C#Cc3ccccc3)cn2)C(=O)OC1(C)C]

Step 1: (RS)-3-Benzyloxycarbonylamino-2-methoxy-propionic acid methyl ester

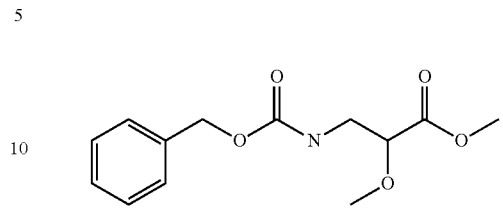

The title compound was obtained using chemistry similar to that described in Example 16 starting from (RS)-3-benzyloxycarbonylamino-2-hydroxy-propionic acid methyl ester, which was directly used in the next step without further characterisation.

Step 2: (RS)-5-Methoxy-6,6-dimethyl-[1,3]oxazinan-2-one

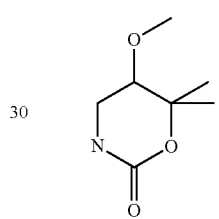

The title compound was obtained as a light yellow oil, MS: m/e=160.2 (M+H⁺), using procedures similar to those described in Example 95, step 2 and Example 72, step 2 from (RS)-3-benzyloxycarbonylamino-2-methoxy-propionic acid methyl ester (Example 114, step 1).

Step 3: (RS)-5-Methoxy-6,6-dimethyl-3-(5-phenylethynyl-pyridin-2-yl)-[1,3]oxazinan-2-one

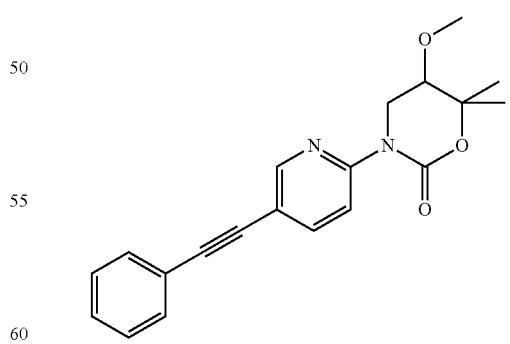

The title compound was obtained as a light yellow oil, MS: m/e=337.3 (M+H⁺), using chemistry similar to that described in Example 37, step 2 from 2-bromo-5-phenylethynyl-pyridine (Example 96, step 1) and (RS)-5-methoxy-6,6-dimethyl-[1,3]oxazinan-2-one (Example 114, step 2).

Example 115

4,4-Dimethyl-1-(5-phenylethynyl-pyrimidin-2-yl)-pyrrolidin-2-one

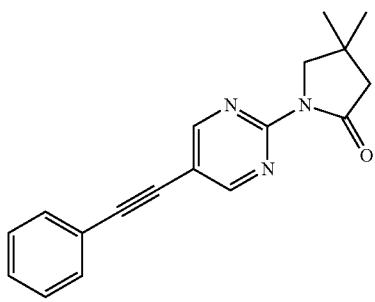

Step 1:
2-Methanesulfonyl-5-phenylethynyl-pyrimidine

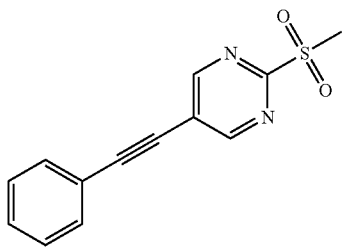 [SMILES: CS(=O)(=O)c1ncc(C#Cc2ccccc2)cn1]

Bis-(triphenylphosphine)-palladium(II)dichloride (1.48 g, 2.11 mmol, 0.05 equiv.) was dissolved in 200 ml THF. (10 g, 42.2 mmol) 5-Bromo-2-(methylsulfonyl)pyrimidine and phenylacetylene (9.26 ml, 84.4 mmol, 2 equiv.) were added at room temperature. Triethylamine (17.6 ml, 127 mmol, 3 equiv.), triphenylphosphine (330 mg, 1.3 mmol, 0.03 equiv.) and copper(I)iodide (80 mg, 420 µmol, 0.01 equiv.) were added and the mixture was stirred for 4 hours at 65° C. The reaction mixture was cooled and extracted with saturated NaHCO₃ solution and two times with EtOAc. The organic layers were extracted with water, dried over sodium sulfate and evaporated to dryness. The crude product was purified by flash chromatography on a silica gel column and eluting with an ethyl acetate:heptane gradient 0:100 to 100:0. The desired 2-methanesulfonyl-5-phenylethynyl-pyrimidine (6.2 g, 57% yield) was obtained as a yellow solid, MS: m/e=259.1 (M+H$^+$).

Step 2: 4,4-Dimethyl-1-(5-phenylethynyl-pyrimidin-2-yl)-pyrrolidin-2-one

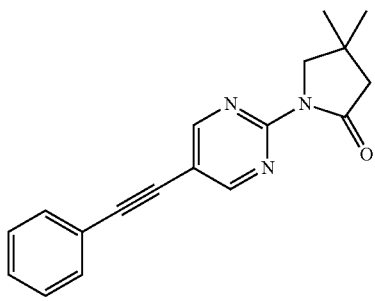 [SMILES: CC1(C)CC(=O)N(c2ncc(C#Cc3ccccc3)cn2)C1]

(100 mg, 0.39 mmol) 2-Methanesulfonyl-5-phenylethynyl-pyrimidine (Example 115, step 1) was dissolved in 1 ml dioxane. 4,4-Dimethylpyrrolidin-2-one (53 mg, 465 µmol, 1.2 equiv.) and cesium carbonate (190 mg, 580 µmol, 1.5 equiv.) were added at room temperature. The mixture was stirred for 4 hours at 100° C. The reaction mixture was cooled, evaporated and extracted with saturated NaHCO₃ solution and two times with a small volume of dichloromethane. The crude product was purified by flash chromatography by directly loading the dichloromethane layers onto a silica gel column and eluting with an ethyl acetate:heptane gradient 0:100 to 100:0. The desired 4,4-dimethyl-1-(5-phenylethynyl-pyrimidin-2-yl)-pyrrolidin-2-one (32 mg, 28% yield) was obtained as a light yellow solid, MS: m/e=292.1 (M+H$^+$).

Example 116

5,5-Dimethyl-1-(5-phenylethynyl-pyrimidin-2-yl)-piperidin-2-one

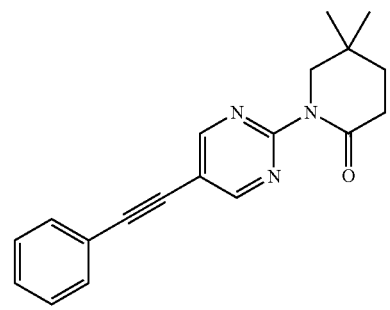 [SMILES: CC1(C)CCC(=O)N(c2ncc(C#Cc3ccccc3)cn2)C1]

The title compound was obtained as a brown oil, MS: m/e=306.2 (M+H$^+$), using chemistry similar to that described in Example 115, step 2 from 2-methanesulfonyl-5-phenylethynyl-pyrimidine (Example 115, step 1) and 5,5-dimethylpiperidin-2-one (CAS 4007-79-8).

Example 117

2-(5-Phenylethynyl-pyrimidin-2-yl)-2-aza-spiro[4.4]nonan-3-one

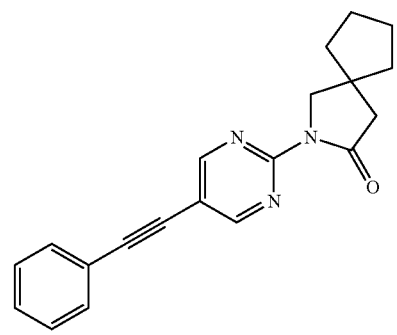

The title compound was obtained as a light yellow solid, MS: m/e=318.2 (M+H$^+$), using chemistry similar to that described in Example 115, step 2 from 2-methanesulfonyl-5-phenylethynyl-pyrimidine (Example 115, step 1) and 2-aza-spiro[4.4]nonan-3-one (CAS 75751-72-3).

Example 118

1-[5-(3-Fluoro-phenylethynyl)-pyrimidin-2-yl]-4,4-dimethyl-pyrrolidin-2-one

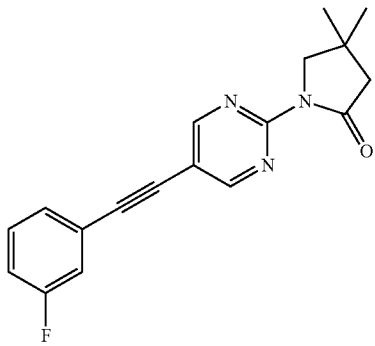 [SMILES: CC1(C)CC(=O)N(c2ncc(C#Cc3cccc(F)c3)cn2)C1]

Step 1: 1-(5-Bromo-pyrimidin-2-yl)-4,4-dimethyl-pyrrolidin-2-one

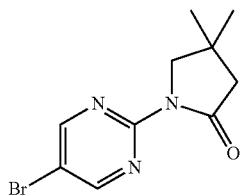

The title compound was obtained as a light yellow solid, MS: m/e=270.1/272.2 (M+H$^+$), using chemistry similar to that described in Example 115, step 2 from 5-bromo-2-fluoropyrimidine and 4,4-dimethylpyrrolidin-2-one.

Step 2: 1-[5-(3-Fluoro-phenylethynyl)-pyrimidin-2-yl]-4,4-dimethyl-pyrrolidin-2-one

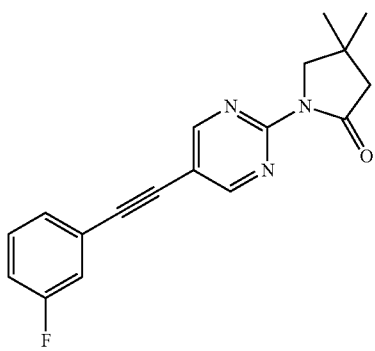 [SMILES: CC1(C)CC(=O)N(c2ncc(C#Cc3cccc(F)c3)cn2)C1]

The title compound was obtained as a light yellow solid, MS: m/e=310.2 (M+H$^+$), using chemistry similar to that described in Example 115, step 1 from 1-(5-bromo-pyrimidin-2-yl)-4,4-dimethyl-pyrrolidin-2-one (Example 118, step 1) and 1-ethynyl-3-fluoro-benzene.

Example 119

1-[5-(3-Chloro-phenylethynyl)-pyrimidin-2-yl]-4,4-dimethyl-pyrrolidin-2-one

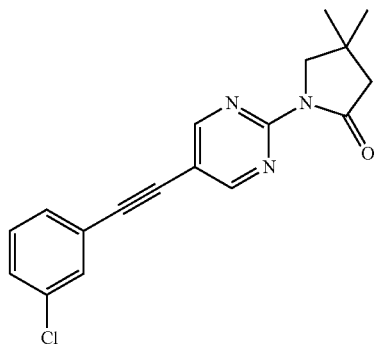 [SMILES: CC1(C)CC(=O)N(c2ncc(C#Cc3cccc(Cl)c3)cn2)C1]

Step 1: 2-Chloro-5-(3-chloro-phenylethynyl)-pyrimidine

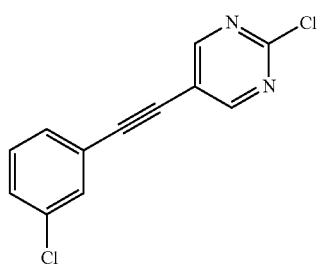 [SMILES: Clc1cccc(C#Cc2cnc(Cl)nc2)c1]

The title compound was obtained as a light brown solid, MS: m/e=248/250 (M+H$^+$), using chemistry similar to that described in Example 115, step 1 from 2-chloro-5-iodopyrimidine and 1-chloro-3-ethynyl-benzene.

Step 2: 1-[5-(3-Chloro-phenylethynyl)-pyrimidin-2-yl]-4,4-dimethyl-pyrrolidin-2-one

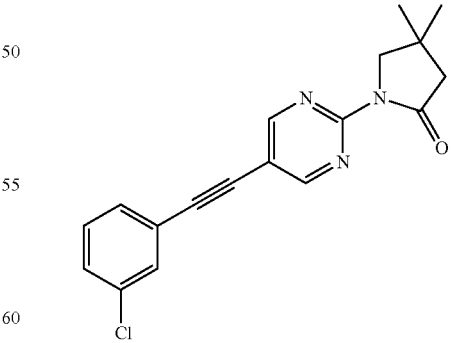

The title compound was obtained as a light yellow solid, MS: m/e=326.3/328.3 (M+H$^+$), using chemistry similar to that described in Example 115, step 2 from 2-chloro-5-(3-chloro-phenylethynyl)-pyrimidine (Example 119, step 1) and 4,4-dimethylpyrrolidin-2-one.

Example 120

1-[5-(4-Fluoro-phenylethynyl)-pyrimidin-2-yl]-4,4-dimethyl-pyrrolidin-2-one

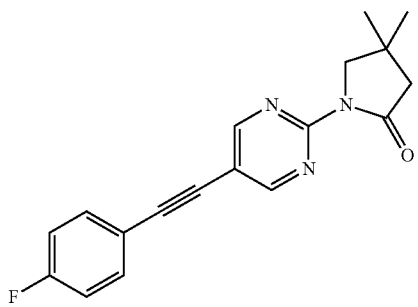 [SMILES: CC1(C)CC(=O)N(c2ncc(C#Cc3ccc(F)cc3)cn2)C1]

Step 1: 2-Bromo-5-trimethylsilanylethynyl-pyrimidine

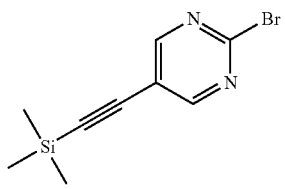

2-Bromo-5-iodopyrimidine (1.2 g, 4.2 mmol) was dissolved under nitrogen in 25 ml THF. Bis-(triphenylphosphine)-palladium(II)dichloride (300 mg, 420 µmol, 0.1 equiv.), ethynyltrimethylsilane (540 mg, 0.77 ml, 5.48 mmol, 1.3 equiv.), triethylamine (0.85 g, 1.17 ml, 8.4 mmol, 2 equiv.) and copper(I)iodide (40 mg, 210 µmol, 0.05 equiv.) were added and the mixture was stirred for 4 hours at 50° C. The reaction mixture was cooled and evaporated to dryness. The crude product was purified by flash chromatography on silica gel, eluting with an ethyl acetate:heptane gradient 0:100 to 40:60. The desired 2-bromo-5-trimethylsilanylethynyl-pyrimidine (0.75 g, 70% yield) was obtained as a yellow solid, MS: m/e=255/257 (M+H$^+$).

Step 2: 4,4-Dimethyl-1-(5-trimethylsilanylethynyl-pyrimidin-2-yl)-pyrrolidin-2-one

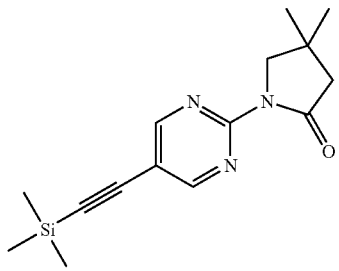 [SMILES: CC1(C)CC(=O)N(c2ncc(C#C[Si](C)(C)C)cn2)C1]

(200 mg, 0.78 mmol) 2-Bromo-5-trimethylsilanylethynyl-pyrimidine (Example 120, step 1) was dissolved in toluene (7 ml) and 4,4-dimethylpyrrolidin-2-one (89 mg, 0.78 mmol, 1.0 equiv.), cesium carbonate (410 mg, 1.25 mmol, 1.6 equiv.), xantphos (CAS 161265-03-8) (18 mg, 0.03 mmol, 0.04 equiv.) and Pd$_2$(dba)$_3$ (14 mg, 0.01 mmol, 0.02 equiv.) were added under nitrogen. The mixture was stirred for 2 hours at 90° C. The crude product was purified by flash chromatography by directly loading the toluene mixture onto a silica gel column and eluting with an ethyl acetate:heptane gradient 0:100 to 100:0. The desired 4,4-dimethyl-1-(5-trimethylsilanylethynyl-pyrimidin-2-yl)-pyrrolidin-2-one (164 mg, 73% yield) was obtained as a light red solid, MS: m/e=288.1 (M+H$^+$).

Step 3: 1-[5-(4-Fluoro-phenylethynyl)-pyridin-2-yl]-4,4-dimethyl-pyrrolidin-2-one

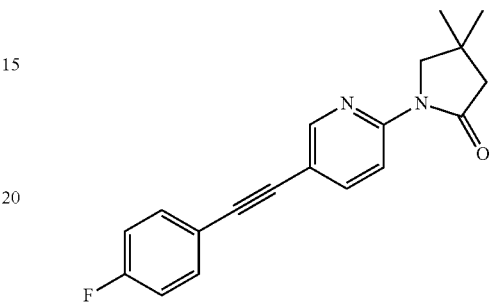

4,4-Dimethyl-1-(5-trimethylsilanylethynyl-pyrimidin-2-yl)-pyrrolidin-2-one (Example 120, step 2) (30 mg, 0.1 mmol) was dissolved in DMF (1 ml). 1-Fluoro-4-iodobenzene (32 mg, 0.14 mmol, 1.4 equiv.), Et$_3$N (43 µl, 0.31 mmol, 3 equiv.), Bis-(triphenylphosphine)-palladium(II)dichloride (4 mg, 5.2 µmol, 0.05 equiv.) and copper(I)iodide (0.6 mg, 3.1 µmol, 0.03 equiv.) were added under nitrogen and the mixture was heated to 70° C. TBAF 1M in THF (115 µl, 0.115 mmol, 1.1 equiv.) was added dropwise in 20 minutes at 70° C. The reaction mixture was stirred for 30 minutes at 70° C. and evaporated with isolute to dryness. The crude product was purified by flash chromatography with a 20 g silica gel column and eluting with heptane:ethyl acetate 100:0->0:100. The desired 1-[5-(4-fluoro-phenylethynyl)-pyridin-2-yl]-4,4-dimethyl-pyrrolidin-2-one (24 mg, 73% yield) was obtained as a white solid, MS: m/e=310.1 (M+H$^+$).

Example 121

1-[5-(2,5-Difluoro-phenylethynyl)-pyrimidin-2-yl]-4,4-dimethyl-pyrrolidin-2-one

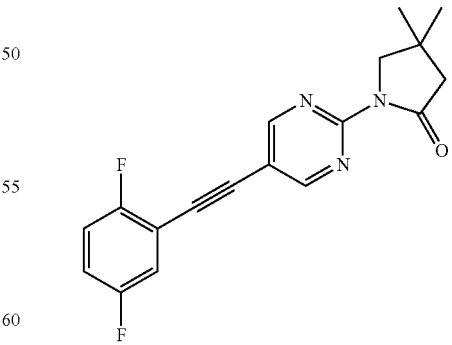

The title compound was obtained as a white solid, MS: m/e=328.2 (M+H$^+$), using chemistry similar to that described in Example 120, step 3 from 4,4-dimethyl-1-(5-trimethylsilanylethynyl-pyrimidin-2-yl)-pyrrolidin-2-one (Example 120, step 2) and 1,4-difluoro-2-iodobenzene.

Example 122

3,4,4-Trimethyl-1-(5-phenylethynyl-pyrimidin-2-yl)-imidazolidin-2-one

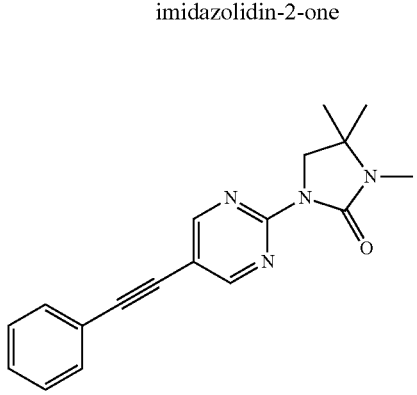

Step 1: 1-(5-Iodo-pyrimidin-2-yl)-4,4-dimethyl-imidazolidin-2-one

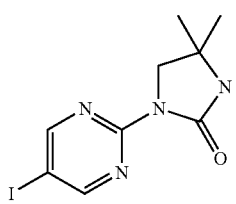

The title compound was obtained as a light yellow solid, MS: m/e=319 (M+H⁺), using chemistry similar to that described in Example 115, step 2 from 2-chloro-5-iodopyrimidine and 4,4-dimethyl-imidazolidin-2-one (CAS 24572-33-6).

Step 2: 1-(5-Iodo-pyrimidin-2-yl)-3,4,4-trimethyl-imidazolidin-2-one

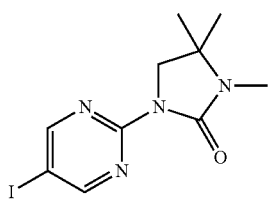 [SMILES: CN1C(=O)N(c2ncc(I)cn2)CC1(C)C]

(55 mg, 173 µmol) 1-(5-Iodo-pyrimidin-2-yl)-4,4-dimethyl-imidazolidin-2-one (Example 122, step 1) was dissolved in DMF (1 ml) and cooled to 0-5° C. NaH (55%) (9 mg, 225 µmol, 1.3 equiv.) was added and the mixture was stirred for 30 min at 0-5° C. Iodomethane (13 µl, 200 µmol, 1.2 equiv.) was added and the mixture was stirred for 30 min without cooling bath. The reaction mixture was treated with sat. NaHCO₃ solution and extracted twice with a small volume of CH₂Cl₂. The organic layers were loaded directly to silica gel column and the crude material was purified by flash chromatography on silica gel (20 gr, ethyl acetate/heptane gradient, 0:100 to 100:0). The desired 1-(5-iodo-pyrimidin-2-yl)-3,4,4-trimethyl-imidazolidin-2-one (31 mg, 54% yield) was obtained as a white solid, MS: m/e=333.1 (M+H⁺).

Step 3: 3,4,4-Trimethyl-1-(5-phenylethynyl-pyrimidin-2-yl)-imidazolidin-2-one

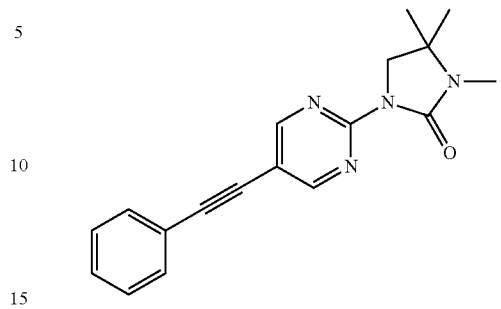

The title compound was obtained as a yellow oil, MS: m/e=307.4 (M+H⁺), using chemistry similar to that described in Example 115, step 1 from 1-(5-iodo-pyrimidin-2-yl)-3,4,4-trimethyl-imidazolidin-2-one (Example 122, step 2) and phenylacetylene.

Example 123

1-[5-(3-Fluoro-phenylethynyl)-pyrimidin-2-yl]-3,4,4-trimethyl-imidazolidin-2-one

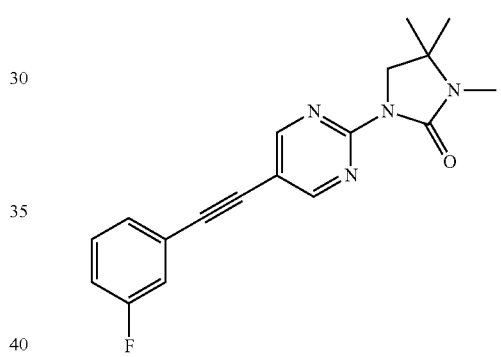

The title compound was obtained as a light yellow solid, MS: m/e=325.2 (M+H⁺), using chemistry similar to that described in Example 115, step 1 from 1-(5-iodo-pyrimidin-2-yl)-3,4,4-trimethyl-imidazolidin-2-one (Example 122, step 2) and 1-ethynyl-3-fluoro-benzene.

Example 124

1-[5-(2,5-Difluoro-phenylethynyl)-pyrimidin-2-yl]-3,4,4-trimethyl-imidazolidin-2-one

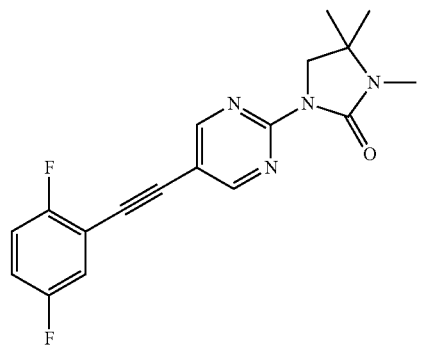 [SMILES: CN1C(=O)N(c2ncc(C#Cc3cc(F)ccc3F)cn2)CC1(C)C]

Step 1: 4,4-Dimethyl-1-(5-trimethylsilanylethynyl-pyrimidin-2-yl)-imidazolidin-2-one

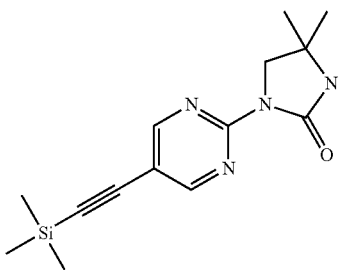

The title compound was obtained as a light yellow solid, MS: m/e=289.0 (M+H⁺), using chemistry similar to that described in Example 120, step 2 from 2-bromo-5-trimethylsilanylethynyl-pyrimidine (Example 120, step 1) and 4,4-dimethyl-imidazolidin-2-one (CAS 24572-33-6).

Step 2: 1-[5-(2,5-Difluoro-phenylethynyl)-pyrimidin-2-yl]-4,4-dimethyl-imidazolidin-2-one

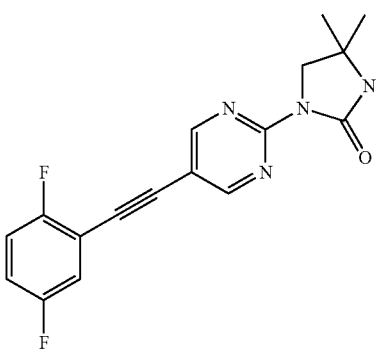 [SMILES: CC1(C)CN(c2ncc(C#Cc3cc(F)ccc3F)cn2)C(=O)N1]

The title compound was obtained as a light brown solid, MS: m/e=329.2 (M+H⁺), using chemistry similar to that described in Example 120, step 3 from 4,4-dimethyl-1-(5-trimethylsilanylethynyl-pyrimidin-2-yl)-imidazolidin-2-one (Example 124, step 1) and 1,4-difluoro-2-iodobenzene.

Step 3: 1-[5-(2,5-Difluoro-phenylethynyl)-pyrimidin-2-yl]-3,4,4-trimethyl-imidazolidin-2-one

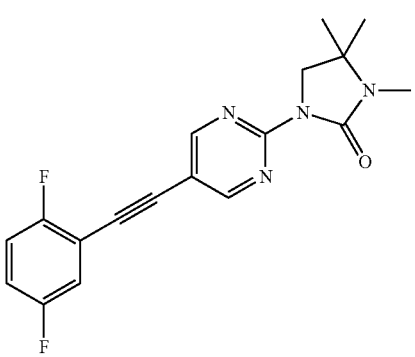 [SMILES: CN1C(=O)N(c2ncc(C#Cc3cc(F)ccc3F)cn2)CC1(C)C]

The title compound was obtained as a white solid, MS: m/e=343.1 (M+H⁺), using chemistry similar to that described in Example 122, step 2 from 1-[5-(2,5-difluoro-phenylethynyl)-pyrimidin-2-yl]-4,4-dimethyl-imidazolidin-2-one (Example 124, step 2) and iodomethane.

Example 125

1-[5-(4-Fluoro-phenylethynyl)-pyrimidin-2-yl]-3,4,4-trimethyl-imidazolidin-2-one

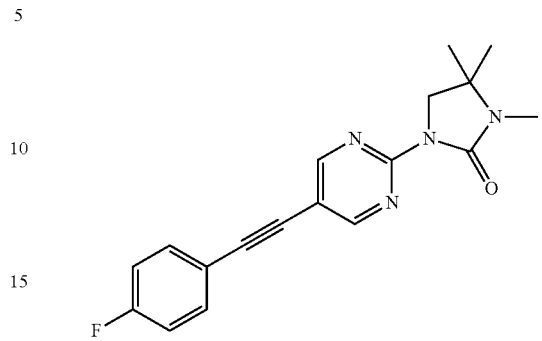

The title compound was obtained as a light brown solid, MS: m/e=325.2 (M+H⁺), using chemistry similar to that described in Example 115, step 1 from 1-(5-iodo-pyrimidin-2-yl)-3,4,4-trimethyl-imidazolidin-2-one (Example 122, step 2) and 1-ethynyl-4-fluoro-benzene.

Example 126

1-[5-(3,4-Difluoro-phenylethynyl)-pyrimidin-2-yl]-3,4,4-trimethyl-imidazolidin-2-one

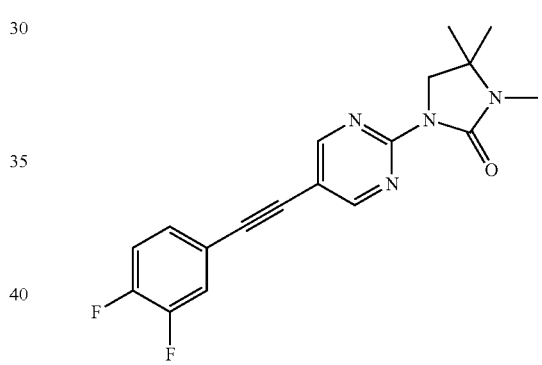

The title compound was obtained as a light brown solid, MS: m/e=343.1 (M+H⁺), using chemistry similar to that described in Example 115, step 1 from 1-(5-iodo-pyrimidin-2-yl)-3,4,4-trimethyl-imidazolidin-2-one (Example 122, step 2) and 4-ethynyl-1,2-difluoro-benzene.

Example 127

(RS)-3-Methoxy-4,4-dimethyl-1-(5-phenylethynyl-pyrimidin-2-yl)-pyrrolidin-2-one

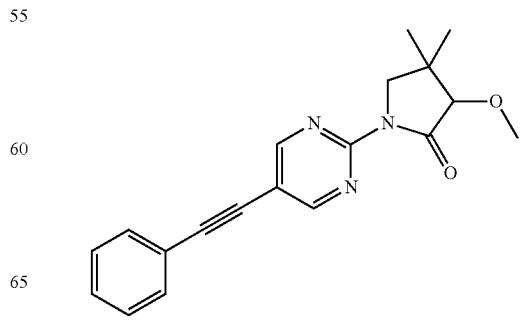

Step 1: (RS)-4-Iodo-N-(5-iodo-pyrimidin-2-yl)-2-methoxy-3,3-dimethyl-butyramide

The title compound was obtained as an orange solid, MS: m/e=476.0 (M+H⁺), using chemistry similar to that described in patent WO9637466, page 17, step 2 starting from (RS)-3-methoxy-4,4-dimethyl-dihydro-furan-2-one (CAS 100101-82-4) instead of 3-t-butylcarbamoyloxy-tetrahydrofuran-2-one and by using 2-amino-5-iodopyrimidine instead of 2-amino-4-trifluoromethylpyridine.

Step 2: (RS)-1-(5-Iodo-pyrimidin-2-yl)-3-methoxy-4,4-dimethyl-pyrrolidin-2-one

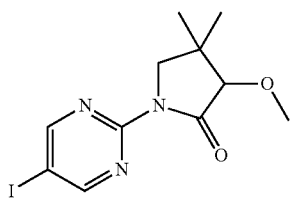 [SMILES: COC1C(=O)N(c2ncc(I)cn2)CC1(C)C]

The title compound was obtained as a light yellow solid, MS: m/e=348.0 (M+H⁺), using chemistry similar to that described in patent WO9637466, page 17, step 3 from (RS)-4-iodo-N-(5-iodo-pyrimidin-2-yl)-2-methoxy-3,3-dimethyl-butyramide (Example 127, step 1).

Step 3: (RS)-3-Methoxy-4,4-dimethyl-1-(5-phenyl-ethynyl-pyrimidin-2-yl)-pyrrolidin-2-one

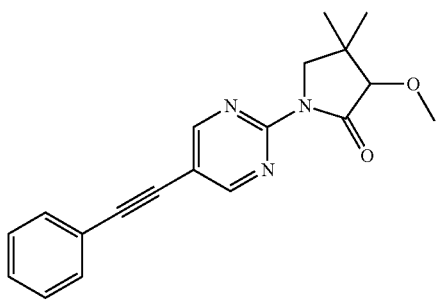 [SMILES: COC1C(=O)N(c2ncc(C#Cc3ccccc3)cn2)CC1(C)C]

The title compound was obtained as a light yellow solid, MS: m/e=322.2 (M+H⁺), using chemistry similar to that described in Example 115, step 1 from (RS)-1-(5-iodo-pyrimidin-2-yl)-3-methoxy-4,4-dimethyl-pyrrolidin-2-one (Example 127, step 2) and phenylacetylene.

Example 128

(5R or 5S)-5-Methoxymethyl-3-(5-phenylethynyl-pyrimidin-2-yl)-oxazolidin-2-one

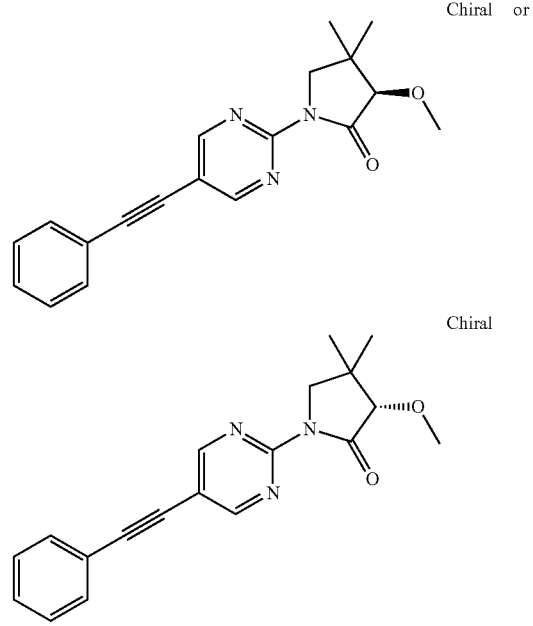

The title compound, a light yellow solid, MS: m/e=322.3 (M+H⁺), was prepared by separation of (RS)-3-methoxy-4,4-dimethyl-1-(5-phenylethynyl-pyrimidin-2-yl)-pyrrolidin-2-one (Example 127) using a chiral column (chiralpak AD with heptane:isopropanol 90:10 as solvent).

Example 129

(5S or 5R)-5-Methoxymethyl-3-(5-phenylethynyl-pyrimidin-2-yl)-oxazolidin-2-one

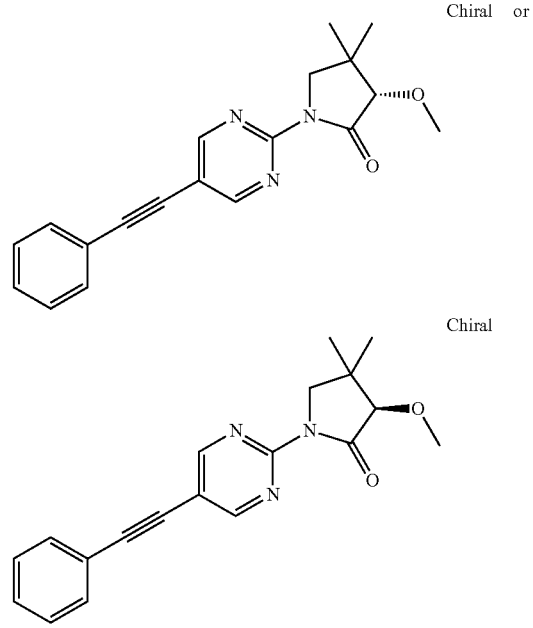

The title compound, a light yellow solid, MS: m/e=322.3 (M+H+), was prepared by separation of (RS)-3-methoxy-4,4-dimethyl-1-(5-phenylethynyl-pyrimidin-2-yl)-pyrrolidin-2-one (Example 127) using a chiral column (chiralpak AD with heptane:isopropanol 90:10 as solvent).

Example 130

(RS)-1-[5-(3-Fluoro-phenylethynyl)-pyrimidin-2-yl]-3-methoxy-4,4-dimethyl-pyrrolidin-2-one

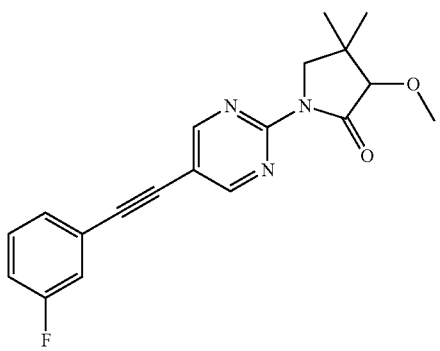 [SMILES: COC1C(=O)N(c2ncc(C#Cc3cccc(F)c3)cn2)CC1(C)C]

The title compound was obtained as a yellow solid, MS: m/e=340.2 (M+H+), using chemistry similar to that described in Example 115, step 1 from (RS)-1-(5-iodo-pyrimidin-2-yl)-3-methoxy-4,4-dimethyl-pyrrolidin-2-one (Example 127, step 2) and 1-ethynyl-3-fluoro-benzene.

Example 131

(R or S)-1-[5-(3-Fluoro-phenylethynyl)-pyrimidin-2-yl]-3-methoxy-4,4-dimethyl-pyrrolidin-2-one

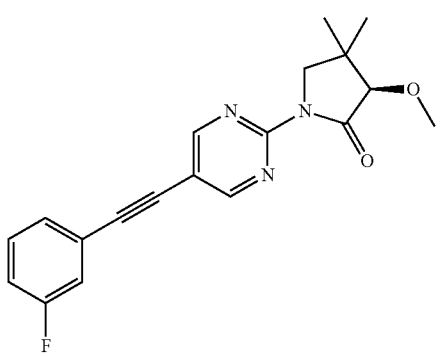

The title compound, a white solid, MS: m/e=340.3 (M+H+), was prepared by separation of (RS)-1-[5-(3-fluoro-phenylethynyl)-pyrimidin-2-yl]-3-methoxy-4,4-dimethyl-pyrrolidin-2-one (Example 130) using a chiral column (chiralpak AD with heptane:isopropanol 90:10 as solvent).

Example 132

(S or R)-1-[5-(3-Fluoro-phenylethynyl)-pyrimidin-2-yl]-3-methoxy-4,4-dimethyl-pyrrolidin-2-one

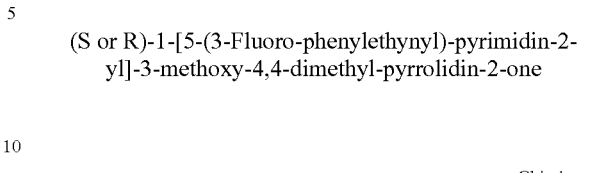

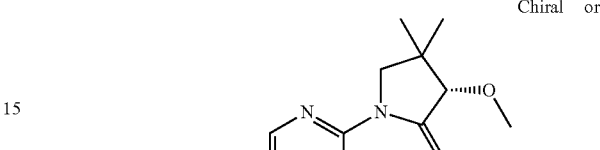

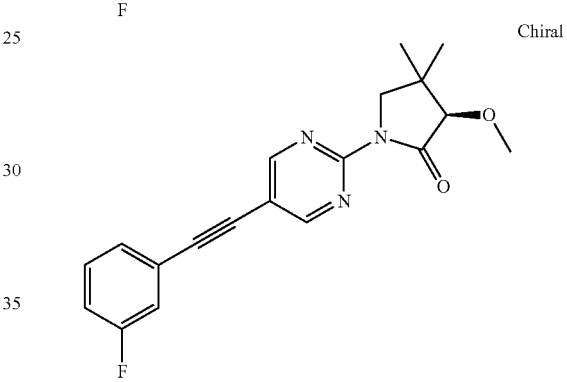

The title compound, a white solid, MS: m/e=340.3 (M+H+), was prepared by separation of (RS)-1-[5-(3-fluoro-phenylethynyl)-pyrimidin-2-yl]-3-methoxy-4,4-dimethyl-pyrrolidin-2-one (Example 130) using a chiral column (chiralpak AD with heptane:isopropanol 90:10 as solvent).

Example 133

(R or S)-1-[5-(2,5-Difluoro-phenylethynyl)-pyrimidin-2-yl]-3-methoxy-4,4-dimethyl-pyrrolidin-2-one

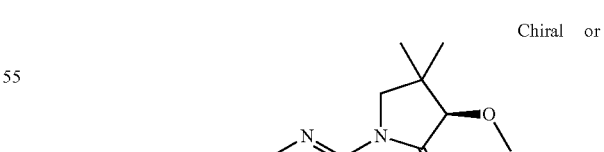

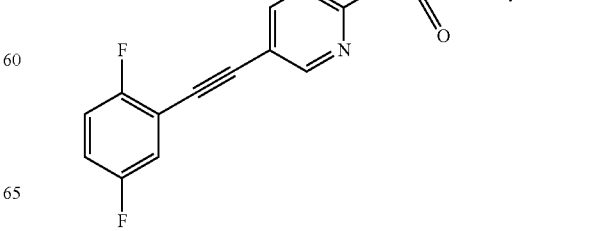

-continued

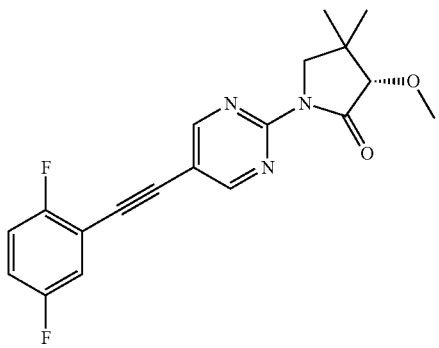

Step 1: (RS)-3-Methoxy-4,4-dimethyl-1-(5-trimethylsilanylethynyl-pyrimidin-2-yl)-pyrrolidin-2-one

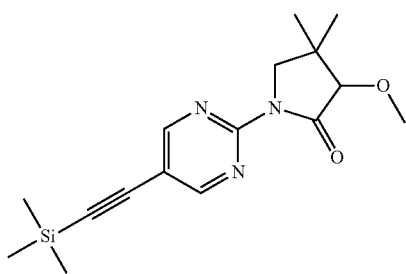

The title compound was obtained as a light brown solid, MS: m/e=318.1 (M+H$^+$), using chemistry similar to that described in Example 115, step 1 from (RS)-1-(5-iodo-pyrimidin-2-yl)-3-methoxy-4,4-dimethyl-pyrrolidin-2-one (Example 127, step 2) and ethynyl-trimethyl-silane.

Step 2: (RS)-1-[5-(2,5-Difluoro-phenylethynyl)-pyrimidin-2-yl]-3-methoxy-4,4-dimethyl-pyrrolidin-2-one

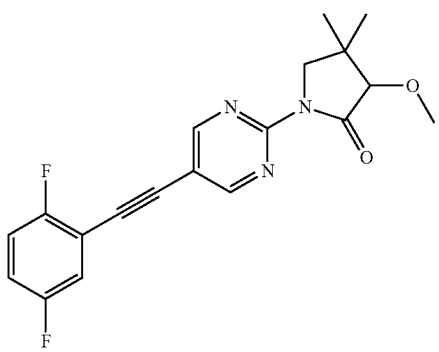 [SMILES: COC1C(=O)N(c2ncc(C#Cc3cc(F)ccc3F)cn2)CC1(C)C]

The title compound was obtained as a yellow solid, MS: m/e=358.1 (M+H$^+$), using chemistry similar to that described in Example 120, step 3 from (RS)-3-methoxy-4,4-dimethyl-1-(5-trimethylsilanylethynyl-pyrimidin-2-yl)-pyrrolidin-2-one (Example 133, step 1) and 1,4-difluoro-2-iodo-benzene.

Step 3: (R or S)-1-[5-(2,5-Difluoro-phenylethynyl)-pyrimidin-2-yl]-3-methoxy-4,4-dimethyl-pyrrolidin-2-one

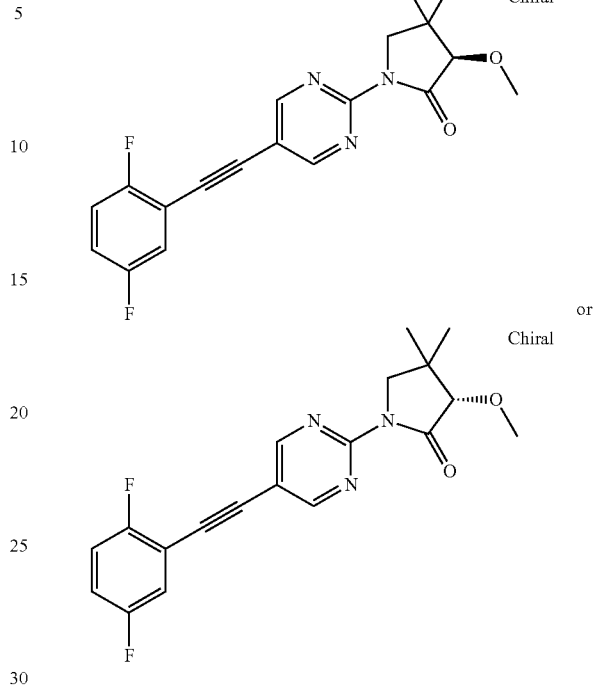

The title compound, a white solid, MS: m/e=358.1 (M+H$^+$), was prepared by separation of (RS)-1-[5-(2,5-difluoro-phenylethynyl)-pyrimidin-2-yl]-3-methoxy-4,4-dimethyl-pyrrolidin-2-one (Example 133, step 2) using a chiral column (Reprosil Chiral NR with heptane:EtOH 70:30 as solvent).

Example 134

4,4-Dimethyl-1-(5-phenylethynyl-pyrimidin-2-yl)-piperidin-2-one

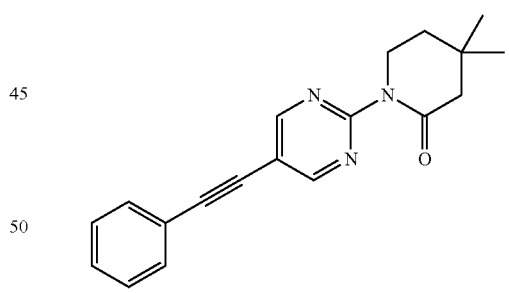

Step 1: 4,4-Dimethyl-1-(5-trimethylsilanylethynyl-pyrimidin-2-yl)-piperidin-2-one

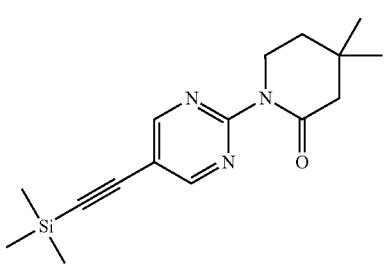

The title compound was obtained as a light yellow solid, MS: m/e=302.2 (M+H+), using chemistry similar to that described in Example 115, step 1 from 2 from 2-bromo-5-trimethylsilanylethynyl-pyrimidine (Example 120, step 1) and 4,4-dimethyl-piperidin-2-one (CAS 55047-81-9).

Step 2: 4,4-Dimethyl-1-(5-phenylethynyl-pyrimidin-2-yl)-piperidin-2-one

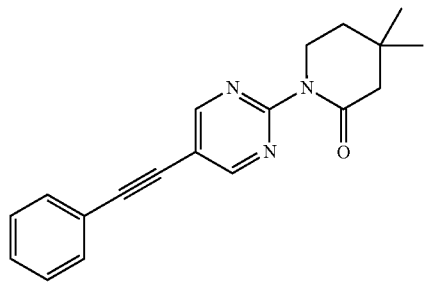 [SMILES: CC1(C)CCN(c2ncc(C#Cc3ccccc3)cn2)C(=O)C1]

The title compound was obtained as a white solid, MS: m/e=306.3 (M+H+), using chemistry similar to that described in Example 120, step 3 from 4,4-dimethyl-1-(5-trimethylsilanylethynyl-pyrimidin-2-yl)-piperidin-2-one (Example 134, step 1) and iodobenzene.

Example 135

1-[5-(3-Fluoro-phenylethynyl)-pyrimidin-2-yl]-4,4-dimethyl-piperidin-2-one

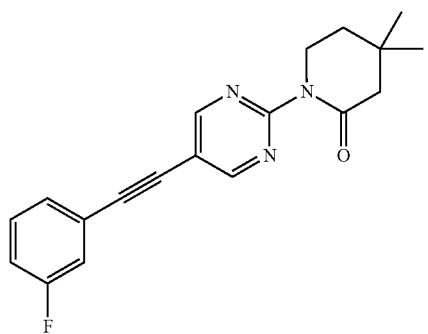 [SMILES: CC1(C)CCN(c2ncc(C#Cc3cccc(F)c3)cn2)C(=O)C1]

The title compound was obtained as a white solid, MS: m/e=324.2 (M+H+), using chemistry similar to that described in Example 120, step 3 from 4,4-dimethyl-1-(5-trimethylsilanylethynyl-pyrimidin-2-yl)-piperidin-2-one (Example 134, step 1) and 1-fluoro-3-iodobenzene.

Example 136

1-[5-(2,5-Difluoro-phenylethynyl)-pyrimidin-2-yl]-4,4-dimethyl-piperidin-2-one

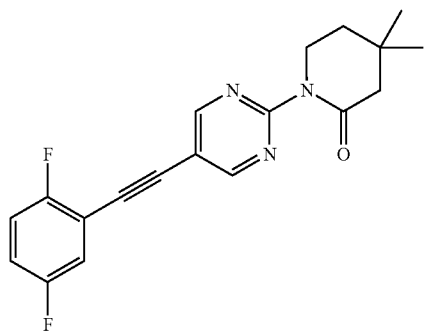 [SMILES: CC1(C)CCN(c2ncc(C#Cc3cc(F)ccc3F)cn2)C(=O)C1]

The title compound was obtained as a light yellow solid, MS: m/e=342.3 (M+H+), using chemistry similar to that described in Example 120, step 3 from 4,4-dimethyl-1-(5-trimethylsilanylethynyl-pyrimidin-2-yl)-piperidin-2-one (Example 134, step 1) and 2,5-difluoro-3-iodobenzene.

Example 137

3,4,4-Trimethyl-5'-phenylethynyl-3,4,5,6-tetrahydro-[1,2']bipyrimidinyl-2-one

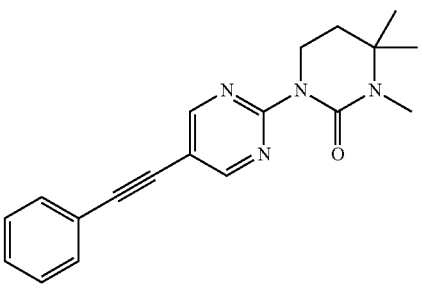 [SMILES: CN1C(=O)N(c2ncc(C#Cc3ccccc3)cn2)CCC1(C)C]

Step 1: 4,4-Dimethyl-tetrahydro-pyrimidin-2-one

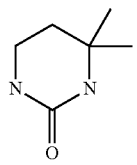

(3.4 g, 14.3 mmol) (3-Amino-3-methyl-butyl)-carbamic acid tert-butyl ester hydrochloride was dissolved in THF (60 ml) and KOtBu (6.4 g, 57.1 mmol, 4 equiv.) was added. The mixture was stirred for 16 hours at 60° C. and evaporated then with isolute to dryness. The crude product was purified by flash chromatography by directly loading the residue onto a silica gel column and eluting with an ethyl acetate:methanol gradient 100:0 to 70:30. The desired 4,4-dimethyl-tetrahydro-pyrimidin-2-one (1.65 g, 90% yield) was obtained as a light yellow solid, MS: m/e=129.1 (M+H+).

Step 2: 4,4-Dimethyl-5'-trimethylsilanylethynyl-3,4,5,6-tetrahydro-[1,2']bipyrimidinyl-2-one

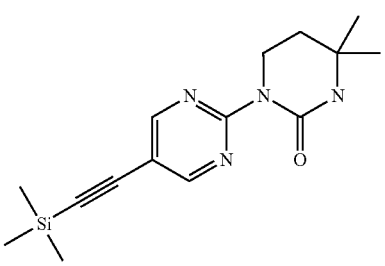

The title compound was obtained as a brown solid, MS: m/e=303.2 (M+H+), using chemistry similar to that described in Example 120, step 2 from 2 from 2-bromo-5-trimethylsilanylethynyl-pyrimidine (Example 120, step 1) and 4,4-dimethyl-tetrahydro-pyrimidin-2-one (Example 137, step 1).

Step 3: 4,4-Dimethyl-5'-phenylethynyl-3,4,5,6-tetrahydro-[1,2']bipyrimidinyl-2-one

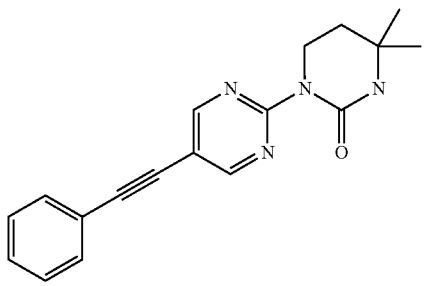

The title compound was obtained as a yellow solid, MS: m/e=329.2 (M+H$^+$), using chemistry similar to that described in Example 120, step 3 from 4,4-dimethyl-5'-trimethylsilanylethynyl-3,4,5,6-tetrahydro-[1,2']bipyrimidinyl-2-one (Example 137, step 2) and iodobenzene.

Step 4: 3,4,4-Trimethyl-5'-phenylethynyl-3,4,5,6-tetrahydro-[1,2']bipyrimidinyl-2-one

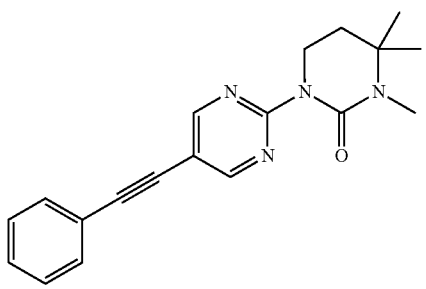

The title compound was obtained as a light yellow solid, MS: m/e=321.1 (M+H$^+$), using chemistry similar to that described in Example 122, step 2 from 4,4-dimethyl-5'-phenylethynyl-3,4,5,6-tetrahydro-[1,2']bipyrimidinyl-2-one (Example 137, step 3) and iodomethane.

Example 138

5'-(3-Fluoro-phenylethynyl)-3,4,4-trimethyl-3,4,5,6-tetrahydro-[1,2']bipyrimidinyl-2-one

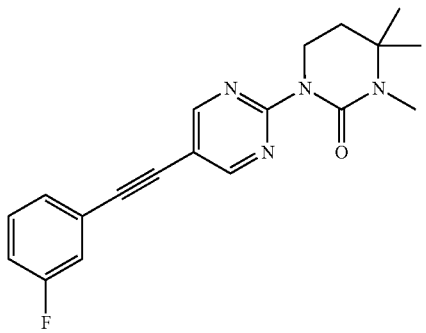 [SMILES: CN1C(=O)N(c2ncc(C#Cc3cccc(F)c3)cn2)CCC1(C)C]

Step 1: 5'-(3-Fluoro-phenylethynyl)-4,4-dimethyl-3,4,5,6-tetrahydro-[1,2']bipyrimidinyl-2-one

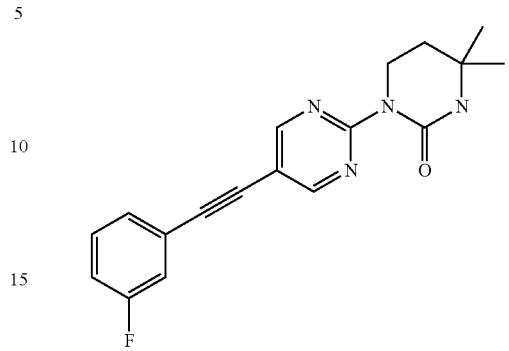

The title compound was obtained as a light brown solid, MS: m/e=325.2 (M+H$^+$), using chemistry similar to that described in Example 120, step 3 from 4,4-dimethyl-5'-trimethylsilanylethynyl-3,4,5,6-tetrahydro-[1,2']bipyrimidinyl-2-one (Example 137, step 2) and 1-fluoro-3-iodobenzene.

Step 2: 5'-(3-Fluoro-phenylethynyl)-3,4,4-trimethyl-3,4,5,6-tetrahydro-[1,2']bipyrimidinyl-2-one

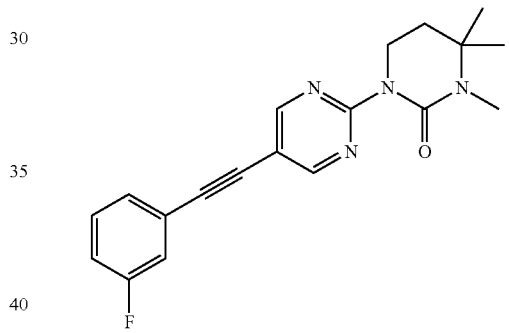

The title compound was obtained as a yellow oil, MS: m/e=339.2 (M+H$^+$), using chemistry similar to that described in Example 122, step 2 from 5'-(3-fluoro-phenylethynyl)-4,4-dimethyl-3,4,5,6-tetrahydro-[1,2']bipyrimidinyl-2-one (Example 138, step 1) and iodomethane.

Example 139

5'-(2,5-Difluoro-phenylethynyl)-3,4,4-trimethyl-3,4,5,6-tetrahydro-[1,2']bipyrimidinyl-2-one

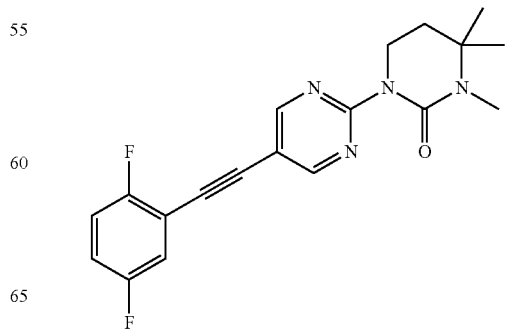

213

Step 1: 5'-(2,5-Difluoro-phenylethynyl)-4,4-dimethyl-3,4,5,6-tetrahydro-[1,2']bipyrimidinyl-2-one

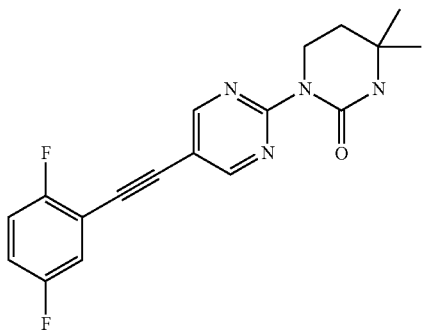

The title compound was obtained as a light brown solid, MS: m/e=343.1 (M+H$^+$), using chemistry similar to that described in Example 120, step 3 from 4,4-dimethyl-5'-trimethylsilanylethynyl-3,4,5,6-tetrahydro-[1,2']bipyrimidinyl-2-one (Example 137, step 2) and 1,4-difluoro-2-iodobenzene.

Step 2: 5'-(2,5-Difluoro-phenylethynyl)-3,4,4-trimethyl-3,4,5,6-tetrahydro-[1,2']bipyrimidinyl-2-one

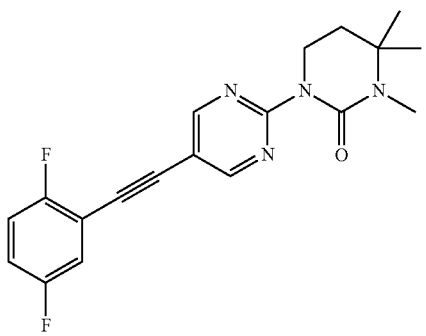

The title compound was obtained as a light yellow solid, MS: m/e=357.2 (M+H$^+$), using chemistry similar to that described in Example 122, step 2 from 5'-(2,5-difluoro-phenylethynyl)-4,4-dimethyl-3,4,5,6-tetrahydro-[1,2']bipyrimidinyl-2-one (Example 139, step 1) and iodomethane.

Example 140

3-Isopropyl-4,4-dimethyl-1-(5-phenylethynyl-pyrimidin-2-yl)-imidazolidin-2-one

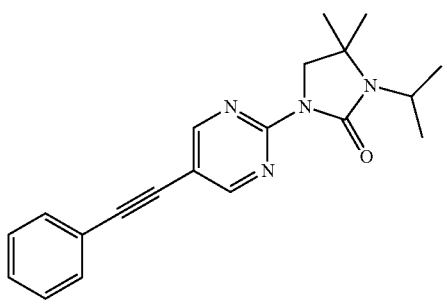 [SMILES: CC(C)N1C(=O)N(c2ncc(C#Cc3ccccc3)cn2)CC1(C)C]

214

Step 1: 1-(5-Iodo-pyrimidin-2-yl)-3-isopropyl-4,4-dimethyl-imidazolidin-2-one

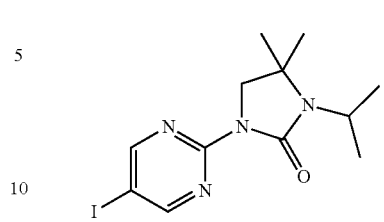

The title compound was obtained as a light yellow oil, MS: m/e=361.0 (M+H$^+$), using chemistry similar to that described in Example 122, step 2 from 1-(5-iodo-pyrimidin-2-yl)-4,4-dimethyl-imidazolidin-2-one (Example 122, step 1) and 2-iodopropane.

Step 2: 3-Isopropyl-4,4-dimethyl-1-(5-phenylethynyl-pyrimidin-2-yl)-imidazolidin-2-one

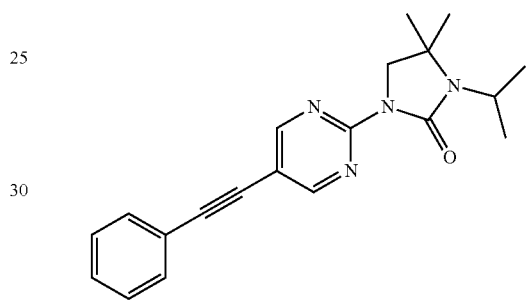

The title compound was obtained as a light brown solid, MS: m/e=335.2 (M+H$^+$), using chemistry similar to that described in Example 115, step 1 from 1-(5-iodo-pyrimidin-2-yl)-3-isopropyl-4,4-dimethyl-imidazolidin-2-one (Example 140, step 1) and phenylacetylene.

Example 141

1-[5-(3-Fluoro-phenylethynyl)-pyrimidin-2-yl]-3-isopropyl-4,4-dimethyl-imidazolidin-2-one

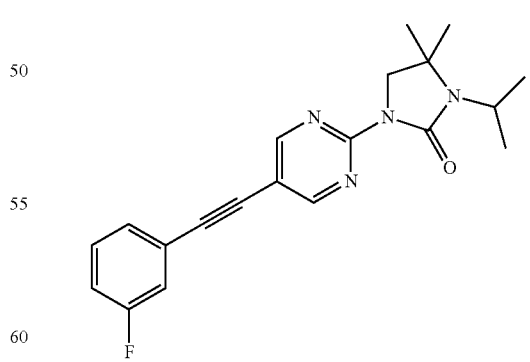

The title compound was obtained as a light brown solid, MS: m/e=353.3 (M+H$^+$), using chemistry similar to that described in Example 115, step 1 from 1-(5-iodo-pyrimidin-2-yl)-3-isopropyl-4,4-dimethyl-imidazolidin-2-one (Example 140, step 1) and 1-ethynyl-3-fluorobenzene.

Example 142

1-[5-(4-Fluoro-phenylethynyl)-pyrimidin-2-yl]-3-isopropyl-4,4-dimethyl-imidazolidin-2-one

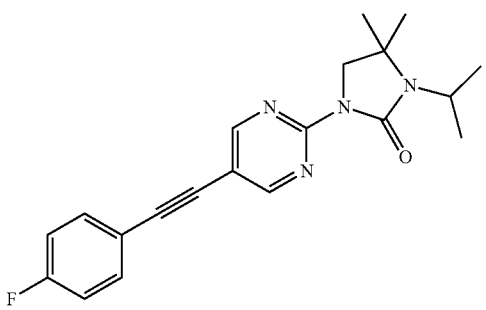 [SMILES: CC(C)N1C(=O)N(c2ncc(C#Cc3ccc(F)cc3)cn2)CC1(C)C]

The title compound was obtained as a light brown solid, MS: m/e=353.3 (M+H⁺), using chemistry similar to that described in Example 115, step 1 from 1-(5-iodo-pyrimidin-2-yl)-3-isopropyl-4,4-dimethyl-imidazolidin-2-one (Example 140, step 1) and 1-ethynyl-4-fluorobenzene.

Example 143

1-[5-(4-Fluoro-phenylethynyl)-pyrimidin-2-yl]-3-ethyl-4,4-dimethyl-imidazolidin-2-one

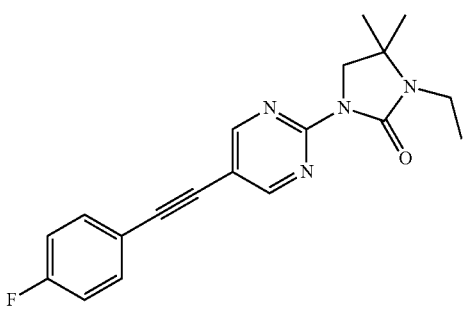 [SMILES: CCN1C(=O)N(c2ncc(C#Cc3ccc(F)cc3)cn2)CC1(C)C]

Step 1: 1-(5-Bromo-pyrimidin-2-yl)-4,4-dimethyl-imidazolidin-2-one

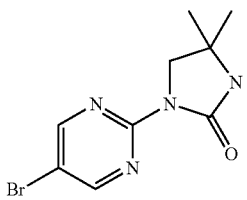

The title compound was obtained as a light brown solid, MS: m/e=271.1/273.1 (M+H⁺), using chemistry similar to that described in Example 120, step 2 from 5-bromo-2-iodopyrimidine and 4,4-dimethyl-imidazolidin-2-one (CAS 24572-33-6).

Step 2: 1-(5-Bromo-pyrimidin-2-yl)-3-ethyl-4,4-dimethyl-imidazolidin-2-one

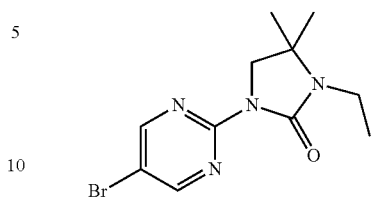

The title compound was obtained as a brown solid, MS: m/e=299.2/301.2 (M+H⁺), using chemistry similar to that described in Example 122, step 2 from 1-(5-bromo-pyrimidin-2-yl)-4,4-dimethyl-imidazolidin-2-one (Example 143, step 1) and ethyl iodide.

Step 3: 1-(5-Iodo-pyrimidin-2-yl)-3-ethyl-4,4-dimethyl-imidazolidin-2-one

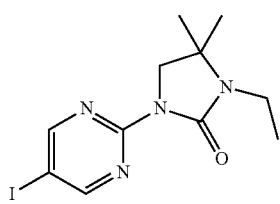 [SMILES: CCN1C(=O)N(c2ncc(I)cn2)CC1(C)C]

(350 mg, 1.17 mmol) 1-(5-Bromo-pyrimidin-2-yl)-3-ethyl-4,4-dimethyl-imidazolidin-2-one (Example 143, step 2) was dissolved in dioxane (20 ml) and sodium iodide (700 mg, 4.68 mmol, 4 equiv.), copper(I)iodide (21 mg, 0.234 mmol, 0.2 equiv.) and trans-N,N'-dimethylcyclohexane-1,2-diamine (33 mg, 37 µl, 0.234 mmol, 0.2 equiv.) were added. The mixture was stirred for 16 hours at 100° C. The reaction mixture was cooled and extracted with saturated NaHCO₃ solution and two times ethyl acetate. The organic layers were extracted with brine, dried over sodium sulfate and evaporated to dryness. The desired 1-(5-iodo-pyrimidin-2-yl)-3-ethyl-4,4-dimethyl-imidazolidin-2-one (350 mg, 86% yield) was obtained as a brown solid, MS: m/e=347.0 (M+H⁺) and was used without further purification in the next step.

Step 4: 1-[5-(4-Fluoro-phenylethynyl)-pyrimidin-2-yl]-3-ethyl-4,4-dimethyl-imidazolidin-2-one

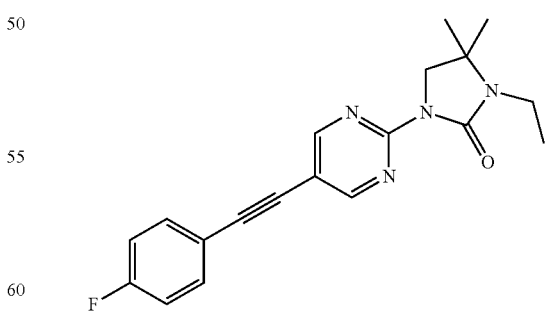

The title compound was obtained as a brown solid, MS: m/e=339.3 (M+H⁺), using chemistry similar to that described in Example 115, step 1 from 1-(5-iodo-pyrimidin-2-yl)-3-ethyl-4,4-dimethyl-imidazolidin-2-one (Example 143, step 3) and 1-ethynyl-4-fluorobenzene.

Example 144

1-[5-(3-Fluoro-phenylethynyl)-pyrimidin-2-yl]-3-ethyl-4,4-dimethyl-imidazolidin-2-one

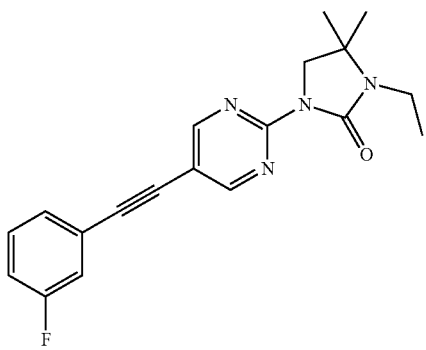 [SMILES: CCN1C(=O)N(c2ncc(C#Cc3cccc(F)c3)cn2)CC1(C)C]

The title compound was obtained as a light brown solid, MS: m/e=339.3 (M+H⁺), using chemistry similar to that described in Example 115, step 1 from 1-(5-iodo-pyrimidin-2-yl)-3-ethyl-4,4-dimethyl-imidazolidin-2-one (Example 143, step 3) and 1-ethynyl-3-fluorobenzene.

Example 145

(RS)-5,6,6-Trimethyl-3-(5-phenylethynyl-pyrimidin-2-yl)-[1,3]oxazinan-2-one

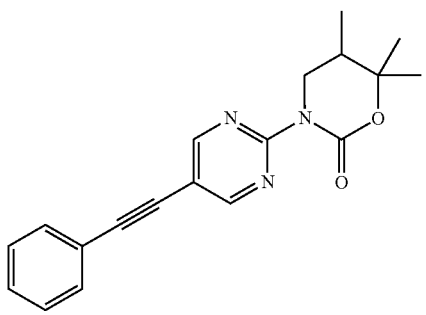 [SMILES: CC1CN(c2ccc(C#Cc3ccccc3)cn2)C(=O)OC1(C)C]

Step 1: (RS)-(3-Hydroxy-2,3-dimethyl-butyl)-carbamic acid tert-butyl ester

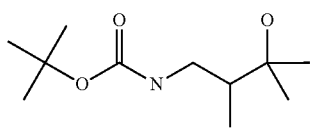

The title compound was obtained as a colorless oil, MS: m/e=218.3 (M+H⁺), using chemistry similar to that described in Example 95, step 2 from methyl 3-(tert-butoxycarbonylamino)-2-methylpropanoate (CAS 182486-16-4).

Step 2: (RS)-5,6,6-Trimethyl-[1,3]oxazinan-2-one

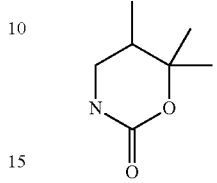

The title compound was obtained as a yellow solid, MS: m/e=144.0 (M+H⁺), using chemistry similar to that described in Example 72, step 2 from (RS)-(3-hydroxy-2,3-dimethyl-butyl)-carbamic acid tert-butyl ester (Example 145, step 1).

Step 3: 2-Bromo-5-phenylethynyl-pyrimidine

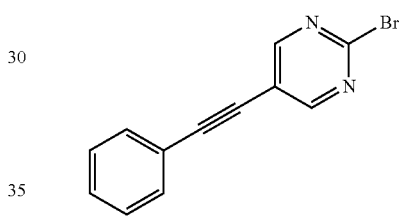

The title compound was obtained as a white solid using chemistry similar to that described in Example 120, step 1 from 2-bromo-5-iodopyrimidine and phenylacetylene.

Step 4: (RS)-5,6,6-Trimethyl-3-(5-phenylethynyl-pyrimidin-2-yl)-[1,3]oxazinan-2-one

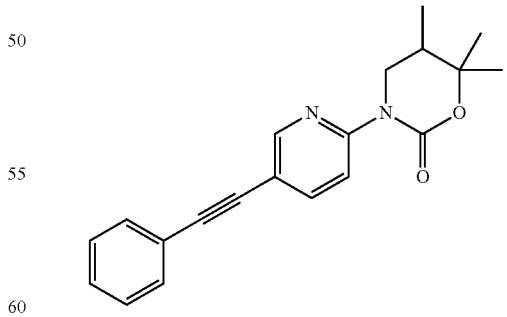

The title compound was obtained as a yellow solid, MS: m/e=322.2 (M+H⁺), using chemistry similar to that described in Example 120, step 2 from 2-bromo-5-phenylethynyl-pyrimidine (Example 145, step 3) and (RS)-5,6,6-trimethyl-[1,3]oxazinan-2-one (Example 145, step 2).

Example 146

(RS)-3-[5-(2,5-Difluoro-phenylethynyl)-pyrimidin-2-yl]-5,6,6-trimethyl-[1,3]oxazinan-2-one

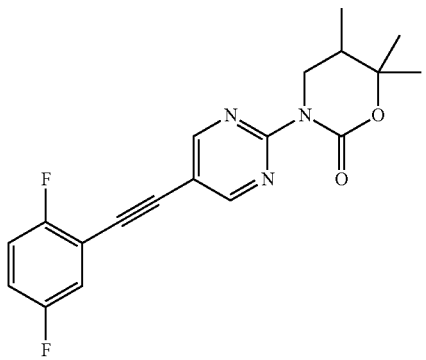 [SMILES: CC1CN(c2ncc(C#Cc3cc(F)ccc3F)cn2)C(=O)OC1(C)C]

Step 1: (RS)-5,6,6-Trimethyl-3-(5-trimethylsilanyl-ethynyl-pyrimidin-2-yl)-[1,3]oxazinan-2-one

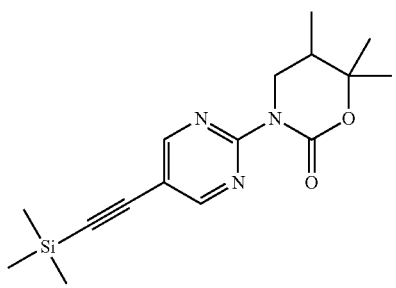

The title compound was obtained as a brown solid, MS: m/e=318.1 (M+H$^+$), using chemistry similar to that described in Example 120, step 2 from 2-bromo-5-trimethylsilanyl-ethynyl-pyrimidine (Example 120, step 1) and (RS)-5,6,6-trimethyl-[1,3]oxazinan-2-one (Example 145, step 2).

Step 2: (RS)-3-[5-(2,5-Difluoro-phenylethynyl)-pyrimidin-2-yl]-5,6,6-trimethyl-[1,3]oxazinan-2-one

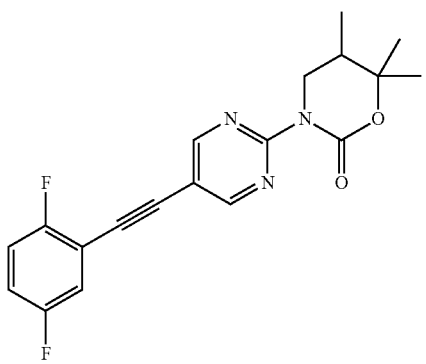 [SMILES: CC1CN(c2ncc(C#Cc3cc(F)ccc3F)cn2)C(=O)OC1(C)C]

The title compound was obtained as a white solid, MS: m/e=358.4 (M+H$^+$), using chemistry similar to that described in Example 120, step 3 from (RS)-5,6,6-trimethyl-3-(5-trimethylsilanylethynyl-pyrimidin-2-yl)-[1,3]oxazinan-2-one (Example 146, step 1) and 1,4-difluoro-2-iodobenzene.

Example 147

4-Methyl-6-(5-phenylethynyl-pyrimidin-2-yl)-4,6-diaza-spiro[2.4]heptan-5-one

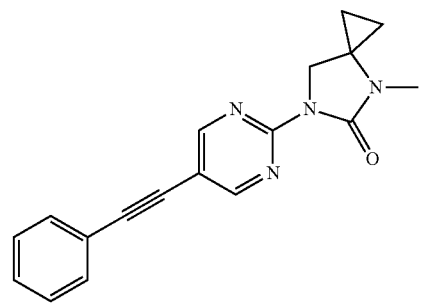 [SMILES: CN1C(=O)N(c2ncc(C#Cc3ccccc3)cn2)CC12CC2]

Step 1: 4-Methyl-4,6-diaza-spiro[2.4]heptan-5-one

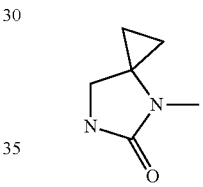

The title compound was obtained as a white solid using procedures similar to those described in Example 106, step 1 to 3 from starting from 1-((tert-butoxycarbonylamino)methyl)cyclopropanecarboxylic acid instead of (rac)-cis-2-(tert-butoxycarbonylamino)cyclopentanecarboxylic acid.

Step 2: 4-Methyl-6-(5-phenylethynyl-pyrimidin-2-yl)-4,6-diaza-spiro[2.4]heptan-5-one

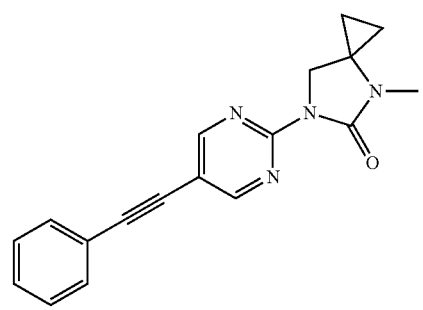

The title compound was obtained as a white solid, MS: m/e=305.3 (M+H$^+$), using chemistry similar to that described in Example 120, step 2 from 2-bromo-5-phenylethynyl-pyrimidine (Example 145, step 3) and 4-methyl-4,6-diaza-spiro[2.4]heptan-5-one (Example 147, step 1).

Example 148

(RS)-3-[5-(3-Fluoro-phenylethynyl)-pyrimidin-2-yl]-5,6,6-trimethyl-[1,3]oxazinan-2-one

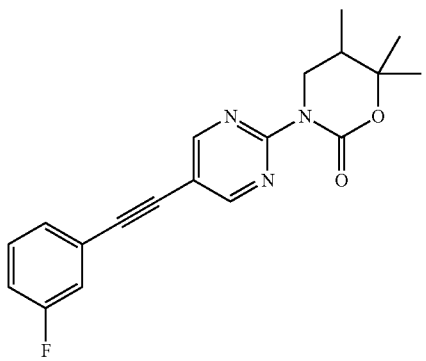 [SMILES: CC1CN(c2ncc(C#Cc3cccc(F)c3)cn2)C(=O)OC1(C)C]

The title compound was obtained as a yellow solid, MS: m/e=340.1 (M+H$^+$), using chemistry similar to that described in Example 120, step 3 from (RS)-5,6,6-trimethyl-3-(5-trimethylsilanylethynyl-pyrimidin-2-yl)-[1,3]oxazinan-2-one (Example 146, step 1) and 1-fluoro-3-iodobenzene.

Example 149

(RS)-3-[5-(4-Fluoro-phenylethynyl)-pyrimidin-2-yl]-5,6,6-trimethyl-[1,3]oxazinan-2-one

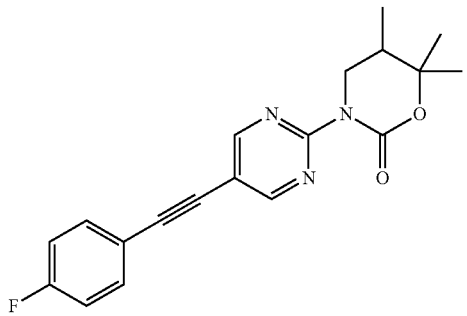 [SMILES: CC1CN(c2ncc(C#Cc3ccc(F)cc3)cn2)C(=O)OC1(C)C]

The title compound was obtained as a yellow solid, MS: m/e=340.1 (M+H$^+$), using chemistry similar to that described in Example 120, step 3 from (RS)-5,6,6-trimethyl-3-(5-trimethylsilanylethynyl-pyrimidin-2-yl)-[1,3]oxazinan-2-one (Example 146, step 1) and 1-fluoro-4-iodobenzene.

Example 150

4,4-Dimethyl-1-(6-(phenylethynyl)pyridazin-3-yl)pyrrolidin-2-one

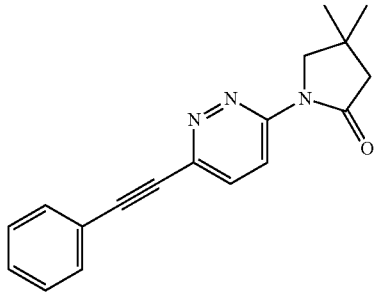 [SMILES: CC1(C)CC(=O)N(c2ccc(C#Cc3ccccc3)nn2)C1]

To a solution of 3-chloro-6-(phenylethynyl)pyridazine (CAS 77778-15-5) (180 mg, 839 μmol) and 4,4-dimethylpyrrolidin-2-one (CAS 66899-02-3) (142 mg, 1.26 mmol, 1.5 equiv.) in 2 ml of DMF were added cesium carbonate (546 mg, 1.68 mmol, 2 equiv.). The suspension was heated 16 hours at 120° C. and then allowed to cool to room temperature. Ethyl acetate (10 ml) were added and the unsoluble salts were filtered off. After concentration in vaccuo, the residue was dissolved in 10 ml of ethyl acetate. Silicagel (4 g) were added and the suspension was evaporated to dryness. The silicagel with the adsorbed crude mixture was loaded onto a 20 g silicagel flash chromatography column and eluted three min. with heptane followed by a heptane to 45% ethyl acetate/heptane gradient over 25 min to yield 36 mg (15% yield) of the title compound as a cristalline yellow solid, MS: m/e=292.3 (M+H$^+$).

Example 151

4,4-Dimethyl-1-(6-(phenylethynyl)pyridazin-3-yl)piperidin-2-one

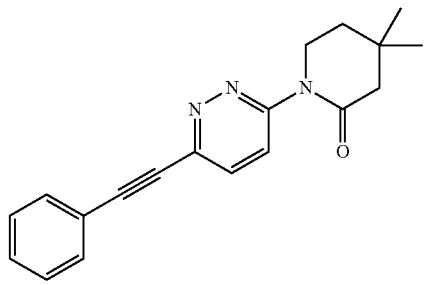

Step 1: 3-Iodo-6-(phenylethynyl)pyridazine

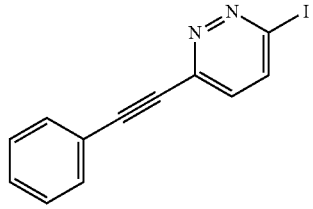 [SMILES: Ic1ccc(C#Cc2ccccc2)nn1]

To a solution of 100 mg (0.466 mmol) of 3-chloro-6-(phenylethynyl)pyridazine in 5 ml of acetonitrile were added sodium iodide (209 mg, 1.4 mmol, 3 equiv.), acetic acid (56 mg, 53.3 ml, 0.93 mmol, 2 equiv.), and 95% sulfuric acid (4.6 mg, 2.5 ml, 0.47 mmol, 1 equiv.). The orange solution was stirred for 8 hours at 70° C. and then left to cool overnight. After standard workup with ethyl acetate/water, the residue was adsorbed onto 4 g of silicagel and purified by flash chromatography over a 20 g silicagel column over a heptane to 50% ethyl acetate in heptane gradient to yield 82 mg (58% yield) of the title compound as a crystalline light yellow solid, MS: m/e=307.1 (M+H$^+$).

Step 2: 4,4-Dimethyl-1-(6-(phenylethynyl)pyridazin-3-yl)piperidin-2-one

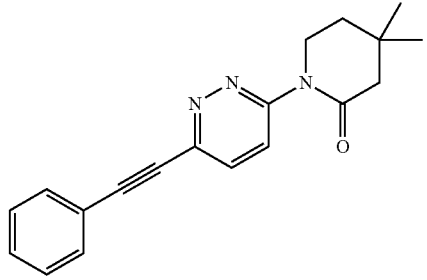

To a well stirred suspension of 3-iodo-6-(phenylethynyl) pyridazine (Example 151, step 1) (80 mg, 261 μmol), 4,4-dimethylpiperidin-2-one (66.5 mg, 314 μmol, 1.2 equiv.) and 4,5-bis(diphenylphosphino)-9,9-dimethylxanthene (xantphos) (6.05 mg, 10.5 μmol, 0.04 equiv.) in 2-ml of toluene were added under argon atmosphere tris(dibenzylideneacetone)dipalladium(0) (Pd$_2$(dba)$_3$), (4.79 mg, 5.23 μmol, 0.02 equiv.) and the mixture was stirred for 4 hours at 100° C. The crude mixture was directly purified by flash chromatography over a 20 g silicagel column using a heptane to 50% ethyl acetate in heptane gradient, and yielded 18 mg (23% yield) of the title compound as a white solid, MS: m/e=306.2 (M+H$^+$).

Example 152

5,5-Dimethyl-3-(6-(phenylethynyl)pyridazin-3-yl) oxazolidin-2-one

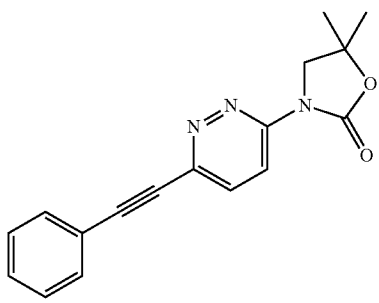 [SMILES: CC1(C)CN(c2ccc(C#Cc3ccccc3)nn2)C(=O)O1]

Step 1: 2-Methyl-1-(6-phenylethynyl-pyridazin-3-ylamino)-propan-2-ol

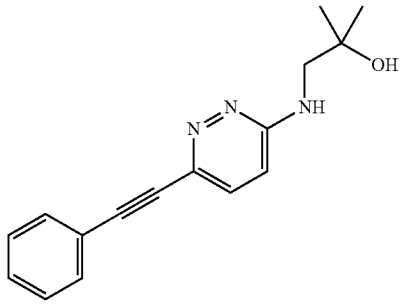 [SMILES: CC(C)(O)CNc1ccc(C#Cc2ccccc2)nn1]

A solution of 3-chloro-6-(phenylethynyl)pyridazine (CAS 77778-15-5) (300 mg, 1.4 mmol) and 1-amino-2-methylpropan-2-ol (137 mg, 147 μl, 1.54 mmol, 1.1 equiv.) in 3 ml of pyridine was heated 20 hours at 120° C. in a sealed tube. The solvent was removed in vaccuo. The residue was taken up in ethyl acetate/methanol, adsorbed onto 4 g of silica and purified on a 20 g flash chromatography column using a heptane to ethyl acetate gradient to yield 90 mg (24% yield) of the title compound as a crystalline light yellow solid, MS: m/e=268.2 (M+H$^+$).

Step 2: 5,5-Dimethyl-3-(6-(phenylethynyl)pyridazin-3-yl)oxazolidin-2-one

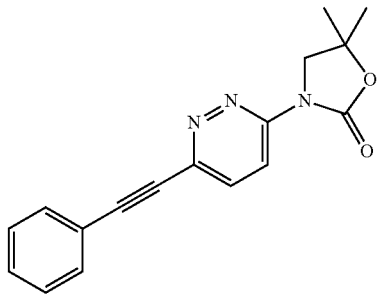 [SMILES: CC1(C)CN(c2ccc(C#Cc3ccccc3)nn2)C(=O)O1]

A solution of 2-methyl-1-(6-(phenylethynyl)pyridazin-3-ylamino)propan-2-ol (Example 152, step 1) (90 mg, 337 μmol) and triethylamine (102 mg, 141 μl, 1.01 mmol, 3 equiv.) in 4 ml of THF was cooled to 0-5° C. and then triphosgene (99.9 mg, 337 μmol, 1 equiv.) was added and the reaction was stirred for 1 hour at 0-5° C. The mixture was quenched with 5 ml of 5% sodium bicarbonate solution and worked up with ethyl acetate/water. The crude material was adsorbed onto silicagel and purified by flash chromatography over a heptane to 50% ethyl acetate in heptane gradient to yield the title compound (51 mg, 52% yield) as a crystalline light yellow solid, MS: m/e=294.2 (M+H$^+$).

Example 153

6,6-Dimethyl-3-(6-(phenylethynyl)pyridazin-3-yl)-1,3-oxazinan-2-one

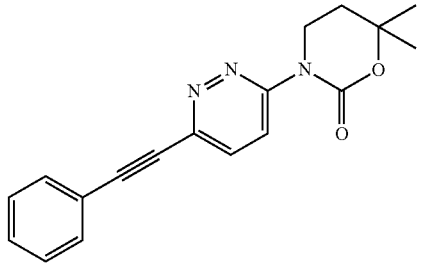 [SMILES: CC1(C)CCN(c2ccc(C#Cc3ccccc3)nn2)C(=O)O1]

Step 1: 2-Methyl-4-(6-phenylethynyl-pyridazin-3-ylamino)-butan-2-ol

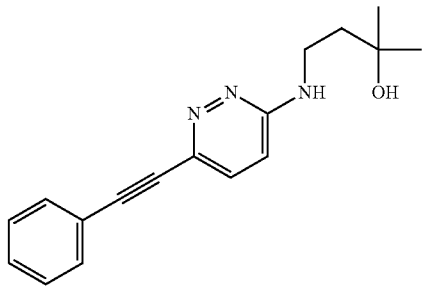

A solution of 3-chloro-6-(phenylethynyl)pyridazine (CAS 77778-15-5) (125 mg, 0.582 mmol) and 4-amino-2-methylbutan-2-ol hydrochloride (244 mg, 1.75 mmol, 3 equiv.)

and triethylamine (206 mg, 284 ml, 2.04 mmol, 2 equiv.) in 1.25 ml of pyridine was heated 20 hours at 85° C. The solvent was removed in vaccuo. The residue was taken up in ethyl acetate/methanol, adsorbed onto 4 g of silica and purified on a 20 g flash chromatography column using a heptane/ethyl acetate 85:15 to 15:85 gradient to yield 44 mg (27% yield) of the title compound as a crystalline white solid, MS: m/e=282.2 (M+H⁺).

Step 2: 6,6-Dimethyl-3-(6-(phenylethynyl)pyridazin-3-yl)-1,3-oxazinan-2-one

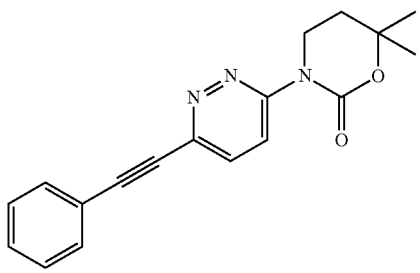 [SMILES: CC1(C)CCN(c2ccc(C#Cc3ccccc3)nn2)C(=O)O1]

The title compound, a crystalline light yellow solid, MS: m/e=308.3 (M+H⁺), was prepared in accordance with the general method of Example 152, step 2 starting from 2-methyl-4-(6-phenylethynyl-pyridazin-3-ylamino)-butan-2-ol (Example 153, step 1) and triphosgene.

Example 154

3,4,4-Trimethyl-1-(6-(m-tolylethynyl)pyridazin-3-yl)imidazolidin-2-one

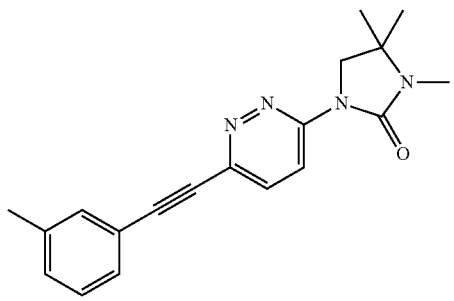

Step 1: N-1-(6-Iodo-pyridazin-3-yl)-2-methyl-propane-1,2-diamine

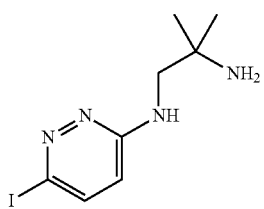

A suspension of 3-chloro-6-iodo-pyridazine (CAS 135034-10-5) (500 mg, 2.08 mmol) and 2-methylpropane-1,2-diamine (220 mg, 262 μl, 2.5 mmol, 1.2 equiv.) in 4 ml of pyridine was heated 16 hours at 100° C. The solvent was removed in vaccuo. The crude material (508 mg) was directly used in the next step.

Step 2: 1-(6-Chloro-pyridazin-3-yl)-4,4-dimethyl-imidazolidin-2-one

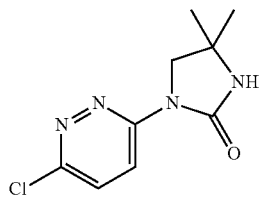

To a solution of crude N-1-(6-iodopyridazin-3-yl)-2-methylpropane-1,2-diamine (Example 154, step 1) (580 mg, 1.99 mmol) and pyridine (346 mg, 353 μl, 4.37 mmol, 2.2 equiv.) in 5 ml of dichloromethane were added (1.96 g, 2.1 ml, 3.97 mmol, 2 equiv.) of a 20% solution of phosgene in toluene dropwise at 0-2° C. over a period of 10 min. After stirring for 2 hours at 0-4° C., the reaction was allowed to warm up to room temperature overnight. The mixture was quenched with 5 ml of 5% sodium bicarbonate solution and worked up with dichloromethane/water. The crude material was adsorbed onto silicagel and purified by flash chromatography using a heptane to 80% ethyl acetate in heptane gradient to yield the title compound (where the iodine was completely exchanged for chlorine) (140 mg, 31% yield) as a crystalline white solid, MS: m/e=227.2, 229.4 (M+H⁺).

Step 3: 1-(6-Chloro-pyridazin-3-yl)-3,4,4-trimethyl-imidazolidin-2-one

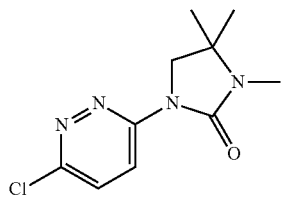 [SMILES: CN1C(=O)N(c2ccc(Cl)nn2)CC1(C)C]

To a solution of 1-(6-chloropyridazin-3-yl)-4,4-dimethylimidazolidin-2-one (Example 154, step 2) (140 mg, 618 μmol) in DMF (3 ml) was added 60% sodium hydride suspension (37.1 mg, 926 μmol, 1.5 equiv.). After stirring at room temperature for 10 min, iodomethane (132 mg, 57.9 μl, 926 μmol, 1.5 equiv.) was added and the suspension was stirred for 1 hour at room temperature. The solvent was removed in vaccuo and the residue was worked up with ethyl acetate/water. The title compound was obtained as a crystalline light brown solid (129 mg, 87% yield), MS: m/e=241.2, 243.4 (M+H⁺).

Step 4: 1-(6-Iodo-pyridazin-3-yl)-3,4,4-trimethyl-imidazolidin-2-one

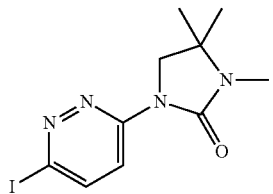 [SMILES: CN1C(=O)N(c2ccc(I)nn2)CC1(C)C]

The title compound, crystalline light yellow solid (149 mg, 86%), MS: m/e=333.0 (M+H⁺), was prepared from 1-(6- chloro-pyridazin-3-yl)-3,4,4-trimethyl-imidazolidin-2-one (Example 154, step 3) in accordance with the general method of Example 151, step 1 by acid catalyzed chlorine-iodine exchange.

Step 5: 3,4,4-Trimethyl-1-(6-(m-tolylethynyl)pyridazin-3-yl)imidazolidin-2-one

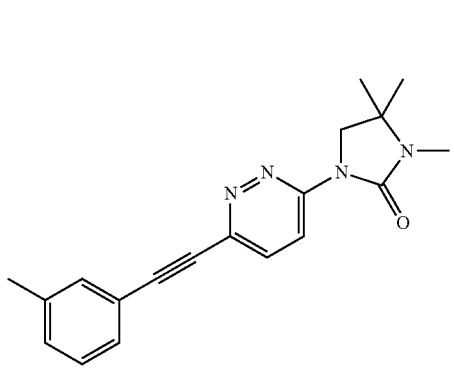

To a solution of 1-(6-iodopyridazin-3-yl)-3,4,4-trimethylimidazolidin-2-one (Example 154, step 4) (75 mg, 226 μmol), 1-ethynyl-3-methylbenzene (44.6 mg, 49.5 μl, 384 μmol, 1.7 equiv.), triethylamine (68.5 mg, 94.4 μl, 677 μmol, 3 equiv.), bis(triphenylphosphine)palladium (II) chloride (9.51 mg, 13.5 μmol, 0.06 equiv.) and triphenylphosphine (1.78 mg, 6.77 μmol, 0.03 equiv.) in 2 ml of THF was added under an Argon atmosphere copper (I) iodide (1.29 mg, 6.77 μmol, 0.03 equiv.). The suspension was warmed to 60° C. for 2 hours, taken up in 5 ml of ethyl acetate and adsorbed on 4 g of silica. Purification by flash chromatography on silicagel using a heptane to 50% ethyl acetate/heptane gradient yielded the title compound as a crystalline light yellow solid (18 mg, 25% yield), MS: m/e=321.2 (M+H$^+$).

Example 155

1-(6-((3-Chlorophenyl)ethynyl)pyridazin-3-yl)-3,4,4-trimethylimidazolidin-2-one

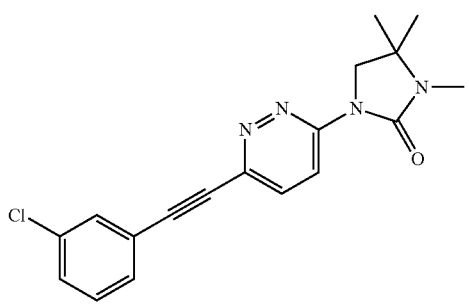 [SMILES: CN1C(=O)N(c2ccc(C#Cc3cccc(Cl)c3)nn2)CC1(C)C]

The title compound, a crystalline light yellow solid (36 mg, 47% yield), MS: m/e=341.2, 343.3 (M+H$^+$), was prepared in accordance with the general method of Example 154, step 5; starting from 1-(6-iodo-pyridazin-3-yl)-3,4,4-trimethyl-imidazolidin-2-one (Example 154, step 4) and 3-chlorophenylacetylene.

Example 156

3,4,4-Trimethyl-1-(5-(phenylethynyl)pyrazin-2-yl)imidazolidin-2-one

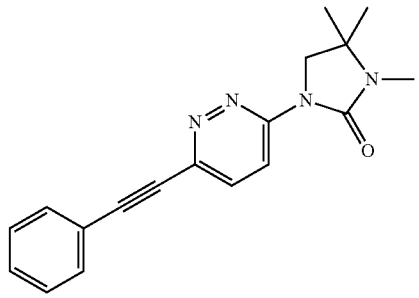 [SMILES: CN1C(=O)N(c2ccc(C#Cc3ccccc3)nn2)CC1(C)C]

Step 1: N-1-(5-Iodo-pyrazin-2-yl)-2-methyl-propane-1,2-diamine

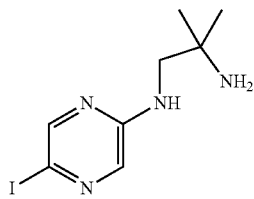

To a solution of 2-bromo-5-iodopyrazine (CAS 622392-04-5) (250 mg, 878 μmol) in 0.7 ml of pyridine, was added 2-methylpropane-1,2-diamine (116 mg, 138 μl, 1.32 mmol, 1.5 equiv.) at room temperature. The colorless solution was stirred for 16 hours at 100° C. The reaction mixture was cooled and concentrated in vacuo. The crude material was used directly in the next step.

Step 2: 1-(5-Iodo-pyrazin-2-yl)-4,4-dimethyl-imidazolidin-2-one

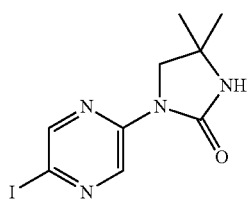

The title compound, an off-white solid (72 mg, 26% yield), was prepared in accordance with the general method of Example 154, step 2; starting from N-1-(5-iodo-pyrazin-2-yl)-2-methyl-propane-1,2-diamine (Example 156, step 1) and cyclisation with phosgene. The crude material was directly used in the next step without further characterization.

Step 3: 1-(5-Iodo-pyrazin-2-yl)-3,4,4-trimethyl-imidazolidin-2-one

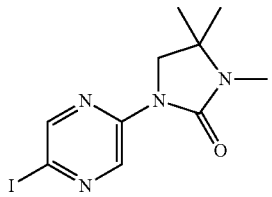 [SMILES: CN1C(=O)N(c2cnc(I)cn2)CC1(C)C]

The title compound, an off-white solid (77 mg, 99% yield), was prepared in accordance with the general method of Example 154, step 3; by alkylation of 1-(5-iodo-pyrazin-2-yl)-4,4-dimethyl-imidazolidin-2-one (Example 156, step 2) with methyl iodide. The crude material was directly used in the next step without further characterization.

Step 4: '3,4,4-Trimethyl-1-(5-(phenylethynyl)pyrazin-2-yl)imidazolidin-2-one

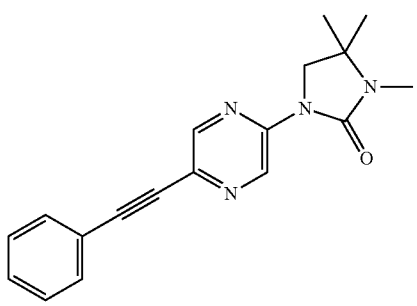 [SMILES: CN1C(=O)N(c2cnc(C#Cc3ccccc3)cn2)CC1(C)C]

The title compound, a crystalline light yellow solid (69 mg, 75% yield), MS: m/e=307.3 (M+H$^+$), was prepared in accordance with the general method of Example 154, step 5; starting from 1-(5-iodo-pyrazin-2-yl)-3,4,4-trimethyl-imidazolidin-2-one (Example 156, step 3) and phenylacetylene.

Example 157

3,4,4-Trimethyl-1-(5-(pyridin-3-ylethynyl)pyrazin-2-yl)imidazolidin-2-one

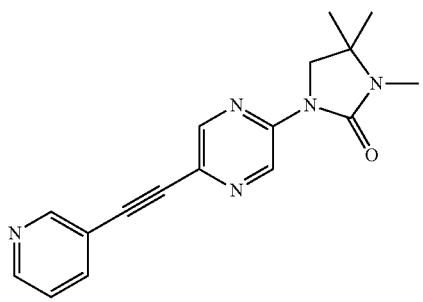 [SMILES: CN1C(=O)N(c2cnc(C#Cc3cccnc3)cn2)CC1(C)C]

The title compound, a crystalline yellow solid, MS: m/e=308.3 (M+H$^+$), was prepared in accordance with the general method of Example 154, step 5; starting from 1-(5-iodo-pyrazin-2-yl)-3,4,4-trimethyl-imidazolidin-2-one (Example 156, step 3) and 3-pyridylacetylene.

Example 158

1-(5-((3-Fluorophenyl)ethynyl)pyrazin-2-yl)-3,4,4-trimethylimidazolidin-2-one

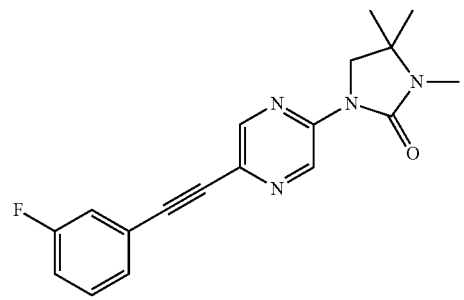 [SMILES: CN1C(=O)N(c2cnc(C#Cc3cccc(F)c3)cn2)CC1(C)C]

The title compound, a crystalline light yellow solid, MS: m/e=325.2 (M+H$^+$), was prepared in accordance with the general method of Example 154, step 5; starting from 1-(5-iodo-pyrazin-2-yl)-3,4,4-trimethyl-imidazolidin-2-one (Example 156, step 3) and 3-fluorophenylacetylene.

Example 159

1-(5-((4-Fluorophenyl)ethynyl)pyrazin-2-yl)-3,4,4-trimethylimidazolidin-2-one

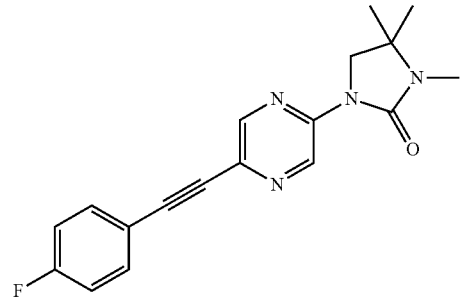 [SMILES: CN1C(=O)N(c2cnc(C#Cc3ccc(F)cc3)cn2)CC1(C)C]

The title compound, a light yellow solid, MS: m/e=325.2 (M+H$^+$), was prepared in accordance with the general method of example 154, step 5; starting from 1-(5-iodo-pyrazin-2-yl)-3,4,4-trimethyl-imidazolidin-2-one (Example 156, step 3) and 4-fluorophenylacetylene.

Example 160

4,4-Dimethyl-1-(5-(pyridin-3-ylethynyl)pyrazin-2-yl)pyrrolidin-2-one

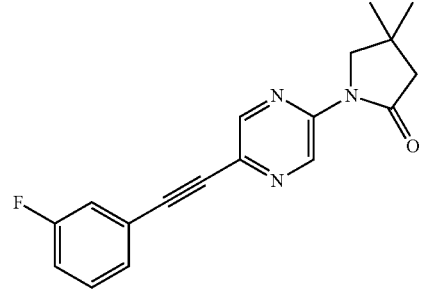 [SMILES: CC1(C)CC(=O)N(c2cnc(C#Cc3cccc(F)c3)cn2)C1]

Step 1: 1-(5-Bromo-pyrazin-2-yl)-4,4-dimethyl-pyrrolidin-2-one

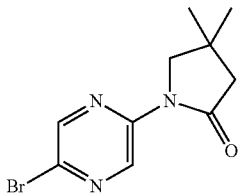

To a well stirred suspension of 2-bromo-5-iodopyrazine (300 mg, 1.05 mmol), 4,4-dimethylpiperidin-2-one (155 mg, 1.37 mmol, 1.3 equiv.) and 4,5-bis(diphenylphosphino)-9,9-dimethylxanthene (xantphos) (24.4 mg, 0.042 mmol, 0.04 equiv.) in 4 ml of toluene were added under argon atmosphere tris(dibenzylideneacetone)dipalladium(0) (Pd$_2$(dba)$_3$), (19.3 mg, 0.021 mmol, 0.02 equiv.) and the mixture was stirred for 5 hours at 100° C. The crude mixture was adsorbed on silicagel and purified by flash chromatography over a 20 g silicagel column using a 2:1 heptane/ethyl acetate mixture as eluant. The title compound (151 mg, 53% yield) was obtained as a white solid, MS: m/e=270.1, 272.1 (M+H$^+$).

Step 2: 4,4-Dimethyl-1-(5-(pyridin-3-ylethynyl)pyrazin-2-yl)pyrrolidin-2-one

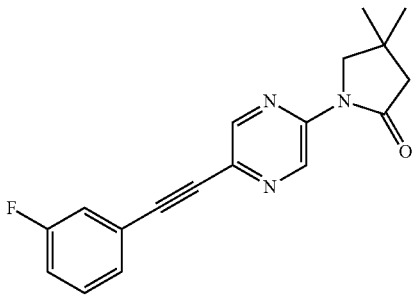

The title compound, a light yellow solid, MS: m/e=310.4 (M+H$^+$), was prepared in accordance with the general method of Example 154, step 5; starting from 1-(5-bromo-pyrazin-2-yl)-4,4-dimethyl-pyrrolidin-2-one (Example 160, step 1) and 3-fluorophenylacetylene.

Example 161

1-(5-((3-Fluorophenyl)ethynyl)pyrazin-2-yl)-4,4-dimethylpiperidin-2-one

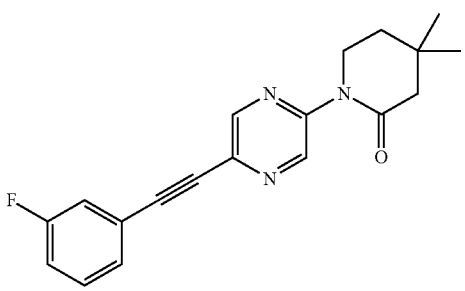 [SMILES: CC1(C)CCN(c2cnc(C#Cc3cccc(F)c3)cn2)C(=O)C1]

Step 1: 1-(5-Bromo-pyrazin-2-yl)-4,4-dimethyl-piperidin-2-one

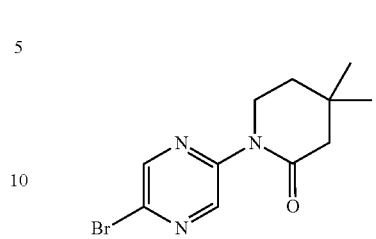

The title compound, an off-white solid, MS: m/e=284.2, 286.0 (M+H$^+$), was prepared in accordance with the general method of Example 160, step 1; starting from 2-bromo-5-iodopyrazine and 4,4-dimethyl-piperidin-2-one.

Step 2: 1-(5-((3-Fluorophenyl)ethynyl)pyrazin-2-yl)-4,4-dimethylpiperidin-2-one

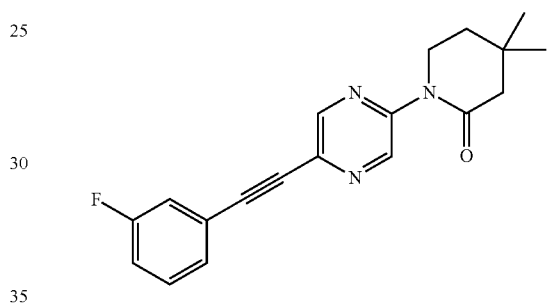

The title compound, an off-white solid, MS: m/e=324.3 (M+H$^+$), was prepared in accordance with the general method of Example 154, step 5; starting from 1-(5-bromo-pyrazin-2-yl)-4,4-dimethyl-piperidin-2-one (Example 161, step 1) and 3-fluorophenylacetylene.

Example 162

4,4-Dimethyl-1-(5-(pyridin-3-ylethynyl)pyrazin-2-yl)piperidin-2-one

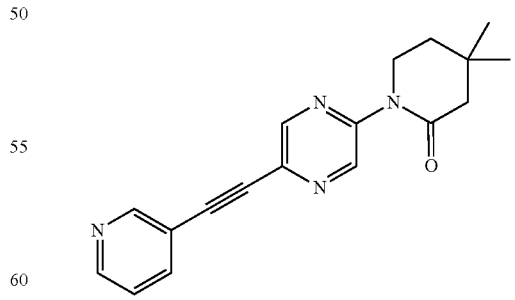

The title compound, an off-white solid, MS: m/e=307.2 (M+H$^+$), was prepared in accordance with the general method of Example 154, step 5; starting from 1-(5-bromo-pyrazin-2-yl)-4,4-dimethyl-piperidin-2-one (Example 161, step 1) and 3-pyridylacetylene.

Example 163

4,4-Dimethyl-1-(5-(phenylethynyl)pyrazin-2-yl)piperidin-2-one

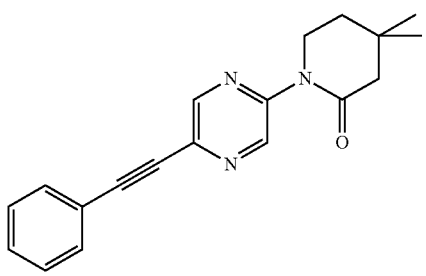 [SMILES: CC1(C)CCN(c2cnc(C#Cc3ccccc3)cn2)C(=O)C1]

The title compound, a yellow solid, MS: m/e=306.2 (M+H⁺), was prepared in accordance with the general method of Example 154, step 5; starting from 1-(5-bromo-pyrazin-2-yl)-4,4-dimethyl-piperidin-2-one (Example 161, step 1) and phenylacetylene.

Example 164

4,4-Dimethyl-1-(5-(phenylethynyl)pyrazin-2-yl)tetrahydropyrimidin-2(1H)-one

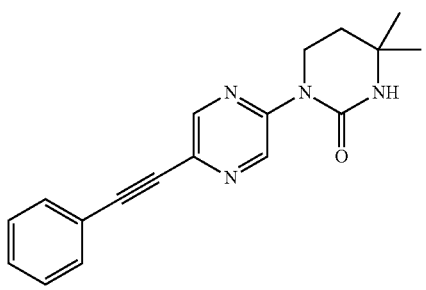

Step 1: 1-(5-Bromo-pyrazin-2-yl)-4,4-dimethyl-tetrahydro-pyrimidin-2-one

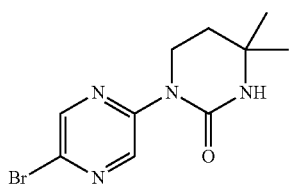 [SMILES: CC1(C)CCN(c2cnc(Br)cn2)C(=O)N1]

The title compound, a light brown solid, MS: m/e=285.0, 287.0 (M+H⁺), was prepared in accordance with the general method of Example 160, step 1; starting from 2-bromo-5-iodopyrazine and 4,4-dimethyl-tetrahydro-pyrimidin-2-one (Example 137, step 1).

Step 2: 4,4-Dimethyl-1-(5-(phenylethynyl)pyrazin-2-yl)tetrahydropyrimidin-2(1H)-one

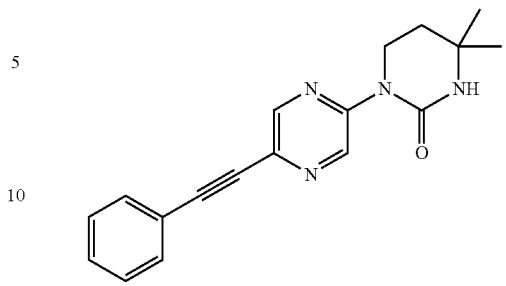

The title compound, a light yellow solid, MS: m/e=307.3 (M+H⁺), was prepared in accordance with the general method of example 45, step 5; starting from 1-(5-bromo-pyrazin-2-yl)-4,4-dimethyl-tetrahydro-pyrimidin-2-one (Example 164, step 1) and phenylacetylene.

Example 165

3,4,4-Trimethyl-1-(5-(phenylethynyl)pyrazin-2-yl)tetrahydropyrimidin-2(1H)-one

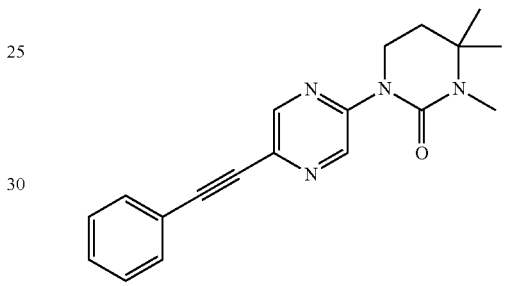

To a solution of 4,4-dimethyl-1-(5-(phenylethynyl)pyrazin-2-yl)tetrahydropyrimidin-2(1H)-one (Example 164, step 2) (30 mg, 0.098 mmol) in 2 ml of DMF was added 60% sodium hydride suspension (4.7 mg, 0.118 mmol, 1.2 equiv.). After stirring at room temperature for 15 min, iodomethane (7.4 ml, 16.7 mg, 0.118 mmol, 1.2 equiv.) was added and the reaction was stirred at room temperature overnight. The reaction mixture was concentrated in vacuo and was worked up with ethyl acetate/water. Flash chromatography over a prepacked 20 g silica column eluting with a heptane to 50% ethyl acetate in heptane gradient yielded the title compound (25.4 mg, 81% yield) as an off-white solid, MS: m/e=321.3 (M+H⁺).

Example 166

1-(5-((3-Fluorophenyl)ethynyl)pyrazin-2-yl)-4,4-dimethyltetrahydropyrimidin-2(1H)-one

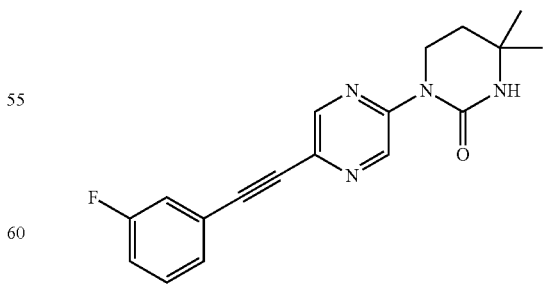

The title compound, an off-white solid, MS: m/e=325.3 (M+H⁺), was prepared in accordance with the general method of Example 154, step 5; starting from 1-(5-bromo-pyrazin-2-yl)-4,4-dimethyl-tetrahydro-pyrimidin-2-one (Example 164, step 1) and 3-fluorophenylacetylene.

Example 167

1-(5-((3-Fluorophenyl)ethynyl)pyrazin-2-yl)-3,4,4-trimethyltetrahydropyrimidin-2(1H)-one

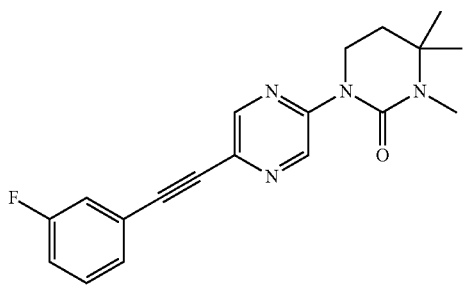 [SMILES: CN1C(=O)N(c2cnc(C#Cc3cccc(F)c3)cn2)CCC1(C)C]

The title compound, a light yellow solid, MS: m/e=339.1 (M+H+), was prepared in accordance with the general method of Example 165, by alkylation of 1-(5-((3-fluorophenyl)ethynyl)pyrazin-2-yl)-4,4-dimethyltetrahydropyrimidin-2(1H)-one (Example 166) with methyl iodide.

Example 168

6,6-Dimethyl-3-(5-(phenylethynyl)pyrazin-2-yl)-1,3-oxazinan-2-one

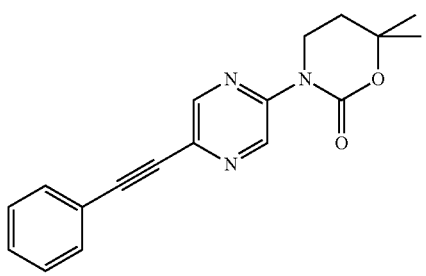 [SMILES: CC1(C)CCN(c2cnc(C#Cc3ccccc3)cn2)C(=O)O1]

Step 1: 2-Bromo-5-phenylethynyl-pyrazine

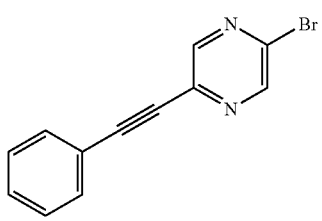 [SMILES: Brc1cnc(C#Cc2ccccc2)cn1]

To a solution of 2-bromo-5-iodopyrazine (500 mg, 1.76 mmol), phenylacetylene (224 mg, 241 μL, 2.19 mmol, 1.25 equiv.), triethylamine (533 mg, 734 μL, 5.27 mmol, 3 equiv.), bis(triphenylphosphine)palladium (II) chloride (73.9 mg, 0.105 mmol, 0.06 equiv.) and triphenyl-phosphine (13.8 mg, 0.053 mmol, 0.03 equiv.) in 10 ml of THF was added under an Argon atmosphere copper (I) iodide (10.0 mg, 0.053 mmol, 0.03 equiv.). The suspension was warmed to 60° C. overnight, taken up in 5 ml of ethyl acetate and adsorbed on 4 g of silica. Purification by flash chromatography on silicagel using a 2:1 ethyl acetate/heptane mixture yielded the title compound as a light brown solid (107 mg, 23% yield). The material was directly used in the next step without further characterization.

Step 2: 2-Methyl-4-(5-phenylethynyl-pyrazin-2-ylamino)-butan-2-ol

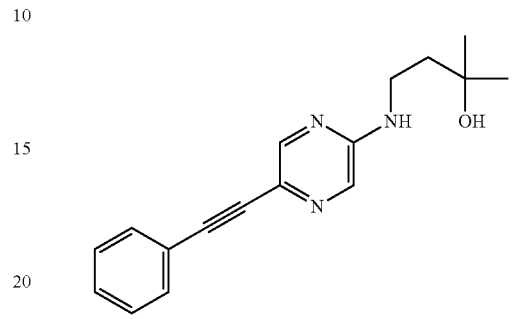

A solution of 2-bromo-5-(phenylethynyl)pyrazine (Example 168, step 1) (158 mg, 0.061 mmol) and 4-amino-2-methylbutan-2-ol hydrochloride (255 mg, 1.83 mmol, 30 equiv.) and triethylamine (185 mg, 255 ul, 1.83 mmol, 30 equiv.) in 3 ml pyridine was stirred overnight at 85° C. The reaction mixture was concentrated in vaccuo. After workup with dichloromethane/water/brine, and drying over magnesium sulfate, the organic phases were concentrated in vacuo. The crude product was chromatographed over a prepacked 20 g silica column eluting with a 25% to 100% ethyl acetate in heptane gradient which yielded the title compound (87.5 mg, 51% yield) as an off-white solid, MS: m/e=282.2 (M+H+).

Step 3: 6,6-Dimethyl-3-(5-(phenylethynyl)pyrazin-2-yl)-1,3-oxazinan-2-one

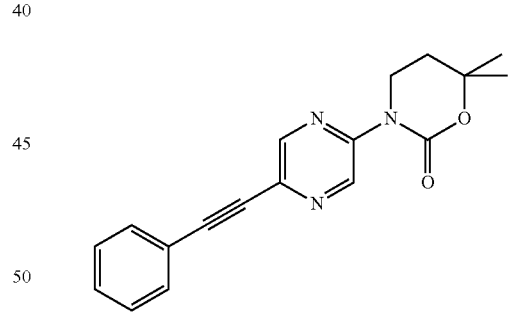

A solution of 2-methyl-4-(5-(phenylethynyl)pyrazin-2-ylamino)butan-2-ol (Example 168, step 2) (84 mg, 0.30 mmol) and triethylamine (91 mg, 125 μl, 0.90 mmol, 3 equiv.) in 2 ml of THF was cooled to 0-5° C. and triphosgene (89 mg, 0.30 mmol, 1 equiv.) was added in portions. The mixture was stirred for 1 hr at 0-5° C. and for 2 hours at room temperature. The reaction mixture was quenched with saturated sodium carbonate solution followed by workup with ethyl acetate/water. The organic layers were combined, dried and concentrated. The crude product was chromatographed over a prepacked 20 g Silica column eluting with a heptane to 50% ethyl acetate in heptane gradient to yield the title compound (66.1 mg, 72% yield) as an off-white solid, MS: m/e=308.3 (M+H+).

Example 169

(RS)-3-[5-(3-Fluoro-phenylethynyl)-pyridin-2-yl]-5-methoxy-6,6-dimethyl-[1,3]oxazinan-2-one

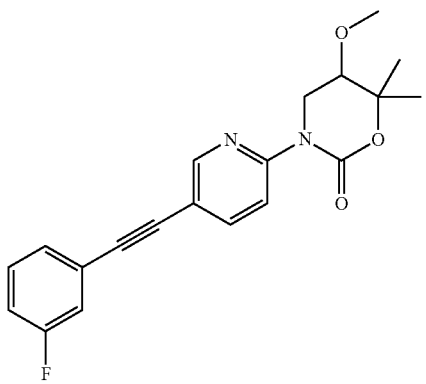 [SMILES: COC1CN(c2ccc(C#Cc3cccc(F)c3)cn2)C(=O)OC1(C)C]

Step 1: (RS)-5-Methoxy-6,6-dimethyl-3-(5-trimethylsilanylethynyl-pyridin-2-yl)-[1,3]oxazinan-2-one

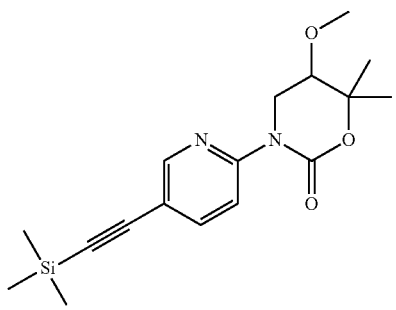

The title compound was obtained as a light brown solid, MS: m/e=333.2 (M+H$^+$), using chemistry similar to that described in Example 37, step 2 from 2-bromo-5-trimethylsilanylethynyl-pyridine (Example 37, step 1) and (RS)-5-methoxy-6,6-dimethyl-[1,3]oxazinan-2-one (Example 114, step 2).

Step 2: (RS)-3-[5-(3-Fluoro-phenylethynyl)-pyridin-2-yl]-5-methoxy-6,6-dimethyl-[1,3]oxazinan-2-one

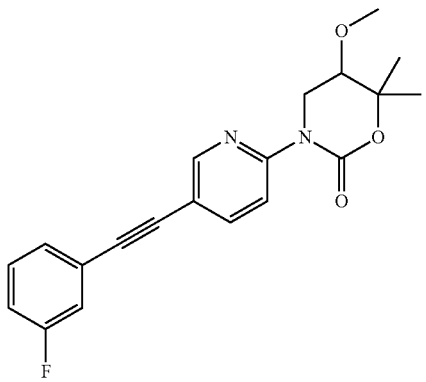 [SMILES: COC1CN(c2ccc(C#Cc3cccc(F)c3)cn2)C(=O)OC1(C)C]

The title compound was obtained as a yellow oil, MS: m/e=355.0 (M+H$^+$), using chemistry similar to that described in Example 37, step 3 from (RS)-5-methoxy-6,6-dimethyl-3-(5-trimethylsilanylethynyl-pyridin-2-yl)-[1,3]oxazinan-2-one (Example 169, step 1) and 1-fluoro-3-iodobenzene.

Example 170

(3aRS,6aSR)-1-Methyl-3-(6-phenylethynyl-pyridazin-3-yl)-hexahydro-cyclopentaimidazol-2-one

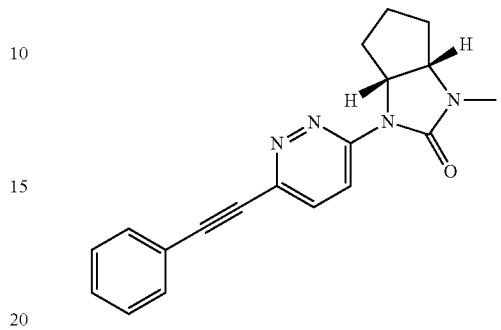

To a solution of (3aRS, 6aSR)-1-methyl-hexahydro-cyclopentaimidazol-2-one (Example 106, step 3) (55 mg, 0.39 mmol, 1.5 equiv.) in 3 ml of DMF was added 60% sodium hydride suspension in mineral oil (17 mg, 0.42 mmol, 1.6 equiv.). The white suspension was stirred for 30 min. at room temperature. Then 3-chloro-6-(phenylethynyl)pyridazine (CAS 77778-15-5) (56 mg, 0.261 mmol) was added and the reaction was stirred for 1 hour at room temperature. After workup with ethyl acetate/water, drying over magnesium sulfate and concentration in vaccuo, the residue was purified by flash chromatography over silica gel eluting with a heptane to 50% ethyl acetate/heptane gradient to yield 40 mg (48% yield) of the title compound as an off-white solid, MS: m/e=319.1 (M+H$^+$).

Example 171

(RS)-6-Methyl-4-(5-phenylethynyl-pyridin-2-yl)-morpholin-3-one

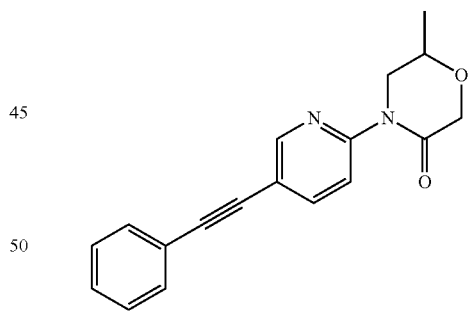

Step 1: (RS)-4-(5-Iodo-pyridin-2-yl)-6-methyl-morpholin-3-one

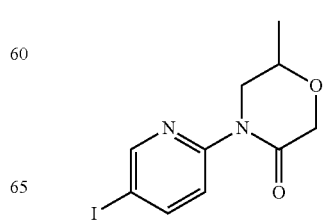

The title compound was obtained as a white solid, MS: m/e=319.0 (M+H⁺), using chemistry similar to that described in Example 37, step 2 from 2,5-diiodopyridine and (RS)-6-methyl-morpholin-3-one (CAS 127958-63-8).

Step 2: (RS)-6-Methyl-4-(5-phenylethynyl-pyridin-2-yl)-morpholin-3-one

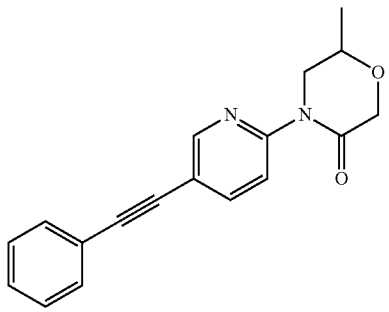 [SMILES: CC1CN(c2ccc(C#Cc3ccccc3)cn2)C(=O)CO1]

The title compound was obtained as a light yellow solid, MS: m/e=293.1 (M+H⁺), using chemistry similar to that described in Example 1, step 3 from (RS)-4-(5-iodo-pyridin-2-yl)-6-methyl-morpholin-3-one (Example 171, step 1) with phenylacetylene.

Example 172

6,6-Dimethyl-4-(5-phenylethynyl-pyridin-2-yl)-morpholin-3-one

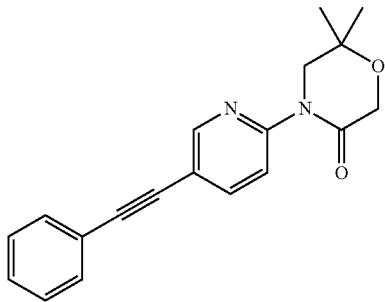 [SMILES: CC1(C)CN(c2ccc(C#Cc3ccccc3)cn2)C(=O)CO1]

Step 1:
(2-Dibenzylamino-1,1-dimethyl-ethoxy)-acetic acid ethyl ester

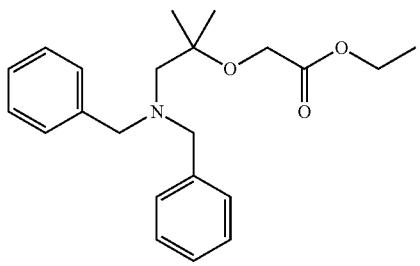 [SMILES: CCOC(=O)COC(C)(C)CN(Cc1ccccc1)Cc1ccccc1]

(4.9 g, 18.2 mmol) 1-(Dibenzylamino)-2-methylpropan-2-ol (CAS 344868-41-3) was dissolved in dichloroethane (50 ml) and ethyl 2-diazoacetate (2.83 ml, 27.3 mmol, 1.5 equiv.) and rhodium(II) acetate dimer (200 mg, 0.455 mmol, 0.025 equiv.) were added carefully at room temperature. The mixture was stirred for 3 hours at 80° C. The reaction mixture was evaporated with isolute and the crude product was purified by flash chromatography by directly loading the residue onto a silica gel column and eluting with a heptane:ethyl acetate gradient 100:0 to 70:30. The desired (2-dibenzylamino-1,1-dimethyl-ethoxy)-acetic acid ethyl ester (1.03 g, 80% purity, 13% yield) was obtained as a colorless liquid, MS: m/e=356.3 (M+H⁺).

Step 2: 6,6-Dimethyl-morpholin-3-one

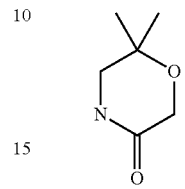

(2-Dibenzylamino-1,1-dimethyl-ethoxy)-acetic acid ethyl ester (Example 172, step 1) was hydrogenated in EtOH with Pd(OH)₂ for 16 hours at 60° C. The desired 6,6-dimethyl-morpholin-3-one (585 mg, 60% purity, quant.) was obtained as a colorless liquid, MS: m/e=129 (M+H⁺) and used in the next step without further purification.

Step 3: 6,6-Dimethyl-4-(5-trimethylsilanylethynyl-pyridin-2-yl)-morpholin-3-one

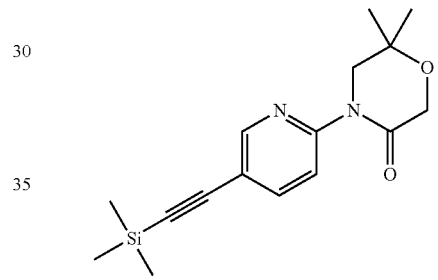

The title compound was obtained as a yellow oil, MS: m/e=303.2 (M+H⁺), using chemistry similar to that described in Example 37, step 2 from 2-bromo-5-trimethylsilanylethynyl-pyridine (Example 37, step 1) and 6,6-dimethyl-morpholin-3-one (Example 172, step 2).

Step 4: 6,6-Dimethyl-4-(5-phenylethynyl-pyridin-2-yl)-morpholin-3-one

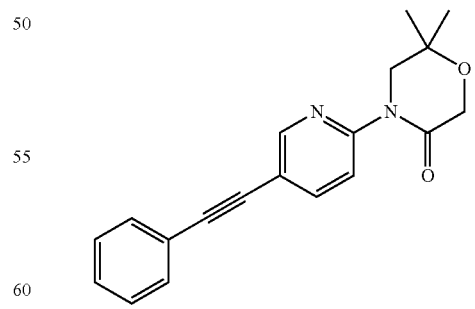

The title compound was obtained as a white solid, MS: m/e=307.3 (M+H⁺), using chemistry similar to that described in Example 37, step 3 from 6,6-dimethyl-4-(5-trimethylsilanylethynyl-pyridin-2-yl)-morpholin-3-one (Example 172, step 3) and iodobenzene.

Example 173

1,1-Dioxo-4-(5-phenylethynyl-pyridin-2-yl)-thiomorpholin-3-one

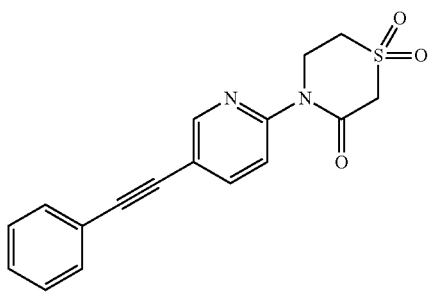 [SMILES: O=C1CS(=O)(=O)CCN1c1ccc(C#Cc2ccccc2)cn1]

Step 1:
4-(5-Bromo-pyridin-2-yl)-thiomorpholin-3-one

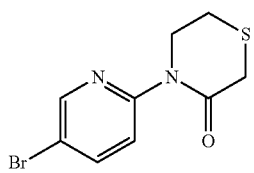 [SMILES: O=C1CSCCN1c1ccc(Br)cn1]

The title compound was obtained as a yellow solid, MS: m/e=273.0/274.9 (M+H$^+$), using chemistry similar to that described in Example 37, step 2 from 2,5-dibromopyridine and thiomorpholin-3-one.

Step 2: 4-(5-Bromo-pyridin-2-yl)-1,1-dioxo-thiomorpholin-3-one

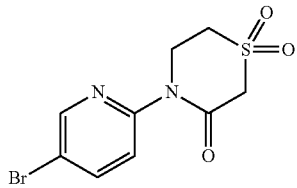

(240 mg, 0.88 mmol) 4-(5-Bromo-pyridin-2-yl)-thiomorpholin-3-one (Example 173, step 1) was dissolved in dichloroethane (10 ml) and mCPBA (300 mg, 1.76 mmol, 2 equiv.) was added at 0-5° C. The mixture was stirred for 2 hours at 20-25° C. The reaction mixture was extracted with saturated NaHCO$_3$ solution and five times dichloromethane. The organic layers were combined, dried over Na$_2$SO$_4$ and evaporated to dryness. The desired 4-(5-bromo-pyridin-2-yl)-1,1-dioxo-thiomorpholin-3-one (167 mg, 62% yield) was obtained as a light brown solid, MS: m/e=305.1/307.1 (M+H$^+$).

Step 3: 1,1-Dioxo-4-(5-phenylethynyl-pyridin-2-yl)-thiomorpholin-3-one

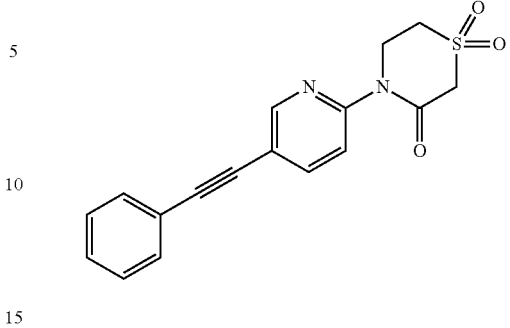

The title compound was obtained as a light brown solid, MS: m/e=327.2 (M+H$^+$), using chemistry similar to that described in Example 1, step 3 from 4-(5-bromo-pyridin-2-yl)-1,1-dioxo-thiomorpholin-3-one (Example 173, step 2) and phenylacetylene.

Example 174

(3aSR,6aRS)-1-[6-(3-Fluoro-phenylethynyl)-pyridazin-3-yl]-3-methyl-hexahydro-cyclopentaimidazol-2-one

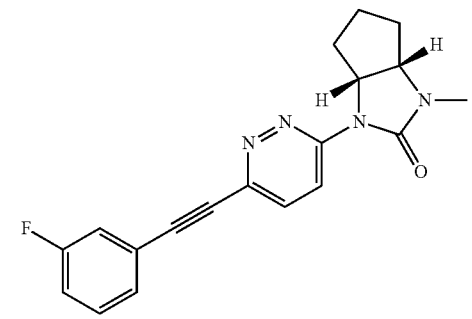 [SMILES: CN1C(=O)N(c2ccc(C#Cc3cccc(F)c3)nn2)[C@@H]2CCC[C@@H]21]

Step 1:
3-Chloro-6-(3-fluoro-phenylethynyl)-pyridazine

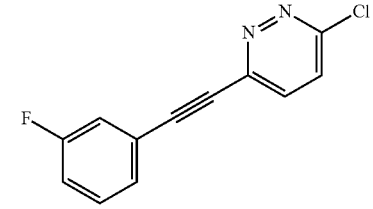 [SMILES: Fc1cccc(C#Cc2ccc(Cl)nn2)c1]

To a well stirred solution of 2-chloro-5-iodopyrazine (600 mg, 2.5 mmol), 3-fluorophenyl-acetylene (315 mg, 303 µl, 2.62 mmol, 1.05 equiv.) in 7 ml of THF were added under argon atmosphere bis(triphenylphosphine)-palladium(II) dichloride (175 mg, 0.250 mmol, 0.02 equiv.), copper(I) iodide (23.8 mg, 0.125 mmol, 0.01 equiv.) and triethylamine (556 mg, 761 ul, 5.49 mmol, 2.2 equiv.). The mixture was stirred for 2 hours at room temperature. The crude mixture was filtered, adsorbed on silicagel and purified by flash chromatography over a 50 g silicagel column using a heptane to 25% ethyl acetate in heptane gradient. The title compound (450 mg, 78% yield) was obtained as a crystalline light-yellow solid, MS: m/e=233.1, 235.0 (M+H$^+$).

Step 2: (3aSR,6aRS)-1-[6-(3-Fluoro-phenylethynyl)-pyridazin-3-yl]-3-methyl-hexahydro-cyclopentaimidazol-2-one

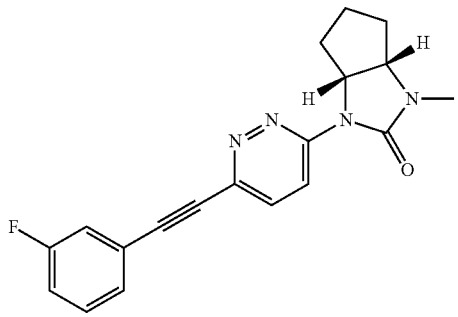 [SMILES: CN1C(=O)N(c2ccc(C#Cc3cccc(F)c3)nn2)[C@@H]2CCC[C@@H]21]

The title compound, an off-white solid, MS: m/e=337.2 (M+H⁺), was prepared in accordance with the general method of Example 170; starting from 3-chloro-6-((3-fluorophenyl)-ethynyl)pyridazine and (3aRS, 6aSR)-1-methyl-hexahydro-cyclopentaimidazol-2-one.

The invention claimed is:

1. The compound of formula I-C1

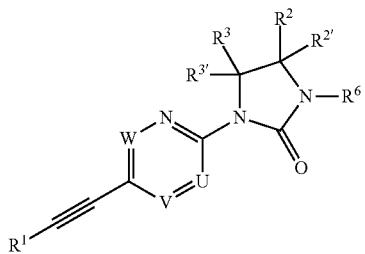

wherein
U is =N— or =C($R^5$)—;
V is —CH= or —N=;
W is —CH= or =N—;
with the proviso that only one of U, V or W is nitrogen.
$R^5$ is hydrogen, methyl or halogen;
$R^6$ is hydrogen or lower alkyl;
$R^1$ is phenyl or heteroaryl, each of which is optionally substituted by one or two substituents, selected from halogen, lower alkyl and lower alkoxy;
$R^2$ and $R^{2'}$ are each independently hydrogen, lower alkyl, hydroxy, lower alkoxy, $C_3$-$C_6$-cycloalkyl, or $CH_2$-lower alkoxy, or together with the carbon atom to which they are attached form a $C_3$-$C_6$-cycloalkyl group or a ring containing —$CH_2OCH_2$—; and
$R^3$ and $R^{3'}$ are each independently hydrogen, lower alkyl, or $CH_2$-lower alkoxy or together with the carbon atom to which they are attached form a $C_3$-$C_6$-cycloalkyl group;
or $R^3$ and $R^2$ together with the carbon atom to which they are attached form a $C_{3-6}$-cycloalkyl group or a ring containing —$(CH_2)_2OCH_2$—;
or $R^6$ and $R^2$ together with the carbon atom and the nitrogen atom to which they are attached form a $C_{3-6}$-cycloalkyl group;
or a pharmaceutically acceptable acid addition salt, a racemic mixture, an enantiomers, an optical isomer and/or stereoisomer thereof.

2. The compound of claim 1, selected from the group consisting of
4,4-dimethyl-1-(5-phenylethynyl-pyridin-2-yl)-imidazolidin-2-one;
3,4,4-trimethyl-1-(5-phenylethynyl-pyridin-2-yl)-imidazolidin-2-one;
3-ethyl-4,4-dimethyl-1-(5-phenylethynyl-pyridin-2-yl)-imidazolidin-2-one;
3-isopropyl-4,4-dimethyl-1-(5-phenylethynyl-pyridin-2-yl)-imidazolidin-2-one;
1-methyl-3-(5-phenylethynyl-pyridin-2-yl)-1,3-diaza-spiro[4.4]nonan-2-one;
(RS)-4-cyclopentyl-3-methyl-1-(5-phenylethynyl-pyridin-2-yl)-imidazolidin-2-one;
3,4,4-trimethyl-1-(5-pyridin-3-ylethynyl-pyridin-2-yl)-imidazolidin-2-one;
1-[5-(5-fluoro-pyridin-3-ylethynyl)-pyridin-2-yl]-3,4,4-trimethyl-imidazolidin-2-one;
3,4,4-trimethyl-1-[5-(1-methyl-1H-pyrazol-4-ylethynyl)-pyridin-2-yl]-imidazolidin-2-one;
1-[5-(5-chloro-pyridin-3-ylethynyl)-pyridin-2-yl]-3,4,4-trimethyl-imidazolidin-2-one;
3,4,4-trimethyl-1-(5-pyridazin-4-ylethynyl-pyridin-2-yl)-imidazolidin-2-one;
or a pharmaceutically acceptable acid addition salt, a racemic mixture, an enantiomer, an optical isomer and/or stereoisomer thereof.

3. The compound of claim 1, selected from the group consisting of
1-[5-(3-fluoro-phenylethynyl)-pyridin-2-yl]-3,4,4-trimethyl-imidazolidin-2-one;
1-[5-(3-chloro-phenylethynyl)-pyridin-2-yl]-3,4,4-trimethyl-imidazolidin-2-one;
3,4,4-trimethyl-1-(5-pyrimidin-5-ylethynyl-pyridin-2-yl)-imidazolidin-2-one;
3,4,4-trimethyl-1-(5-m-tolylethynyl-pyridin-2-yl)-imidazolidin-2-one;
1-[5-(4-fluoro-phenylethynyl)-pyridin-2-yl]-3,4,4-trimethyl-imidazolidin-2-one;
(RS)-2-(5-phenylethynyl-pyridin-2-yl)-hexahydro-imidazo[1,5-a]pyridin-3-one;
(RS)-2-(5-pyridin-3-ylethynyl-pyridin-2-yl)-hexahydro-imidazo[1,5-a]pyridin-3-one;
(RS)-2-[5-(3-fluoro-phenylethynyl)-pyridin-2-yl]-hexahydro-imidazo[1,5-a]pyridin-3-one;
(RS)-4-cyclopropyl-3-methyl-1-(5-phenylethynyl-pyridin-2-yl)-imidazolidin-2-one;
(3aSR,7aRS)-(3aRS,7RS)-1-methyl-3-(5-phenylethynyl-pyridin-2-yl)-octahydro-benzoimidazol-2-one;
(3aSR,7aRS)-(3aRS,7RS)-1-methyl-3-(5-pyridin-3-yl-ethynyl-pyridin-2-yl)-octahydro-benzoimidazol-2-one;
or a pharmaceutically acceptable acid addition salt, a racemic mixture, an enantiomer, an optical isomer and/or stereoisomer thereof.

4. The compound of claim 1, selected from the group consisting of (3aSR,7aRS)-(3aRS,7RS)-1-[5-(5-fluoro-pyridin-3-ylethynyl)-pyridin-2-yl]-3-methyl-octahydro-benzoimidazol-2-one;
4-methyl-6-(5-phenylethynyl-pyridin-2-yl)-4,6-diaza-spiro[2.4]heptan-5-one;
(3aSR,7aRS)-(3aRS,7RS)-1-ethyl-3-(5-phenylethynyl-pyridin-2-yl)-octahydro-benzoimidazol-2-one;
(3aSR,7aRS)-(3aRS,7RS)-1-ethyl-3-(5-pyridin-3-ylethynyl-pyridin-2-yl)-octahydro-benzoimidazol-2-one;
(3aSR,7aRS)-(3aRS,7RS)-1-isopropyl-3-(5-phenylethynyl-pyridin-2-yl)-octahydro-benzoimidazol-2-one;

(3aRS, 6aSR)-1-methyl-3-(5-(phenylethynyl)pyridin-2-yl)hexahydrocyclopenta[d]imidazol-2(1H)-one;
(RS)-4-tert-butyl-3-methyl-1-(5-phenylethynyl-pyridin-2-yl)-imidazolidin-2-one;
1-[5-(3-fluoro-phenylethynyl)-3-methyl-pyridin-2-yl]-3,4,4-trimethyl-imidazolidin-2-one;
(3aSR,6aRS)-1-[5-(3-fluoro-phenylethynyl)-pyridin-2-yl]-3-methyl-hexahydro-cyclopenta-imidazol-2-one;
1-[3-fluoro-5-(4-fluoro-phenylethynyl)-pyridin-2-yl]-3,4,4-trimethyl-imidazolidin-2-one;
1-[3-fluoro-5-(3-fluoro-phenylethynyl)-pyridin-2-yl]-3,4,4-trimethyl-imidazolidin-2-one;
or a pharmaceutically acceptable acid addition salt, a racemic mixture, an enantiomer, an optical isomer and/or stereoisomer thereof.

5. The compound of claim 1, selected from the group consisting of
6-[5-(4-fluoro-phenylethynyl)-pyridin-2-yl]-4-methyl-4,6-diaza-spiro[2.4]heptan-5-one;
6-[5-(3-fluoro-phenylethynyl)-pyridin-2-yl]-4-methyl-4,6-diaza-spiro[2.4]heptan-5-one;
3,4,4-trimethyl-1-(5-phenylethynyl-pyrimidin-2-yl)-imidazolidin-2-one;
1-[5-(3-fluoro-phenylethynyl)-pyrimidin-2-yl]-3,4,4-trimethyl-imidazolidin-2-one;
1-[5-(2,5-difluoro-phenylethynyl)-pyrimidin-2-yl]-3,4,4-trimethyl-imidazolidin-2-one;
1-[5-(4-fluoro-phenylethynyl)-pyrimidin-2-yl]-3,4,4-trimethyl-imidazolidin-2-one;
1-[5-(3,4-di-fluoro-phenylethynyl)-pyrimidin-2-yl]-3,4,4-trimethyl-imidazolidin-2-one;
3-isopropyl-4,4-dimethyl-1-(5-phenylethynyl-pyrimidin-2-yl)-imidazolidin-2-one;
1-[5-(3-fluoro-phenylethynyl)-pyrimidin-2-yl]-3-isopropyl-4,4-dimethyl-imidazolidin-2-one;
1-[5-(4-fluoro-phenylethynyl)-pyrimidin-2-yl]-3-isopropyl-4,4-dimethyl-imidazolidin-2-one;
1-[5-(4-fluoro-phenylethynyl)-pyrimidin-2-yl]-3-ethyl-4,4-dimethyl-imidazolidin-2-one;
or a pharmaceutically acceptable acid addition salt, a racemic mixture, an enantiomer, an optical isomer and/or stereoisomer thereof.

6. The compound of claim 1, selected from the group consisting of
1-[5-(3-fluoro-phenylethynyl)-pyrimidin-2-yl]-3-ethyl-4,4-dimethyl-imidazolidin-2-one;
4-methyl-6-(5-phenylethynyl-pyrimidin-2-yl)-4,6-diazaspiro[2.4]heptan-5-one;
3,4,4-trimethyl-1-(6-(m-tolylethynyl)pyridazin-3-yl)imidazolidin-2-one;
1-(6-((3-chlorophenyl)ethynyl)pyridazin-3-yl)-3,4,4-trimethylimidazolidin-2-one;
3,4,4-trimethyl-1-(5-(phenylethynyl)pyrazin-2-yl)imidazolidin-2-one;
3,4,4-trimethyl-1-(5-(pyridin-3-ylethynyl)pyrazin-2-yl)imidazolidin-2-one;
1-(5-((3-fluorophenyl)ethynyl)pyrazin-2-yl)-3,4,4-trimethylimidazolidin-2-one;
1-(5-((4-fluorophenyl)ethynyl)pyrazin-2-yl)-3,4,4-trimethylimidazolidin-2-one;
(3aRS,6aSR)-1-methyl-3-(6-phenylethynyl-pyridazin-3-yl)-hexahydro-cyclopentaimidazol-2-one;
(3aSR,6aRS)-1-[6-(3-fluoro-phenylethynyl)-pyridazin-3-yl]-3-methyl-hexahydro-cyclopentaimidazol-2-one;
or a pharmaceutically acceptable acid addition salt, a racemic mixture, an enantiomer, an optical isomer and/or stereoisomer thereof.

7. The compound of claim 1, wherein said compound is 1-methyl-3-(5-(phenylethynyl)pyridin-2-yl)hexahydrocyclopenta[d]imidazol-2(1H)-one or a pharmaceutically acceptable acid addition salt, a racemic mixture, an enantiomer, an optical isomer and/or stereoisomer thereof.

8. The compound of claim 7, wherein said compound is (3aRS, 6aSR)-1-methyl-3-(5-(phenylethynyl)pyridin-2-yl)hexahydrocyclopenta[d]imidazol-2(1H)-one.

* * * * *

UNITED STATES PATENT AND TRADEMARK OFFICE
CERTIFICATE OF CORRECTION

PATENT NO. : 9,315,498 B2  
APPLICATION NO. : 14/085064  
DATED : April 19, 2016  
INVENTOR(S) : Luke Green et al.

Page 1 of 1

It is certified that error appears in the above-identified patent and that said Letters Patent is hereby corrected as shown below:

TITLE PAGE

Item 73, "Hoffman-La Roche Inc." should be replaced with "Hoffmann-La Roche Inc."

Signed and Sealed this  
Twenty-first Day of June, 2016

Michelle K. Lee  
*Director of the United States Patent and Trademark Office*